(12) United States Patent
Rawat et al.

(10) Patent No.: US 9,567,316 B2
(45) Date of Patent: Feb. 14, 2017

(54) AMINOQUINOLINE DERIVATIVES AND USES THEREOF

(71) Applicant: THE MCLEAN HOSPITAL CORPORATION, Belmont, MA (US)

(72) Inventors: Diwan S. Rawat, Delhi (IN); Sunny Manohar, Delhi (IN); Ummadisetty Chinna Rajesh, Delhi (IN); Deepak Kumar, Delhi (IN); Anuj Thakur, Delhi (IN); Mohit Tripathi, Delhi (IN); Panyala Linga Reddy, Delhi (IN); Shamseer Kulangara Kandi, Delhi (IN); Satyapavan Vardhineni, Delhi (IN); Kwang-Soo Kim, Lexington, MA (US); Chun-Hyung Kim, Lexington, MA (US)

(73) Assignees: THE MCLEAN HOSPITAL CORPORATION, Belmont, MA (US); UNIVERSITY OF DELHI, Delhi (IN)

( * ) Notice: Subject to any disclaimer, the term of this patent is extended or adjusted under 35 U.S.C. 154(b) by 0 days.

(21) Appl. No.: 14/382,727

(22) PCT Filed: Feb. 28, 2013

(86) PCT No.: PCT/US2013/028329
§ 371 (c)(1),
(2) Date: Sep. 3, 2014

(87) PCT Pub. No.: WO2013/134047
PCT Pub. Date: Sep. 12, 2013

(65) Prior Publication Data
US 2015/0023930 A1   Jan. 22, 2015

(30) Foreign Application Priority Data
Mar. 7, 2012 (IN) .............................. 661/DEL/2012

(51) Int. Cl.
C07D 401/12 (2006.01)
C07D 401/14 (2006.01)
(Continued)

(52) U.S. Cl.
CPC .......... *C07D 401/12* (2013.01); *A61K 31/506* (2013.01); *A61K 31/5355* (2013.01); *A61K 45/06* (2013.01);
(Continued)

(58) Field of Classification Search
None
See application file for complete search history.

(56) References Cited

U.S. PATENT DOCUMENTS

| 3,196,155 A | 7/1965 | Gailliot et al. |
| 2003/0119026 A1 | 6/2003 | Le et al. |

(Continued)

FOREIGN PATENT DOCUMENTS

| WO | WO00/59510 A1 | 10/2000 |
| WO | 03/070244 A1 | 8/2003 |

(Continued)

OTHER PUBLICATIONS

Park 2011 "Fine tuning of receptor polarity for the development of selective naked eye anion receptor" Tetrahedron letters 52:3361-3366.*

(Continued)

*Primary Examiner* — Adam M Weidner
(74) *Attorney, Agent, or Firm* — David S. Resnick; Nixon Peabody LLP

(57) ABSTRACT

Described herein are aminoquinoline and aminoacridine based hybrids, pharmaceutical compositions and medicaments that include such aminoquinoline and aminoacridine based hybrids, and methods of using such compounds for diagnosing and/or treating infections, neurodegerative dis- (Continued)

AQ

CQ eases or disorders, inflammation, inflammation associated diseases and disorders, and/or diseases or disorders that are treatable with dopamine agonists such as the restless leg syndrome.

6 Claims, 39 Drawing Sheets

(51) Int. Cl.
  A61K 31/506 (2006.01)
  A61K 45/06 (2006.01)
  C12N 5/0793 (2010.01)
  A61K 31/5355 (2006.01)
(52) U.S. Cl.
  CPC ........... *C07D 401/14* (2013.01); *C12N 5/0619* (2013.01); *C12N 2506/02* (2013.01)

(56) References Cited

U.S. PATENT DOCUMENTS

| | | | |
|---|---|---|---|
| 2003/0229119 A1 | 12/2003 | Kym et al. | |
| 2004/0072818 A1* | 4/2004 | Dunning | C07D 215/46 514/210.21 |
| 2005/0186591 A1 | 8/2005 | Bumcrot et al. | |
| 2009/0226401 A1* | 9/2009 | Kim | A61K 31/4706 424/93.7 |
| 2011/0251210 A1* | 10/2011 | Peyton | A61K 31/047 514/252.18 |

FOREIGN PATENT DOCUMENTS

| | | | | |
|---|---|---|---|---|
| WO | WO2004/002960 A1 | 1/2004 | | |
| WO | WO2008036374 | * | 3/2008 | ............ A61K 35/30 |
| WO | 2009148659 A2 | 12/2009 | | |
| WO | WO2010/059738 A1 | 5/2010 | | |
| WO | 2010/065932 A1 | 6/2010 | | |

OTHER PUBLICATIONS

Arambula et al. "A simple ligand that selectively targets CUG trinucleotide repeats and inhibits MBNL protein binding." Proceedings of the National Academy of Sciences of the United States of America (PNAS), 2009, 106 (38), pp. 16068-16073.
Manohar et al. "Synthesis, antimalarial and cytotoxicity of 4-aminoquinoline-triazine conjugates." Bioorganic & Medicinal Chemistry Letters, 2010, 20 pp. 322-325.
Sunduru et al. "Synthesis of oxalamide and triazine derivatives as novel class of hybrid 4-aminoquinoline with potent antiplasmodial activity." Bioorganic & Medicinal Chemistry, 2009, 17, pp. 6451-6462.
Melato et al. "A combinatorial approach to 2,4,6-trisubstituted triazines with potent antimalarial activity: combining conventional synthesis and microwave-assistance." ChemMedChem, 2008, 3, pp. 873-876.
Bolte et al. "Synthetic models of DNA complexes with antimalarial compounds. 2. The problem of guanine specicicity in chloroquine binding." J. of Medicinal Chemistry, 1977, 20(1), pp. 106-113.
Melato et al. "Novel 4-aminoquinolines through microwave-assisted SnAr reactions: a practical route to antimalarial agents." European J. of Organic Chemistry, 2007, 36, pp. 6118-6123.
Atheaya et al., "Synthesis, thermal stability, antimalarial activity of symmetrically and asymmetrically substituted tetraoxanes", Bioorg. Med. Chem. Lett. 18:1446-1449 (2008).
Blandini et al., "Time-course of nigrostriatal damage, basal ganglia metabolic changes and behavioural alterations following intrastriatal injection of 6-hydroxydopamine in the rat: new clues from an old model", Eur. J. Neurosci. 25:397-405 (2007).
Bonifati, "Genetics of Parkinson's disease", Minerva Med. 96(3):175-186 (2005).

Castillo et al., "Dopamine Biosynthesis Is Selectively Abolished in Substantia Nigra/Ventral Tegmental Area but Not in Hypothalamic Neurons in Mice with Targeted Disruption of the Nurr1 Gene", Mol. Cell. Neurosci. 11:36-46 (1998).
Chu et al., "Nurr1 in Parkinson's Disease and Related Disorders" J. Comp. Neurol. 494:495-514 (2006).
Chung et al., "ES cell-derived renewable and functional midbrain dopaminergic progenitors", Proc. Natl. Acad. Sci. U.S.A. 108(23):9703-9708 (2011).
Cookson et al., "How genetics research in Parkinson's disease is enhancing understanding of the common idiopathic forms of the disease", Curr. Opin. Neurol. 18:706-711 (2005).
D'Amato et al., "Selectivity of the Parkinsonian Neurotoxin MPTP: Toxic Metabolite MPP+ Binds to Neuromelanin", Science 231:987-989 (1986).
D'Amato et al., "Evidence for neuromelanin involvement in MPTP-induced neurotoxicity", Nature 327:324-326 (1987).
Dauer et al., "Parkinson's Disease: Mechanisms and Models", Neuron 39:889-909 (2003).
Dekundy et al., "Modulation of L-DOPA-induced abnormal involuntary movements by clinically tested compounds: Further validation of the rat dyskinesia model", Behav. Brain Res. 179:76-89 (2007).
Espino et al., "Chronic effects of single intrastriatal injections of 6-hydroxydopamine or 1-methyl-4-phenylpyridinium studied by microdialysis in freely moving rats", Brain. Res. 695:151-157 (1995).
Glass et al., "The coregulator exchange in transcriptional functions of nuclear receptors", Genes Dev. 14:121-141 (2000).
Glass et al., "Mechanisms Underlying Inflammation in Neurodegeneration", Cell 140:918-934 (2010).
Hwang et al., "3,4-Dihydroxyphenylalanine Reverses the Motor Deficits in Pitx3—Deficient Aphakia Mice: Behavioral Characterization of a Novel Genetic Model of Parkinson's Disease", J. Neurosci. 25(8):2132-2137 (2005).
Kadkhodaei et al., "Nurr1 is Required for Maintenance of Maturing and Adult Midbrain Dopamine Neurons", J. Neurosci. 29(50):15923-15932 (2009).
Kim et al., "Orphan nuclear receptor Nurr1 directly transactivates the promoter activity of the tyrosine hydroxylase gene in a cell-specific manner", J. Neurochem. 85:622-634 (2003).
Kumar et al., "Synthesis, antimalarial activity and cytotoxicity of substituted 3,6-diphenyl-[1,2,4,5]tetraoxanes", Bioorg. Med. Chem. 17:5632-5638 (2009).
Kumar et al., "Synthesis and in vitro antimalarial activity of tetraoxane-amine/amide conjugates", Eur. J. Med. Chem. 46(7):2816-2827 (2011).
Le et al., "Mutations in NR4A2 associated with familial Parkinson disease", Nat. Genet. 33:85-89 (2003).
Manohar et al., "Synthesis, antimalarial activity and cytotoxicity of 4-aminoquinoline-triazine conjugates", Bioorg. Med. Chem. Lett. 20(1):322-325 (2010).
Manohar et al., "Synthesis of 4-aminoquinoline-1,2,3-triazole and 4-aminoquinoline-1,2,3-triazole-1,3,5-triazine Hybrids as Potential Antimalarial Agents", Chem. Biol. Drug Des. 78(1):124-136 (2011).
Manohar et al., "Novel 4-Aminoquinoline-Pyrimidine Based Hybrids with Improved in Vitro and in Vivo Antimalarial Activity", ACS Med. Chem. Lett. 3(7):555-559 (2012).
Manohar et al., "4-Aminoquinoline-Triazine-Based Hybrids with Improved In Vitro Antimalarial Activity Against CQ-Sensitive and CQ-Resistant Strains of Plasmodium falciparum", Chem. Biol. Drug Des. 81:625-630 (2013).
McMorrow et al., "Inflammation: a role for NR4A orphan nuclear receptors?", Biochem. Soc. Trans. 39(2):688-693 (2011).
Obeso et al., "Missing pieces in the Parkinson's disease puzzle", Nat. Med. 16(6):653-661 (2010).
Park et al., "Acupuncture prevents 6-hydroxydopamine-induced neuronal death in the nigrostriatal dopaminergic system in the rat Parkinson's disease model", Exp. Neurol. 180:92-97 (2003).
Park et al., "Proneural bHLH neurogenin 2 differentially regulates Nurr1-induced dopamine neuron differentiation in rat and mouse neural precursor cells in vitro", FEBS Lett. 582:537-542 (2008).

(56) References Cited

OTHER PUBLICATIONS

Paxinos et al., "The Rat Brain in Stereotaxic Coordinates", San Diego, CA: Academic Press (1997).

Ringe et al., "Reaction of Myoglobin with Phenylhydrazine: A Molecular Doorstop", Biochemistry 23:2-4 (1984).

Saijo et al., "A Nurr1/CoREST Pathway in Microglia and Astrocytes Protects Dopaminergic Neurons from Inflammation-Induced Death", Cell 137:47-59 (2009).

Saucedo-Cardenas et al., "Nurr1 is essential for the induction of the dopaminergic phenotype and the survival of ventral mesencephalic late dopaminergic precursor neurons", Proc. Natl. Acad. Sci. U.S.A. 95:4013-4018 (1998).

Schlichting et al., "The Catalytic Pathway of Cytochrome P450cam at Atomic Resolution", Science 287:1615-1622 (2000).

Voutilainen et al., "Mesencephalic Astrocyte-Derived Neurotrophic Factor Is Neurorestorative in Rat Model of Parkinson's Disease", J. Neurosci. 29(30):9651-9659 (2009).

Wang et al., "Structure and function of Nurr1 identifies a class of ligand-independent nuclear receptors", Nature 423:555-560 (2003).

Webster et al., "The Yeast UASG Is a Transcriptional Enhancer in Human HeLa Cells in the Presence of the GAL4 Trans-Activator", Cell 52:169-178 (1988).

Zetterstrom et al., "Dopamine Neuron Agenesis in Nurr1-Deficient Mice", Science 276:248-250 (1997).

Carlier et al., "Heterodimeric Tacrine-Based Acetylcholinesterase Inhibitors: Investigating Ligand-Peripheral Site Interactions", J. Med. Chem. 42(20):4225-4231 (1999).

Nava-Zuazo et al., "Design, synthesis, and in vitro antiprotozoal, antimycobacterial activities of N-{2-[(7-chloroquinolin-4-yl)amino]ethyl}ureas", Bioorg. Med. Chem. 18(17):6398-6403 (2010).

Sondhi et al., "Synthesis of sulpha drug acridine derivatives and their evaluation for anit-inflammatory, analgesic and anticancer activity", Indian J. Chem. 41B:2659-2666 (2002).

Sunduru et al., "Synthesis of novel thiourea, thiazolidinedione and thioparabanic acid derivatives of 4-aminoquinoline as potent antimalarials", Bioorg. Med. Chem. Lett. 19(9):2570-2573 (2009).

Kumar et al., "Synthesis and bioevaluation of hybrid 4-aminoquinoline triazines as a new class of antimalarial agents", Bioorganic & Medicinal Chemistry Letters 18(24):6530-6533 (2008).

Kumar et al., "Synthesis of new 4-aminoquinolines and quinoline-acridine hybrids as antimalarial agents", Bioorganic & Medicinal Chemistry Letters 20(23):7059-7063 (2010).

\* cited by examiner

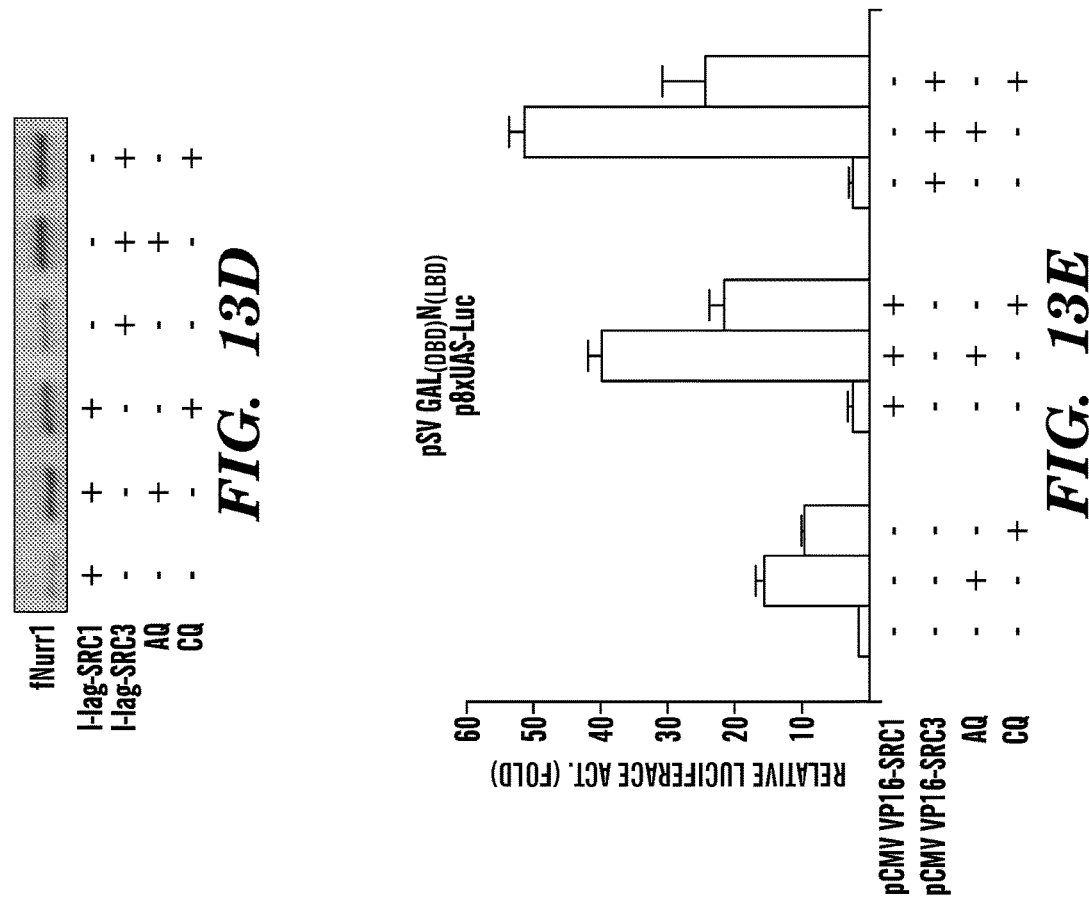
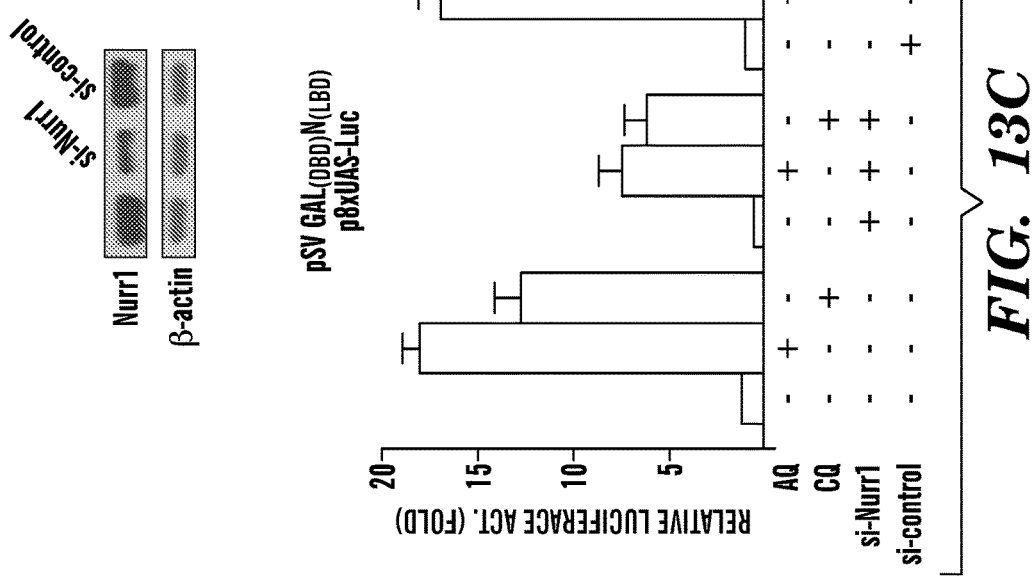
FIG. 13C
FIG. 13D
FIG. 13E

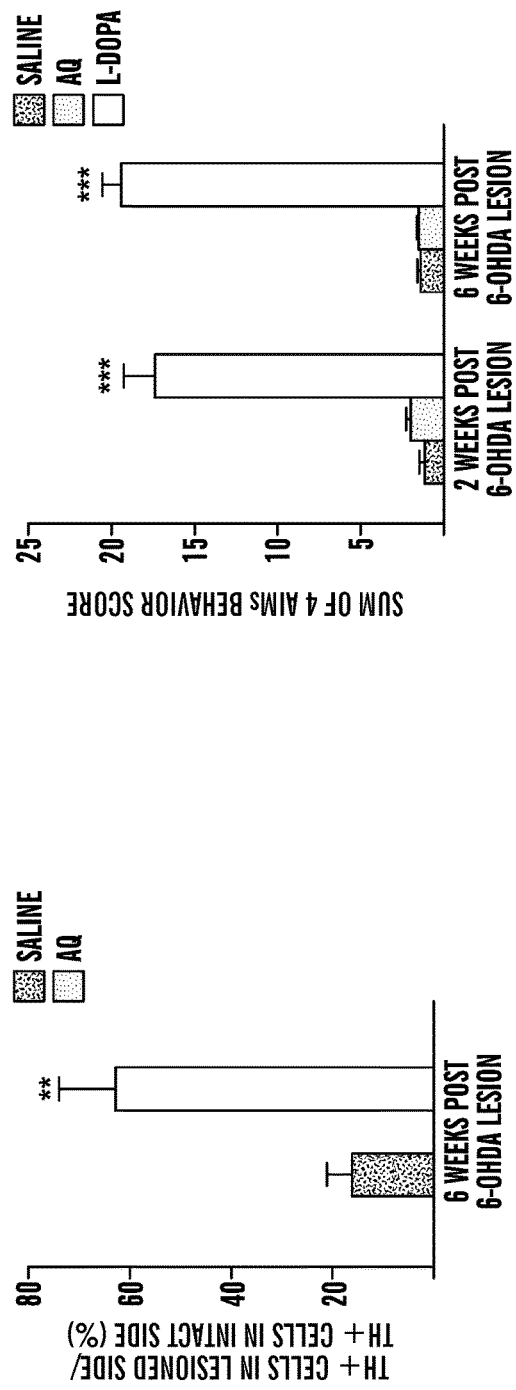
*FIG. 15F*
*FIG. 15D*
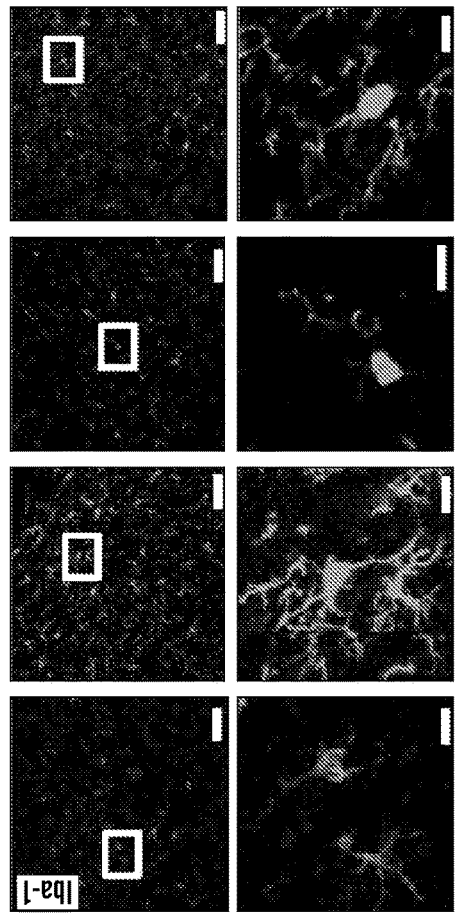
*FIG. 15E*

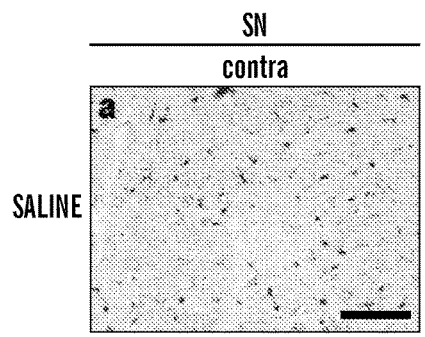
FIG. 24A  FIG. 24B
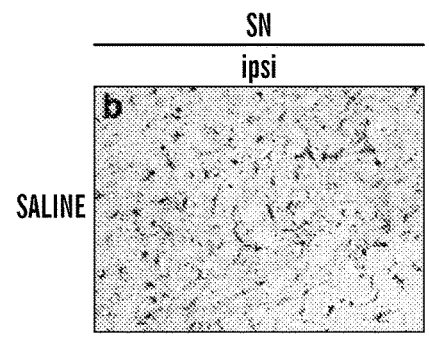
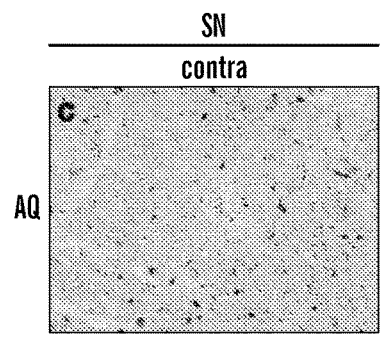
FIG. 24C  FIG. 24D
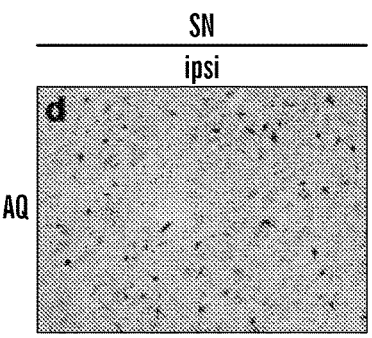
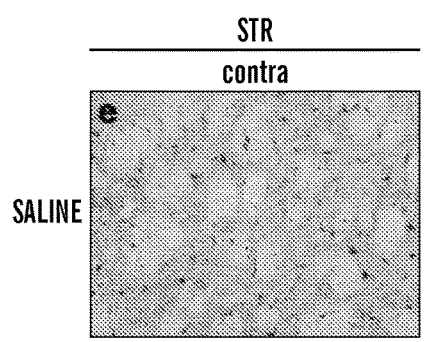
FIG. 24E  FIG. 24F
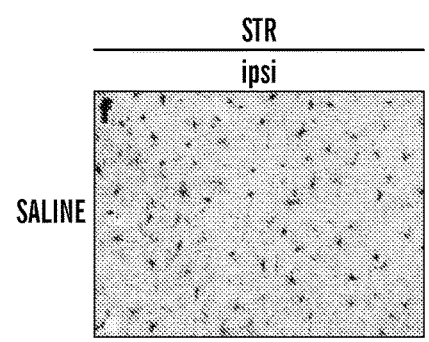
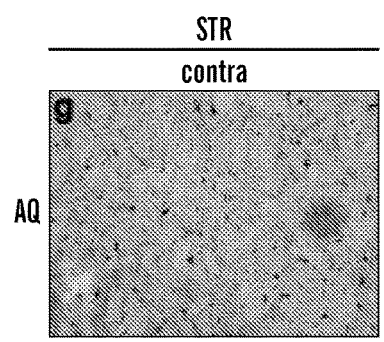
FIG. 24G  FIG. 24H
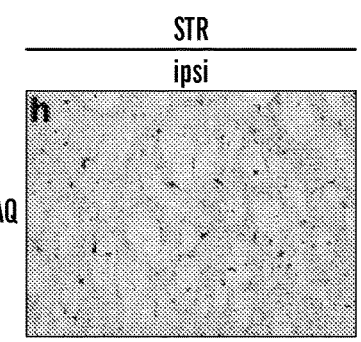

AMINOQUINOLINE DERIVATIVES AND USES THEREOF

This invention was made with Government support under Grant Number MH048866 awarded by the National Institutes of Mental Health. The Government has certain rights in this invention.

CROSS REFERENCE TO RELATED APPLICATIONS

This application is a 35 U.S.C. §371 National Phase Entry Application of International Application No. PCT/US2013/028239 filed Feb. 28, 2013, which designates the U.S., and which claims benefit under one or more of 35 U.S.C. §119(a)-119(d) of Indian Patent Application No. 661/DEL/2012, filed Mar. 7, 2012, the content of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 28, 2015, is named 063476-076541-US_SL.txt and is 8,494 bytes in size.

TECHNICAL FIELD

The present disclosure relates generally to aminoquinoline and aminoacridine based hybrids, pharmaceutical compositions and medicaments that include such aminoquinoline and aminoacridine based hybrids, and methods of using such compounds for diagnosing and/or treating infections, neurodegerative diseases or disorders, inflammation, and/or inflammation associated diseases and disorders.

BACKGROUND

PD, primarily caused by selective degeneration of midbrain dopamine (mDA) neurons, is the most prevalent movement disorder, affecting 1-2% of the global population over the age of 65[1-3]. Currently available pharmacological treatments (e.g., L-DOPA) are largely symptomatic and lose their efficacy over time, with accompanying severe side effects such as dyskinesia. Thus, there is an unmet clinical need to develop mechanism-based and/or disease-modifying treatments[2,3]. The orphan nuclear receptor Nurr1 (also known as NR4A2) is essential not only for development and maintenance of mDA neurons[4-7] but also for their protection from inflammation-induced death[8]. Furthermore, previous studies showed decreased Nurr1 expression in postmortem brains of PD patients[9] and functional mutant forms in rare familial PD cases[10], strongly suggesting that Nurr1 is a promising target for the development of novel disease-modifying therapeutics for PD[11]. Thus, there is a need in the art for agonists of Nurr1.

SUMMARY

In continuation of inventors efforts to develop new structurally diverse molecular scaffolds for the treatment of malaria [Rawat, D. S. Bioorg. Med. Chem. Lett. 2008, 18, 1446; Rawat, D. S. Bioorg. Med. Chem., 2009, 17, 5632; Rawat, D. S. Eur. J. Med. Chem. 2011, 46, 2816; Manohar, S., Khan, S. I., Rawat, D. S. Bioorg. Med. Chem. Lett. 2010, 20, 322; Manohar, S., Khan, S. I., Rawat, D. S. Chem. Biol. Drug Des. 2011, 78, 124; Manohar, S., Rajesh, U. C., Khan, S. I., Tekwani, B. L., Rawat, D. S. ACS Med. Chem. Lett. 2012, 3, 555; and Manohar, S., Khan, S. I., Rawat, D. S. Chem. Biol. Drug Des., Accepted, 2013 (DOI: 10.1111/cbdd.12108)], an effort has been initiated to link 4-aminoquinoline and pyrimidine entities together via flexible linker so that molecule has enough flexibility to fit in the binding site of the target and as a result this kind of hybrid molecules may show better antimalarial activity.

In one aspect, the disclosure provides a compound of formula (I), (II), (III), (IV), (V) (VI), (VII), (VIII), or (IX):

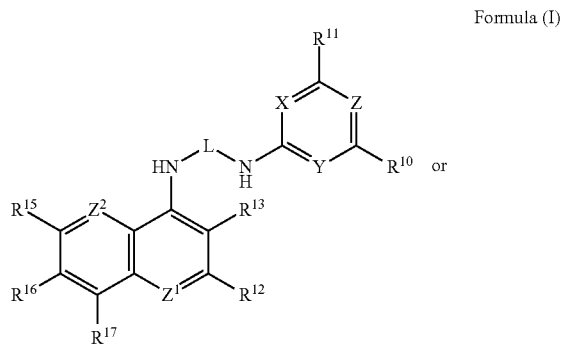

Formula (I)

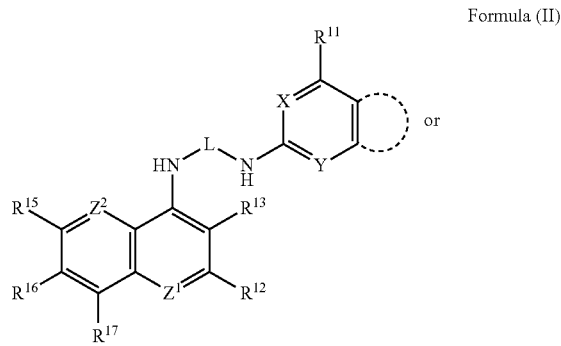

Formula (II)

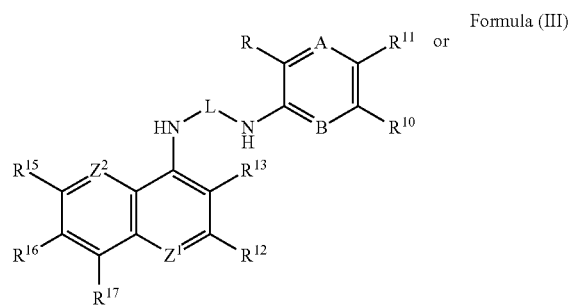

Formula (III)

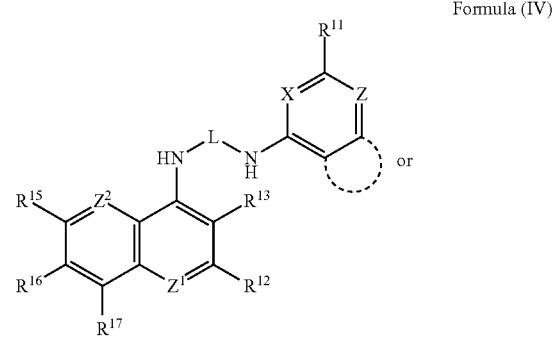

Formula (IV)

Formula (V)

Formula (VI)

Formula (VII)

Formula (VIII)

Formula (IX)

wherein:
X, Y, and Z are independently CR$^{18}$, N, O, or S;
A and B are independently CR$^{18}$ or N;
one of Z$^1$ and Z$^2$ is N and the other is CR$^{14}$;
R and R$^{10}$-R$^{28}$ independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted;
----- forms a cyclyl, heterocyclyl, aryl, or heteroaryl, each of which can be optionally substituted; and
L is a linker The compounds disclosed herein include pharmaceutically acceptable salts, hydrates, solvates, esters, stereoisomer mixtures, and enantiomers thereof.

The disclosure also provides a pharmaceutical composition comprising a compound disclosed herein and a pharmaceutically acceptable diluent, carrier, or excipient.

In yet another aspect, the disclosure provides a method of treating a disease state when a decrease Nurr1 activity contributes to the pathology or symptomology of the disease, the method comprising administering a therapeutically effective amount of a disclosed herein to a subject in need thereof.

In one aspect, the disclosure provides a method of treating a neurodegenative disease or disorder in a subject, the method comprising administering a therapeutically effective amount of a disclosed herein to a subject in need thereof.

In yet another aspect, the disclosure provides a method of treating a neurodegenative disease or disorder in a subject, the method comprising administering a therapeutically effective amount of a disclosed herein to a subject in need thereof.

In still another aspect, the disclosure provides a method of treating inflammation or inflammation associated disorder in a subject in need thereof, the method comprising administering to the subject a therapeutically effective amount of a compound described herein.

In yet still another aspect, the disclosure provides a kit that includes a compound disclosed herein together with instructions for administering the compound to subject in need thereof.

The disclosure further provides a method for causing differentiation of a cell, e.g., a stem cell, into a dopaminergic neuron by contacting the cell with a compound disclosed herein.

The disclosure additionally features a method for treating a neurodegerative disease or disorder in a subject, comprising: co-administering: (i) a composition containing stem cells into the subject and (ii) a compound disclosed herein in an amount sufficient to induce differentiation of the stem cells.

In some embodiments, the neurodegereative disease is Parkinson's disease (PD).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 13A-13I show identification of amodiaquine (AQ) and chloroquine (CQ) as Nurr1 activators. (FIG. 13A) Chemical structures of three hit compounds that activate Nurr1's transcriptional function. Notably, all compounds contain an identical scaffold, 4-amino-7-chloroquinoline (highlighted by red color), strongly suggesting a structure-activity relationship regarding Nurr1 activation. (FIG. 13B) AQ and CQ increase the transcriptional activity of Nurr1-based reporter constructs: full-length Nurr1-dependent (fNurr; left panel) and Nurr1 LBD-dependent (right panel) transcriptional activities. The basal level of transcriptional activity was normalized to 1. The bars represent means±SEM from three independent experiments. (FIG. 13C) Effect of Nurr1 specific siRNA on Nurr1 LBD's transactivation activity. A knock-down of Nurr1 expression by treatment with Nurr1-specific siRNA reduced the reporter gene activity of the Nurr1 LBD construct, suggesting that this activity is mediated through Nurr1. (FIG. 13D) Human neuroblastoma SK-N-BE(2)C cells were transfected with the N-terminal flag-tagged SRC1 or SRC3 and the C-terminal myc-tagged full-length Nurr1. Twenty hours after transfection, cells were treated with 30 μM AQ or 100 μM CQ for 16 hours. Cell lysates were immunoprecipitated (IP) using anti-flag antibodies and analyzed by immunoblotting (IB) using anti-myc antibodies. (FIG. 13E) Effect of SRC proteins on AQ and CQ-induced Nurr1 transactivation. SK-N-BE(2)C cells were transfected with VP16-SRC1 or VP16-SRC3, an effector plasmid (pSV GAL$_{(DBD)}$-N$_{(LBD)}$), and a reporter plasmid (p8xUAS-Luc), and were treated with 30 μM AQ or 100 μM CQ for 16 hours. The fold induction was derived by comparing each luciferase activity to basal level obtained by non-SRC transfection. (FIG. 13F) AQ showed highly specific interaction with Nurr1 LBD as evaluated by surface plasmon resonance (SPR) analysis. The sensorgrams were obtained from injection of a series of concentrations of AQ over immobilized Nurr1-LBD and RXR-LBD. The concentrations (μM) are shown next to the arrows. (FIG. 13G) Fluorescence spectra of Nurr1-LBD and RXR-LBD in the presence of increasing concentrations of AQ following excitation at 280 nm in PBS (pH 7.2). The arrows indicate signal changes as AQ concentration increases (0, 0.1 nM, 1 nM, 10 nM, 100 nM and 1 μM). (FIG. 13H) Saturation binding of the recombinant Nurr1-LBD protein using [$^3$H]-CQ. Nurr1-LBD protein was incubated for overnight at 4° C. with increasing concentrations (3.9, 7.8, 15.5, 31, 62.5, 125, 250, 500, 1000 nM) of [$^3$H]-CQ. Non-specific binding was determined in the presence of a 1000-fold molar excess of unlabeled CQ. Specific binding was calculated as the difference of total and non-specific binding. The insert indicates Scatchard analysis of the specific binding. (FIG. 13I) Competition of AQ, CQ and primaquine (PQ) with [$^3$H]-CQ for binding to the Nurr1-LBD. Increasing concentrations of unlabeled AQ, CQ or PQ were incubated with 500 nM [$^3$H]-CQ and Nurr1-LBD. The data represent the average of triplicate from three independent experiments. All graphs, $K_d$, $K_i$, and $B_{max}$ values were generated using the non-linear regression program Prism version 5.02.

(FIGS. 14A and 14B) AQ stimulated the generation and gene expression of DA neurons from neural progenitors isolated from E14.5 rat cortex in a dose-dependent manner. Cortical precursors were transduced with Nurr1-expressing retrovirus and the TH+ cells were visualized by immunostaining against TH protein. Differentiation was induced by withdrawal of bFGF a day after viral infection and AQ was added for 2 hours during the differentiation period. Immunocytochemical analyses for TH (FIG. 14A) and yields of TH+/DAPI cells (FIG. 14B) for each treatment group were obtained following in vitro differentiation for 3d and 9d. Significantly different from control in 3 independent cultures. (FIG. 14C) Schematic representation of the location of primers used in the rat TH promoter (upper panel). Primer sequences are shown in materials and methods. ChIP assay shows AQ- or CQ-dependent Nurr1 recruitment to the TH promoters NL1 and NL3. Rat PC12 cells were treated with 20 μM AQ or 70 μM CQ for 15 hrs. ChIP assay was carried out with IgG or α-Nurr1 (E-20) antibody. *p<0.05 and **p<0.005 versus untreated. Results are expressed as the average of three independent experiments. Error bars represent standard deviations. (FIGS. 14D-14F) Primary cultures of rat mesencephalic DA neurons were treated with 20 μM 6-OHDA for 24 hr in the presence or absence of 5 μM AQ and 20 μM CQ. (FIG. 14D) The number of TH-positive neurons and (FIG. 14E) the rate of [$^3$H]DA uptake were measured. (FIG. 14F) Cell survival was measured by the MTT reduction assay in DA cells treated with 6-OHDA alone or in combination with AQ. Values from each treatment were expressed as a percentage of untreated control for the MTT assay. (FIG. 14G) AQ suppresses LPS-induced expression of proinflammatory cytokines. Primary microglia from P1 rat brains were treated with 1 ng/ml LPS for 4 hrs in the presence or absence of AQ (10 and 20 μM). Levels of mRNA expression were analyzed by quantitative real-time PCR and normalized with GAPDH. Each bar represents means±SEM of n=4-5. *p<0.05, p<0.01, *p<0.001, compared to the LPS only-treated group.

FIG. 15A-15E show effects of AQ treatments on 6-OHDA-lesioned rat model of PD. (FIG. 15A) Schematic representation of the administration of AQ to 6-OHDA lesioned rats. Unilateral striatal 6-OHDA lesioned rats were treated with AQ or saline for 2 weeks, starting from 1 day prior to lesioning. The grey shade indicates L-DOPA treatment for 2 weeks as control of AIMs test. (FIG. 15B) Amphetamine-induced rotational test was performed at 4 and 6 weeks (right panel) after 6-OHDA lesion. There was significant difference in the number of amphetamine-induced rotational behavior between the two groups at 4 and 6 weeks. (FIG. 15C) TH$^+$ fibers and neurons were plentiful in the ST and SN of normal site whereas their marked depletion was observed in the right ST and SN by 6-OHDA lesioning. In contrast, abundant TH-immunopositive cells were spared not only in the striatum and but also in the SN in AQ-treated group, when examined at 6 weeks post lesion. Scale bar: black=200, while=100, red=20 μm. (FIG. 15D) Stereological counting in AQ-treated rats show that approximately 60% of TH+ neurons are spared in the lesion side, whereas it remained about 10% in saline-treated animals. (FIG. 15E) Iba1+ microglial activation by 6-OHDA lesion was dramatically decreased by AQ treatment. Scale bar: while=50, red=10 μm. (FIG. 15F) Treatment of 6-OHDA-lesioned rats with L-DOPA, but not with AQ, exhibited severe side effects, as measured by AIMs scores. Rats were monitored for four types of AIMs (Axial, Forelimb, Orolingual, and Locomoter AIMS) at 2 and 6 weeks post lesioning. Each AIM behavior was monitored and scored with 0-4 scale and summed. Bars represent the mean±SEM (#p<0.06, *p<0.01, p<0.0003, *p<0.0001).

(FIG. 20A) AQ showed no interaction with Nur77-LBD as evaluated by SPR analysis. Sensorgrams were obtained from injection of a series of AQ concentrations over immobilized Nur77-LBD proteins. (FIGS. 20B and 20C) Fluorescence spectra of Nur77-LBD in the presence of increasing concentrations of AQ (0, 0.1 nM, 1 nM, 10 nM, 100 nM and 1 μM) (FIG. 20B), or of RXR-LBD in the presence of increasing concentration of 9-cis retinoic acid (0, 0.1 nM, 1 nM, 10 nM, 100 nM and 1 μM) as a positive control (FIG. 20C) following the excitation at 280 nm at PBS (pH 7.2).

(FIG. 22A) AQ suppresses LPS-induced expression of pro-inflammatory cytokines in murine microglial BV-2 cell that treated with 10 ng/ml LPS for 4 hrs in the presence or absence of AQ (10 and 15 μM). (FIG. 22B) CQ suppresses LPS-induced expression of proinflammatory cytokines. Primary microglia from P1 rat brains were treated with 10 ng/ml LPS for 4 hrs in the presence or absence of 10 μM CQ. Levels of mRNA expression were analyzed by quantitative real-time PCR and normalized with GAPDH. Each bar represents means±SEM of n=6. *p<0.05, p<0.01, *p<0.001, compared to the LPS only-treated group.

FIGS. 24A-24J. AQ reduces microglial activation in 6-OHDA-injected rat brains. Rats were administered saline (FIGS. 24A, 24B, 24E, and 24F) or AQ (FIGS. 24C, 24D, 24G, and 24H) for 2 weeks, then were sacrificed and brains sectioned. Brain sections including the SN (FIGS. 24A-24D) and STR regions (FIGS. 24E-H) were immunostained with anti-Iba-1 antibody and Iba-1+ cells were counted in both lesion and intact sides. FIGS. 24I-24J are bargraphs showing percentage of Iba-1 + cells in lesioned side/Iba-1 + cells in intact side for SN and STR regions respectively. Data represent the mean±SEM. (p<0.01, *p<0.001). Scale bar=200 μm.

DETAILED DESCRIPTION

Figure 1:
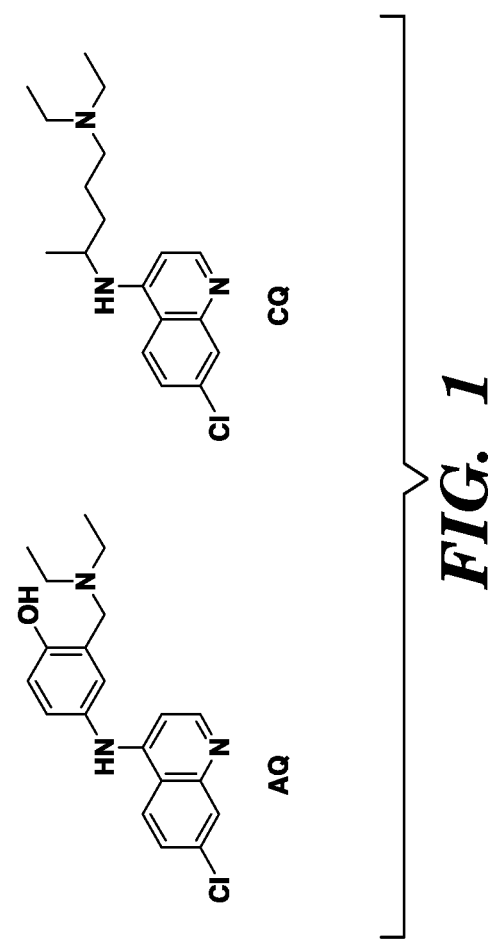
FIG. 1 shows the structures of amordiaquine (AQ) and chloroquine (CQ).
Figure 2:
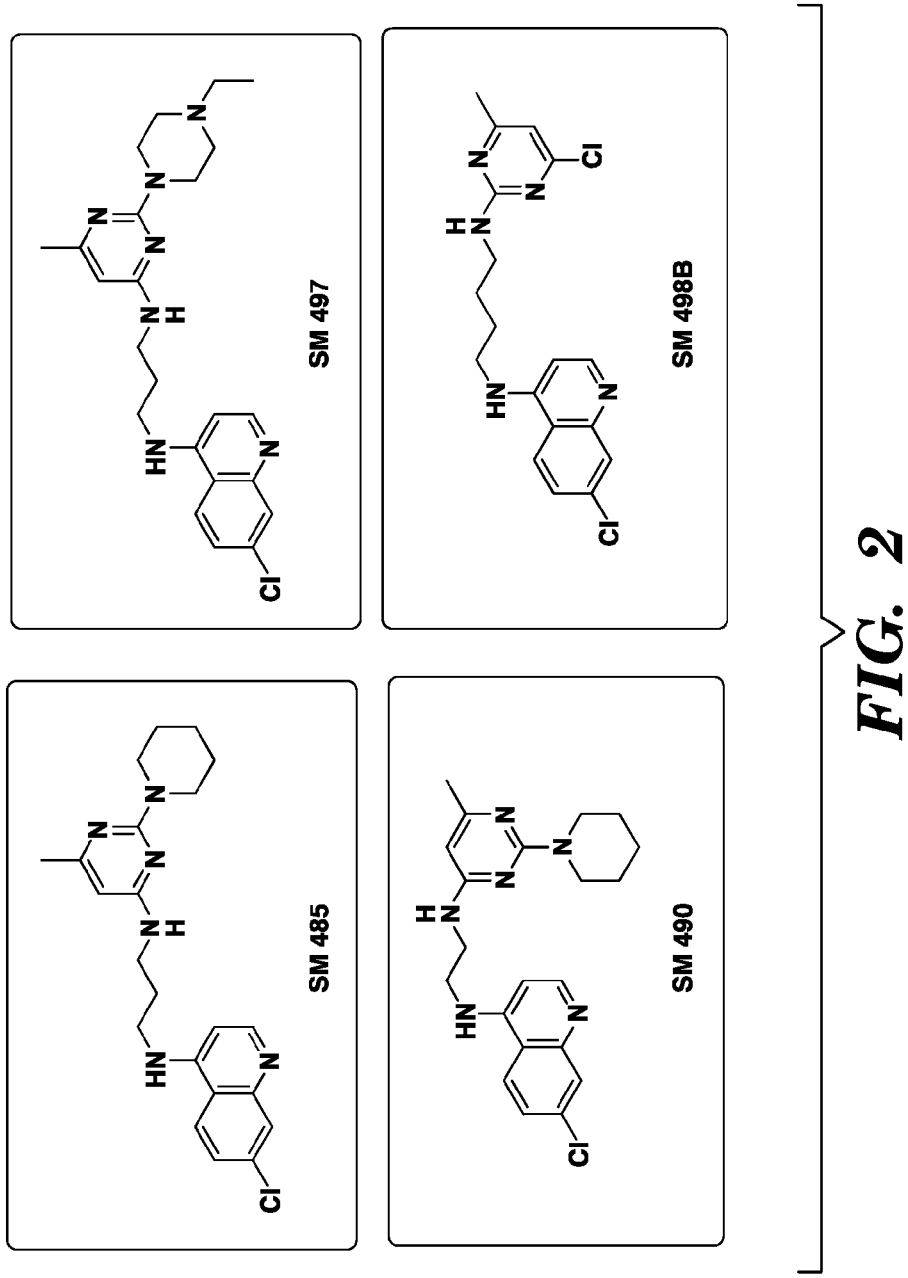
FIG. 2 shows structure of some exemplary aminoquinoline-pyrimidine analogs according to embodiments of the compounds disclosed herein.

One object of the invention is to develop a method for the preparation aminoquinoline based hybrids in which 4-aminoquinoline, 8-aminoquinoline, mefloquine, amidoquine, are covalently attached to pyrimidine, pyrazine, triazine C7/C5 curcuminods, heteroaromatics, aromatics, amino acids, peptides, sugar, steroids, or any other antimalarial pharmacophores and all related possible combinations. Another object of the invention is to synthesis aminoquinoline based hybrids in which aminoquinoline is attached with various pharamacophores which are known for their antimalarial activity. An additional object of this invention is to use these aminoquinoline based hybrids for the treatment of malarial using any delivery agent. Yet another object of the invention is to use these aminoquinoline based hybrids for treatment of disease when a decrease Nurr1 activity contributes to the pathology or symptomology of the disease. Still another object of the invention is to use these aminoquinoline based hybrids for treating a neurodegenative disease or disorder. Still another aspect of the invention is using these aminoquinoline based hybrids for treating inflammation or inflammation associated disorder. Yet another object of the invention is to attach these aminoquinoline based hybrids to biocompatible polymers, dendimers and nano materials for the treatment of infectious diseases. Further object of the invention is to use these compounds for the treatment of antimalarial as such or in combination of any other antimalarial drugs. The foregoing has outlined some of the pertinent objectives of the invention. These objectives should be construed to be merely illustrative of some of the more prominent features and applications of the intended invention. Many other beneficial results can be obtained by applying the disclosed invention in a different manner or modifying the invention within the scope of disclosure. Accordingly, other objectives and a full understanding of the invention and the detailed description of the preferred embodiment in addition to the scope of invention are to be defined by the claims.

As will be appreciated by one of skill in the art, the compounds of formula (I)-(V) disclosed herein are based on the 4-aminoquinoline or the 8-aminoquinoline skeleton. Accordingly, in some embodiments, $Z^1$ is N and $Z^2$ is $CR^{14}$ (e.g., the 4-aminoquinoline skeleton). In some other embodiments, $Z^1$ is $CR^{14}$ and $Z^2$ is N (e.g., the 8-aminoquinoline skeleton).

Without limitations, variables $R^{12}$-$R^{17}$ can all be the same, all different or any combinations of same and different. In one non-limiting example, at least one (e.g., one, two, three, four, five, or all six) of $R^{12}$-$R^{17}$ can be H. In some embodiments, $R^{12}$, $R^{13}$, $R^{15}$, and $R^{17}$ are all H. In some embodiments, $R^{12}$, $R^{13}$, $R^{15}$, and $R^{17}$ are all same; $Z^1$ is N and $Z^2$ is CH. In one embodiment, $R^{12}$, $R^{13}$, $R^{15}$, and $R^{17}$ are all H; $Z^1$ is N and $Z^2$ is CH.

In another non-limiting example, at least one (e.g., one, two, three, four, five, or all six) of $R^{12}$-$R^{17}$ is not H. In some embodiments, at least one (e.g., one, two, three, four, five, or all six) of $R^{12}$-$R^{17}$ is halogen, alkyl, cyclyl, hydroxyl, alkoxy, thio, alkylthio, $SO_2R^{10}$, amino, alkylamino, amino acid, or carbohydrate.

In some embodiments, at least one (e.g., one, two, three, four, five, or all six) of $R^{12}$-$R^{17}$ is halogen, e.g., Br, Cl, or F. In some embodiments, $R^{16}$ is halogen, e.g., Br, Cl, or F. In some other embodiments, $R^{17}$ is halogen, e.g., Br, Cl, or F.

In some embodiments, at least one (e.g., one, two, three, four, five, or all six) of $R^{12}$-$R^{17}$ is $C_1$-$C_6$ alkyl, which can be optionally substituted. In some embodiments, $R^{16}$ is $C_1$-$C_6$ alkyl, which can be optionally substituted. In some other embodiments, $R^{17}$ is $C_1$-$C_6$ alkyl, which can be optionally substituted.

In some embodiments, at least one (e.g., one, two, three, four, five, or all six) of $R^{12}$-$R^{17}$ is $CO_2H$. In some embodiments, $R^{16}$ is $CO_2H$. In some other embodiments, $R^{17}$ is $CO_2H$.

In some embodiments, at least one (e.g., one, two, three, four, five, or all six) of $R^{12}$-$R^{17}$ is hydroxyl. In some embodiments, $R^{16}$ is hydroxyl. In some other embodiments, $R^{17}$ is hydroxyl.

In some embodiments, at least one (e.g., one, two, three, four, five, or all six) of $R^{12}$-$R^{17}$ is alkoxy. In some embodiments, $R^{16}$ is alkoxy. In some other embodiments, $R^{17}$ is alkoxy.

In some embodiments, at least one (e.g., one, two, three, four, five, or all six) of $R^{12}$-$R^{17}$ is thiol or alkylthio. In some embodiments, $R^{16}$ is thiol or alkylthio. In some other embodiments, $R^{17}$ is thiol or alkylthio.

In some embodiments, at least one (e.g., one, two, three, four, five, or all six) of $R^{12}$-$R^{17}$ is amino or alkylamino. In some embodiments, $R^{16}$ is amino or alkylamino. In some other embodiments, $R^{17}$ is amino or alkylamino.

In some embodiments, at least one (e.g., one, two, three, four, five, or all six) of $R^{12}$-$R^{17}$ is cyano. In some embodiments, $R^{16}$ is cyano. In some other embodiments, $R^{17}$ is cyano.

In some embodiments, $R^{18}$ is a hydrogen, halogen, cyano, nitro, $C_1$-$C_6$ alkyl, or optionally substituted phenyl.

In some embodiments, $R^{18}$ is hydrogen. In some embodiments, $R^{18}$ is a 4-substituted phenyl. In one embodiment $R^{18}$ is

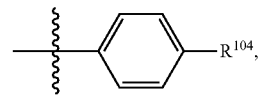

wherein $R^{104}$ is linear or branched alkyl, linear or branched alkenyl, linear or branched alkynyl, cyclyl, heterocyclyl, aryl, heteroaryl, halogen, alkoxy, nitro, cyano, carbonyl, hydroxyl, phenoxy, amino, alkylamino, thiol, or alkylthio, each of which can be optionally substituted. In some embodiments, $R^{104}$ is Br.

In some embodiments, $R^{12}$, $R^{13}$, $R^{15}$, and $R^{17}$ are H; $R^{16}$ is chloro; $Z^1$ is N; and $Z^2$ is CH. In some other embodiments, $R^{12}$, $R^{13}$, $R^{15}$, $R^{16}$, and $R^{17}$ are H, $Z^1$ is CH; and $Z^2$ is N.

In still some other embodiments, $R^{12}$, $R^{13}$, $R^{15}$, $R^{16}$, and $R^{17}$ are H, $Z^1$ is N; and $Z^2$ is CH.

Without limitations, variables $R^{21}$-$R^{28}$ can all be the same, all different or any combinations of same and different. In one non-limiting example, at least one (e.g., one, two, three, four, five, six, seven, or all eight) of $R^{21}$-$R^{28}$ can be H. In some embodiments, $R^{21}$, $R^{22}$, $R^{24}$, $R^{25}$, $R^{27}$ and $R^{28}$ are all H. In another non-limiting example, at least one (e.g., one, two, three, four, five, six, seven, or all eight)) of $R^{21}$-$R^{28}$ is not H. In some embodiments, at least one (e.g., one, two, three, four, five, six, seven, or all eight) of $R^{21}$-$R^{28}$ is halogen, alkyl, cyclyl, hydroxyl, alkoxy, thio, alkylthio, $SO_2R^{10}$, amino, alkylamino, amino acid, or carbohydrate.

In some embodiments, at least one (e.g., one, two, three, four, five, six, seven, or all eight) of $R^{21}$-$R^{28}$ is halogen, e.g., Br, Cl, or F. In some embodiments, $R^{23}$ is halogen, e.g., Br, Cl, or F.

In some embodiments, at least one (e.g., one, two, three, four, five, six, seven, or all eight) of $R^{21}$-$R^{28}$ is $C_1$-$C_6$ alkoxy. In some embodiments, at least one (e.g., one, two, three, four, five, six, seven, or all eight) of $R^{21}$-$R^{28}$ is methoxy. In some embodiments, $R^{26}$ is $C_1$-$C_6$alkoxy. In one embodiment, $R^{26}$ is methoxy.

In one embodiment, $R^{21}$, $R^{22}$, $R^{24}$, $R^{25}$, $R^{27}$ and $R^{28}$ are all H; $R^{23}$ is Cl; and $R^{26}$ methoxy.

In the ring comprising the variables X, Y, and Z, the variables X, Y, and Z can all be same, all different, or any combination of same and different, e.g., all three can be same, two same and one different, or all three are different. For example, X, Y, and Z call can be the same; X and Y can be same while Z is different; X and Z can be the same while Y is different; Y and Z can be the same while X is different; or X, Y, Z are all different.

In some embodiments, at least one (e.g., one, two, or all three) of X, Y, and Z are CH. In some embodiments, X, Y, and Z are all CH. In some embodiments, at least one (e.g., one, two, or all three) of X, Y, and Z are N. Various combinations of X, Y, and Z variables include: X, Y, and Z all are N; X and Y are N, and Z is CH; X and Z are N, and Y is CH; X is N, and Y and Z are CH; X is CH, and Y and Z are N; X and Z are CH, and Y is N; X and Y are CH, and Z is N; and X, Y, and Z all are CH. Thus, the compounds disclosed herein can comprise any one of the various combinations disclosed in this paragraph.

In the ring comprising variables A and B, the variables A and B can be the same or different. In some embodiments, A is N and B is CH; A is CH and B is N; or A and B both are N.

In some embodiments, R is H, $C_1$-$C_6$alkyl, halogen, heterocyclyl, amino, arylamino, cyclylamino, and alkylamino, each of which can be optionally substituted. In one embodiment, R is methyl.

Without limitations, variables $R^{10}$ and $R^{11}$ can be same or different. In some embodiments, $R^{10}$ and $R^{11}$ can be selected independently from the group consisting of H, $C_1$-$C_6$alkyl, —NH(CH$_2$)x-OH (wherein x is an integer from 0 to 10), halogen, heterocyclyl, amino, arylamino, cyclylamino, and alkylamino, each of which can be optionally substituted.

In some embodiments, $R^{10}$ can be selected from the group consisting of 2-(7-chloro-4-quinolinylamino)-ethyl amino; 2-alkylaminoethyl amino; 2-aminoethyl amino; 2-hydroxyethyl amino; 2-methylphenyl amino; 3,5-dimethoxyphenyl amino; 3-alkylaminopropyl amino; 3-aminopropyl amino; 3-hydroxypropyl amino; 4-alkylaminobutyl amino; 4-aminopropyl amino; 4-ethylphenyl amino; 4-ethylpiperazinyl; 4-bromophenyl amino; 4-chlorophenyl amino; 4-fluorophenyl amino; 4-hydroxybutyl amino; 4-methoxyphenyl amino; 4-methylphenyl amino; 4-methylpiperazinyl; 4-morpholinyl; 5-hydroxypentyl amino; 6-hexylapentyl amino; alkylaminobutyl amino; aminomethyl amino; Chloro; cycloheptylamino; cyclohexylamino; cyclopenylamino; diethylamino; dimethylamino; hydrogen; hydroxymethyl amino; methyl; phenylamino; piperazinyl; and piperidinyl, each of which can be optionally substituted.

In some embodiments, $R^{11}$ can be selected from the group consisting of 2-(7-chloro-4-quinolinylamino)-ethyl amino; 2-alkylaminoethyl amino; 2-aminoethyl amino; 2-hydroxyethyl amino; 2-methylphenyl amino; 3,5-dimethoxyphenyl amino; 3-alkylaminopropyl amino; 3-aminopropyl amino; 3-hydroxypropyl amino; 4-alkylaminobutyl amino; 4-aminopropyl amino; 4-ethylphenyl amino; 4-ethylpiperazinyl; 4-bromophenyl amino; 4-chlorophenyl amino; 4-fluorophenyl amino; 4-hydroxybutyl amino; 4-methoxyphenyl amino; 4-methylphenyl amino; 4-methylpiperazinyl; 4-morpholinyl; 5-hydroxypentyl amino; 6-hexylapentyl amino; alkylaminobutyl amino; aminomethyl amino; Chloro; cycloheptylamino; cyclohexylamino; cyclopenylamino; diethylamino; dimethylamino; hydrogen; hydroxymethyl amino; methyl; phenylamino; piperazinyl; and piperidinyl, each of which can be optionally substituted.

In some embodiments, $R^{10}$ and $R^{11}$ can be selected independently from the group consisting of 2-(7-chloro-4-quinolinylamino)-ethyl amino; 2-alkylaminoethyl amino; 2-aminoethyl amino; 2-hydroxyethyl amino; 2-methylphenyl amino; 3,5-dimethoxyphenyl amino; 3-alkylaminopropyl amino; 3-aminopropyl amino; 3-hydroxypropyl amino; 4-alkylaminobutyl amino; 4-aminopropyl amino; 4-ethylphenyl amino; 4-ethylpiperazinyl; 4-bromophenyl amino; 4-chlorophenyl amino; 4-fluorophenyl amino; 4-hydroxybutyl amino; 4-methoxyphenyl amino; 4-methylphenyl amino; 4-methylpiperazinyl; 4-morpholinyl; 5-hydroxypentyl amino; 6-hexylapentyl amino; alkylaminobutyl amino; aminomethyl amino; Chloro; cycloheptylamino; cyclohexylamino; cyclopenylamino; diethylamino; dimethylamino; hydrogen; hydroxymethyl amino; methyl; phenylamino; piperazinyl; and piperidinyl, each of which can be optionally substituted.

In some embodiments, one of $R^{10}$ and $R^{11}$ is 4-morpholinyl and the other is 3-hydroxypropyl amino; one is 4-morpholinyl and the other is 2-hydroxyethyl amino; one is 4-morpholinyl and the other is 3,5-dimethoxyphenyl amino; one is 4-morpholinyl and the other is 4-ethylphenyl amino; one is 4-morpholinyl and the other is 4-fluorophenyl amino; one is 4-morpholinyl and the other is 4-hydroxybutyl amino; one is 4-morpholinyl and the other is 4-methoxyphenyl amino; one is 4-morpholinyl and the other is phenylamino; one is 4-piperidinyl and the other is phenylamino; one is chloro and the other is 2-(7-chloro-4-quinolinylamino)-ethyl amino; one is chloro and the other is 4-ethylpiperazinyl; one is chloro and the other is 4-ethylpiperazinyl; one is chloro and the other is 4-methylpiperazinyl; one is chloro and the other is 4-methylpiperazinyl; one is chloro and the other is 4-morpholinyl; one is chloro and the other is diethylamino; one is chloro and the other is piperidinyl; one is chloro and the other one is phenyl amino; one is hydrogen and the other is 4-methoxyphenyl amino; one is hydrogen and the other is 2-hydroxyethyl amino; one is hydrogen and the other is 3,5-dimethoxyphenyl amino; one is hydrogen and the other is 3-hydroxypropyl amino; one is hydrogen and the other is 4-bromophenyl amino; one is hydrogen and the other is 4-chlorophenyl amino; one is hydrogen and the other is 4-fluorophenyl amino; one is hydrogen and the other is 4-hydroxybutyl amino; one is hydrogen and the other is 4-methylphenyl amino; one is hydrogen and the other is 4-morpholinyl; one is hydrogen and the other is 5-hydroxypentyl amino; one is hydrogen and the other is 6-hydroxyhexyl amino; one is hydrogen and the other is chloro; one is hydrogen and the other is phenyl amino; one is hydrogen and the other is piperidinyl; one is methyl and the other is 4-methoxyphenyl amino; one is methyl and the other is 2-hydroxyethyl amino; one is methyl and the other is 3,5-dimethoxyphenyl amino; one is methyl and the other is 3-hydroxypropyl amino; one is methyl and the other is 4-bromophenyl amino; one is methyl and the other is 4-chlorophenyl amino; one is methyl and the other is 4-ethylpiperazinyl; one is methyl and the other is 4-fluorophenyl amino; one is methyl and the other is 4-hydroxybutyl amino; one is methyl and the other is 4-methylphenyl amino; one is methyl and the other is 4-methylpiperazinyl; one is methyl and the other is 4-morpholinyl; one is methyl and the other is 5-hydroxypentyl amino; one is methyl and the other is 6-hydroxyhexyl amino; one is methyl and the other is chloro; one is methyl and the other is phenyl amino; one is methyl and the other is piperidinyl; one is piperidinyl 2-hydroxyethyl amino; one is piperidinyl and the other is 3,5-dimethoxyphenyl amino; one is piperidinyl and the other is 3-hydroxypropyl amino; one is piperidinyl and the other is 4-ethylphenyl amino; one is piperidinyl and the other is 4-fluorophenyl amino; one is piperidinyl and the other is 4-hydroxybutyl amino; or one is piperidinyl and the other is 4-methoxyphenyl amino.

In some embodiments, both $R^{10}$ and $R^{11}$ are chloro; both are phenylamino; both are 4-morpholinyl; both are 2-methylphenyl amino; both are cyclohexyl amino; or both are hydrogen.

In some embodiments, one of $R^{10}$ and $R^{11}$ is hydrogen or methyl and the other is cyploroylamine; cyclopentylamine; cyclohexylamine; cycloheptylamine; 1-adamantylamine; pyrrolidinyl; 4-thiomorpholinyl; 4-alkyl-piperazinyl; pyrazolyl; 1H-pyrazolyl; imidazolyl; N-imidazolyl; 3,5-dimethyl-pyrazolyl; or 3,5-dimethyl-1H-pyrazolyl.

In some embodiments, one of $R^{10}$ and $R^{11}$ is

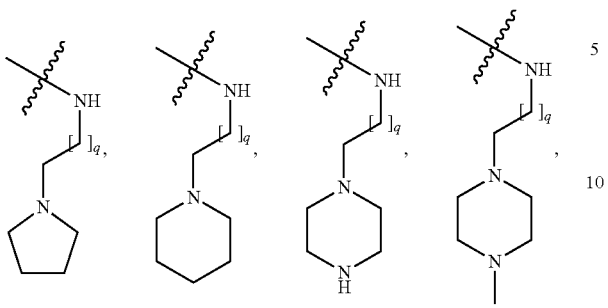

wherein q is an integer from 0 to 20. In some embodiments, q is 0, 1, 2, 3, 4, 5, or 6. In one embodiment, q is 1, 2, 3, or 4.

In some embodiments, one of $R^{10}$ and $R^{11}$ is H or methyl and the other is

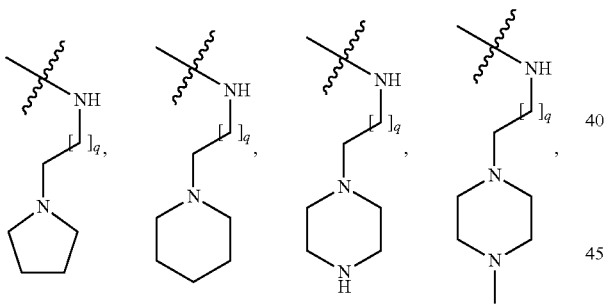

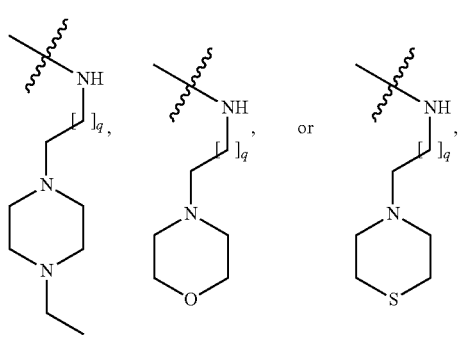

wherein q is an integer from 0 to 20. In some embodiments, q is 0, 1, 2, 3, 4, 5, or 6. In one embodiment, q is 1, 2, 3, or 4.

In some embodiments, one of $R^{10}$ and $R^{11}$ is

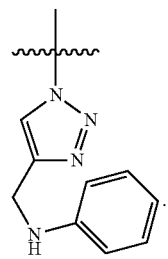 [SMILES: *n1cc(CNc2ccccc2)nn1]

In some embodiments, one of $R^{10}$ and $R^{11}$ is H, methyl or chloro and the other is

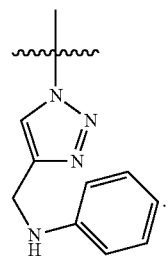 [SMILES: *n1cc(CNc2ccccc2)nn1]

In some embodiments, one of $R^{10}$ and $R^{11}$ is

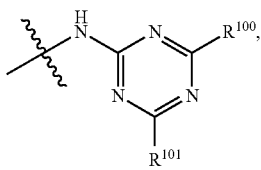

wherein $R^{100}$ and $R^{101}$ are independently amino, alkylamino, cycloamino, heterocyclyamino, arylamino, heteroarylamino, or heterocyclyl linked by a ring nitrogen, each of which can be optionally substituted.

In some embodiments, one of $R^{10}$ and $R^{11}$ is H, methyl or chloro and the other

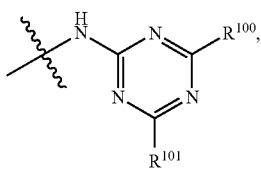

wherein $R^{100}$ and $R^{101}$ are independently amino, alkylamino, cycloamino, heterocyclyamino, arylamino, heteroarylamino, heterocyclyl linked by a ring nitrogen, or amino acid, each of which can be optionally substituted. In some embodiments, $R^{100}$ and $R^{101}$ both are same. In some embodiments, $R^{100}$ and $R^{101}$ are different.

In some embodiments, $R^{18}$ is optionally substituted aryl. For example, $R^{18}$ can be an optionally substituted phenyl. In some embodiments, $R^{18}$ is 4-bromophenyl.

In one embodiment, one of $R^{10}$ and $R^{11}$ is

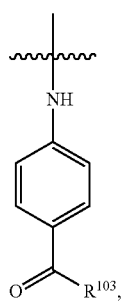

wherein $R^{103}$ is amino, alkylamino, cycloamino, heterocyclyamino, arylamino, heteroarylamino, heterocyclyl linked by a ring nitrogen, or amino acid, each of which can be optionally substituted. In one embodiment, $R^{103}$ is

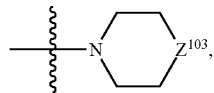

wherein $Z^{103}$ is $CH_2$, O, NH, N-methyl, N-ethyl. or S.

In some embodiments, $R^{11}$ is

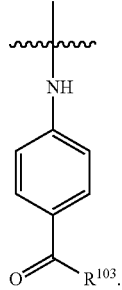

In some embodiments, the compound of formula (I) is of formula (IA):

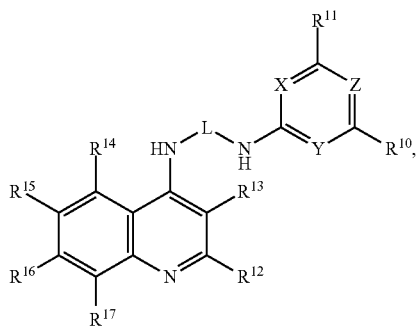

Formula (IA)

wherein the variables are as defined above.

In some embodiments, the compound of formula (I) is of formula (IB), (IC), (ID) or (IE):

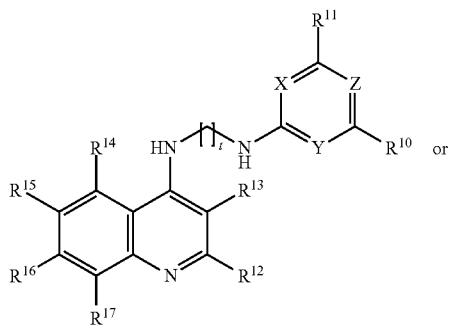

Formula (IB)

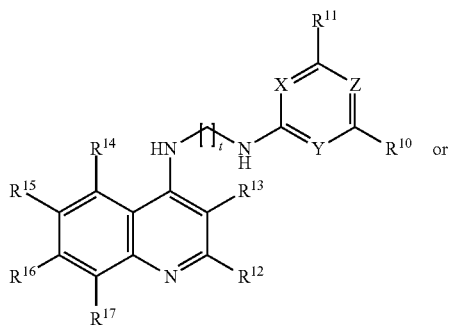

Formula (IC)

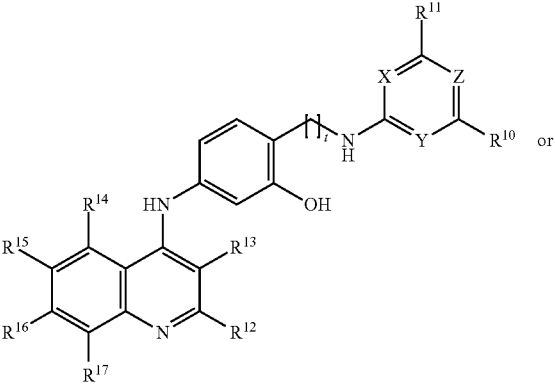

Formula (ID)

Formula (IE)

wherein t is an integer from 0 to 20, and the other variables are as defined above.

In some embodiments, t is 0, 1, 2, 3, 4, 5, 6, 7, or 8.

In some embodiments, the compound of formula (I) is of formula (IF) or (IG):

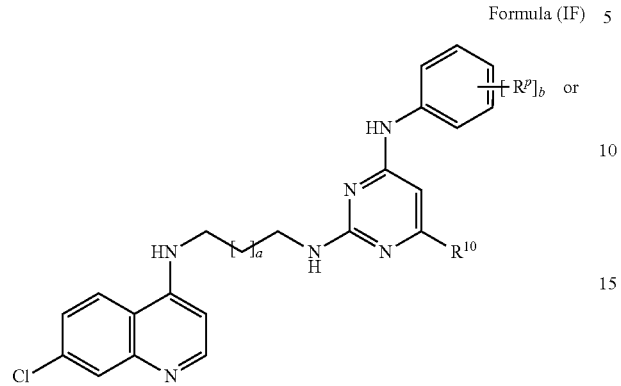

Formula (IF)

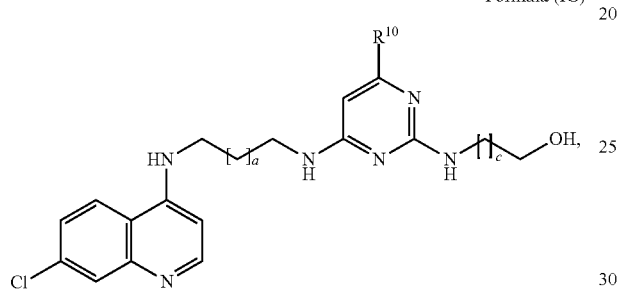

Formula (IG)

wherein a and c are independently an integer from 0 to 20; c is an integer from 0 to 5; $R^p$ is absent or linear or branched alkyl, linear or branched alkenyl, linear or branched alkynyl, cyclyl, heterocyclyl, aryl, heteroaryl, halogen, alkoxy, nitro, cyano, carbonyl, carboxy, hydroxyl, phenoxy, amino, alkylamino, thiol, sulfinyl, sulfonyl, thiocarbonyl, or alkylthio, each of which can be optionally substituted; and the other variables are as defined above.

In some embodiments, a is 0, 1, 2, 3, 4, 5, or 6.

In some embodiment, b is 0, 1, or 2.

In some embodiments, c is 0, 1, 2, 3, 4, 5, or 6.

In some embodiments of formula (IF) or (IG), $R^{10}$ is hydrogen or methyl.

In some embodiments of formula (IF) or (IG), $R^p$ is absent. In some other embodiments, $R^p$ is methyl, bromo, chloro, fluoro, or methoxy.

In some embodiments, a compound of formula (IV) is of formula (IVA)

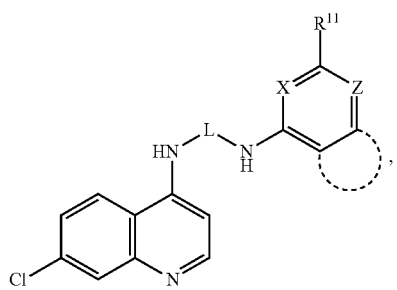

Formula (IVA)

wherein the variables are as defined above.

In some embodiments. a compound of formula (V) is of formula (VA):

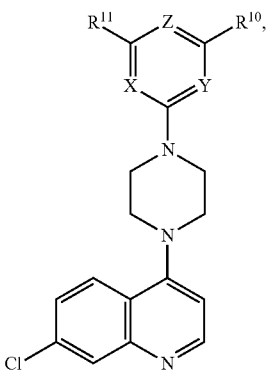

Formula (VA)

wherein variable are as defined above.

In some embodiments, a compound of formula (VI) is of formula (VIA) or (VIB):

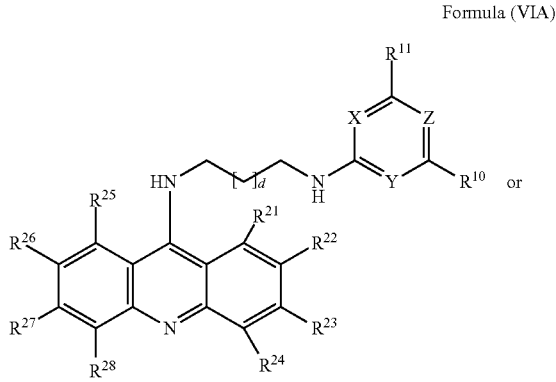

Formula (VIA)

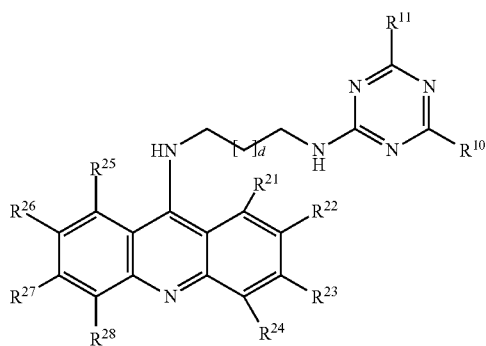

Formula (VIB)

wherein d is an integer from 0 to 20; and the other variables are as defined above.

In some embodiments, d is 0, 1, 2, 3, 4, 5, or 6.

As used herein, the term "linker" refers to an organic moiety that connects two parts of a compound. Linkers typically comprise a direct bond or an atom such as oxygen or sulfur, a unit such as $NR^N$, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), SO$_2$, N(R$^{N'}$)$_2$, C(O), cleavable linking group, substituted or unsubstituted aryl, substituted or unsubstituted heteroaryl, substituted or unsubstituted heterocyclic; where R$^{N'}$ is hydrogen, acyl, aliphatic or substituted aliphatic.

The exact structure and size of the linker can vary considerably, and many variations of the linker are within the scope of the inventions disclosed herein. As used herein, the "linker" can comprise a wide variety of structures. In many embodiments it is desirable that the linker be of sufficient size and character that it provides some space and/or flexibility in the connection between the two parts of the molecule the linker is connecting together, but does not become of such high molecular weight so as to impair the water solubility or trans-membrane absorbability of the resulting compounds.

Accordingly, in some embodiments, the linker is selected from the group consisting of branched or linear alkylene, branched or linear alkenylene, branched or linear alkynylene, cyclyl, heterocyclyl, aryl, heteroaryl, O, NH, S, S, SS, SO$_2$, O-alkylene, NH-alkylene, S-alkylene, amino acid, carbohydrate, and any combinations thereof.

In some embodiments, the linker is —(CH$_2$)$_n$— or —CH(CH$_3$)—(CH$_2$)$_n$—, wherein n is 0, 1, 2, 3, 4, 5, 6, 7, 8, 9, 10, 11, 12, 13, 14, 15, 16, 17, 18, 19, or 20. In some embodiments, n is 1. In some embodiments, n is 2. In some other embodiments, n is 3. In yet some other embodiment, n is 4. In yet still some other embodiments, n is 5. In some other embodiments, n is 6. In still some other embodiments, n is 7. In one embodiment, n is 8.

In some embodiments, the linker is

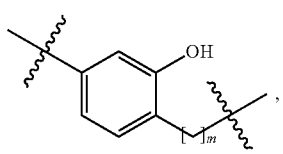

wherein m is 0, 1, 2, 3, 4, 5, 6, 7, 8, 9, 10, 11, 12, 13, 14, 15, 16, 17, 18, 19, or 20. In some embodiments, m is 0. In some other embodiments, m is 1. In yet some other embodiment, m is 2. In yet still some other embodiments, m is 3.

In some embodiments, the linker is

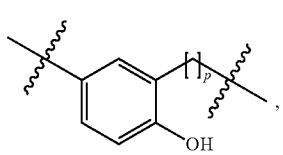

wherein p is 0, 1, 2, 3, 4, 5, 6, 7, 8, 9, 10, 11, 12, 13, 14, 15, 16, 17, 18, 19, or 20. In some embodiments, p is 0. In some other embodiments, p is 1. In yet some other embodiment, p is 2. In yet still some other embodiments, p is 3.

Additional exemplary linkers that can be used are shown in Table 1.

TABLE 1

Examples of hetero-bifunctional cross linking agents.
Hetero-Bifunctional Cross Linking Agents

| Linker | Reactive Toward | Advantages and Applications | Spacer Arm Length after crosslinking (angstroms) |
|---|---|---|---|
| SMPT | Primary amines Sulfhydryls | Greater stability | 11.2 |
| SPDP | Primary amines Sulfhydryls | Thiolation Cleavable cross-linking | 6.8 |
| LC-SPDP | Primary amines Sulfhydryls | Extended spacer arm | 15.6 |
| Sulfo-LC-SPDP | Primary amines Sulfhydryls | Extended spacer arm Water soluble | 15.6 |
| SMCC | Primary amines Sulfhydryls | Stable maleimide reactive group Enzyme-antibody conjugation Hapten-carrier protein conjugation | 11.6 |
| Sulfo-SMCC | Primary amines Sulfhydryls | Stable maleimide reactive group Enzyme-antibody conjugation | 11.6 |
| MBS | Primary amines Sulfhydryls | Enzyme-antibody conjugation Hapten-carrier protein conjugation | 9.9 |
| Sulfo-MBS | Primary amines Sulfhydryls | Water soluble | 9.9 |
| SIAB | Primary amines Sulfhydryls | Enzyme-antibody conjugation | 10.6 |
| Sulfo-SIAB | Primary amines Sulfhydryls | Water soluble | 10.6 |
| SMPB | Primary amines Sulfhydryls | Extended spacer arm Enzyme-antibody conjugation | 14.5 |
| Sulfo-SMPB | Primary amines Sulfhydryls | Extended spacer arm Water-soluble | 14.5 |
| EDC/ Sulfo-NHS | Primary amines Carboxyl groups | Hapten-carrier conjugation | 0 |
| ABH | Carbohydrates Non-selective | Reacts with sugar moieties | 11.9 |

In some embodiments, a compound of the invention is as shown in Table 2.

TABLE 2

Embodiments of compounds of the inventions.

| S. No. | Prototype Structure | Variable groups | |
|---|---|---|---|
| | | R₁ | R₂ |
| 1. | [7-chloroquinolin-4-yl-NH-(CH₂)ₙ-NH-pyrimidine with R₁ at 2-position and R₂ at 6-position]; n = 2, 3, 4, 6 [7-chloroquinolin-4-yl-NH-(CH₂)ₙ-NH-pyrimidine with R₁ at 4-position and R₂ at 6-position]; n = 2, 3, 4, 6 | cyclopropylamine, cyclopentylamine, cyclohexylamine, cycloheptylamine, 1-adamantylamine, pyrrolidine, thiomorpholine, methylamine, dimethylamine, diethylamine, 1H-pyrazole, 1H-imidazole, 3,5-dimethyl-1H-pyrazole, 1-methylpiperazine, 1-ethylpiperazine, 1-isopropylpiperazine, 1-tert-butylpiperazine, 1-(adamantyl)piperazine, 1-benzoylpiperazine, 1-(isonicotinoyl)piperazine, 1-(4-aminobenzoyl)piperazine, 1-(4-nitrobenzoyl)piperazine | N, Me, Cl, CN, CF₃ |

TABLE 2-continued
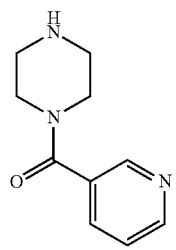 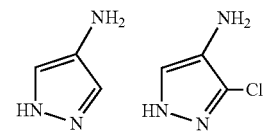
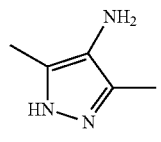 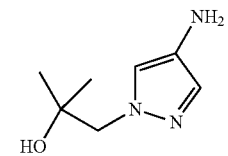
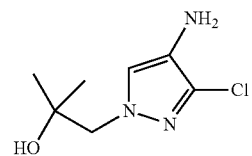
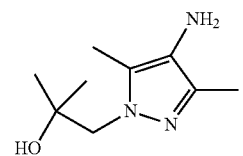
| | | | |
|---|---|---|---|
| 2. | 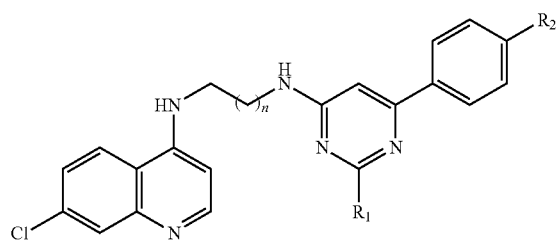<br>n = 2, 3, 4, 6 | $R_1$ can be same | H, F, Cl, OMe, Et |
| 3. | 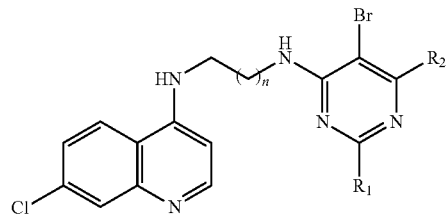<br>n = 2, 3, 4, 6 | $R_1$ can be same | H, Me, Cl, CN, CF$_3$ |

TABLE 2-continued

| # | Structure | R1 | R2, R3 |
|---|---|---|---|
| 4. | (7-chloroquinolin-4-yl)-NH-(CH₂)ₙ-NH-[4-(4-R₃-phenyl)-6-R₂-2-R₁-pyrimidine]; n = 2, 3, 4, 6 | R1 can be same | R₂: H, Me; R₃: H, F, Cl, OMe, Et |
| 5. | (7-chloroquinolin-4-yl)-NH-(CH₂)ₙ-piperazine-[6-R₂-2-R₁-pyrimidine]; n = 1, 2 | R1 can be same | H, Me, Cl |
| 6. | (7-chloroquinolin-4-yl)-NH-(CH₂)ₙ-NH-[2-R₁-quinazolin-4-yl]; n = 2, 3, 4, 6 | R1 can be same | — |
| 7. | (7-chloroquinolin-4-yl)-NH-[4-(CH₂-NH-[6-R₂-2-R₁-pyrimidin-4-yl])phenyl] | R1 can be same | H, Me, Cl |
| 8. | (7-chloroquinolin-4-yl)-NH-[3-(CH₂-NH-[6-R₂-2-R₁-pyrimidin-4-yl])phenyl] | R1 can be same | H, Me, Cl |

TABLE 2-continued

| 9. | [Structure: 7-chloroquinoline-NH-CH(4-Cl-phenyl)-phenyl-CH2-piperazine-pyrimidine(methyl)(R1)] | R1 can be same | No R2 |

In some embodiments, the compound of the invention is a compound shown in Table 3.

TABLE 3

Some exemplary compounds of the invention.

| S. NO. | CODE | STRUCTURE | MOL. FOR. | MOL. WT. | QUANT (mg) | SOLU- BILITY | CLASS OF COM- POUND |
|---|---|---|---|---|---|---|---|
| 1. | SM 484A | [Structure] | $C_{17}H_{17}Cl_2N_5$ | 362.26 | 5.7 | DMSO | AQ-pyrimidine |
| 2. | SM 484B | [Structure] | $C_{17}H_{17}Cl_2N_5$ | 362.26 | 5.9 | DMSO | AQ-pyrimidine |
| 3. | SM 485 | [Structure] | $C_{22}H_{27}ClN_6$ | 410.94 | 4.5 | DMSO | AQ-pyrimidine |
| 4. | SM 488A | [Structure] | $C_{16}H_{15}Cl_2N_5$ | 348.23 | 1.6 | DMSO | AQ-pyrimidine |

TABLE 3-continued

Some exemplary compounds of the invention.

| S. NO. | CODE | STRUCTURE | MOL. FOR. | MOL. WT. | QUANT (mg) | SOLU- BILITY | CLASS OF COM- POUND |
|---|---|---|---|---|---|---|---|
| 5. | SM 488B | 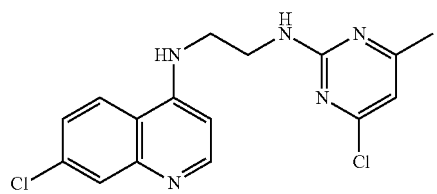 [SMILES: Cc1cc(Cl)nc(NCCNc2ccnc3cc(Cl)ccc23)n1] | $C_{16}H_{15}Cl_2N_5$ | 348.23 | 3.5 | DMSO | AQ- pyrimi- dine |
| 6. | SM 489 | 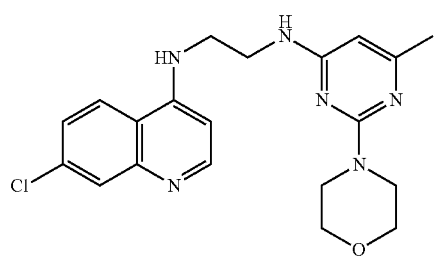 [SMILES: Cc1cc(NCCNc2ccnc3cc(Cl)ccc23)nc(N2CCOCC2)n1] | $C_{20}H_{23}ClN_6O$ | 398.89 | 1.5 | DMSO | AQ- pyrimi- dine |
| 7. | SM 490 | 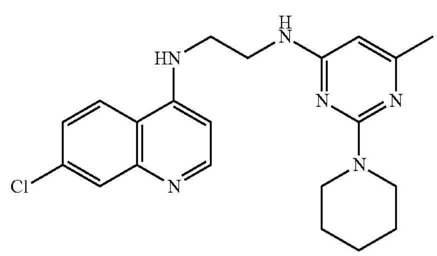 [SMILES: Cc1cc(NCCNc2ccnc3cc(Cl)ccc23)nc(N2CCCCC2)n1] | $C_{21}H_{25}ClN_6$ | 396.92 | 3.8 | DMSO | AQ- pyrimi- dine |
| 8. | SM 491 | 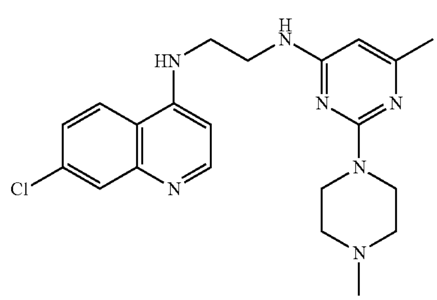 [SMILES: Cc1cc(NCCNc2ccnc3cc(Cl)ccc23)nc(N2CCN(C)CC2)n1] | $C_{21}H_{26}ClN_7$ | 411.93 | 4.2 | DMSO | AQ- pyrimi- dine |
| 9. | SM 493 | 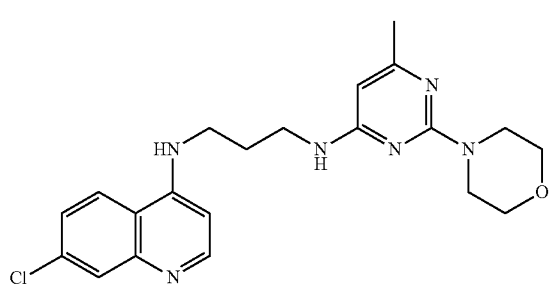 [SMILES: Cc1cc(NCCCNc2ccnc3cc(Cl)ccc23)nc(N2CCOCC2)n1] | $C_{21}H_{25}ClN_6O$ | 412.92 | 3.7 | DMSO | AQ- pyrimi- dine |

TABLE 3-continued
Some exemplary compounds of the invention.
| S. NO. | CODE | STRUCTURE | MOL. FOR. | MOL. WT. | QUANT (mg) | SOLU- BILITY | CLASS OF COM- POUND |
|---|---|---|---|---|---|---|---|
| 10. | SM 494 | 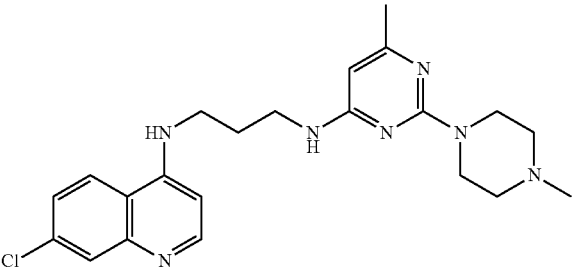 [SMILES: Cc1cc(NCCCNc2ccnc3cc(Cl)ccc23)nc(N2CCN(C)CC2)n1] | $C_{22}H_{28}ClN_7$ | 425.96 | 2.3 | DMSO | AQ- pyrimi- dine |
| 11. | SM 497 | 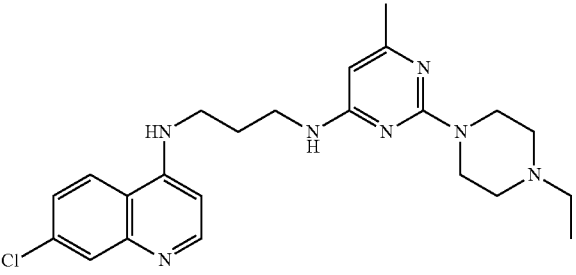 [SMILES: CCN1CCN(c2nc(C)cc(NCCCNc3ccnc4cc(Cl)ccc34)n2)CC1] | $C_{23}H_{30}ClN_7$ | 439.98 | 1.7 | DMSO | AQ- pyrimi- dine |
| 12. | SM 498A | 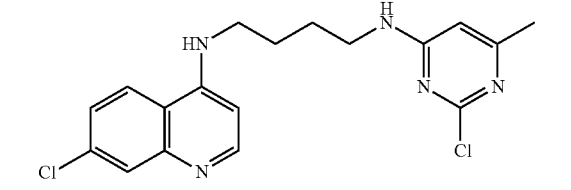 [SMILES: Cc1cc(NCCCCNc2ccnc3cc(Cl)ccc23)nc(Cl)n1] | $C_{18}H_{19}Cl_2N_5$ | 376.28 | 6.2 | DMSO | AQ- pyrimi- dine |
| 13. | SM 498B | 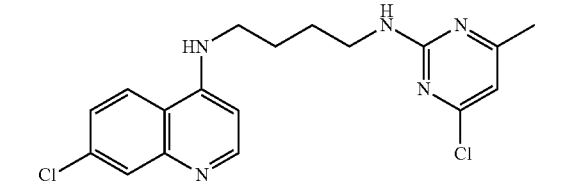 [SMILES: Cc1cc(Cl)nc(NCCCCNc2ccnc3cc(Cl)ccc23)n1] | $C_{18}H_{19}Cl_2N_5$ | 376.28 | 8.7 | DMSO | AQ- pyrimi- dine |
| 14. | SM 499 | 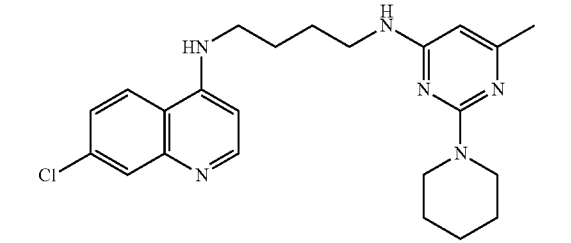 [SMILES: Cc1cc(NCCCCNc2ccnc3cc(Cl)ccc23)nc(N2CCCCC2)n1] | $C_{23}H_{29}ClN_6$ | 424.97 | 4.5 | DMSO | AQ- pyrimi- dine |
| 15. | SM 500 | 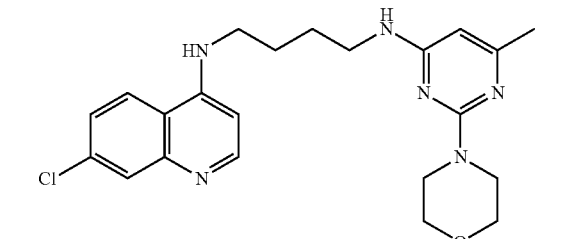 | $C_{22}H_{27}ClN_6O$ | 426.94 | 4.6 | DMSO | AQ- pyrimi- dine |

TABLE 3-continued
Some exemplary compounds of the invention.
| S. NO. | CODE | STRUCTURE | MOL. FOR. | MOL. WT. | QUANT (mg) | SOLU- BILITY | CLASS OF COM- POUND |
|---|---|---|---|---|---|---|---|
| 16. | SM 501 | 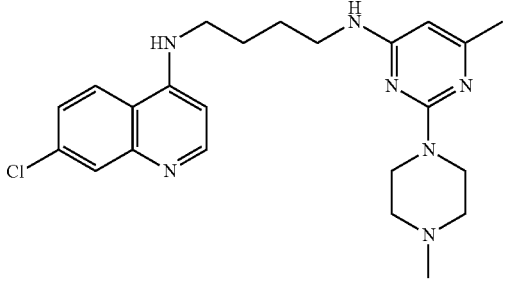 [SMILES: Cc1cc(NCCCCNc2ccnc3cc(Cl)ccc23)nc(N2CCN(C)CC2)n1] | $C_{23}H_{30}ClN_7$ | 439.98 | 3.1 | DMSO | AQ- pyrimi- dine |
| 17. | SM 502 | 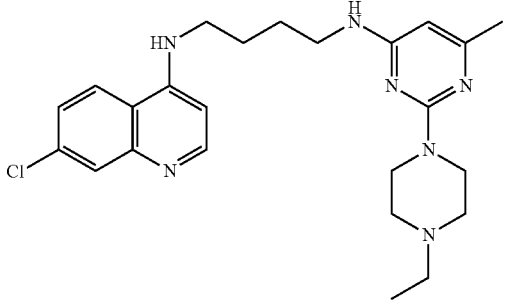 [SMILES: CCN1CCN(c2nc(C)cc(NCCCCNc3ccnc4cc(Cl)ccc34)n2)CC1] | $C_{24}H_{32}ClN_7$ | 454.01 | 3.8 | DMSO | AQ- pyrimi- dine |
| 18. | SM 504A | 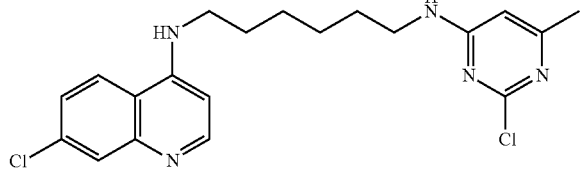 | $C_{20}H_{23}Cl_2N_5$ | 404.34 | 3.5 | DMSO | AQ- pyrimi- dine |
| 19. | SM 504B | 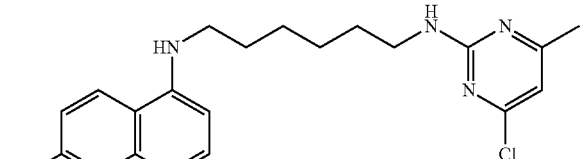 | $C_{20}H_{23}Cl_2N_5$ | 404.34 | 2.5 | DMSO | AQ- pyrimi- dine |
| 20. | SM 505 | 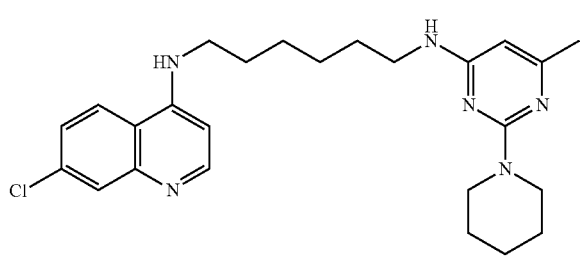 [SMILES: Cc1cc(NCCCCCCNc2ccnc3cc(Cl)ccc23)nc(N2CCCCC2)n1] | $C_{25}H_{33}ClN_6$ | 453.02 | 7.2 | DMSO | AQ- pyrimi- dine |
| 21. | SM 506 | 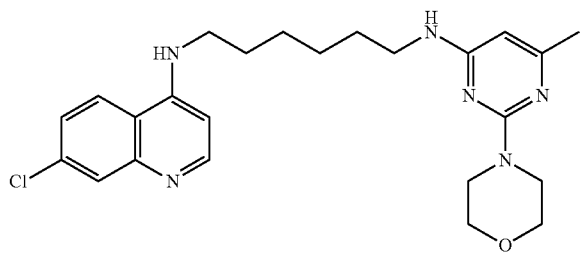 [SMILES: Cc1cc(NCCCCCCNc2ccnc3cc(Cl)ccc23)nc(N2CCOCC2)n1] | $C_{24}H_{31}ClN_6O$ | 455.00 | 3.1 | DMSO | AQ- pyrimi- dine |

TABLE 3-continued
Some exemplary compounds of the invention.
| S. NO. | CODE | STRUCTURE | MOL. FOR. | MOL. WT. | QUANT (mg) | SOLU-BILITY | CLASS OF COMPOUND |
|---|---|---|---|---|---|---|---|
| 22. | SM 507 | 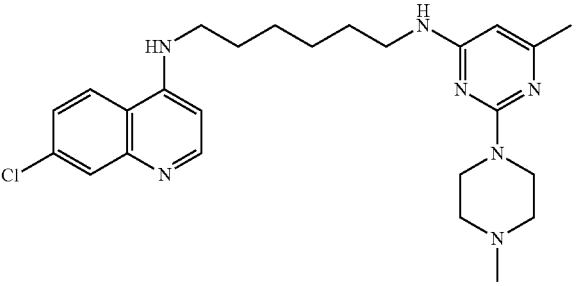 [SMILES: Cc1cc(NCCCCCCNc2ccnc3cc(Cl)ccc23)nc(N2CCN(C)CC2)n1] | $C_{25}H_{34}ClN_7$ | 468.04 | 2.0 | DMSO | AQ-pyrimidine |
| 23. | SM 695A | 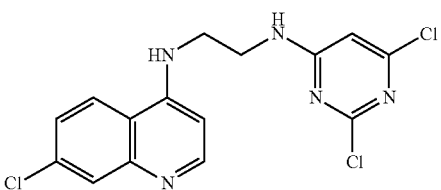 [SMILES: Clc1ccc2c(NCCNc3cc(Cl)nc(Cl)n3)ccnc2c1] | $C_{15}H_{12}Cl_3N_5$ | 368.65 | 7.6 | DMSO | AQ-pyrimidine |
| 24. | SM 695B | 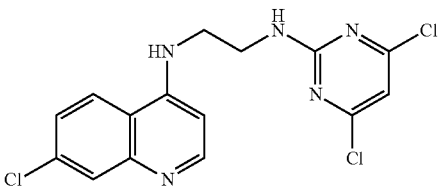 [SMILES: Clc1ccc2c(NCCNc3nc(Cl)cc(Cl)n3)ccnc2c1] | $C_{15}H_{12}Cl_3N_5$ | 368.65 | 5.4 | DMSO | AQ-pyrimidine |
| 25. | SM 696 | 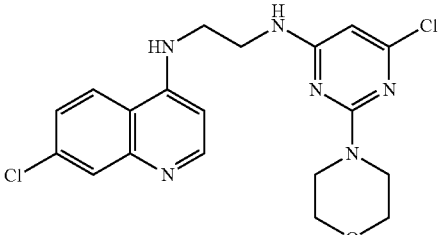 | $C_{19}H_{20}Cl_2N_6O$ | 419.31 | 5.2 | DMSO | AQ-pyrimidine |
| 26. | SM 697 | 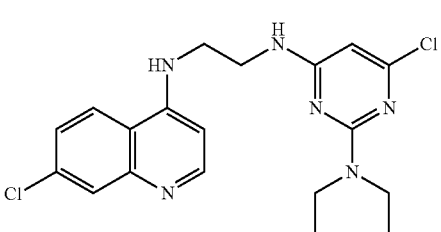 | $C_{20}H_{22}Cl_2N_6$ | 417.33 | 6.4 | DMSO | AQ-pyrimidine |
| 27. | SM 699 | 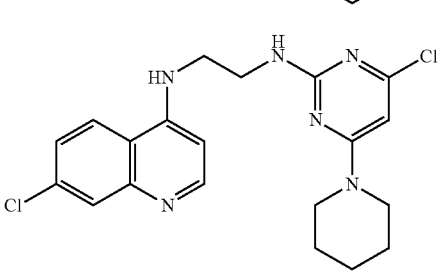 | $C_{20}H_{22}Cl_2N_6$ | 417.33 | 6.7 | DMSO | AQ-pyrimidine |

TABLE 3-continued

Some exemplary compounds of the invention.

| S. NO. | CODE | STRUCTURE | MOL. FOR. | MOL. WT. | QUANT (mg) | SOLU-BILITY | CLASS OF COM-POUND |
|---|---|---|---|---|---|---|---|
| 28. | SM 700 | 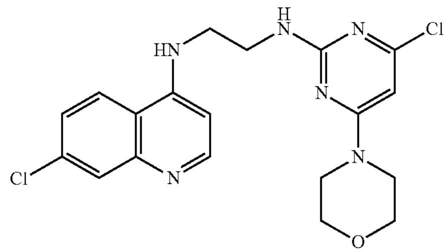 [SMILES: Clc1ccc2c(NCCNc3nc(Cl)cc(N4CCOCC4)n3)ccnc2c1] | $C_{19}H_{20}Cl_2N_6O$ | 419.31 | 7.9 | DMSO | AQ-pyrimidine |
| 29. | SM 701 | 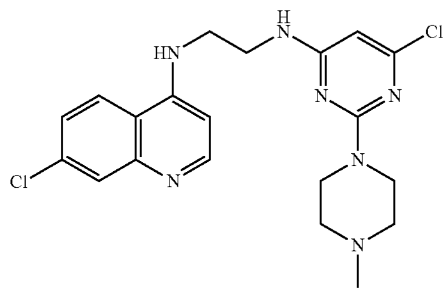 [SMILES: CN1CCN(c2nc(Cl)cc(NCCNc3ccnc4cc(Cl)ccc34)n2)CC1] | $C_{20}H_{23}Cl_2N_7$ | 432.35 | 5.8 | DMSO | AQ-pyrimidine |
| 30. | SM 702 | 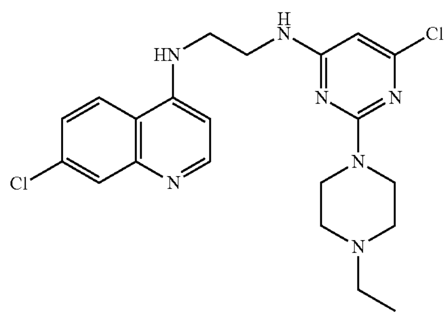 [SMILES: CCN1CCN(c2nc(Cl)cc(NCCNc3ccnc4cc(Cl)ccc34)n2)CC1] | $C_{21}H_{25}Cl_2N_7$ | 446.38 | 3.8 | DMSO | AQ-pyrimidine |
| 31. | SM 703 | 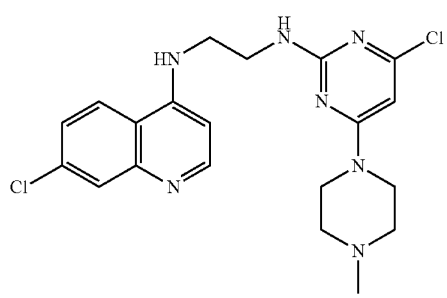 [SMILES: CN1CCN(c2cc(Cl)nc(NCCNc3ccnc4cc(Cl)ccc34)n2)CC1] | $C_{20}H_{23}Cl_2N_7$ | 432.35 | 7.2 | DMSO | AQ-pyrimidine |
| 32. | SM 704 | 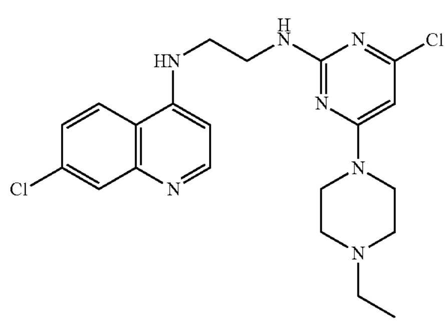 [SMILES: CCN1CCN(c2cc(Cl)nc(NCCNc3ccnc4cc(Cl)ccc34)n2)CC1] | $C_{21}H_{25}Cl_2N_7$ | 446.38 | 4.0 | DMSO | AQ-pyrimidine |

TABLE 3-continued
Some exemplary compounds of the invention.
| S. NO. | CODE | STRUCTURE | MOL. FOR. | MOL. WT. | QUANT (mg) | SOLU- BILITY | CLASS OF COM- POUND |
|---|---|---|---|---|---|---|---|
| 33. | SM 710A | 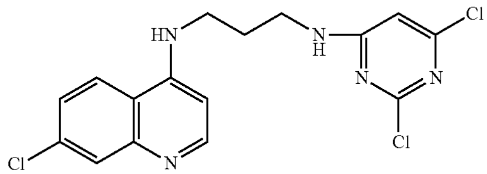 [SMILES: Clc1ccc2c(NCCCNc3cc(Cl)nc(Cl)n3)ccnc2c1] | $C_{16}H_{14}Cl_3N_5$ | 382.67 | 6.7 | DMSO | AQ- pyrimi- dine |
| 34. | SM 710B | 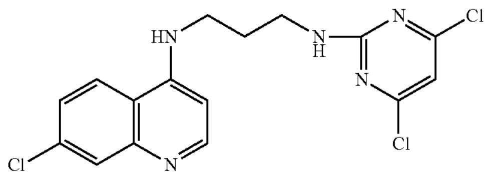 [SMILES: Clc1ccc2c(NCCCNc3nc(Cl)cc(Cl)n3)ccnc2c1] | $C_{16}H_{14}Cl_3N_5$ | 382.67 | 6.1 | DMSO | AQ- pyrimi- dine |
| 35. | SM 711 | 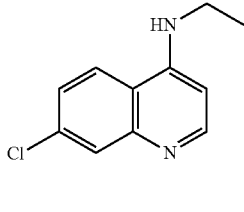 | $C_{21}H_{24}Cl_2N_6$ | 431.36 | 4.4 | DMSO | AQ- pyrimi- dine |
| 36. | SM 712 | 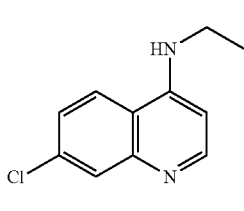 | $C_{20}H_{22}Cl_2N_6O$ | 433.33 | 6.2 | DMSO | AQ- pyrimi- dine |
| 37. | SM 713 | 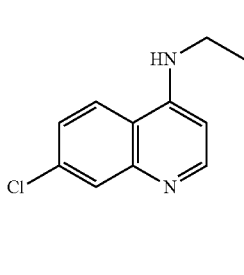 | $C_{21}H_{25}Cl_2N_7$ | 446.38 | 4.3 | DMSO | AQ- pyrimi- dine |
| 38. | SM 714 | 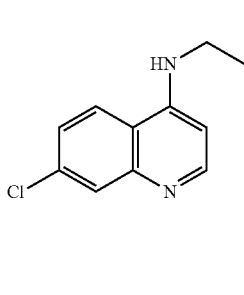 | $C_{22}H_{27}Cl_2N_7$ | 460.40 | 5.6 | DMSO | AQ- pyrimi- dine |

TABLE 3-continued

Some exemplary compounds of the invention.

| S. NO. | CODE | STRUCTURE | MOL. FOR. | MOL. WT. | QUANT (mg) | SOLU-BILITY | CLASS OF COMPOUND |
|---|---|---|---|---|---|---|---|
| 39. | SM 715 | 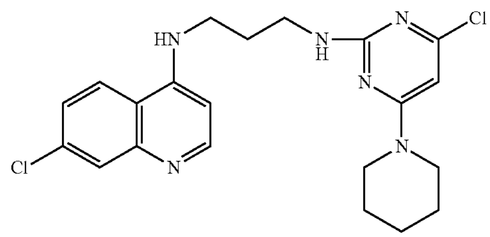 [SMILES: Clc1ccc2c(NCCCNc3nc(Cl)cc(N4CCCCC4)n3)ccnc2c1] | $C_{21}H_{24}Cl_2N_6$ | 431.36 | 6.8 | DMSO | AQ-pyrimidine |
| 40. | SM 716 | 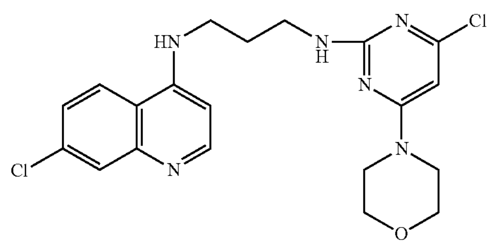 [SMILES: Clc1ccc2c(NCCCNc3nc(Cl)cc(N4CCOCC4)n3)ccnc2c1] | $C_{20}H_{22}Cl_2N_6O$ | 433.33 | 6.1 | DMSO | AQ-pyrimidine |
| 41. | SM 717 | 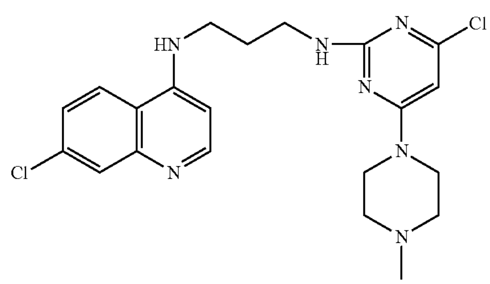 [SMILES: CN1CCN(c2cc(Cl)nc(NCCCNc3ccnc4cc(Cl)ccc34)n2)CC1] | $C_{21}H_{25}Cl_2N_7$ | 446.38 | 2.5 | DMSO | AQ-pyrimidine |
| 42. | SM 718 | 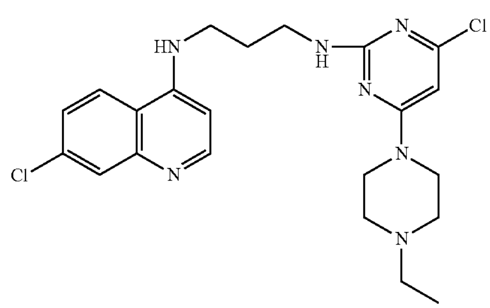 [SMILES: CCN1CCN(c2cc(Cl)nc(NCCCNc3ccnc4cc(Cl)ccc34)n2)CC1] | $C_{22}H_{27}Cl_2N_7$ | 460.40 | 3.5 | DMSO | AQ-pyrimidine |
| 43. | SM 719A | 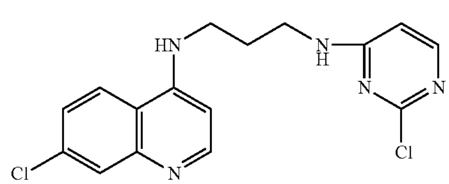 [SMILES: Clc1ccc2c(NCCCNc3ccnc(Cl)n3)ccnc2c1] | $C_{16}H_{15}Cl_2N_5$ | 348.23 | 5.6 | DMSO | AQ-pyrimidine |
| 44. | SM 719B | 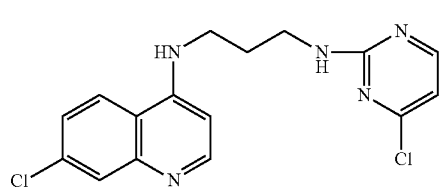 [SMILES: Clc1ccc2c(NCCCNc3nccc(Cl)n3)ccnc2c1] | $C_{16}H_{15}Cl_2N_5$ | 348.23 | 8.0 | DMSO | AQ-pyrimidine |

TABLE 3-continued

Some exemplary compounds of the invention.

| S. NO. | CODE | STRUCTURE | MOL. FOR. | MOL. WT. | QUANT (mg) | SOLU-BILITY | CLASS OF COM-POUND |
|---|---|---|---|---|---|---|---|
| 45. | SM 720 | 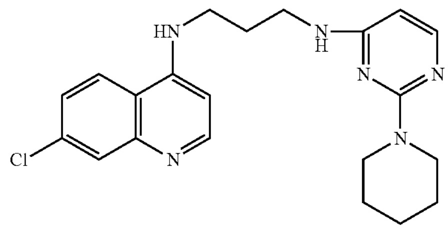 [SMILES: Clc1ccc2c(NCCCNc3ccnc(N4CCCCC4)n3)ccnc2c1] | $C_{21}H_{25}ClN_6$ | 396.92 | 5.2 | DMSO | AQ-pyrimidine |
| 46. | SM 721 | 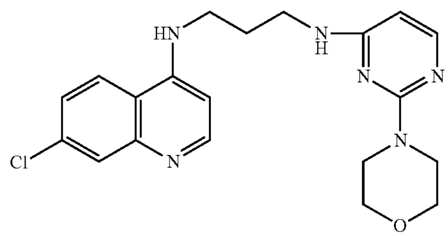 [SMILES: Clc1ccc2c(NCCCNc3ccnc(N4CCOCC4)n3)ccnc2c1] | $C_{20}H_{23}ClN_6O$ | 398.89 | 5.8 | DMSO | AQ-pyrimidine |
| 47. | SM 722 | 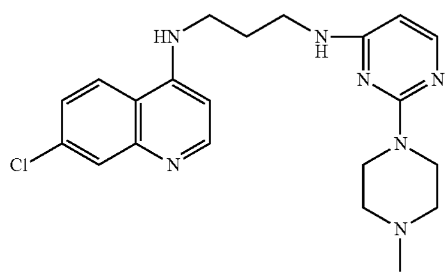 [SMILES: CN1CCN(c2nccc(NCCCNc3ccnc4cc(Cl)ccc34)n2)CC1] | $C_{21}H_{26}ClN_7$ | 411.93 | 1.3 | DMSO | AQ-pyrimidine |
| 48. | SM 723 | 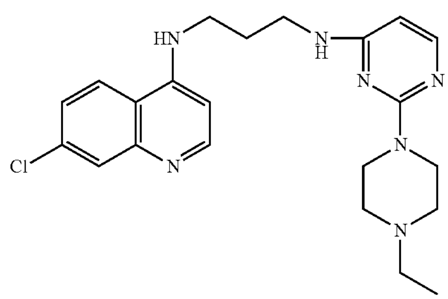 [SMILES: CCN1CCN(c2nccc(NCCCNc3ccnc4cc(Cl)ccc34)n2)CC1] | $C_{22}H_{28}ClN_7$ | 425.96 | 4.1 | DMSO | AQ-pyrimidine |
| 49. | SM 724 | 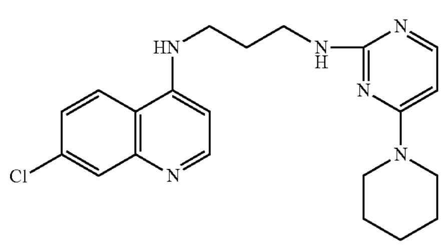 [SMILES: Clc1ccc2c(NCCCNc3nccc(N4CCCCC4)n3)ccnc2c1] | $C_{21}H_{25}ClN_6$ | 396.92 | 5.0 | DMSO | AQ-pyrimidine |

TABLE 3-continued

Some exemplary compounds of the invention.

| S. NO. | CODE | STRUCTURE | MOL. FOR. | MOL. WT. | QUANT (mg) | SOLU- BILITY | CLASS OF COM- POUND |
|---|---|---|---|---|---|---|---|
| 50. | SM 725 | 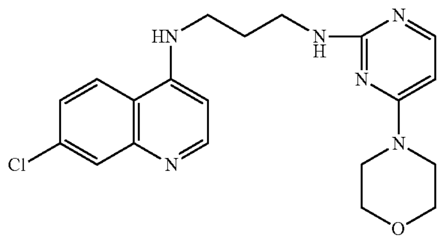 [SMILES: Clc1ccc2c(NCCCNc3nccc(N4CCOCC4)n3)ccnc2c1] | $C_{20}H_{23}ClN_6O$ | 398.89 | 6.7 | DMSO | AQ- pyrimi- dine |
| 51. | SM 726 | 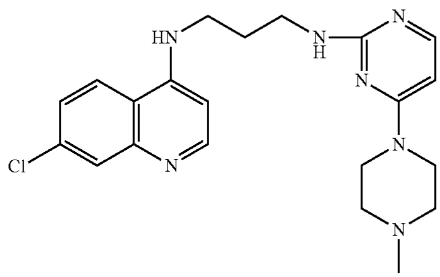 [SMILES: CN1CCN(c2ccnc(NCCCNc3ccnc4cc(Cl)ccc34)n2)CC1] | $C_{21}H_{26}ClN_7$ | 411.93 | 5.7 | DMSO | AQ- pyrimi- dine |
| 52. | SM 727 | 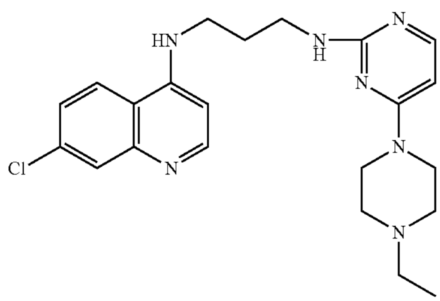 [SMILES: CCN1CCN(c2ccnc(NCCCNc3ccnc4cc(Cl)ccc34)n2)CC1] | $C_{22}H_{28}ClN_7$ | 425.96 | 7.7 | DMSO | AQ- pyrimi- dine |
| 53. | SM 728A | 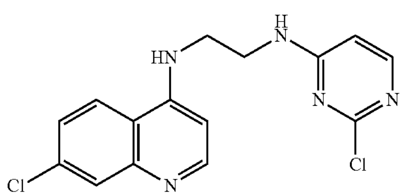 [SMILES: Clc1ccc2c(NCCNc3ccnc(Cl)n3)ccnc2c1] | $C_{15}H_{13}Cl_2N_5$ | 334.20 | 7.2 | DMSO | AQ- pyrimi- dine |
| 54. | SM 728B | 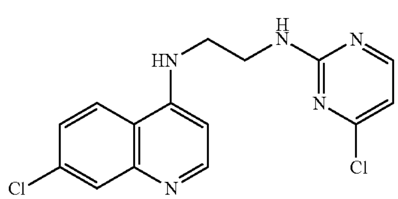 [SMILES: Clc1ccc2c(NCCNc3nccc(Cl)n3)ccnc2c1] | $C_{15}H_{13}Cl_2N_5$ | 334.20 | 5.8 | DMSO | AQ- pyrimi- dine |
| 55. | SM 730 | 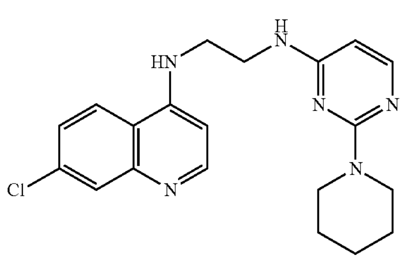 [SMILES: Clc1ccc2c(NCCNc3ccnc(N4CCCCC4)n3)ccnc2c1] | $C_{20}H_{23}ClN_6$ | 382.89 | 6.6 | DMSO | AQ- pyrimi- dine |

TABLE 3-continued

Some exemplary compounds of the invention.

| S. NO. | CODE | STRUCTURE | MOL. FOR. | MOL. WT. | QUANT (mg) | SOLU-BILITY | CLASS OF COM-POUND |
|---|---|---|---|---|---|---|---|
| 56. | SM 731 | 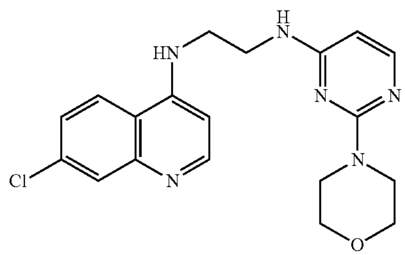 [SMILES: Clc1ccc2c(NCCNc3ccnc(N4CCOCC4)n3)ccnc2c1] | $C_{19}H_{21}ClN_6O$ | 384.86 | 4.4 | DMSO | AQ-pyrimi-dine |
| 57. | SM 732 | 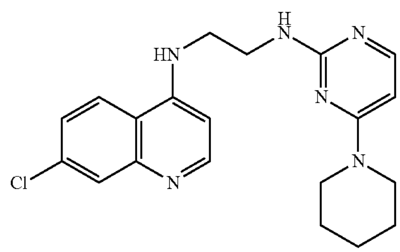 [SMILES: Clc1ccc2c(NCCNc3nccc(N4CCCCC4)n3)ccnc2c1] | $C_{20}H_{23}ClN_6$ | 382.89 | 4.1 | DMSO | AQ-pyrimi-dine |
| 58. | SM 733 | 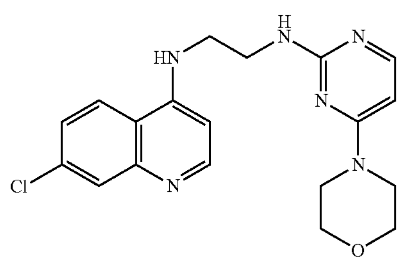 [SMILES: Clc1ccc2c(NCCNc3nccc(N4CCOCC4)n3)ccnc2c1] | $C_{19}H_{21}ClN_6O$ | 384.86 | 1.0 | DMSO | AQ-pyrimi-dine |
| 59 | SM 734 | 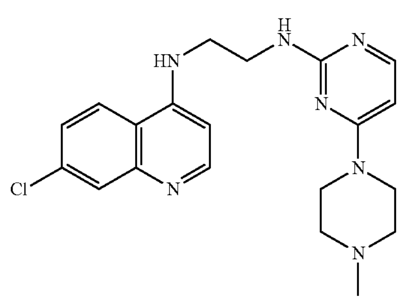 [SMILES: CN1CCN(c2ccnc(NCCNc3ccnc4cc(Cl)ccc34)n2)CC1] | $C_{20}H_{24}ClN_7$ | 397.90 | 3.2 | DMSO | AQ-pyrimi-dine |
| 60. | SM 332 | 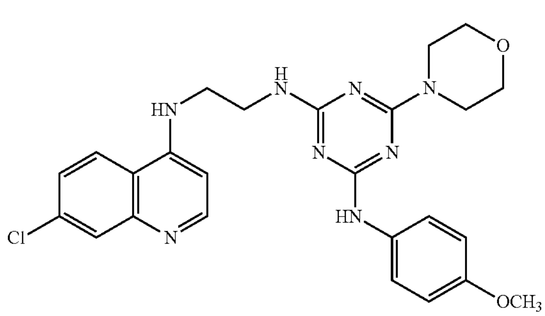 [SMILES: COc1ccc(Nc2nc(NCCNc3ccnc4cc(Cl)ccc34)nc(N3CCOCC3)n2)cc1] | $C_{25}H_{27}ClN_8O_2$ | 506.99 | 1.5 | DMSO | AQ-triazine |

TABLE 3-continued

Some exemplary compounds of the invention.

| S. NO. | CODE | STRUCTURE | MOL. FOR. | MOL. WT. | QUANT (mg) | SOLU- BILITY | CLASS OF COM- POUND |
|---|---|---|---|---|---|---|---|
| 61. | SM 334 | 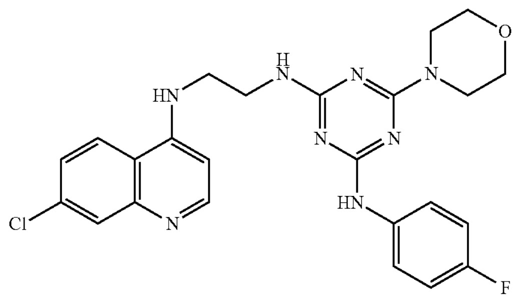 [SMILES: Fc1ccc(Nc2nc(NCCNc3ccnc4cc(Cl)ccc34)nc(N3CCOCC3)n2)cc1] | $C_{24}H_{24}ClFN_8O$ | 494.95 | 1.5 | DMSO | AQ-triazine |
| 62. | SM 335 | 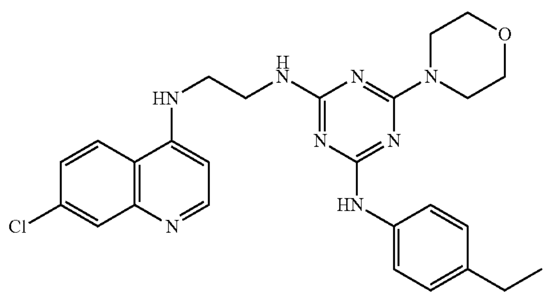 [SMILES: CCc1ccc(Nc2nc(NCCNc3ccnc4cc(Cl)ccc34)nc(N3CCOCC3)n2)cc1] | $C_{26}H_{29}ClN_8O$ | 505.01 | 3.2 | DMSO | AQ-triazine |
| 63. | SM 336 | 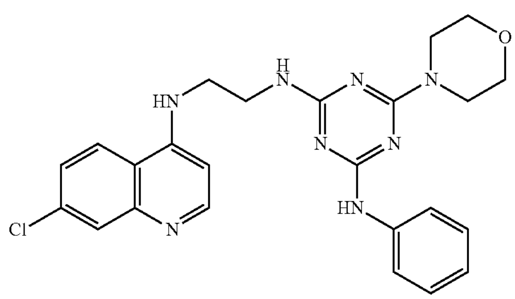 [SMILES: Clc1ccc2c(NCCNc3nc(Nc4ccccc4)nc(N4CCOCC4)n3)ccnc2c1] | $C_{24}H_{25}ClN_8O$ | 476.96 | 4.3 | DMSO | AQ-triazine |
| 64. | SM 337 | 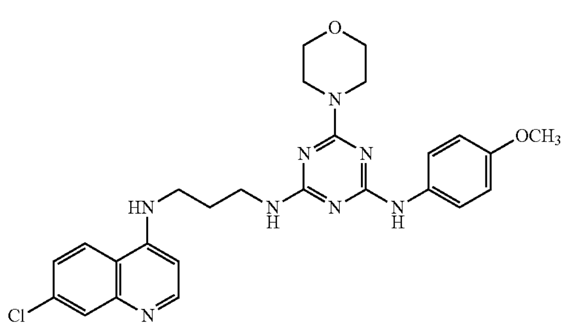 [SMILES: COc1ccc(Nc2nc(NCCCNc3ccnc4cc(Cl)ccc34)nc(N3CCOCC3)n2)cc1] | $C_{26}H_{29}ClN_8O_2$ | 521.01 | 8.1 | DMSO | AQ-triazine |

TABLE 3-continued

Some exemplary compounds of the invention.

| S. NO. | CODE | STRUCTURE | MOL. FOR. | MOL. WT. | QUANT (mg) | SOLU- BILITY | CLASS OF COM- POUND |
|---|---|---|---|---|---|---|---|
| 65. | SM 339 | 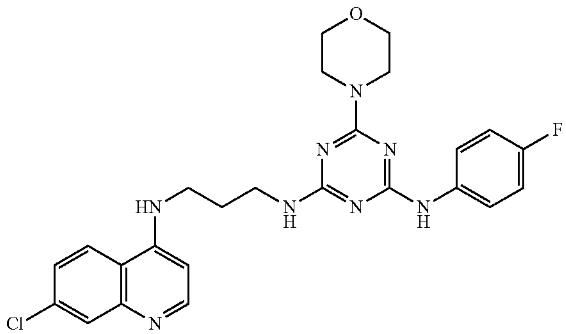 [SMILES: Fc1ccc(Nc2nc(NCCCNc3ccnc4cc(Cl)ccc34)nc(N3CCOCC3)n2)cc1] | $C_{25}H_{26}ClFN_8O$ | 508.98 | 3.8 | DMSO | AQ-triazine |
| 66. | SM 340 | 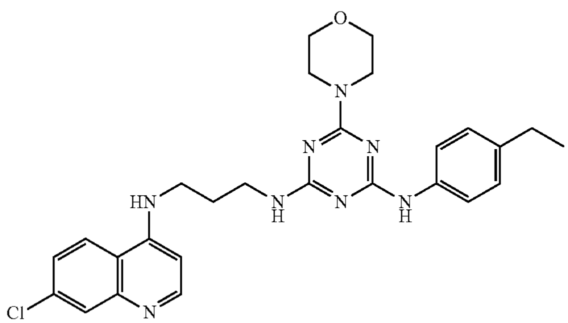 [SMILES: CCc1ccc(Nc2nc(NCCCNc3ccnc4cc(Cl)ccc34)nc(N3CCOCC3)n2)cc1] | $C_{27}H_{31}ClN_8O$ | 519.04 | 3.3 | DMSO | AQ-triazine |
| 67. | SM 341 | 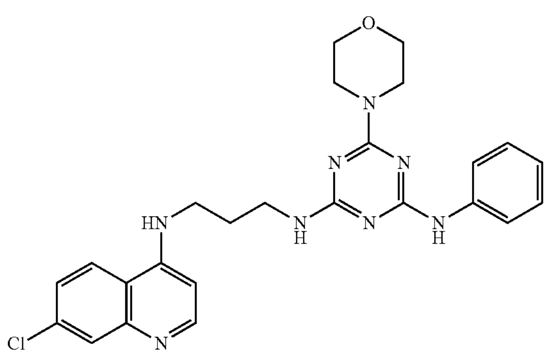 [SMILES: Clc1ccc2c(NCCCNc3nc(Nc4ccccc4)nc(N4CCOCC4)n3)ccnc2c1] | $C_{25}H_{27}ClN_8O$ | 490.99 | 3.3 | DMSO | AQ-triazine |
| 68. | SM 345 | 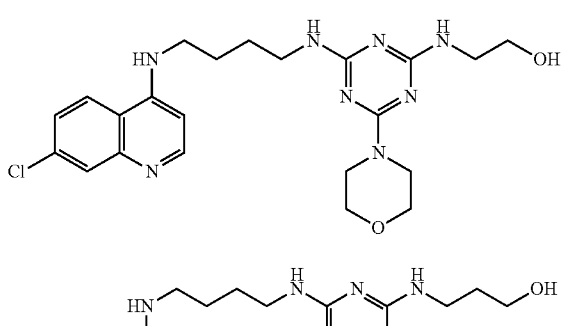 | $C_{22}H_{29}ClN_8O_2$ | 472.97 | 1.7 | DMSO | AQ-triazine |
| 69. | SM 349 | 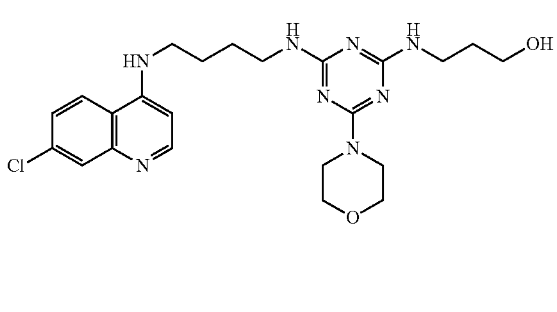 [SMILES: OCCCNc1nc(NCCCCNc2ccnc3cc(Cl)ccc23)nc(N2CCOCC2)n1] | $C_{23}H_{31}ClN_8O_2$ | 487.00 | 3.7 | DMSO | AQ-triazine |

TABLE 3-continued

Some exemplary compounds of the invention.

| S. NO. | CODE | STRUCTURE | MOL. FOR. | MOL. WT. | QUANT (mg) | SOLU-BILITY | CLASS OF COMPOUND |
|---|---|---|---|---|---|---|---|
| 70. | SM 350 | 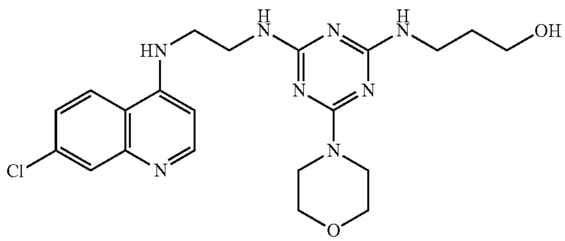 [SMILES: OCCCNc1nc(NCCNc2ccnc3cc(Cl)ccc23)nc(N2CCOCC2)n1] | $C_{21}H_{27}ClN_8O_2$ | 458.94 | 5.7 | DMSO | AQ-triazine |
| 71. | SM 351 | 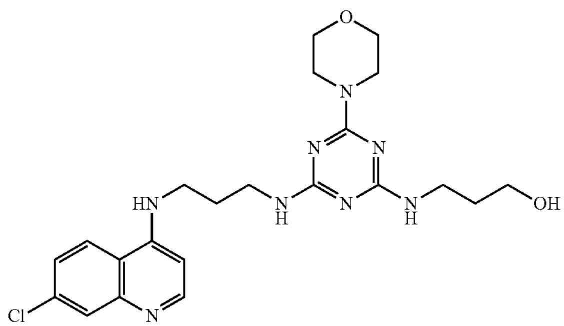 [SMILES: OCCCNc1nc(NCCCNc2ccnc3cc(Cl)ccc23)nc(N2CCOCC2)n1] | $C_{22}H_{29}ClN_8O_2$ | 472.97 | 3.2 | DMSO | AQ-triazine |
| 72. | SM 352 | 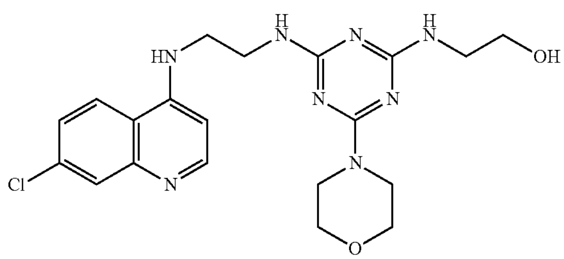 [SMILES: OCCNc1nc(NCCNc2ccnc3cc(Cl)ccc23)nc(N2CCOCC2)n1] | $C_{20}H_{25}ClN_8O_2$ | 444.92 | 3.7 | DMSO | AQ-triazine |
| 73. | SM 353 | 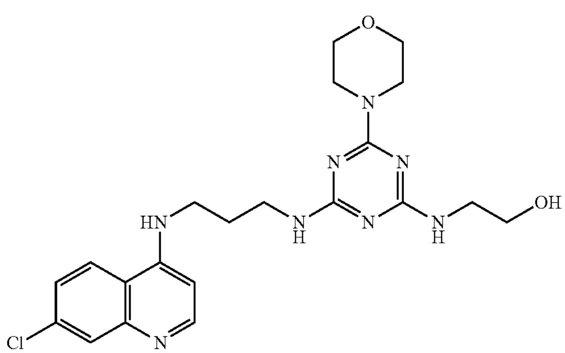 [SMILES: OCCNc1nc(NCCCNc2ccnc3cc(Cl)ccc23)nc(N2CCOCC2)n1] | $C_{21}H_{27}ClN_8O_2$ | 458.94 | 3.2 | DMSO | AQ-triazine |
| 74. | SM 356 | 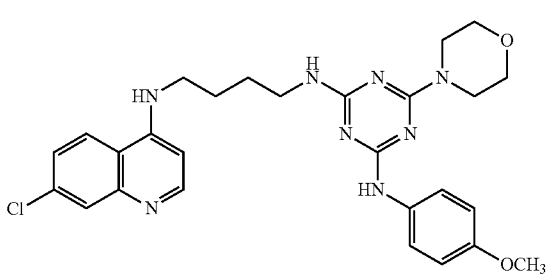 [SMILES: COc1ccc(Nc2nc(NCCCCNc3ccnc4cc(Cl)ccc34)nc(N3CCOCC3)n2)cc1] | $C_{27}H_{31}ClN_8O_2$ | 535.04 | 3.7 | DMSO | AQ-triazine |

TABLE 3-continued

Some exemplary compounds of the invention.

| S. NO. | CODE | STRUCTURE | MOL. FOR. | MOL. WT. | QUANT (mg) | SOLU-BILITY | CLASS OF COM-POUND |
|---|---|---|---|---|---|---|---|
| 75. | SM 357 | 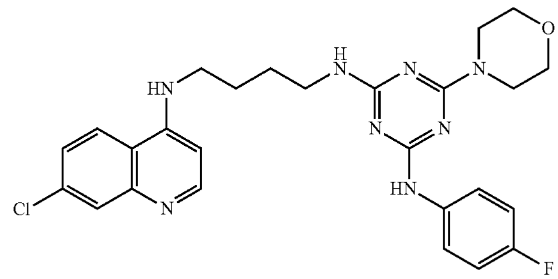 [SMILES: Fc1ccc(Nc2nc(NCCCCNc3ccnc4cc(Cl)ccc34)nc(N3CCOCC3)n2)cc1] | $C_{26}H_{28}ClN_8O$ | 523.00 | 3.1 | DMSO | AQ-triazine |
| 76 | SM 358 | 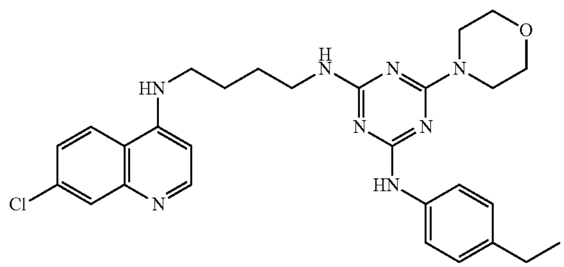 [SMILES: CCc1ccc(Nc2nc(NCCCCNc3ccnc4cc(Cl)ccc34)nc(N3CCOCC3)n2)cc1] | $C_{28}H_{33}ClN_8O$ | 533.07 | 3.5 | DMSO | AQ-triazine |
| 77. | SM 359 | 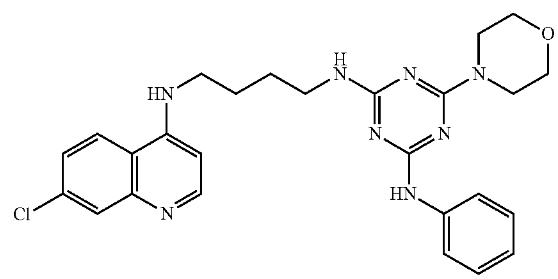 [SMILES: Clc1ccc2c(NCCCCNc3nc(Nc4ccccc4)nc(N4CCOCC4)n3)ccnc2c1] | $C_{26}H_{29}ClN_8O$ | 505.01 | 4.0 | DMSO | AQ-triazine |
| 78. | SM 360 | 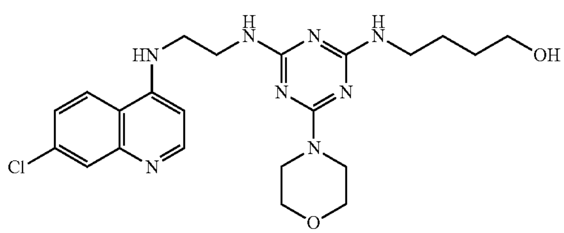 [SMILES: OCCCCNc1nc(NCCNc2ccnc3cc(Cl)ccc23)nc(N2CCOCC2)n1] | $C_{22}H_{29}ClN_8O_2$ | 472.97 | 5.3 | DMSO | AQ-triazine |
| 79. | SM 361 | 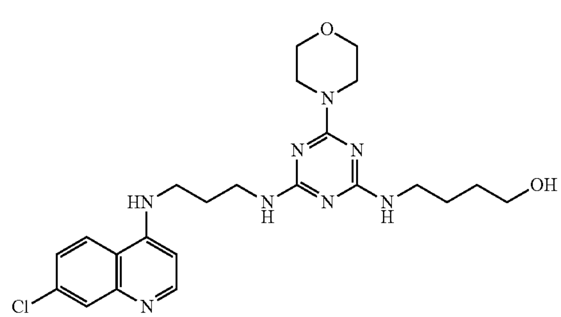 [SMILES: OCCCCNc1nc(NCCCNc2ccnc3cc(Cl)ccc23)nc(N2CCOCC2)n1] | $C_{23}H_{31}ClN_8O_2$ | 487.00 | 5.3 | DMSO | AQ-triazine |

TABLE 3-continued
Some exemplary compounds of the invention.
| S. NO. | CODE | STRUCTURE | MOL. FOR. | MOL. WT. | QUANT (mg) | SOLU- BILITY | CLASS OF COM- POUND |
|---|---|---|---|---|---|---|---|
| 80. | SM 362 | 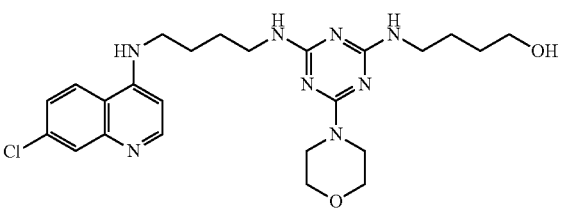 [SMILES: OCCCCNc1nc(NCCCCNc2ccnc3cc(Cl)ccc23)nc(N2CCOCC2)n1] | $C_{24}H_{33}ClN_8O_2$ | 501.02 | 4.0 | DMSO | AQ-triazine |
| 81. | SM 365 | 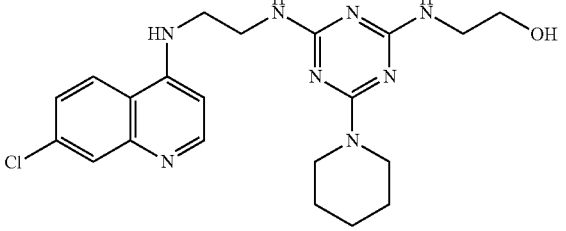 | $C_{21}H_{27}ClN_8O$ | 442.95 | 4.8 | DMSO | AQ-triazine |
| 82. | SM 367 | 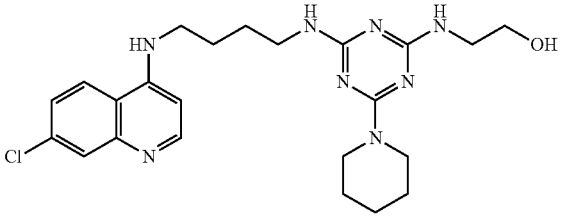 [SMILES: OCCNc1nc(NCCCCNc2ccnc3cc(Cl)ccc23)nc(N2CCCCC2)n1] | $C_{23}H_{31}ClN_8O$ | 471.00 | 3.0 | DMSO | AQ-triazine |
| 83. | SM 370 | 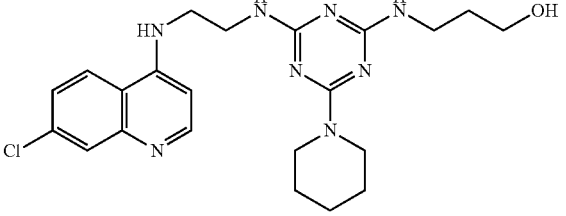 | $C_{22}H_{29}ClN_8O$ | 456.97 | 5.7 | DMSO | AQ-triazine |
| 84. | SM 372 | 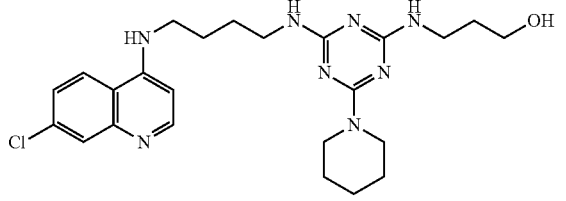 [SMILES: OCCCNc1nc(NCCCCNc2ccnc3cc(Cl)ccc23)nc(N2CCCCC2)n1] | $C_{24}H_{33}ClN_8O$ | 485.02 | 1.5 | DMSO | AQ-triazine |
| 85. | SM 373 | 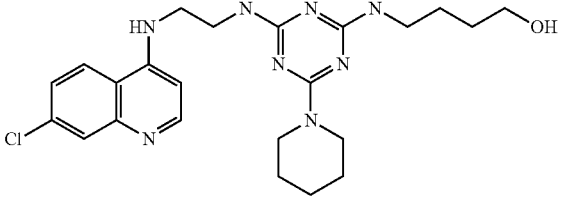 | $C_{23}H_{31}ClN_8O$ | 471.00 | 3.8 | DMSO | AQ-triazine |

TABLE 3-continued
Some exemplary compounds of the invention.
| S. NO. | CODE | STRUCTURE | MOL. FOR. | MOL. WT. | QUANT (mg) | SOLU-BILITY | CLASS OF COMPOUND |
|---|---|---|---|---|---|---|---|
| 86. | SM 375 | 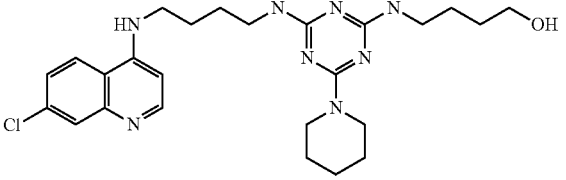 | $C_{25}H_{35}ClN_8O$ | 499.05 | 4.5 | DMSO | AQ-triazine |
| 87. | SM 129 | 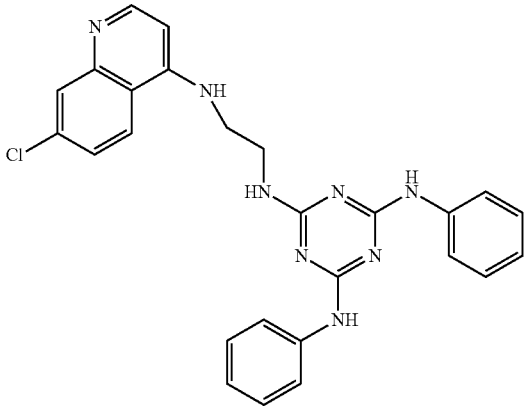 [SMILES: Clc1ccc2c(NCCNc3nc(Nc4ccccc4)nc(Nc4ccccc4)n3)ccnc2c1] | $C_{26}H_{23}ClN_8$ | 482.97 | 1.7 | DMSO | AQ-triazine |
| 88. | SM 130 | 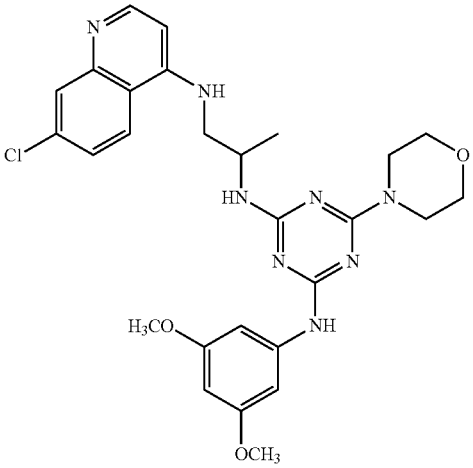 [SMILES: COc1cc(Nc2nc(NC(C)CNc3ccnc4cc(Cl)ccc34)nc(N3CCOCC3)n2)cc(OC)c1] | $C_{27}H_{31}ClN_8O_3$ | 551.04 | 11.0 | DMSO | AQ-triazine |
| 89. | SM 132 | 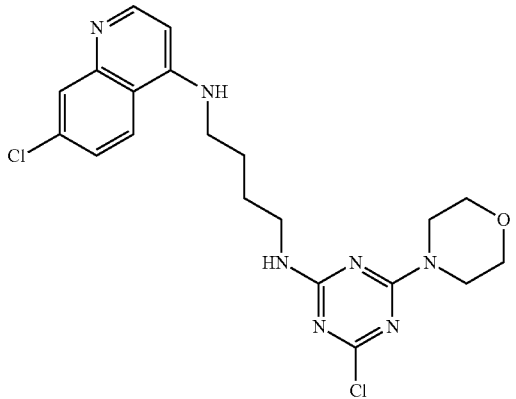 | $C_{28}H_{33}ClN_8O_3$ | 567.07 | 12.1 | DMSO | AQ-triazine |

TABLE 3-continued

Some exemplary compounds of the invention.

| S. NO. | CODE | STRUCTURE | MOL. FOR. | MOL. WT. | QUANT (mg) | SOLU-BILITY | CLASS OF COM-POUND |
|---|---|---|---|---|---|---|---|
| 90. | SM 133 | | $C_{25}H_{22}Cl_3N_9$ | 554.86 | 2.7 | DMSO | AQ-triazine |
| 91. | SM 135 | | $C_{20}H_{23}Cl_2N_7O$ | 448.35 | 3.1 | DMSO | AQ-triazine |
| 92. | SM 136 | | $C_{20}H_{17}Cl_2N_7$ | 426.30 | 2.0 | DMSO | AQ-triazine |
| 93. | SM 137 | | $C_{18}H_{21}Cl_2N_7$ | 406.31 | 2.2 | DMSO | AQ-triazine |

TABLE 3-continued

Some exemplary compounds of the invention.

| S. NO. | CODE | STRUCTURE | MOL. FOR. | MOL. WT. | QUANT (mg) | SOLU-BILITY | CLASS OF COM-POUND |
|---|---|---|---|---|---|---|---|
| 94. | SM 140 | 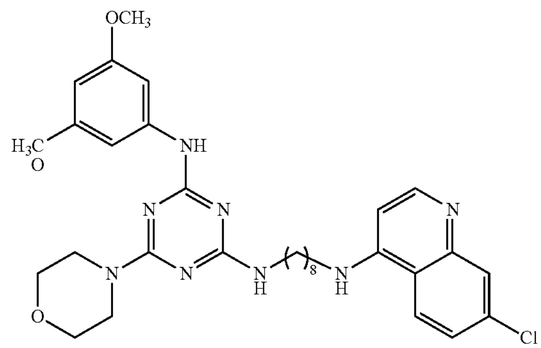 | $C_{32}H_{41}ClN_8O_3$ | 622.17 | 5.5 | DMSO | AQ-triazine |
| 95. | SM 142 | 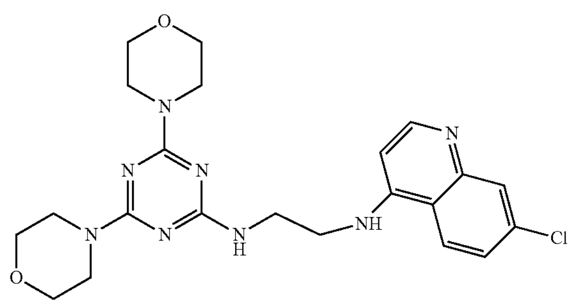 [SMILES: Clc1ccc2c(NCCNc3nc(N4CCOCC4)nc(N4CCOCC4)n3)ccnc2c1] | $C_{22}H_{27}ClN_8O_2$ | 470.96 | 2.5 | DMSO | AQ-triazine |
| 96. | SM 143 | 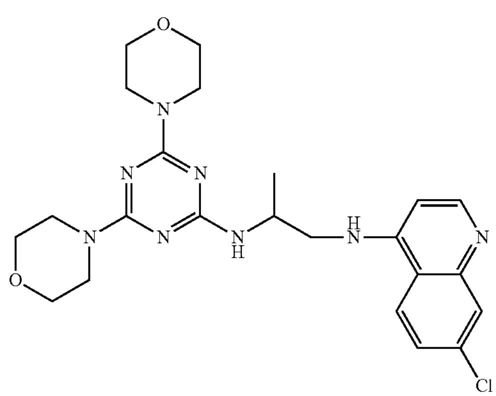 [SMILES: CC(CNc1ccnc2cc(Cl)ccc12)Nc1nc(N2CCOCC2)nc(N2CCOCC2)n1] | $C_{23}H_{29}ClN_8O_2$ | 484.98 | 2.3 | DMSO | AQ-triazine |
| 97. | SM 144 | 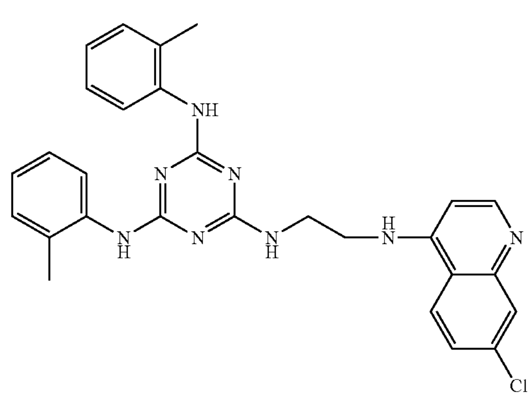 [SMILES: Cc1ccccc1Nc1nc(NCCNc2ccnc3cc(Cl)ccc23)nc(Nc2ccccc2C)n1] | $C_{28}H_{27}ClN_8$ | 511.02 | 4.4 | DMSO | AQ-triazine |

TABLE 3-continued

Some exemplary compounds of the invention.

| S. NO. | CODE | STRUCTURE | MOL. FOR. | MOL. WT. | QUANT (mg) | SOLU- BILITY | CLASS OF COM- POUND |
|---|---|---|---|---|---|---|---|
| 98. | SM 146 | 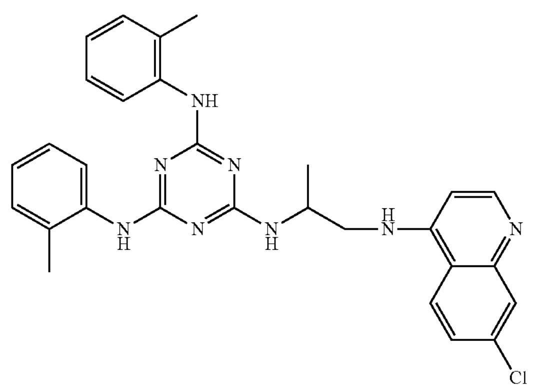 [SMILES: Cc1ccccc1Nc1nc(Nc2ccccc2C)nc(NC(C)CNc2ccnc3cc(Cl)ccc23)n1] | $C_{29}H_{29}ClN_8$ | 525.05 | 3.5 | DMSO | AQ-triazine |
| 99. | SM 148 | 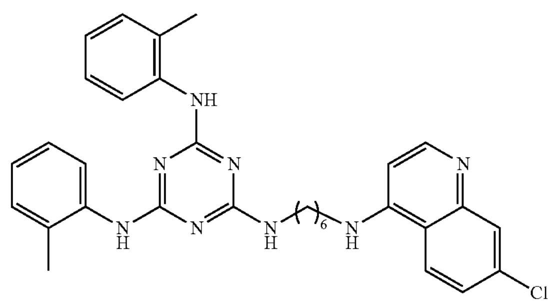 | $C_{32}H_{35}ClN_8$ | 567.13 | 4.1 | DMSO | AQ-triazine |
| 100. | SM 151 | 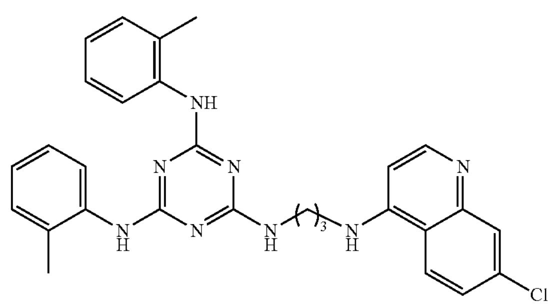 | $C_{29}H_{29}ClN_8$ | 525.05 | 7.4 | DMSO | AQ-triazine |
| 101. | SM 189 | 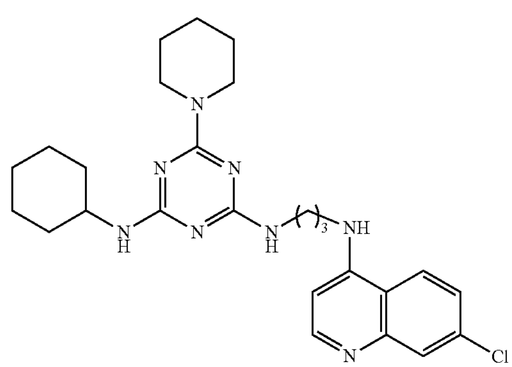 | $C_{26}H_{35}ClN_8$ | 495.06 | 2.1 | DMSO | AQ-triazine |

TABLE 3-continued

Some exemplary compounds of the invention.

| S. NO. | CODE | STRUCTURE | MOL. FOR. | MOL. WT. | QUANT (mg) | SOLU- BILITY | CLASS OF COM- POUND |
|---|---|---|---|---|---|---|---|
| 102. | SM 190 | 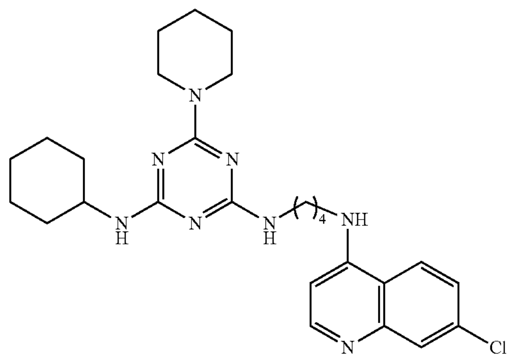 | $C_{27}H_{37}ClN_8$ | 509.09 | 8.0 | DMSO | AQ-triazine |
| 103. | ATH 158 | 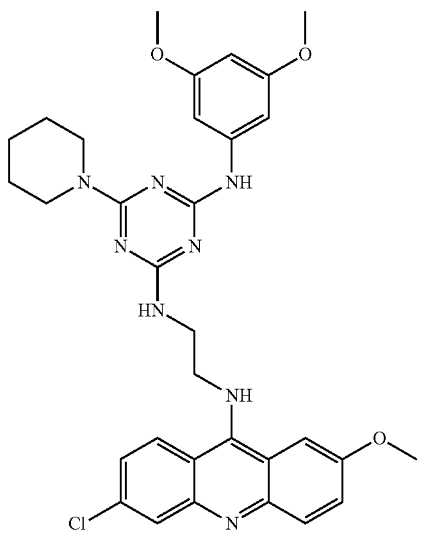 [SMILES: COc1cc(Nc2nc(NCCNc3c4ccc(Cl)cc4nc4ccc(OC)cc34)nc(N3CCCCC3)n2)cc(OC)c1] | $C_{32}H_{35}ClN_8O_3$ | 615.13 | 5.0 | DMSO | ACR-triazine |
| 104. | ATH 159 | 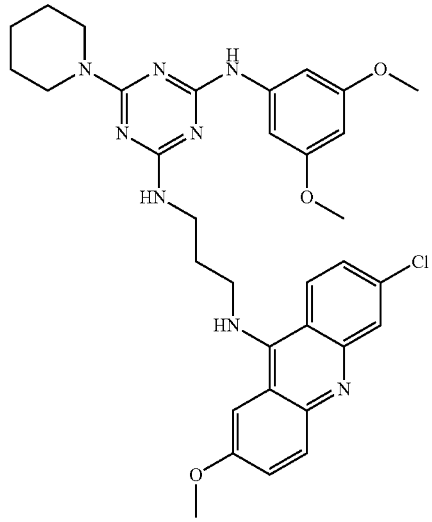 [SMILES: COc1cc(Nc2nc(NCCCNc3c4ccc(Cl)cc4nc4ccc(OC)cc34)nc(N3CCCCC3)n2)cc(OC)c1] | $C_{33}H_{37}ClN_8O_3$ | 629.15 | 5.0 | DMSO | ACR-triazine |

TABLE 3-continued
Some exemplary compounds of the invention.
| S. NO. | CODE | STRUCTURE | MOL. FOR. | MOL. WT. | QUANT (mg) | SOLU- BILITY | CLASS OF COM- POUND |
|---|---|---|---|---|---|---|---|
| 105. | ATH 164 | 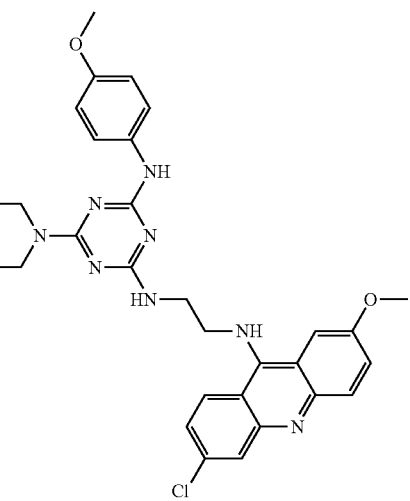 | $C_{36}H_{36}ClN_9O_2$ | 662.18 | 5.0 | DMSO | ACR- triazine |
| 106. | ATH 165 | 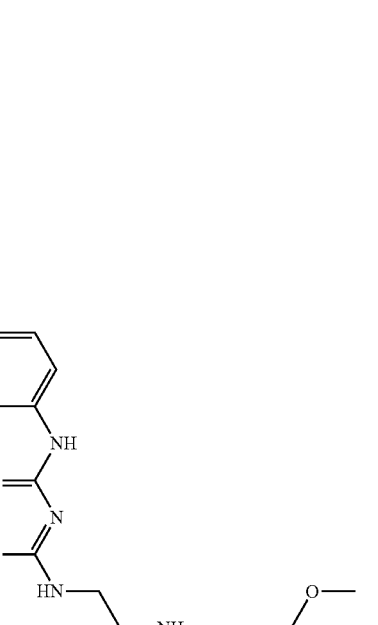 | $C_{28}H_{29}ClN_8O_2$ | 545.04 | 5.0 | DMSO | ACR- triazine |

TABLE 3-continued

Some exemplary compounds of the invention.

| S. NO. | CODE | STRUCTURE | MOL. FOR. | MOL. WT. | QUANT (mg) | SOLU- BILITY | CLASS OF COM- POUND |
|---|---|---|---|---|---|---|---|
| 107. | ATH 166 | | $C_{29}H_{31}ClN_8O_2$ | 559.06 | 5.0 | DMSO | ACR- triazine |
| 108 | ATH 170 | | $C_{37}H_{38}ClN_9O_3$ | 692.21 | 5.0 | DMSO | ACR- triazine |

TABLE 3-continued

Some exemplary compounds of the invention.

| S. NO. | CODE | STRUCTURE | MOL. FOR. | MOL. WT. | QUANT (mg) | SOLU-BILITY | CLASS OF COM-POUND |
|---|---|---|---|---|---|---|---|
| 109. | ATH 171 | 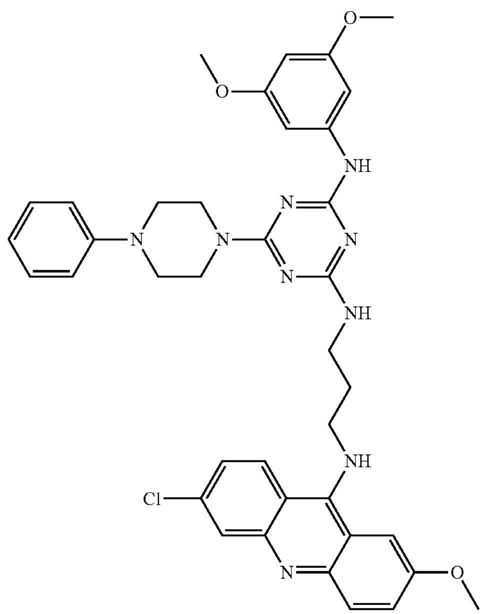 [SMILES: COc1cc(Nc2nc(NCCCNc3c4ccc(Cl)cc4nc4ccc(OC)cc34)nc(N3CCN(c4ccccc4)CC3)n2)cc(OC)c1] | $C_{38}H_{40}ClN_9O_3$ | 706.24 | 5.0 | DMSO | ACR-triazine |
| 110. | ATH 178 | 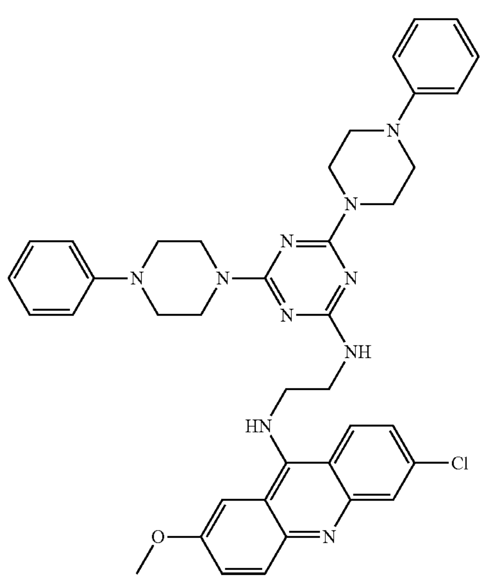 [SMILES: COc1ccc2nc3cc(Cl)ccc3c(NCCNc3nc(N4CCN(c5ccccc5)CC4)nc(N4CCN(c5ccccc5)CC4)n3)c2c1] | $C_{39}H_{41}ClN_{10}O$ | 701.26 | 5.0 | DMSO | ACR-triazine |

TABLE 3-continued

Some exemplary compounds of the invention.

| S. NO. | CODE | STRUCTURE | MOL. FOR. | MOL. WT. | QUANT (mg) | SOLU-BILITY | CLASS OF COM-POUND |
|---|---|---|---|---|---|---|---|
| 111. | ATH 179 | 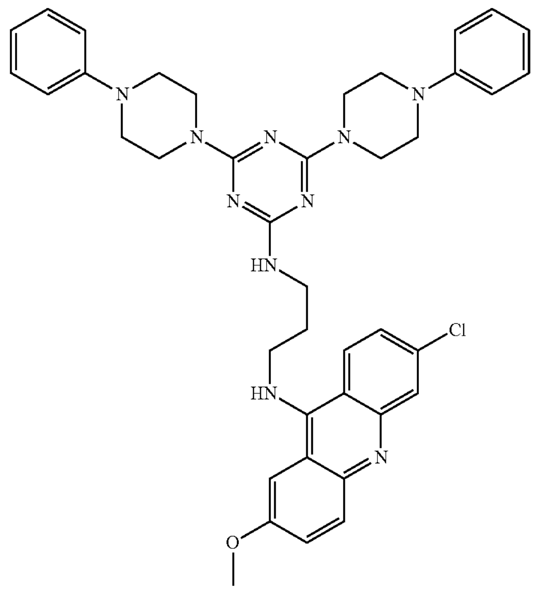 [SMILES: COc1ccc2nc3cc(Cl)ccc3c(NCCCNc3nc(N4CCN(c5ccccc5)CC4)nc(N4CCN(c5ccccc5)CC4)n3)c2c1] | $C_{40}H_{43}ClN_{10}O$ | 715.29 | 5.0 | DMSO | ACR-triazine |
| 112. | ATH 182 | 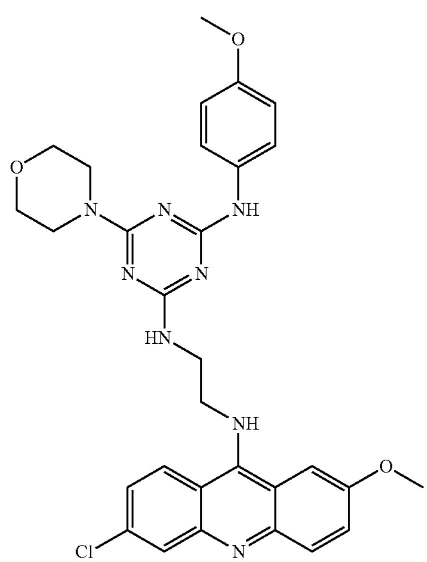 [SMILES: COc1ccc(Nc2nc(NCCNc3c4ccc(Cl)cc4nc4ccc(OC)cc34)nc(N3CCOCC3)n2)cc1] | $C_{30}H_{31}ClN_8O_3$ | 587.07 | 5.0 | DMSO | ACR-triazine |

TABLE 3-continued

Some exemplary compounds of the invention.

| S. NO. | CODE | STRUCTURE | MOL. FOR. | MOL. WT. | QUANT (mg) | SOLU-BILITY | CLASS OF COMPOUND |
|---|---|---|---|---|---|---|---|
| 113. | ATH 184 | 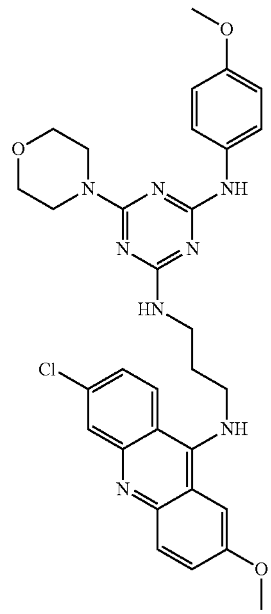 [SMILES: COc1ccc(Nc2nc(NCCCNc3c4ccc(Cl)cc4nc4ccc(OC)cc34)nc(N3CCOCC3)n2)cc1] | $C_{31}H_{33}ClN_8O_3$ | 601.10 | 5.0 | DMSO | ACR-triazine |
| 114. | ATH 189 | 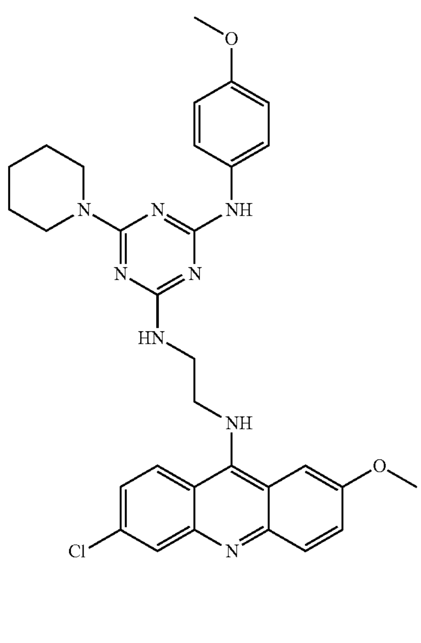 [SMILES: COc1ccc(Nc2nc(NCCNc3c4ccc(Cl)cc4nc4ccc(OC)cc34)nc(N3CCCCC3)n2)cc1] | $C_{31}H_{33}ClN_8O_2$ | 585.10 | 5.0 | DMSO | ACR-triazine |

TABLE 3-continued

Some exemplary compounds of the invention.

| S. NO. | CODE | STRUCTURE | MOL. FOR. | MOL. WT. | QUANT (mg) | SOLU- BILITY | CLASS OF COM- POUND |
|---|---|---|---|---|---|---|---|
| 115. | ATH 191 | 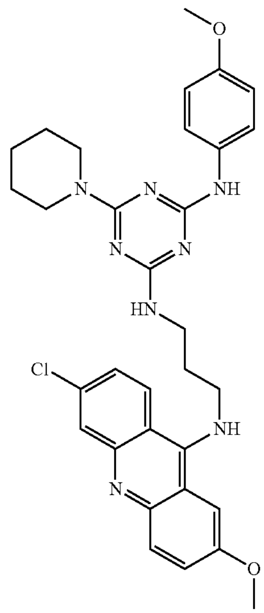 [SMILES: COc1ccc(Nc2nc(NCCCNc3c4ccc(Cl)cc4nc4ccc(OC)cc34)nc(N3CCCCC3)n2)cc1] | $C_{32}H_{35}ClN_8O_2$ | 599.13 | 5.0 | DMSO | ACR-triazine |
| 116. | ATH 192 | 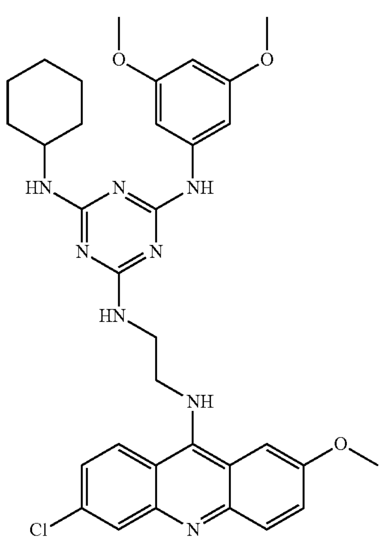 [SMILES: COc1cc(Nc2nc(NCCNc3c4ccc(Cl)cc4nc4ccc(OC)cc34)nc(NC3CCCCC3)n2)cc(OC)c1] | $C_{33}H_{37}ClN_8O_3$ | 629.15 | 5.0 | DMSO | ACR-triazine |

TABLE 3-continued

Some exemplary compounds of the invention.

| S. NO. | CODE | STRUCTURE | MOL. FOR. | MOL. WT. | QUANT (mg) | SOLU-BILITY | CLASS OF COMPOUND |
|---|---|---|---|---|---|---|---|
| 117. | ATH 194 | 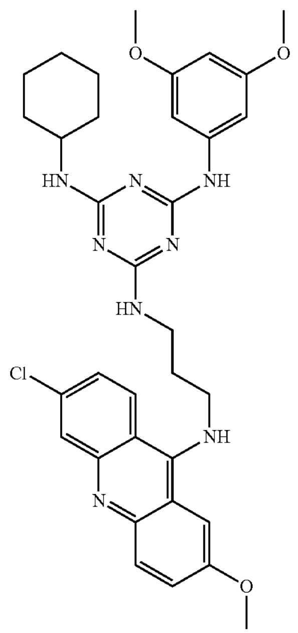 [SMILES: COc1cc(Nc2nc(NCCCNc3c4ccc(Cl)cc4nc4ccc(OC)cc34)nc(NC3CCCCC3)n2)cc(OC)c1] | $C_{34}H_{39}ClN_8O_3$ | 643.18 | 5.0 | DMSO | ACR-triazine |
| 118. | ATH 195 | 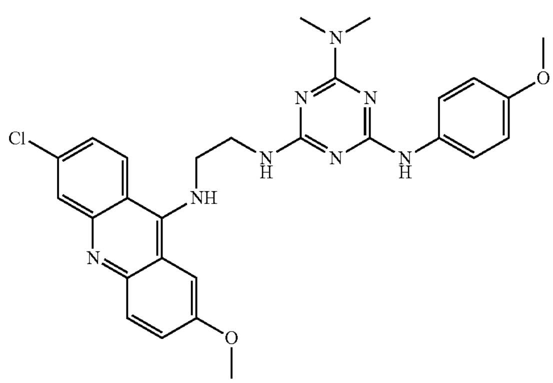 [SMILES: COc1ccc(Nc2nc(NCCNc3c4ccc(Cl)cc4nc4ccc(OC)cc34)nc(N(C)C)n2)cc1] | $C_{28}H_{29}ClN_8O_2$ | 545.04 | 5.0 | DMSO | ACR-triazine |

TABLE 3-continued

Some exemplary compounds of the invention.

| S. NO. | CODE | STRUCTURE | MOL. FOR. | MOL. WT. | QUANT (mg) | SOLU-BILITY | CLASS OF COM-POUND |
|---|---|---|---|---|---|---|---|
| 119. | ATH 196 | 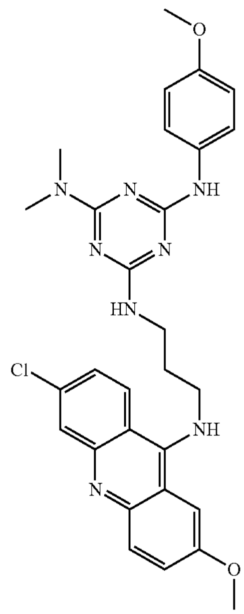 [SMILES: COc1ccc(Nc2nc(NCCCNc3c4ccc(Cl)cc4nc4ccc(OC)cc34)nc(N(C)C)n2)cc1] | $C_{29}H_{31}ClN_8O_2$ | 559.06 | 5.0 | DMSO | ACR-triazine |
| 120. | ATH 198 | 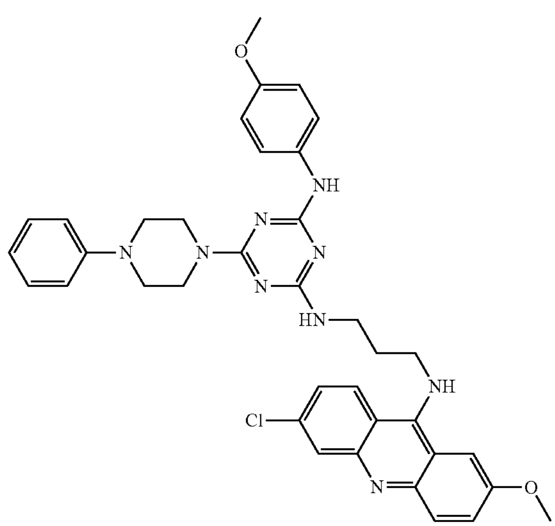 [SMILES: COc1ccc(Nc2nc(NCCCNc3c4ccc(Cl)cc4nc4ccc(OC)cc34)nc(N3CCN(c4ccccc4)CC3)n2)cc1] | $C_{37}H_{38}ClN_9O_2$ | 676.21 | 5.0 | DMSO | ACR-triazine |

TABLE 3-continued
Some exemplary compounds of the invention.
| S. NO. | CODE | STRUCTURE | MOL. FOR. | MOL. WT. | QUANT (mg) | SOLU-BILITY | CLASS OF COM-POUND |
|---|---|---|---|---|---|---|---|
| 121. | ATH 200 | 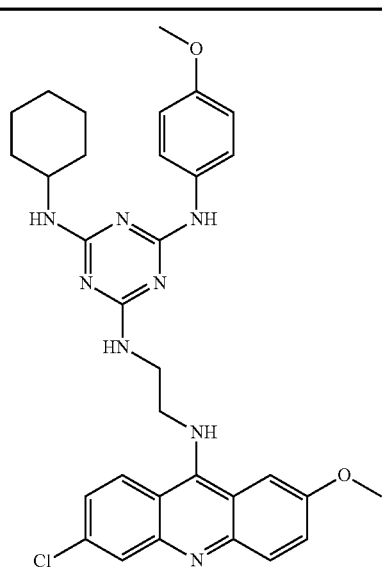 | $C_{32}H_{35}ClN_8O_2$ | 599.13 | 5.0 | DMSO | ACR-triazine |
| 122. | ATH 201 | 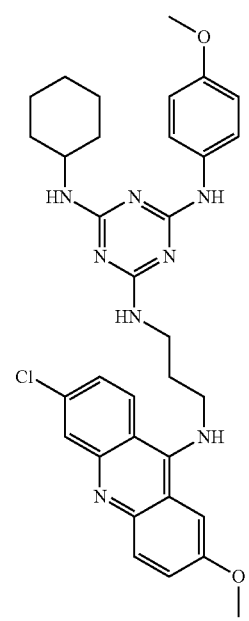 [SMILES: COc1ccc(Nc2nc(NCCCNc3c4ccc(Cl)cc4nc4ccc(OC)cc34)nc(NC3CCCCC3)n2)cc1] | $C_{33}H_{37}ClN_8O_2$ | 613.15 | 5.0 | DMSO | ACR-triazine |
| 123. | ATH 214 | 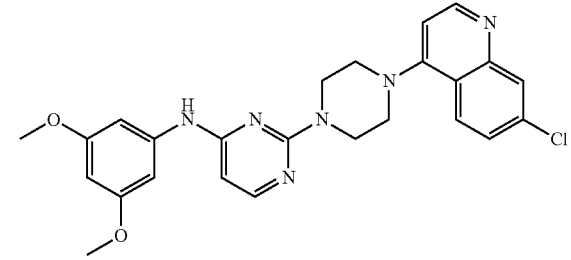 [SMILES: COc1cc(Nc2ccnc(N3CCN(c4ccnc5cc(Cl)ccc45)CC3)n2)cc(OC)c1] | $C_{25}H_{25}ClN_6O_2$ | 476.96 | 8.7 | DMSO | AQ-pyrimidine |

TABLE 3-continued
Some exemplary compounds of the invention.
| S. NO. | CODE | STRUCTURE | MOL. FOR. | MOL. WT. | QUANT (mg) | SOLU-BILITY | CLASS OF COMPOUND |
|---|---|---|---|---|---|---|---|
| 124. | ATH 218 | 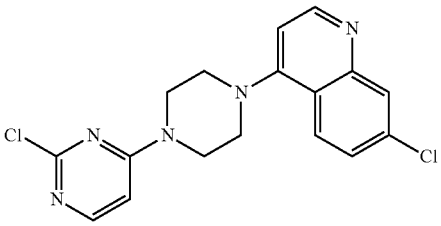 [SMILES: Clc1ccc2c(N3CCN(c4ccnc(Cl)n4)CC3)ccnc2c1] | $C_{17}H_{15}Cl_2N_5$ | 360.24 | 7.0 | DMSO | AQ-pyrimidine |
| 125. | ATH 220 | 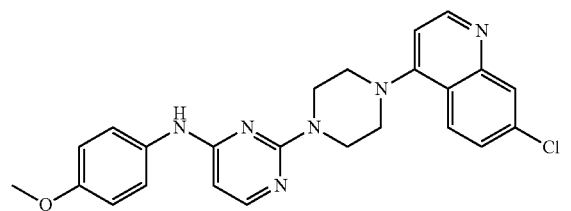 [SMILES: COc1ccc(Nc2ccnc(N3CCN(c4ccnc5cc(Cl)ccc45)CC3)n2)cc1] | $C_{24}H_{23}ClN_6O$ | 446.93 | 8.2 | DMSO | AQ-pyrimidine |
| 126. | ATH 223 | 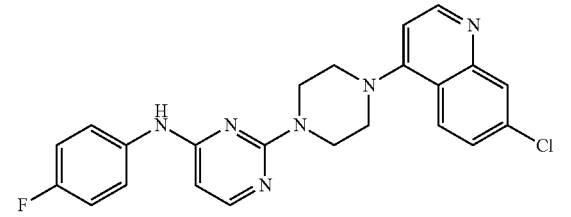 [SMILES: Fc1ccc(Nc2ccnc(N3CCN(c4ccnc5cc(Cl)ccc45)CC3)n2)cc1] | $C_{23}H_{20}ClFN_6$ | 434.90 | 11.9 | DMSO | AQ-pyrimidine |
| 127. | ATH 226 | 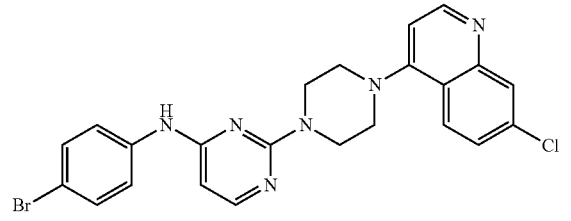 [SMILES: Clc1ccc(Nc2ccnc(N3CCN(c4ccnc5cc(Cl)ccc45)CC3)n2)cc1] | $C_{23}H_{20}BrClN_6$ | 495.80 | 7.2 | DMSO | AQ-pyrimidine |
| 128. | ATH 227 | 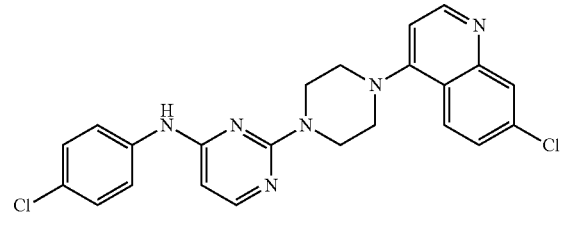 | $C_{23}H_{20}Cl_2N_6$ | 451.35 | 7.1 | DMSO | AQ-pyrimidine |
| 129. | ATH 228 | 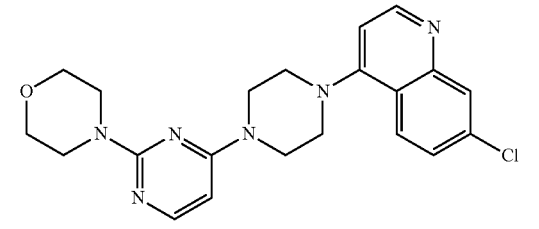 [SMILES: Clc1ccc2c(N3CCN(c4ccnc(N5CCOCC5)n4)CC3)ccnc2c1] | $C_{21}H_{23}ClN_6O$ | 410.90 | 7.5 | DMSO | AQ-pyrimidine |

TABLE 3-continued

Some exemplary compounds of the invention.

| S. NO. | CODE | STRUCTURE | MOL. FOR. | MOL. WT. | QUANT (mg) | SOLU-BILITY | CLASS OF COMPOUND |
|---|---|---|---|---|---|---|---|
| 130. | ATH 231 | 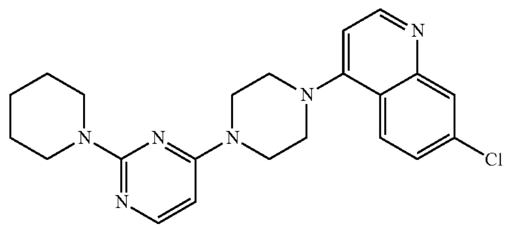 [SMILES: Clc1ccc2c(N3CCN(c4ccnc(N5CCCCC5)n4)CC3)ccnc2c1] | $C_{22}H_{25}ClN_6$ | 408.93 | 7.9 | DMSO | AQ-pyrimidine |
| 131. | ATH 232 | 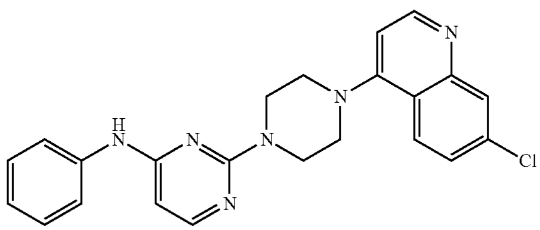 [SMILES: Clc1ccc2c(N3CCN(c4nccc(Nc5ccccc5)n4)CC3)ccnc2c1] | $C_{23}H_{21}ClN_6$ | 416.91 | 9.0 | DMSO | AQ-pyrimidine |
| 132. | ATH 236 | 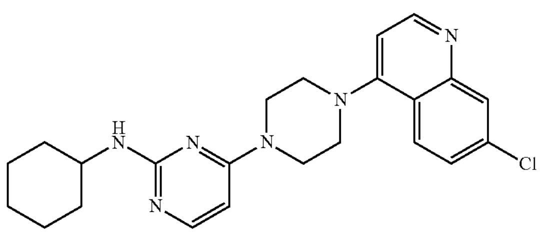 [SMILES: Clc1ccc2c(N3CCN(c4ccnc(NC5CCCCC5)n4)CC3)ccnc2c1] | $C_{23}H_{27}ClN_6$ | 422.95 | 7.8 | DMSO | AQ-pyrimidine |
| 133. | ATH 237 | 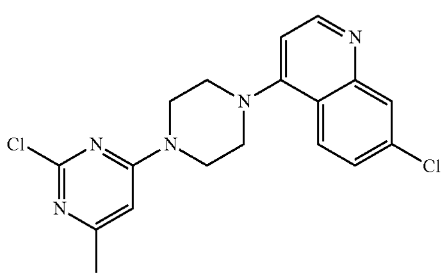 [SMILES: Cc1cc(N2CCN(c3ccnc4cc(Cl)ccc34)CC2)nc(Cl)n1] | $C_{18}H_{17}Cl_2N_5$ | 374.27 | 8.5 | DMSO | AQ-pyrimidine |
| 134. | ATH 239 | 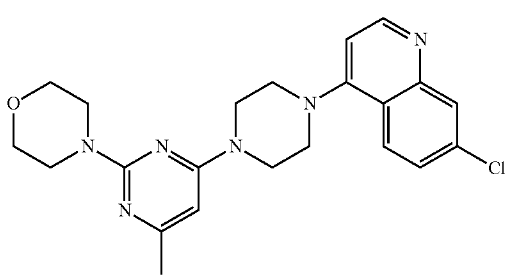 [SMILES: Cc1cc(N2CCN(c3ccnc4cc(Cl)ccc34)CC2)nc(N2CCOCC2)n1] | $C_{22}H_{25}ClN_6O$ | 424.93 | 6.1 | DMSO | AQ-pyrimidine |

TABLE 3-continued
Some exemplary compounds of the invention.
| S. NO. | CODE | STRUCTURE | MOL. FOR. | MOL. WT. | QUANT (mg) | SOLU-BILITY | CLASS OF COM-POUND |
|---|---|---|---|---|---|---|---|
| 135. | ATH 240 | 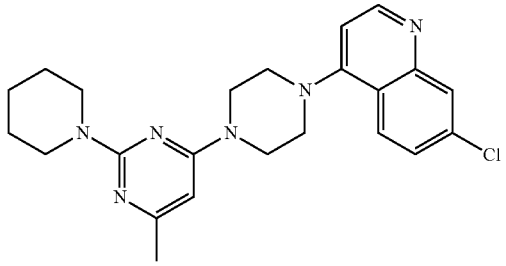 [SMILES: Cc1cc(N2CCN(c3ccnc4cc(Cl)ccc34)CC2)nc(N2CCCCC2)n1] | $C_{23}H_{27}ClN_6$ | 422.95 | 7.9 | DMSO | AQ-pyrimidine |
| 136. | ATH 241 | 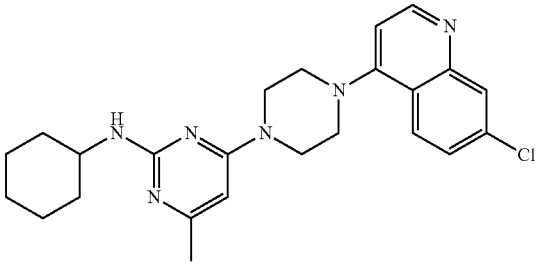 [SMILES: Cc1cc(N2CCN(c3ccnc4cc(Cl)ccc34)CC2)nc(NC2CCCCC2)n1] | $C_{24}H_{29}ClN_6$ | 436.98 | 7.4 | DMSO | AQ-pyrimidine |
| 137. | ATH 244 | 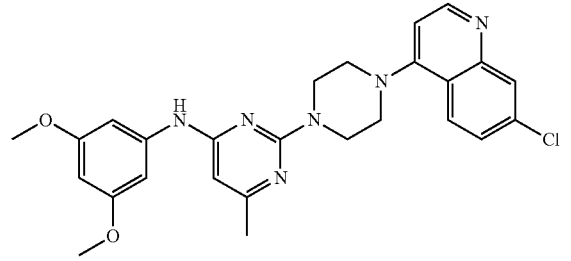 [SMILES: COc1cc(Nc2cc(C)nc(N3CCN(c4ccnc5cc(Cl)ccc45)CC3)n2)cc(OC)c1] | $C_{26}H_{27}ClN_6O_2$ | 490.98 | 7.2 | DMSO | AQ-pyrimidine |
| 138. | ATH 245 | 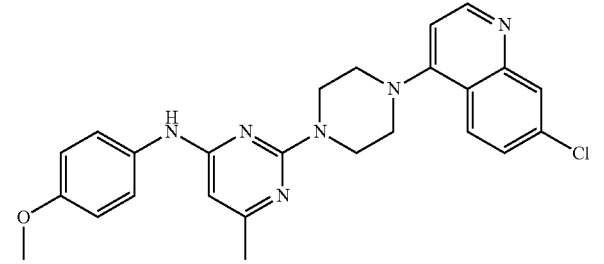 [SMILES: COc1ccc(Nc2cc(C)nc(N3CCN(c4ccnc5cc(Cl)ccc45)CC3)n2)cc1] | $C_{25}H_{25}ClN_6O$ | 460.96 | 7.1 | DMSO | AQ-pyrimidine |
| 139. | ATH 247 | 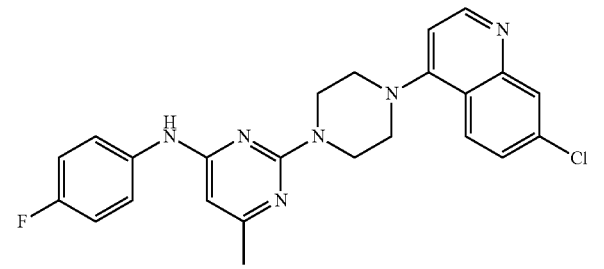 [SMILES: Cc1cc(Nc2ccc(F)cc2)nc(N2CCN(c3ccnc4cc(Cl)ccc34)CC2)n1] | $C_{24}H_{22}ClFN_6$ | 448.92 | 6.2 | DMSO | AQ-pyrimidine |

TABLE 3-continued

Some exemplary compounds of the invention.

| S. NO. | CODE | STRUCTURE | MOL. FOR. | MOL. WT. | QUANT (mg) | SOLU-BILITY | CLASS OF COM-POUND |
|---|---|---|---|---|---|---|---|
| 140. | ATH 252 | 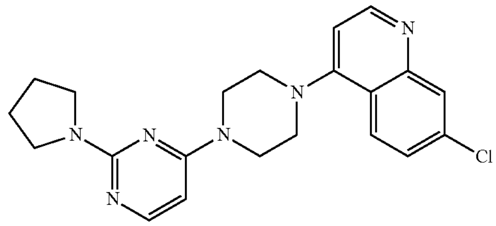 [SMILES: Clc1ccc2c(N3CCN(c4ccnc(N5CCCC5)n4)CC3)ccnc2c1] | $C_{21}H_{23}ClN_6$ | 394.90 | 9.0 | DMSO | AQ-pyrimi-dine |
| 141. | ATH 254 | 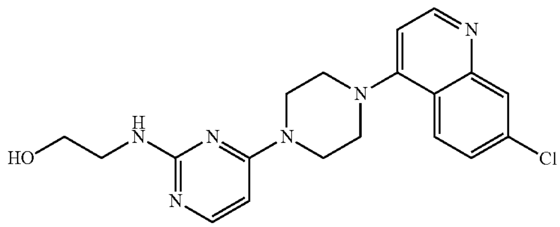 [SMILES: OCCNc1nccc(N2CCN(c3ccnc4cc(Cl)ccc34)CC2)n1] | $C_{19}H_{21}ClN6O$ | 384.86 | 7.3 | DMSO | AQ-pyrimi-dine |
| 142. | ATH 255 | 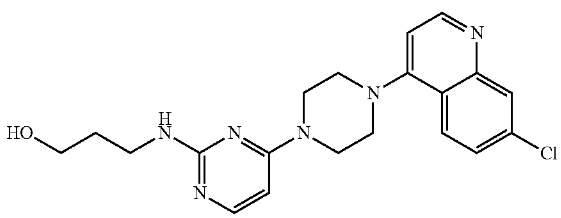 [SMILES: OCCCNc1nccc(N2CCN(c3ccnc4cc(Cl)ccc34)CC2)n1] | $C_{20}H_{23}ClN_6O$ | 398.89 | 8.3 | DMSO | AQ-pyrimi-dine |
| 143. | ATH 256 | 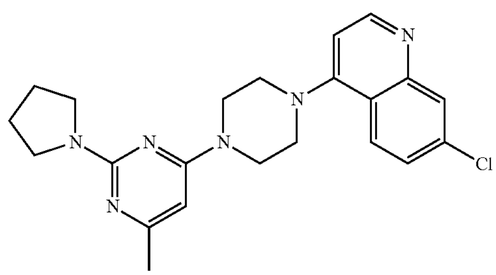 [SMILES: Cc1cc(N2CCN(c3ccnc4cc(Cl)ccc34)CC2)nc(N2CCCC2)n1] | $C_{22}H_{25}ClN_6$ | 408.93 | 8.8 | DMSO | AQ-pyrimi-dine |
| 144. | ATH 257 | 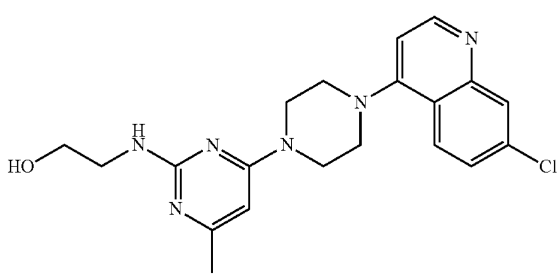 [SMILES: Cc1cc(N2CCN(c3ccnc4cc(Cl)ccc34)CC2)nc(NCCO)n1] | $C_{19}H_{21}ClN_6O$ | 384.86 | 7.0 | DMSO | AQ-pyrimi-dine |

In some embodiments, the compound of the invention is a compound shown in Table 4.

TABLE 4

Some exemplary compounds of the invention.

| S. No. | Code | Structure | Mol. formula | Mol. Wt. | Solubility | Quantity |
|---|---|---|---|---|---|---|
| 1 | DKG805 | 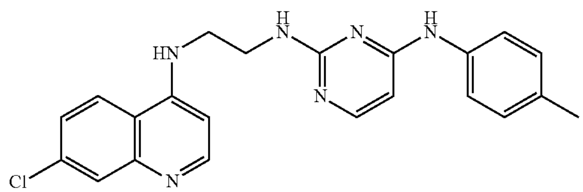 [SMILES: Cc1ccc(Nc2ccnc(NCCNc3ccnc4cc(Cl)ccc34)n2)cc1] | C22H21ClN6 | 404.15162 | DMSO | 11.0 mg |
| 2 | DKG806 | 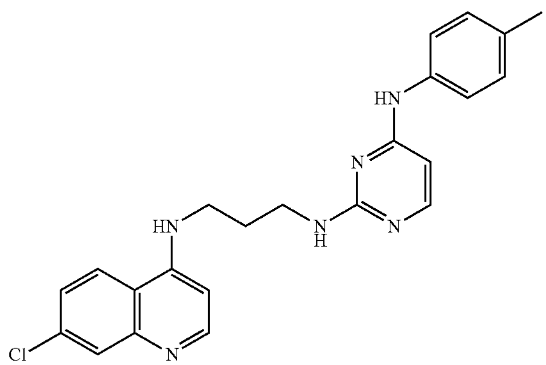 [SMILES: Cc1ccc(Nc2ccnc(NCCCNc3ccnc4cc(Cl)ccc34)n2)cc1] | C23H23ClN6 | 418.16727 | DMSO | 11.2 mg |
| 3 | DKG807 | 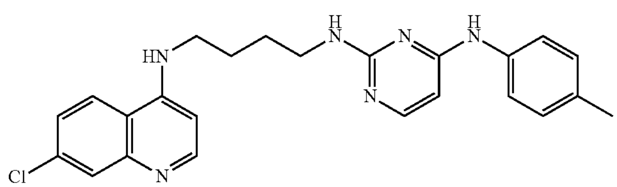 [SMILES: Cc1ccc(Nc2ccnc(NCCCCNc3ccnc4cc(Cl)ccc34)n2)cc1] | C24H25ClN6 | 432.18292 | DMSO | 11.1 mg |
| 4 | DKG809 | 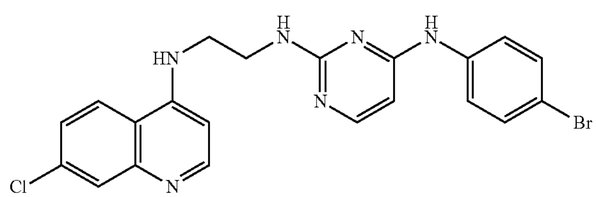 [SMILES: Clc1ccc2c(NCCNc3nccc(Nc4ccc(Br)cc4)n3)ccnc2c1] | C21H18BrClN6 | 468.04648 | DMSO | 11.8 mg |
| 5 | DKG810 | 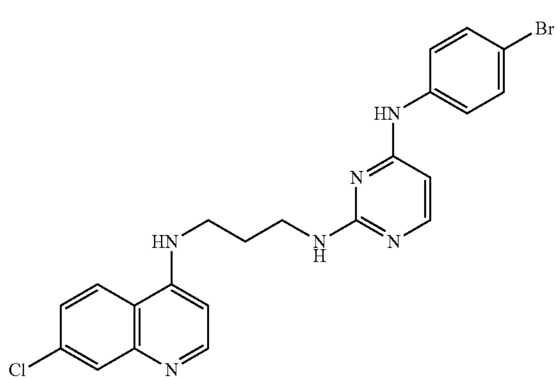 [SMILES: Clc1ccc2c(NCCCNc3nccc(Nc4ccc(Br)cc4)n3)ccnc2c1] | C22H20BrClN6 | 482.06213 | DMSO | 16.0 mg |
| 6 | DKG811 | 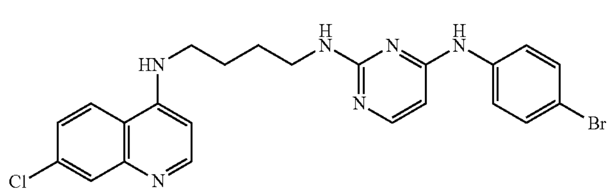 [SMILES: Clc1ccc2c(NCCCCNc3nccc(Nc4ccc(Br)cc4)n3)ccnc2c1] | C23H22BrClN6 | 496.07778 | DMSO | 10.8 mg |

TABLE 4-continued

Some exemplary compounds of the invention.

| S. No. | Code | Structure | Mol. formula | Mol. Wt. | Solubility | Quantity |
|---|---|---|---|---|---|---|
| 7 | DKG813 | 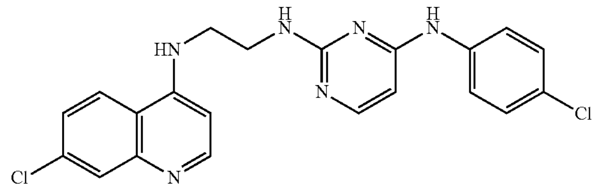 [SMILES: Clc1ccc(Nc2ccnc(NCCNc3ccnc4cc(Cl)ccc34)n2)cc1] | C21H18Cl2N6 | 424.09700 | DMSO | 11.0 mg |
| 8 | DKG814 | 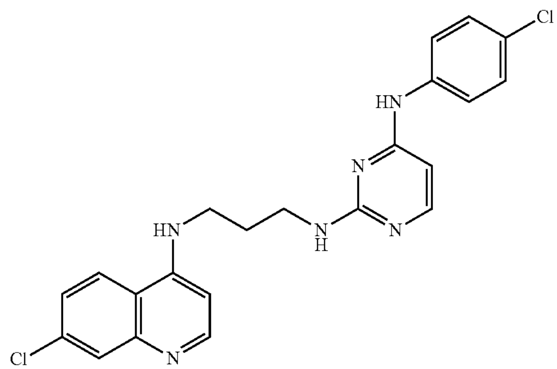 [SMILES: Clc1ccc(Nc2ccnc(NCCCNc3ccnc4cc(Cl)ccc34)n2)cc1] | C22H20Cl2N6 | 438.11265 | DMSO | 16.2 mg |
| 9 | DKG815 | 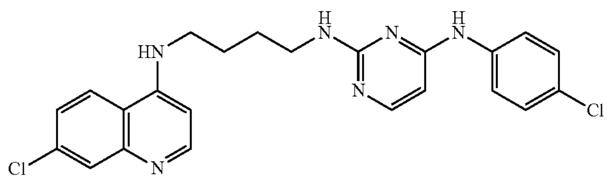 [SMILES: Clc1ccc(Nc2ccnc(NCCCCNc3ccnc4cc(Cl)ccc34)n2)cc1] | C23H22Cl2N6 | 452.12830 | DMSO | 16.8 mg |
| 10 | DKG817 | 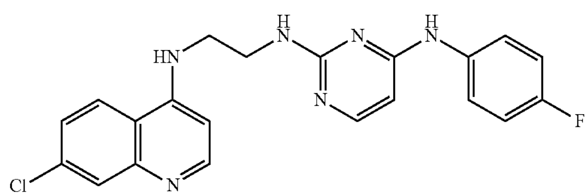 [SMILES: Fc1ccc(Nc2ccnc(NCCNc3ccnc4cc(Cl)ccc34)n2)cc1] | C21H18ClFN6 | 408.12655 | DMSO | 14.5 mg |
| 11 | DKG818 | 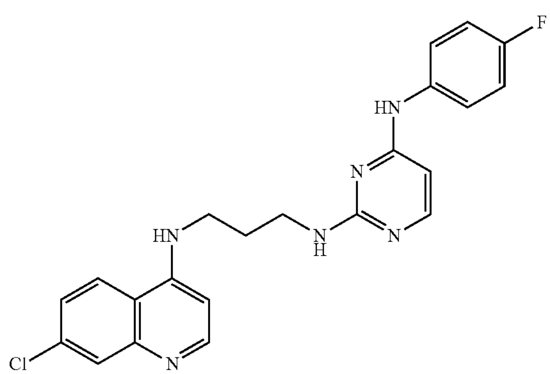 [SMILES: Fc1ccc(Nc2ccnc(NCCCNc3ccnc4cc(Cl)ccc34)n2)cc1] | C22H20ClFN6 | 422.14220 | DMSO | 16.0 mg |
| 12 | DKG819 | 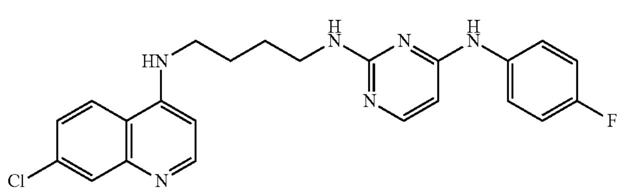 [SMILES: Fc1ccc(Nc2ccnc(NCCCCNc3ccnc4cc(Cl)ccc34)n2)cc1] | C23H22ClFN6 | 436.15785 | DMSO | 15.6 mg |

TABLE 4-continued
Some exemplary compounds of the invention.
| S. No. | Code | Structure | Mol. formula | Mol. Wt. | Solubility | Quantity |
|---|---|---|---|---|---|---|
| 13 | DKG821 | 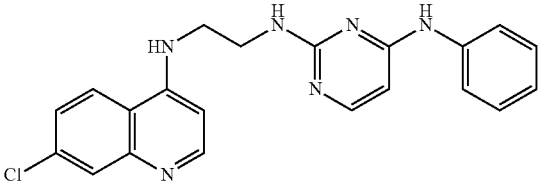 [SMILES: Clc1ccc2c(NCCNc3nccc(Nc4ccccc4)n3)ccnc2c1] | C21H19ClN6 | 390.13597 | DMSO | 11.8 mg |
| 14 | DKG822 | 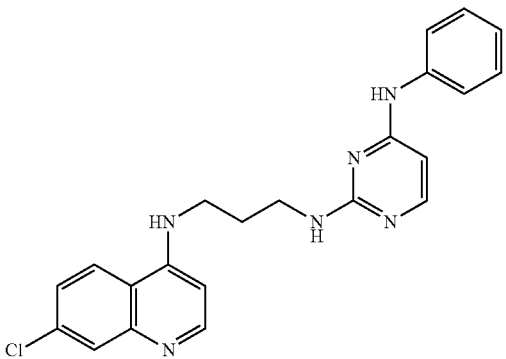 [SMILES: Clc1ccc2c(NCCCNc3nccc(Nc4ccccc4)n3)ccnc2c1] | C22H21ClN6 | 404.15162 | DMSO | 11.0 mg |
| 15 | DKG823 | 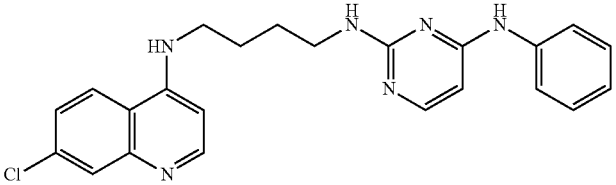 [SMILES: Clc1ccc2c(NCCCCNc3nccc(Nc4ccccc4)n3)ccnc2c1] | C23H23ClN6 | 418.16727 | DMSO | 17.8 mg |
| 16 | DKG825 | 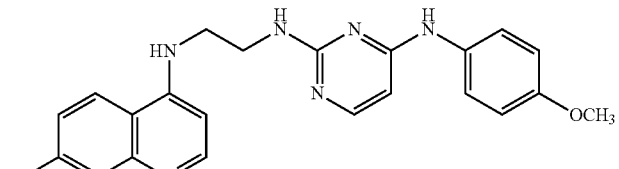 | C22H21ClN6O | 420.14654 | DMSO | 14.4 mg |
| 17 | DKG826 | 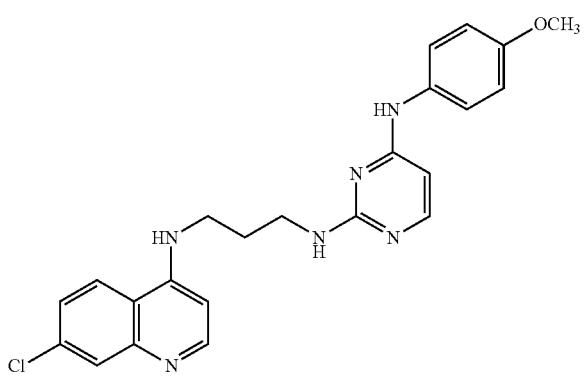 [SMILES: COc1ccc(Nc2ccnc(NCCCNc3ccnc4cc(Cl)ccc34)n2)cc1] | C23H23ClN6O | 434.16219 | DMSO | 13.5 mg |
| 18 | DKG827 | 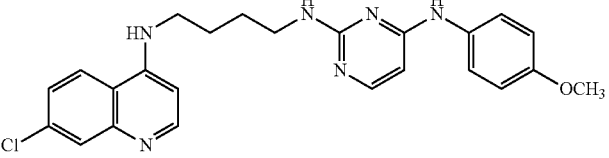 | C24H25ClN6O | 448.17784 | DMSO | 15.6 mg |

TABLE 4-continued

Some exemplary compounds of the invention.

| S. No. | Code | Structure | Mol. formula | Mol. Wt. | Solubility | Quantity |
|---|---|---|---|---|---|---|
| 19 | DKG829 | 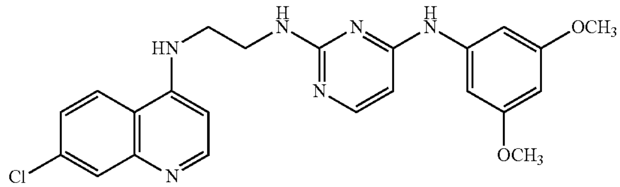 [SMILES: COc1cc(Nc2ccnc(NCCNc3ccnc4cc(Cl)ccc34)n2)cc(OC)c1] | C23H23ClN6O2 | 450.15710 | DMSO | 20.8 mg |
| 20 | DKG830 | 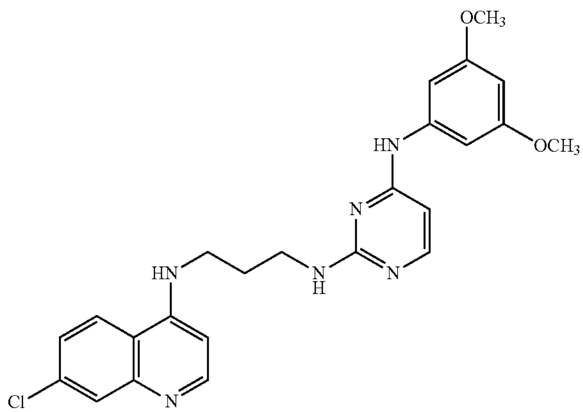 [SMILES: COc1cc(Nc2ccnc(NCCCNc3ccnc4cc(Cl)ccc34)n2)cc(OC)c1] | C24H25ClN6O2 | 464.17275 | DMSO | 16.5 mg |
| 21 | DKG831 | 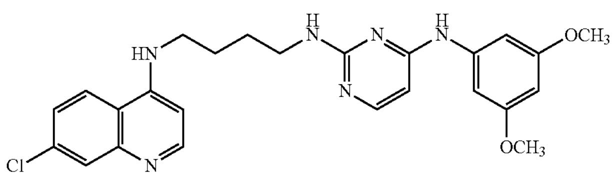 [SMILES: COc1cc(Nc2ccnc(NCCCCNc3ccnc4cc(Cl)ccc34)n2)cc(OC)c1] | C25H27ClN6O2 | 478.18840 | DMSO | 19.2 mg |
| 22 | DKG833 | 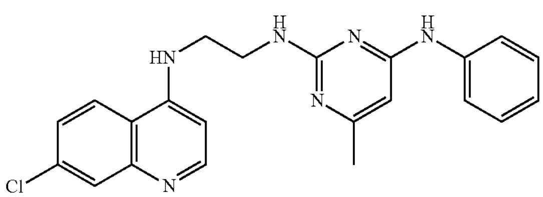 [SMILES: Cc1cc(Nc2ccccc2)nc(NCCNc2ccnc3cc(Cl)ccc23)n1] | C22H21ClN6 | 404.15162 | DMSO | 12.8 mg |
| 23 | DKG834 | 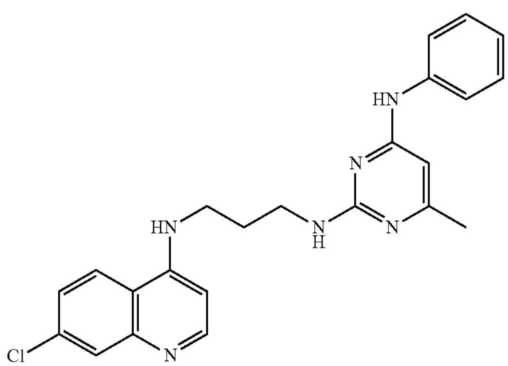 [SMILES: Cc1cc(Nc2ccccc2)nc(NCCCNc2ccnc3cc(Cl)ccc23)n1] | C23H23ClN6 | 418.16727 | DMSO | 15.2 mg |
| 24 | DKG835 | 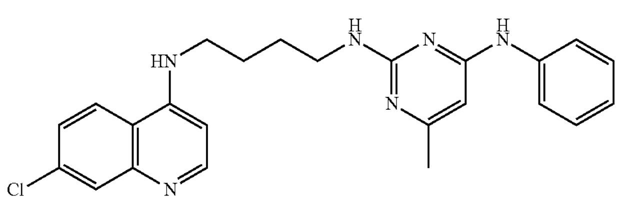 [SMILES: Cc1cc(Nc2ccccc2)nc(NCCCCNc2ccnc3cc(Cl)ccc23)n1] | C24H25ClN6 | 432.18292 | | 13.5 mg |

TABLE 4-continued

Some exemplary compounds of the invention.

| S. No. | Code | Structure | Mol. formula | Mol. Wt. | Solubility | Quantity |
|---|---|---|---|---|---|---|
| 25 | DKG837 | 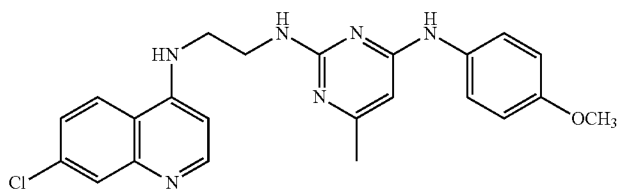 [SMILES: COc1ccc(Nc2cc(C)nc(NCCNc3ccnc4cc(Cl)ccc34)n2)cc1] | C23H23ClN6O | 434.16219 | DMSO | 17.6 mg |
| 26 | DKG838 | 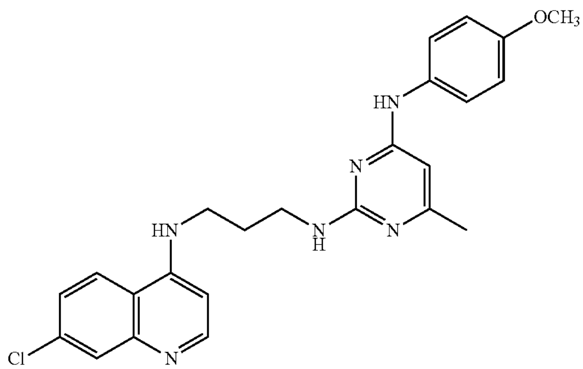 [SMILES: COc1ccc(Nc2cc(C)nc(NCCCNc3ccnc4cc(Cl)ccc34)n2)cc1] | C24H25ClN6O | 448.17784 | DMSO | 12.5 mg |
| 27 | DKG839 | 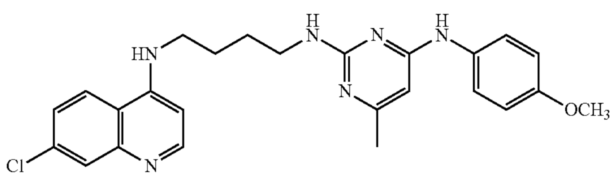 [SMILES: COc1ccc(Nc2cc(C)nc(NCCCCNc3ccnc4cc(Cl)ccc34)n2)cc1] | C25H27ClN6O | 462.19349 | DMSO | 12.1 mg |
| 28 | DKG845 | 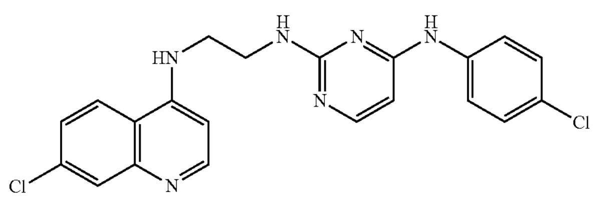 [SMILES: Clc1ccc(Nc2ccnc(NCCNc3ccnc4cc(Cl)ccc34)n2)cc1] | C21H18Cl2N6 | 424.09700 | DMSO | 18.8 mg |
| 29 | DKG846 | 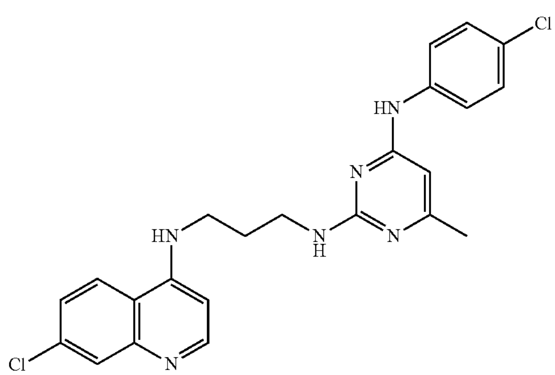 [SMILES: Cc1cc(Nc2ccc(Cl)cc2)nc(NCCCNc2ccnc3cc(Cl)ccc23)n1] | C23H22Cl2N6 | 452.12830 | DMSO | 17.6 mg |
| 30 | DKG847 | 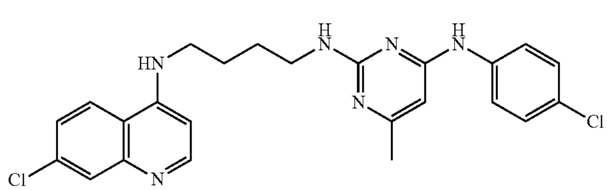 | C24H24Cl2N6 | 466.14395 | DMSO | 15.2 mg |

TABLE 4-continued

Some exemplary compounds of the invention.

| S. No. | Code | Structure | Mol. formula | Mol. Wt. | Solubility | Quantity |
|---|---|---|---|---|---|---|
| 31 | DKG849 | 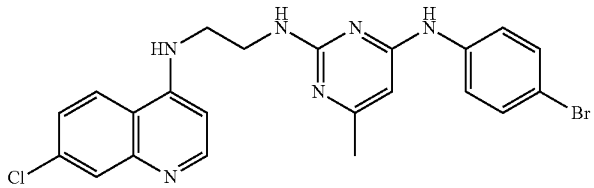 [SMILES: Cc1cc(Nc2ccc(Br)cc2)nc(NCCNc2ccnc3cc(Cl)ccc23)n1] | C22H20BrClN6 | 482.06213 | DMSO | 15.4 mg |
| 32 | DKG850 | 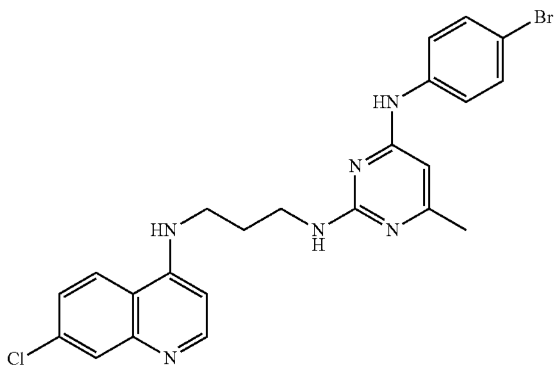 [SMILES: Cc1cc(Nc2ccc(Br)cc2)nc(NCCCNc2ccnc3cc(Cl)ccc23)n1] | C23H22BrClN6 | 496.07778 | DMSO | 16.6 mg |
| 33 | DKG851 | 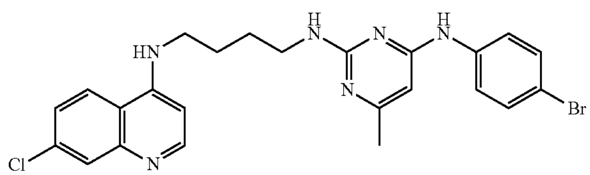 [SMILES: Cc1cc(Nc2ccc(Br)cc2)nc(NCCCCNc2ccnc3cc(Cl)ccc23)n1] | C24H24BrClN6 | 510.09343 | DMSO | 16.5 mg |
| 34 | DKG853 | 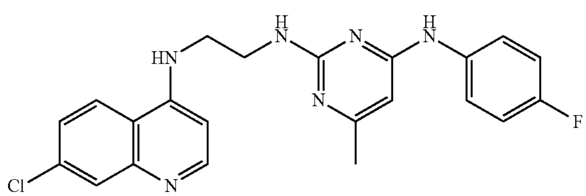 [SMILES: Cc1cc(Nc2ccc(F)cc2)nc(NCCNc2ccnc3cc(Cl)ccc23)n1] | C22H20ClFN6 | 422.14220 | DMSO | 13.8 mg |
| 35 | DKG854 | 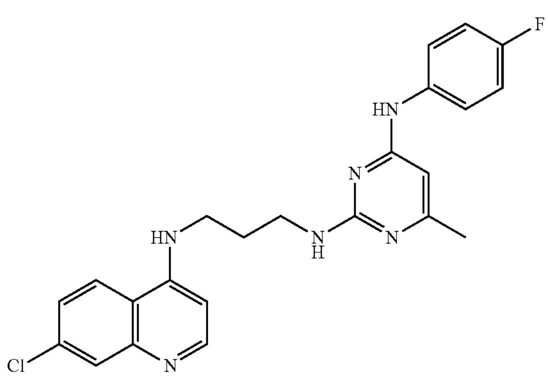 [SMILES: Cc1cc(Nc2ccc(F)cc2)nc(NCCCNc2ccnc3cc(Cl)ccc23)n1] | C23H22ClFN6 | 436.15785 | DMSO | 15.1 mg |
| 36 | DKG855 | 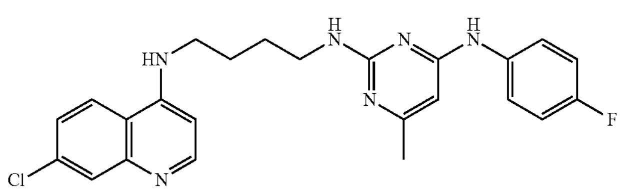 [SMILES: Cc1cc(Nc2ccc(F)cc2)nc(NCCCCNc2ccnc3cc(Cl)ccc23)n1] | C24H24ClFN6 | 450.17350 | DMSO | 13.8 mg |

TABLE 4-continued

Some exemplary compounds of the invention.

| S. No. | Code | Structure | Mol. formula | Mol. Wt. | Solubility | Quantity |
|---|---|---|---|---|---|---|
| 37 | DKG857 | 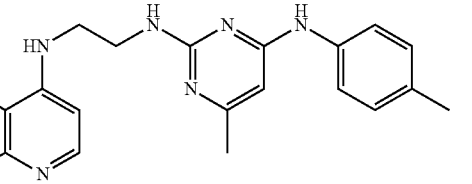 | C23H23ClN6 | 418.16727 | DMSO | 13.1 mg |
| 38 | DKG858 | 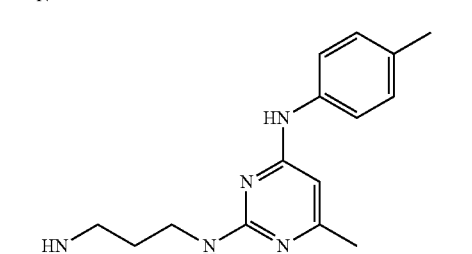 | C24H25ClN6 | 432.18292 | DMSO | 15.6 mg |
| 39 | DKG859 | 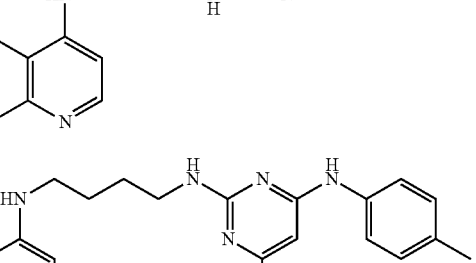 | C25H27ClN6 | 446.19857 | DMSO | 14.5 mg |

In some embodiments, the compound of the invention is a compound shown in Table 5.

TABLE 5

Some exemplary compounds of the invention.

| S. No. | Compound ID | IUPAC Name | Mol. Formula, M.W. | Solubility | Amount (mg) |
|---|---|---|---|---|---|
| 40. | MT1-121 | 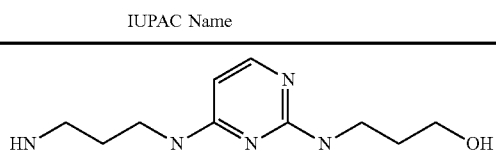 | C19H23ClN6O, 386.88 | MeOH, DMSO | 10.4 |
| 41. | MT1-122 | 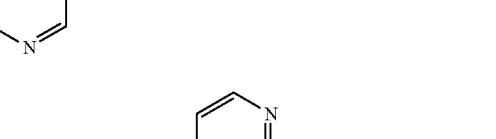 | C20H25ClN6O, 400.91 | MeOH, DMSO | 12.0 |

TABLE 5-continued

Some exemplary compounds of the invention.

| S. No. | Compound ID | IUPAC Name | Mol. Formula, M.W. | Solubility | Amount (mg) |
|---|---|---|---|---|---|
| 42. | MT1-127 | | C18H21ClN6O, 372.85 | MeOH, DMSO | 12.9 |
| 43. | MT1-128 | | C21H27ClN6O, 414.93 | MeOH, DMSO | 13.8 |
| 44. | MT1-132 | | C22H29ClN6O, 428.96 | MeOH, DMSO | 10.7 |
| 45. | MT1-145 | | C19H23ClN6O, 386.88 | MeOH, DMSO | 10.7 |
| 46. | MT1-146 | | C20H25ClN6O, 400.91 | MeOH, DMSO | 10.5 |

TABLE 5-continued

Some exemplary compounds of the invention.

| S. No. | Compound ID | IUPAC Name | Mol. Formula, M.W. | Solubility | Amount (mg) |
|---|---|---|---|---|---|
| 47. | MT1-147 | | C21H27ClN6O, 414.93 | MeOH, DMSO | 13.0 |
| 48. | MT1-148 | | C22H29ClN6O, 428.96 | MeOH, DMSO | 10.3 |
| 49. | MT1-156 | | C19H23ClN6O, 386.88 | MeOH, DMSO | 12.4 |
| 50. | MT1-157 | | C20H25ClN6O, 400.91 | MeOH, DMSO | 11.0 |
| 51. | MT1-158 | | C21H27ClN6O, 414.93 | MeOH, DMSO | 10.9 |

TABLE 5-continued

Some exemplary compounds of the invention.

| S. No. | Compound ID | IUPAC Name | Mol. Formula, M.W. | Solubility | Amount (mg) |
|---|---|---|---|---|---|
| 52. | MT1-162 | | C22H29ClN6O, 428.96 | MeOH, DMSO | 14.0 |
| 53. | MT1-163 | | C23H31ClN6O, 442.98 | MeOH, DMSO | 14.1 |
| 54. | MT1-185 | | C18H21ClN6O, 372.85 | MeOH, DMSO | 12.1 |
| 55. | MT1-186 | | C19H23ClN6O, 386.88 | MeOH, DMSO | 12.3 |

TABLE 5-continued
Some exemplary compounds of the invention.
| S. No. | Compound ID | IUPAC Name | Mol. Formula, M.W. | Solubility | Amount (mg) |
|---|---|---|---|---|---|
| 56. | MT1-189 | 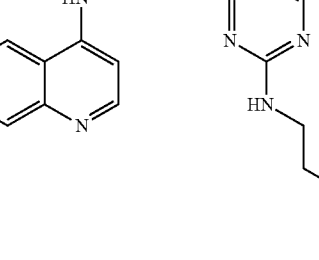 | C20H25ClN6O, 400.91 | MeOH, DMSO | 11.3 |
| 57. | MT1-190 | 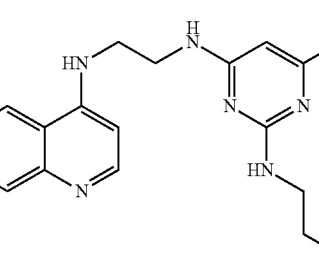 | C21H27ClN6O, 414.93 | MeOH, DMSO | 10.6 |
| 58. | MT1-191 | 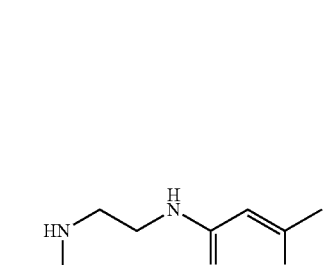 | C22H29ClN6O, 428.96 | MeOH, DMSO | 10.3 |
| 59. | MT1-192 | 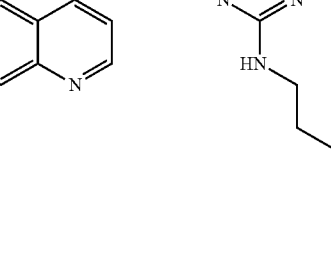 | C20H25ClN6O, 400.91 | MeOH, DMSO | 10.2 |

TABLE 5-continued

Some exemplary compounds of the invention.

| S. No. | Compound ID | IUPAC Name | Mol. Formula, M.W. | Solubility | Amount (mg) |
|---|---|---|---|---|---|
| 60. | MT1-193 | (structure) | C21H27ClN6O, 414.93 | MeOH, DMSO | 11.7 |
| 61. | MT1-194 | (structure) | C22H29ClN6O, 428.96 | MeOH, DMSO | 10.9 |
| 62. | MT1-195 | (structure) | C23H31ClN6O, 442.98 | MeOH, DMSO | 11.3 |
| 6.3 | MT1-196 | (structure) | C24H33ClN6O, 457.01 | MeOH, DMSO | 11.0 |

It should be recognized that the compounds described herein can be present and optionally administered in the form of salts, hydrates and prodrugs that are converted in vivo into the compounds described herein. For example, it is within the scope of the present invention to convert the compounds described herein into and use them in the form of their pharmaceutically acceptable salts derived from various organic and inorganic acids and bases in accordance with procedures well known in the art.

When the compounds described herein possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate andbenzenesulfonate; and other organic acids and their corresponding salts such as acetate, tartrate, maleate, succinate, citrate, benzoate, salicylate and ascorbate. Further acid addition salts amenable to the disclosed compounds include, but are not limited to, adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (frommucic acid), galacturonate, glucoheptaoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds described herein possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g. potassium ethanolate and sodium propanolate; and various organic bases such as ammonium hydroxide, piperidine, diethanolamine and N-methylglutamine. Also included are the aluminum salts of the compounds of the present invention. Further base salts amenable to the disclosed compounds include, but are not limited to, copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine(tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen-containing groups can be quaternized with such agents as $C_1$-$C_4$alkyl halides, e.g., methyl, ethyl, iso-propyl and tert-butyl chlorides, bromides and iodides; di($C_1$-$C_4$alkyl) sulfates, e.g., dimethyl, diethyl and diamyl sulfates; $C_{10}$-$C_{18}$alkyl halides, e.g., decyl, dodecyl, lauryl, myristyl and stearyl chlorides, bromides and iodides; and aryl($C_1$-$C_4$alkyl) halides, e.g., benzyl chloride and phenethyl bromide. Such salts permit the preparation of both water-soluble and oil-soluble compounds described herein.

Prodrug derivatives of compounds described herein can be prepared by modifying substituents of compounds described herein that are then converted in vivo to a different substituent. It is noted that in many instances, the prodrugs themselves also fall within the scope of the range of compounds described herein. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al., 1994, *Bioorganic and Medicinal Chemistry Letters*, Vol. 4, p. 1985.

Protected derivatives of compounds described herein can also be made. Examples of techniques applicable to the creation of protecting groups and their removal can be found in P. G. M. Wuts and T. W. Greene, Greene's Protecting Groups in Organic Synthesis, $4^{th}$ edition, John Wiley & Sons, Inc. 2006.

Compounds described herein can also be conveniently prepared or formed during the process of the invention, as solvates (e.g. hydrates). Hydrates of the compounds described herein can be conveniently prepared by recrystallization from an aqueous/organic solvent mixture, using organic solvents such as dioxin, tetrahydrofuran or methanol.

In some embodiments, the compounds of the present disclosure can be used in the form of a pharmaceutically acceptable salt. A "pharmaceutically acceptable salt", as used herein, is intended to encompass any compound described herein that is utilized in the form of a salt thereof, especially where the salt confers on the compound improved pharmacokinetic properties as compared to the free form of compound or a different salt form of the compound. The pharmaceutically acceptable salt form can also initially confer desirable pharmacokinetic properties on the compound that it did not previously possess, and may even positively affect the pharmacodynamics of the compound with respect to its therapeutic activity in the body. An example of a pharmacokinetic property that can be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Pharmaceutically acceptable salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", J. Pharm. Sci. 66:1-19 (1977), the content of which is herein incorporated by reference in its entirety. Exemplary salts also include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. Suitable acids which are capable of forming salts with the compounds of the disclosure include inorganic acids such as hydrochloric acid, hydrobromic acid, perchloric acid, nitric acid, thiocyanic acid, sulfuric acid, phosphoric acid, and the like; and organic acids such as 1,2-ethanedisulfonic acid, 2-hydroxyethanesulfonic acid, 2-naphthalenesulfonic acid, 3-phenylpropionic acid, 4-methylbicyclo[2.2.2]oct-2-ene-1-carboxylic acid, 4,4'-methylenebis(3-hydroxy-2-ene-1-carboxylic acid), acetic acid, anthranilic acid, benzenesulfonic acid, benzoic acid, camphorsulfonic acid, cinnamic acid, citric acid, cyclopentanepropionic acid, ethanesulfonic acid, formic acid, fumaric acid, glucoheptonic acid, gluconic acid, glutamic acid, glycolic acid, heptanoic acid, hydroxynaphthoic acid, lactic acid, lauryl sulfuric acid, maleic acid, malic acid, malonic acid, mandelic acid, methanesulfonic acid, muconic acid, naphthalene sulfonic acid, o-(4-hydroxybenzoyl)benzoic acid, oxalic acid, p-chlorobenzenesulfonic acid, propionic acid, p-toluenesulfonic acid, pyruvic acid, salicylic acid, stearic acid, succinic acid, sulfanilic acid, tartaric acid, tertiary butylacetic acid, trifluoroacetic acid, trimethylacetic acid, and the like. Suitable bases capable of forming salts with the compounds of the disclosure include inorganic bases such as sodium hydroxide, ammonium hydroxide, sodium carbonate, calcium hydroxide, potassium hydroxide and the like; and organic bases such as mono-, di- and tri-alkyl and aryl amines (e.g., triethylamine, diisopropyl amine, methyl amine, dimethyl amine, N-methylglucamine, pyridine, picoline, dicyclohexylamine, N,N'-dibezylethylenediamine, and the like), and optionally substituted ethanol-amines (e.g., ethanolamine, diethanolamine, trierhanolamine and the like), The compounds according to the disclosure can be prepared by synthetic processes which are known to those skilled in the art, particularly in view of the state of the art and the specific preparatory examples provided below herein. Suitable modification to starting materials by methods well known in the art can also be employed. It is noted, however, that the compounds described herein can also be synthesized by other synthetic routes that others may devise.

It will be readily recognized that certain compounds described herein have atoms with linkages to other atoms that confer a particular stereochemistry to the compound (e.g., chiral centers). It is recognized that synthesis of compounds according to the present invention can result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

The compounds described herein showed significant in vitro/in vivo activity against *Plasmodium falciparum*, without any toxicity. Accordingly, in one aspect, the compounds disclosed herein are useful for treatment of infectious diseases such as malarial or any other disease in question.

Inventors have discovered that the compounds described herein are also unexpectedly, surprisingly agonists of orphan nuclear receptor Nurr1. Accordingly, the compounds described herein can be administered to a subject as part of a therapeutic application. In general, the method can be characterized as including a step of administering a therapeutically effective amount of the compound to a subject in need thereof.

In one embodiment, the compounds and method disclosed herein can be used in treating a subject for a disease state in which a decreased Nurr1 activity contributes to the pathology or symptomology of the disease. Disease states in which Nurr1 activity is decreased include, but are not limited to, neurodegerartive diseases, inflammation diseases or disorders, restless leg syndrome, and the like. The compounds and methods disclosed herein can also be used in treating a subject for a disease for which a dopamine agonist is a useful treatment, for example restless leg syndrome.

The disclosure also provides a method for causing the differentiation of a stem cell, e.g., a human embryonic stem cell, into a dopaminergic neuron by contacting the stem cell with a compound described herein that is present in an amount sufficient to induce differentiation of the stem cell. Without limitation, the stem cell can be contacted with the compounds described herein in a cell culture e.g., in vitro or ex vivo, or administrated to a subject, e.g., in vivo. In some embodiments of the invention, a compound described herein can be administrated to a subject to treat, prevent, and/or diagnose neurodegenerative disorders, including those described herein.

The term "contacting" or "contact" as used herein in connection with contacting a stem cell includes subjecting the cell to an appropriate culture media which comprises the indicated compound. Where the stem cell is in vivo, "contacting" or "contact" includes administering the compound in a pharmaceutical composition to a subject via an appropriate administration route such that the compound contacts the stem cell in vivo.

By "an amount sufficient to induce differentiation" of a stem cell is meant the amount of a compound of the invention required to cause an undifferentiated stem cell to differentiate into a desired cell type, e.g., a neuron.

By "differentiation" is meant the process whereby an unspecialized stem cell acquires the features of a specialized cell, e.g., a nerve cell. Differentiation can also refer to the restriction of the potential of a cell to self-renew and is generally associated with a change in the functional capacity of the cell. Differentiation of a stem cell can be determined by methods well known in the art, including analysis for cell markers or morphological features associated with cells of a defined differentiated state. Examples of such markers and features include measurement of glycoprotein, alkaline phosphatase, and carcinoembryonic antigen expression, where an increase in any one of these proteins is an indicator of differentiation.

By "stem cell" is meant any cell with the potential to self-renew and, under appropriate conditions, differentiate into a dedicated progenitor cell or a specified cell or tissue. Stem cells can be pluripotent or multipotent. Stem cells include, but are not limited to embryonic stem cells, embryonic germ cells, adult stem cells, and umbilical cord blood cells.

Stem cells are unique cell populations that have the ability to divide (self-renew) for indefinite periods of time, and, under the right conditions or signals, to differentiate into the many different cell types that make up an organism. Stem cells derived from the inner cell mass of the blastocyst are known as embryonic stem (ES) cells. Stem cells derived from the primordial germ cells, and which normally develop into mature gametes (eggs and sperm) are known as embryonic germ (EG) cells. Both of these types of stem cells are known as pluripotent cells because of their unique ability to differentiate into derivatives of all three embryonic germ layers (endoderm, mesoderm, and ectoderm).

The pluripotent stem cells can further specialize into another type of multipotent stem cell often derived from adult tissues. Multipotent stem cells are also able to undergo selfrenewal and differentiation, but unlike embryonic stem cells, are committed to give rise to cells that have a particular function. Examples of adult stem cells include hematopoietic stem cells (HSC), which can proliferate and differentiate to produce lymphoid and myeloid cell types; bone marrowderived stem cells (BMSC), which can differentiate into adipocytes, chondrocytes, osteocytes, hepatocytes, cardiomyocytes and neurons; neural stem cells (NSC), which can differentiate into astrocytes, neurons, and oligodendrocytes; and peripheral blood stem cells. Multipotent stem cells have also been derived from epithelial and adipose tissues and umbilical cord blood (UCB).

ES cells, derived from the inner cell mass of preimplantation embryos, have been recognized as the most pluripotent stem cell population and are therefore the preferred cell for the methods of the invention. These cells are capable of unlimited proliferation ex vivo, while maintaining the capacity for differentiation into a Wide variety of somatic and extra-embryonic tissues. ES cells can be male Q(Y) or female (XX); female ES cells are preferred.

Multipotent, adult stem cells can also be used in the methods of the invention. Preferred adult stem cells include hematopoietic stem cells (HSC), Which can proliferate and differentiate throughout life to produce lymphoid and myeloid cell types; bone marrow-derived stem cells (BMSC), Which can differentiate into various cell types including adipocytes, chondrocytes, osteocytes, hepatocytes, cardiomyocytes and neurons; and neural stem cells (NSC), Which can differentiate into astrocytes, neurons, and oligodendrocytes. Multipotent stem cells derived from epithelial and adipose tissues and umbilical cord blood cells can also be used in the methods of the invention.

Stem cells can be derived from source, e.g., any mammal including, but not limited to, mouse, human, and primates. Following acquisition of stem cells, these cells can be used directly in the methods disclosed herein. For example, umbilical cord blood cells can be acquired in sufficient quantity to use directly for therapeutic purposes. Alternatively, stem cells can first be expanded in order to increase the number of available cells. See, for example, U.S. Pat. No. 6,338,942, content of which is incorporated herein by reference in its entirety. Exemplary mouse strains for stem cell preparation include 129, C57BL/6, and a hybrid strain (Brook et al., Proc. Natl. Acad. Sci. U.S.A. 94:5709-5712 (1997), Baharvand et al., In Vitro Cell Dev. Biol. Anim. 40:76-81 (2004), content of both of which is incorporated herein by reference). Methods for preparing mouse, human, or primate stem cells are known in the art and are described, for example, in Nagy et al., Manipulating the mouse embryo: A laboratory manual, 3rd ed., Cold Spring Harbor Laboratory Press (2002); Thomson et al., Science 282:1145-1147 (1998), Marshall et al., Methods Mol. Biol. 158: 1 1-18 (2001); Thomson et al., Trends Biotechnol. 18:5357 (2000); Jones et al., Semin. Reprod. Med. 18:219-223 (2000); Voss et al., Exp. Cell Res. 230:45-49 (1997); and Odorico et al., Stem Cells 19:193-204 (2001), content of all which is incorporated herein by reference in its entirety.

ES cells can be directly derived from the blastocyst or any other early stage of development, or can be a "cloned" stem cell line derived from somatic nuclear transfer and other similar procedures. General methods for culturing mouse, human, or primate ES cells from a blastocyst can be found in Appendix C of the NIH report on stem cells entitled Stem Cells: Scientific Progress and Future Research Directions (June 2001), content of which is incorporated herein by reference. For example, in the first step, the inner cell mass of a preimplantation blastocyst is removed from the trophectoderm that surrounds it. (For cultures of human ES cells, blastocysts are generated by in vitro fertilization and donated for research.) The small plastic culture dishes used to grow the cells contain growth medium supplemented with fetal calf serum, and are sometimes coated with a "feeder" layer of nondividing cells. The feeder cells are often mouse embryonic fibroblast (MEF) cells that have been chemically inactivated so they will not divide. Additional reagents, such as the cytokine leukemia inhibitory factor (LIF), can also be added to the culture medium for mouse ES cells. Second, after several days to a week, proliferating colonies of cells are removed and dispersed into new culture dishes, each of which may or may not contain an MEF feeder layer. If the cells are to be used to human therapeutic purposes, it is preferable that the MEF feeder layer is not included. Under these ex vivo conditions, the ES cells aggregate to form colonies. In the third major step required to generate ES cell lines, the individual, nondifferentiating colonies are dissociated and replated into new dishes, a step called passage. This replating process establishes a "line" of ES cells. The line of cells is termed "clonal" if a single ES cell generates it. Limiting dilution methods can be used to generate a clonal ES cell line. Reagents needed for the culture of stem cells are commercially available, for example, from Invitrogen, Stem Cell Technologies, R&D Systems, and Sigma Aldrich, and are described, for example, in U.S. Patent Publication Nos. 2004/0235159 and 2005/0037492 and Appendix C of the NIH report, Stem Cells: Scientific Progress and Future Research Directions, supra.

For in vivo methods, a therapeutically effective amount of a compound described herein can be administered to a subject. Methods of administering compounds to a subject are known in the art and easily available to one of skill in the art.

As one of skill in the art is aware, promoting stem cell differentiation in a subject can lead to treatment, prevention or amelioration of a number of neurodegenerative disorders. By "neurodegenerative disorder" is meant any disease or disorder caused by or associated with the deterioration of cells or tissues of the nervous system. Exemplary neurodegenerative disorders are polyglutamine expansion disorders (e.g., HD, dentatorubropallidoluysian atrophy, Kennedy's disease (also referred to as spinobulbar muscular atrophy), and spinocerebellar ataxia (e.g., type 1, type 2, type 3 (also referred to as Machado-Joseph disease), type 6, type 7, and type 17)), other trinucleotide repeat expansion disorders (e.g., fragile X syndrome, fragile XE mental retardation, Friedreich's ataxia, myotonic dystrophy, spinocerebellar ataxia type 8, and spinocerebellar ataxia type 12), Alexander disease, Alper's disease, Alzheimer disease, amyotrophic lateral sclerosis (ALS), ataxia telangiectasia, Batten disease (also referred to as Spielmeyer-Vogt-Sjogren-Batten disease), Canavan disease, Cockayne syndrome, corticobasal degeneration, Creutzfeldt-Jakob disease, ischemia stroke, Krabbe disease, Lewy body dementia, multiple sclerosis, multiple system atrophy, Parkinson's Disease, Pelizaeus-Merzbacher disease, Pick's disease, primary lateral sclerosis, Refsum's disease, Sandhoff disease, Schilder's disease, spinal cord injury, spinal muscular atrophy (SMA), SteeleRichardson-Olszewski disease, and Tabes dorsalis.

In some embodiments, the neurodegenerative disease or disorder is Parkinson's Disease.

Methods of diagnosing subjects as having or being at risk of having Parkinson's Disease are well-known in the art. For example, the presence of one or more of the following symptoms can be used as part of a PD diagnosis: trembling, e.g., an involuntary, rhythmic tremor of one arm or one leg; muscular rigidity, stiffness, or discomfort; general slowness in any of the activities of daily living, e.g., akinesia or bradykinesia; difficulty with walking, balance, or posture; alteration in handwriting; emotional changes; memory loss; speech problems; and difficulty sleeping. Review of a subject's symptoms, activity, medications, concurrent medical problems, or possible toxic exposures can be useful in making a PD diagnosis. In addition, a subject can be tested for the presence or absence of genetic mutations that can indicate an increased likelihood of having Parkinson's Disease. For example, the presence of one or more specific mutations or polymorphisms in the NURR1, alpha-synuclein, parkin, MAPT, DJ-1, PINK1, SNCA, NAT2, or LRRK2 genes can be used to diagnose a subject as having or being at risk of having Parkinson's Disease. See, e.g., U.S. Patent Application Publication Nos. 2003-0119026 and 2005-0186591; Bonifati, Minerva Med. 96:175-186, 2005; and Cookson et al., Curr. Opin. Neurol. 18:706-711, 2005, content of each of which is incorporated herein by reference.

Without limitation, the methods for utilizing stem cells described herein can be used for the treatment of diseases treatable through transplantation of differentiated cells derived from ES cells. Stem cells of the invention or produced using the methods disclosed herein can be used to treat neurodegenerative diseases, such as Parkinson's disease, Alzheimer's disease, or traumatic injury to the brain or spinal cord in any subject, e.g. a human.

The inventor have also discovered that the compounds disclosed herein also inhibit or reduce the expression of pro-inflammatory cytokine genes in primary microglia derived from P1 rat brains. Accordingly, the compounds disclosed herein can also be used for treating diseases or disorders characterized by elevated levels pro-inflammatory mediators and/or elevated levels of pro-inflammatory mediator gene expression. Accordingly, in another aspect the disclosure provides a method for treating a subject suffering from a disease or disorder characterized by elevated levels pro-inflammatory mediators and/or elevated levels of pro-inflammatory mediator gene expression, the method comprising administering an effective amount of a compound disclosed herein to the subject. Exemplary pro-inflammatory mediators include, but are not limited to, pro-inflammatory cytokines, leukocytes, leukotiens, prostaglandins and other mediators involved in the initiation and maintenance of inflammation. Pro-inflammatory cytokines and inflammation mediators include, but are not limited to, IL-1-alpha, IL-1-beta, IL-6, IL-8, IL-11, IL-12, IL-17, IL-18, TNF-alpha, leukocyte inhibitory factor (LIF), IFN-gamma, Oncostatin M (OSM), ciliary neurotrophic factor (CNTF), TGF-beta, granulocyte-macrophage colony stimulating factor (GM-CSF), iNOS, and chemokines that chemoattract inflammatory cells. A number of assays for in vivo state of inflammation are known in the art which can be utilized for measuring pro-inflammatory mediator levels. See for example U.S. Pat. Nos. 5,108,899 and 5,550,139, contents of both of which are herein incorporated by reference.

In some embodiments of the aspects described herein, the disease, disorder, or disease condition characterized by elevated levels pro-inflammatory cytokines and/or elevated levels of pro-inflammatory cytokine gene expression is an autoimmune disease, neurodegenerative disease, inflammation, an inflammation associated disorder, a disease characterized by inflammation, or a pathogen or non-pathogen infection.

As used herein, the term "autoimmune disease" refers to disease or disorders wherein the immune system of a subject, e.g., a mammal, mounts a humoral or cellular immune response to the msubject's own tissue or to antigenic agents that are not intrinsically harmful to the subject, thereby producing tissue injury in such a subject. Examples of such disorders include, but are not limited to, systemic lupus erythematosus (SLE), mixed connective tissue disease, scleroderma, Sjögren's syndron, rheumatoid arthritis, and Type I diabetes.

As used herein, the term "neurodegenerative disease or disorder" includes any disease disorder or condition that affects neuronal homeostasis, e.g., results in the degeneration or loss of neuronal cells. Neurodegenerative diseases include conditions in which the development of the neurons, i.e., motor or brain neurons, is abnormal, as well as conditions in which result in loss of normal neuron function. Examples of such neurodegenerative disorders include Alzheimer's disease and other tauopathies such as frontotemporal dementia, frontotemporal dementia with Parkinsonism, frontotemporal lobe dementia, pallidopontonigral degeneration, progressive supranuclear palsy, multiple system tauopathy, multiple system tauopathy with presenile dementia, Wilhelmsen-Lynch disease, disinhibition-dementia-park-insonism-amytrophy complex, Pick's disease, or Pick's disease-like dementia, corticobasal degeneration, frontal temporal dementia, Parkinson's disease, Huntington's disease, amyotrophic lateral sclerosis (ALS), multiple sclerosis, Friedreich's ataxia, Lewybody disease, spinal muscular atrophy, and parkinsonism linked to chromosome 17.

As used herein, the term "inflammation" refers to any cellular processes that lead to the activation of caspase-1, or caspase-5, the production of cytokines IL-I, IL-6, IL-8, TNF-alpha, iNOS, and/or the related downstream cellular events resulting from the actions of the cytokines thus produced, for example, fever, fluid accumulation, swelling, abscess formation, and cell death. As used herein, the term "inflammation" refers to both acute responses (i.e., responses in which the inflammatory processes are active) and chronic responses (i.e., responses marked by slow progression and formation of new connective tissue). Acute and chronic inflammation may be distinguished by the cell types involved. Acute inflammation often involves polymorphonuclear neutrophils; whereas chronic inflammation is normally characterized by a lymphohistiocytic and/or granulomatous response.

As used herein, the term "inflammation" includes reactions of both the specific and non-specific defense systems. A specific defense system reaction is a specific immune system reaction response to an antigen (possibly including an autoantigen). A non-specific defense system reaction is an inflammatory response mediated by leukocytes incapable of immunological memory. Such cells include granulocytes, macrophages, neutrophils and eosinophils. Examples of specific types of inflammation include, but are not limited to, diffuse inflammation, focal inflammation, croupous inflammation, interstitial inflammation, obliterative inflammation, parenchymatous inflammation, reactive inflammation, specific inflammation, toxic inflammation and traumatic inflammation.

As used herein, the term "pathogen infection" refers to infection with a pathogen. As used herein the term "pathogen" refers to an organism, including a microorganism, which causes disease in another organism (e.g., animals and plants) by directly infecting the other organism, or by producing agents that causes disease in another organism (e.g., bacteria that produce pathogenic toxins and the like). As used herein, pathogens include, but are not limited to bacteria, protozoa, fungi, nematodes, viroids and viruses, or any combination thereof, wherein each pathogen is capable, either by itself or in concert with another pathogen, of eliciting disease in vertebrates including but not limited to mammals, and including but not limited to humans. As used herein, the term "pathogen" also encompasses microorganisms which may not ordinarily be pathogenic in a non-immunocompromised host. Specific nonlimiting examples of viral pathogens include Herpes simplex virus (HSV)1, HSV2, Epstein Barr virus (EBV), cytomegalovirus (CMV), human Herpes virus (HHV) 6, HHV7, HHV8, Varicella zoster virus (VZV), hepatitis C, hepatitis B, HIV, adenovirus, Eastern Equine Encephalitis Virus (EEEV), West Nile virus (WNE), JC virus (JCV) and BK virus (BKV).

As used herein, the term "microorganism" includes prokaryotic and eukaryotic microbial species from the Domains of Archaea, Bacteria and Eucarya, the latter including yeast and filamentous fungi, protozoa, algae, or higher Protista. The terms "microbial cells" and "microbes" are used interchangeably with the term microorganism.

As used herein, the term "bacteria," or "bubacteria", refers to a domain of prokaryotic organisms. Bacteria include at least 11 distinct groups as follows: (1) Gram-positive (gram+) bacteria, of which there are two major subdivisions: (i) high G+C group (*Actinomycetes*, Mycobacteria, *Micrococcus*, others) (ii) low G+C group (*Bacillus*, Clostridia, *Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces*; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho* thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram-positive bacteria" include cocci, nonsporulating rods, and sporulating rods. The genera of Grampositive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

As used herein, the term "specific defense system" is intended to refer to that component of the immune system that reacts to the presence of specific antigens. Inflammation is said to result from a response of the specific defense system if the inflammation is caused by, mediated by, or associated with a reaction of the specific defense system. Examples of inflammation resulting from a response of the specific defense system include the response to antigens such as rubella virus, autoimmune diseases such as lupus erythematosus, rheumatoid arthritis, Reynaud's syndrome, multiple sclerosis etc., delayed type hypersensitivity response mediated by T-cells, etc. Chronic inflammatory diseases and the rejection of transplanted tissue and organs are further examples of inflammatory reactions of the specific defense system.

As used herein, a reaction of the "non-specific defense system" is intended to refer to a reaction mediated by leukocytes incapable of immunological memory. Such cells include granulocytes and macrophages. As used herein, inflammation is said to result from a response of the non-specific defense system, if the inflammation is caused by, mediated by, or associated with a reaction of the non-specific defense system. Examples of inflammation which result, at least in part, from a reaction of the non-specific defense system include inflammation associated with conditions such as: adult respiratory distress syndrome (ARDS) or multiple organ injury syndromes secondary to septicemia or trauma; reperfusion injury of myocardial or other tissues; acute glomerulonephritis; reactive arthritis; dermatoses with acute inflammatory components; acute purulent meningitis or other central nervous system inflammatory disorders; thermal injury; hemodialysis; leukophoresis; ulcerative colitis; Crohn's disease; necrotizing enterocolitis; granulocyte transfusion associated syndromes; and cytokine-induced toxicity. The term immune-mediated refers to a process that is either autoimmune or inflammatory in nature.

In some embodiments of the aspects described herein, the inflammation-associated disorder or disease characterized by inflammation is selected from the group consisting of asthma, autoimmune diseases, chronic prostatitis, glomerulonephritis, inflammatory bowl disease, pelvic inflammatory disease, reperfusion injury, arthritis, silicosis, vasculitis, inflammatory myopathies, hypersensitivities, migraine, psoriasis, gout, artherosclerosis, and any combinations thereof.

Exemplary inflammatory diseases include, but are not limited to, rheumatoid arthritis, inflammatory bowel disease, pelvic inflammatory disease, ulcerative colitis, psoriasis, systemic lupus erythematosus, multiple sclerosis, type 1 diabetes mellitus, multiple sclerosis, psoriasis, vaculitis, and allergic inflammation such as allergic asthma, atopic dermatitis, and contact hypersensitivity. Other examples of auto-immune-related diseases or disorders, include but should not be construed to be limited to, rheumatoid arthritis, multiple sclerosis (MS), systemic lupus erythematosus, Graves' disease (overactive thyroid), Hashimoto's thyroiditis (underactive thyroid), Type 1 diabetes mellitus, celiac disease, Crohn's disease and ulcerative colitis, Guillain-Barre syndrome, primary biliary sclerosis/cirrhosis, sclerosing cholangitis, autoimmune hepatitis, Raynaud's phenomenon, scleroderma, Sjogren's syndrome, Goodpasture's syndrome, Wegener's granulomatosis, polymyalgia rheumatica, temporal arteritis/giant cell arteritis, chronic fatigue syndrome CFS), psoriasis, autoimmune Addison's Disease, ankylosing spondylitis, Acute disseminated encephalomyelitis, antiphospholipid antibody syndrome, aplastic anemia, idiopathic thrombocytopenic purpura, Myasthenia gravis, opsoclonus myoclonus syndrome, optic neuritis, Ord's thyroiditis, pemphigus, pernicious anaemia, polyarthritis in dogs, Reiter's syndrome, Takayasu's arteritis, warm autoimmune hemolytic anemia, Wegener's granulomatosis, fibromyalgia (FM), autoinflammatory PAPA syndrome, Familial Mediaterranean Fever, familial cold autoinflammatory syndrome, Muckle-Wells syndrome, and the neonatal onset multisystem inflammatory disease.

As used herein, an anti-inflammation treatment aims to prevent or slow down (lessen) an undesired physiological change or disorder, such as the development or progression of the inflammation. Beneficial or desired clinical results include, but are not limited to, alleviation of symptoms, diminishment of extent of disease, stabilized (i.e., not worsening) state of disease, delay or slowing of inflammation disease progression, amelioration or palliation of the disease state, and remission (whether partial or total), whether detectable or undetectable. An anti-inflammation treatment can also mean prolonging survival as compared to expected survival if not receiving treatment. An anti-inflammation treatment can also completely suppress the inflammation response.

One goal of anti-inflammatory treatment is to bring pro-inflammatory mediator levels down to as close to normal as is safely possible. Accordingly, in one embodiment, level of at least one pro-inflammatory mediator in the subject undergoing treatment is reduced by at least 5%, at least 10%, at least 20%, at least 30%, at least 40%, or at least 50% relative to a reference level. A reference level can be the level of the pro-inflammatory mediator in the subject before onset of treatment regime.

The compounds, compositions, and methods disclosed herein can also be used for research purposes for the study of differentiation or development, and for the generation of transgenic animals useful for research purposes. The stem cells and methods of their use described herein can be used, for example, to create and test animal models of Parkinson's Disease or other neurological disorders. The stem cells and methods of the invention can also be used to study the effects of a particular compound on stem cell differentiation, development, and tissue generation or regeneration.

For administration to a subject, the compounds described herein can be provided in pharmaceutically acceptable (e.g., sterile) compositions. Accordingly, another aspect described herein is a pharmaceutical composition comprising a compound disclosed herein and a pharmaceutically acceptable carrier. These pharmaceutically acceptable compositions comprise an effective amount of one or more of the compounds described herein, formulated together with one or more pharmaceutically acceptable carriers (additives) and/or diluents. As described in detail below, the pharmaceutical compositions of the present disclosure can be specifically formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and/or systemic absorption), boluses, powders, granules, pastes for application to the tongue; (2) parenteral administration, for example, by subcutaneous, intramuscular, intravenous (e.g., bolus or infusion) or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960, content of all of which is herein incorporated by reference.

As used herein, the term "pharmaceutically acceptable" or "pharmacologically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Moreover, for animal (e.g., human) administration, it will be understood that compositions should meet sterility, pyrogenicity, general safety and purity standards as required by FDA Office of Biological Standards.

As used herein, the term "pharmaceutically acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable carrier" or the like are used interchangeably herein.

For liquid formulations, pharmaceutically acceptable carriers can be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions, or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include one or more of the following components: a sterile diluent, including water for injection, saline solution, fixed oils, polyethylene glycols, glycerine, propylene glycol and other synthetic solvents; antibacterial agents, including benzyl alcohol and methyl parabens; antioxidants, including ascorbic acid or sodium bisulfite; chelating agents, including ethylenediaminetetraacetic acid (EDTA); buffers, including acetates, citrates and phosphates, and agents for the adjustment of tonicity, including sodium chloride and dextrose. The pH can be adjusted with acids or bases, including hydrochloric acid and sodium hydroxide.

Liposomes and non-aqueous vehicles such as fixed oils can also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As indicated above, the compositions can further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

It is especially advantageous to formulate oral and intravenous compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals. The pharmaceutical compositions can be included in a container, pack, or dispenser together with instructions for administration.

The amount of a compound described herein that can be combined with a carrier material to produce a single dosage form will generally be an effective amount of the compound. A pharmaceutical composition typically contains an amount of at least 0.01 weight % of active ingredient, i.e., a compound of this disclosure, per weight of total pharmaceutical composition. Generally out of one hundred percent, this amount will range from about 0.01% to 99% of the compound, preferably from about 5% to about 70%, most preferably from 10% to about 30%. A weight % is a ratio by weight of active ingredient to total composition. Thus, for example, 0.1 weight % is 0.1 grams of the compound per 100 grams of total composition.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic, or oily solutions and the like as detailed above.

For intravenous administration, glucuronic acid, L-lactic acid, acetic acid, citric acid or any pharmaceutically acceptable acid/conjugate base with reasonable buffering capacity in the pH range acceptable for intravenous administration can be used as buffers. Sodium chloride solution wherein the pH has been adjusted to the desired range with either acid or base, for example, hydrochloric acid or sodium hydroxide, can also be employed. Typically, a pH range for the intravenous formulation can be in the range of from about 5 to about 12.

Subcutaneous formulations can be prepared according to procedures well known in the art at a pH in the range between about 5 and about 12, which include suitable buffers and isotonicity agents. They can be formulated to deliver a daily dose of the active agent in one or more daily subcutaneous administrations. The choice of appropriate buffer and pH of a formulation, depending on solubility of one or more compounds to be administered, is readily made by a person having ordinary skill in the art. Sodium chloride solution wherein the pH has been adjusted to the desired range with either acid or base, for example, hydrochloric acid or sodium hydroxide, can also be employed in the subcutaneous formulation. Typically, a pH range for the subcutaneous formulation can be in the range of from about 5 to about 12.

Formulations of the invention suitable for oral administration can be in the form of a solid, gel or liquid. For example, the formulation can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like. More specific examples of oral tablets include compressed, chewable lozenges and tablets that can be enteric-coated, sugarcoated or film-coated. Examples of capsules include hard or soft gelatin capsules. Granules and powders can be provided in non-effervescent or effervescent forms. Each can be combined with other ingredients known to those skilled in the art.

In certain embodiments, the compound described herein can be provided as solid dosage forms, preferably capsules or tablets. The tablets, pills, capsules, troches and the like can optionally contain one or more of the following ingredients, or compounds of a similar nature: a binder; a diluent; a disintegrating agent; a lubricant; a glidant; a sweetening agent; and a flavoring agent.

Examples of binders that can be used include, but are not limited to, microcrystalline cellulose, gum tragacanth, glucose solution, acacia mucilage, gelatin solution, sucrose and starch paste.

Examples of lubricants that can be used include, but are not limited to, talc, starch, magnesium or calcium stearate, lycopodium and stearic acid.

Examples of diluents that can be used include, but are not limited to, lactose, sucrose, starch, kaolin, salt, mannitol and dicalcium phosphate.

Examples of glidants that can be used include, but are not limited to, colloidal silicon dioxide.

Examples of disintegrating agents that can be used include, but are not limited to, crosscarmellose sodium, sodium starch glycolate, alginic acid, corn starch, potato starch, bentonite, methylcellulose, agar and carboxymethylcellulose.

Examples of coloring agents that can be used include, but are not limited to, any of the approved certified water soluble FD and C dyes, mixtures thereof; and water insoluble FD and C dyes suspended on alumina hydrate.

Examples of sweetening agents that can be used include, but are not limited to, sucrose, lactose, mannitol and artificial sweetening agents such as sodium cyclamate and saccharin, and any number of spray-dried flavors.

Examples of flavoring agents that can be used include, but are not limited to, natural flavors extracted from plants such as fruits and synthetic blends of compounds that produce a pleasant sensation, such as, but not limited to peppermint and methyl salicylate.

Examples of wetting agents that can be used include, but are not limited to, propylene glycol monostearate, sorbitan monooleate, diethylene glycol monolaurate and polyoxyethylene lauryl ether.

Examples of anti-emetic coatings that can be used include, but are not limited to, fatty acids, fats, waxes, shellac, ammoniated shellac and cellulose acetate phthalates.

Examples of film coatings that can be used include, but are not limited to, hydroxyethylcellulose, sodium carboxymethylcellulose, polyethylene glycol 4000 (PEG 4000) and cellulose acetate phthalate.

If oral administration is desired, the salt of the compound can optionally be provided in a composition that protects it from the acidic environment of the stomach. For example, the composition can be formulated in an enteric coating that maintains its integrity in the stomach and releases the active compound in the intestine. The composition can also be formulated in combination with an antacid or other such ingredient.

When the dosage unit form is a capsule, it can optionally additionally comprise a liquid carrier such as a fatty oil. In addition, dosage unit forms can optionally additionally comprise various other materials that modify the physical form of the dosage unit, for example, coatings of sugar and other enteric agents.

Compounds according to the present invention can also be administered as a component of an elixir, suspension, syrup, wafer, sprinkle, chewing gum or the like. A syrup can optionally comprise, in addition to the active compounds, sucrose as a sweetening agent and certain preservatives, dyes and colorings and flavors.

The compounds described herein can also be mixed with other active materials that do not impair the desired action, or with materials that supplement the desired action. For example, if a compound is used for treating cancer, it can be used with other anti-cancer agents.

Examples of pharmaceutically acceptable carriers that can be included in tablets comprising the compounds described herein include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets can be compressed tablets to which different layers of pharmaceutically acceptable substances are applied. Film-coated tablets can be compressed tablets that have been coated with polymers or other suitable coating. Multiple compressed tablets can be compressed tablets made by more than one compression cycle utilizing the pharmaceutically acceptable substances previously mentioned. Coloring agents can also be used in tablets. Flavoring and sweetening agents can be used in tablets, and are especially useful in the formation of chewable tablets and lozenges.

Examples of liquid oral dosage forms that can be used include, but are not limited to, aqueous solutions, emulsions, suspensions, solutions and/or suspensions reconstituted from non-effervescent granules and effervescent preparations reconstituted from effervescent granules.

Examples of aqueous solutions that can be used include, but are not limited to, elixirs and syrups. As used herein, elixirs refer to clear, sweetened, hydroalcoholic preparations. Examples of pharmaceutically acceptable carriers that can be used in elixirs include, but are not limited to solvents. Particular examples of solvents that can be used include glycerin, sorbitol, ethyl alcohol and syrup. As used herein, syrups refer to concentrated aqueous solutions of a sugar, for example, sucrose. Syrups can optionally further comprise a preservative.

Emulsions refer to two-phase systems in which one liquid is dispersed in the form of small globules throughout another liquid. Emulsions can optionally be oil-in-water or water-in oil emulsions. Examples of pharmaceutically acceptable carriers that can be used in emulsions include, but are not limited to non-aqueous liquids, emulsifying agents and preservatives.

Examples of pharmaceutically acceptable substances that can be used in non-effervescent granules, to be reconstituted into a liquid oral dosage form, include diluents, sweeteners and wetting agents.

Examples of pharmaceutically acceptable substances that can be used in effervescent granules, to be reconstituted into a liquid oral dosage form, include organic acids and a source of carbon dioxide.

Coloring and flavoring agents can optionally be used in all of the above dosage forms.

Particular examples of preservatives that can be used include glycerin, methyl and propylparaben, benzoic add, sodium benzoate and alcohol.

Particular examples of non-aqueous liquids that can be used in emulsions include mineral oil and cottonseed oil.

Particular examples of emulsifying agents that can be used include gelatin, acacia, tragacanth, bentonite, and surfactants such as polyoxyethylene sorbitan monooleate.

Particular examples of suspending agents that can be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that can be used include propylene glycol monostearate, sorbitan monooleate, diethylene glycol monolaurate and polyoxyethylene lauryl ether.

Particular examples of organic acids that can be used include citric and tartaric acid.

Sources of carbon dioxide that can be used in effervescent compositions include sodium bicarbonate and sodium carbonate. Coloring agents include any of the approved certified water-soluble FD and C dyes, and mixtures thereof.

Particular examples of flavoring agents that can be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. No. 4,328,245; No. 4,409,239; and No. 4,410,545, content of all of which is incorporated herein by reference in their entirety. For a liquid dosage form, the solution, e.g., for example, in a polyethylene glycol, can be diluted with a sufficient quantity of a pharmaceutically acceptable liquid carrier, e.g. water, to be easily measured for administration.

Alternatively, liquid or semi-solid oral formulations can be prepared by dissolving or dispersing the active compound or salt in vegetable oils, glycols, triglycerides, propylene glycol esters (e.g. propylene carbonate) and other such carriers, and encapsulating these solutions or suspensions in hard or soft gelatin capsule shells. Other useful formulations include those set forth in U.S. Pat. No. Re 28,819 and No. 4,358,603, content of both of which is incorporated herein by reference in their entirety.

The present invention is also directed to compositions designed to administer the compounds described herein by parenteral administration, generally characterized by injection, either subcutaneously, intramuscularly or intravenously. Injectables can be prepared in any conventional form, for example as liquid solutions or suspensions, solid forms suitable for solution or suspension in liquid prior to injection, or as emulsions.

Examples of excipients that can be used in conjunction with injectables according to the present invention include, but are not limited to water, saline, dextrose, glycerol or ethanol. The injectable compositions can also optionally comprise minor amounts of non-toxic auxiliary substances 50 such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained-release system, such that a constant level of dosage is maintained is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that can optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that can optionally be used include Sodium Chloride Injection, Ringers Injection, Isotonic Dextrose Injection, Sterile Water Injection, Dextrose and Lactated Ringers Injection.

Examples of nonaqueous parenteral vehicles that can optionally be used include fixed oils of vegetable origin, cottonseed oil, corn oil, sesame oil and peanut oil.

Antimicrobial agents in bacteriostatic or fungistatic concentrations can be added to parenteral preparations, particularly when the preparations are packaged in multiple-dose containers and thus designed to be stored and multiple aliquots to be removed. Examples of antimicrobial agents that can be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that can be used include sodium chloride and dextrose. Examples of buffers that can be used include phosphate and citrate. Examples of antioxidants that can be used include sodium bisulfate. Examples of local anesthetics that can be used include procaine hydrochloride. Examples of suspending and dispersing agents that can be used include sodium carboxymethylcellulose, hydroxypropyl methylcellulose and polyvinylpyrrolidone. Examples of emulsifying agents that can be used include Polysorbate 80 (TWEEN 80). A sequestering or chelating agent of metal ions include EDTA.

Pharmaceutical carriers can also optionally include ethyl alcohol, polyethylene glycol and propylene glycol for water miscible vehicles and sodium hydroxide, hydrochloric acid, citric acid or lactic acid for pH adjustment.

The concentration of the compound in the parenteral formulation can be adjusted so that an injection administers a pharmaceutically effective amount sufficient to produce the desired pharmacological effect.

Injectables can be designed for local and systemic administration.

Unit-dose parenteral preparations can be packaged in an ampoule, a vial or a syringe with a needle. All preparations for parenteral administration should be sterile, as is known and practiced in the art.

The compounds described herein can optionally be suspended in micronized or other suitable form or can be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and can be empirically determined.

The compounds described herein can also be prepared as lyophilized powders, which can be reconstituted for administration as solutions, emulsions and other mixtures. The lyophilized powders can also be formulated as solids or gels.

Sterile, lyophilized powder can be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder can optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a compound described herein is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial can contain a single dosage or multiple dosages of the compound described herein.

The compounds described herein can also be administered as topical mixtures. Topical mixtures can be used for local and systemic administration. The resulting mixture can be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds described herein can be formulated as aerosols for topical application, such as by inhalation (see, U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a micro fine powder for insufflation, alone or in combination with an inert carrier such as lactose. In such a case, the particles of the formulation will typically have diameters of less than 50 microns, preferably less than 10 microns.

The compounds described herein can also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the compound alone or in combination with other pharmaceutically acceptable excipients can also be administered.

Depending upon the disease state being treated, other routes of administration, such as topical application, transdermal patches, and rectal administration, can also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases can be used. Agents to raise the melting point of suppositories include spermaceti and wax. Rectal suppositories can be prepared either by the compressed method or by molding. The typical weight of a rectal suppository is about 2 to 3 gm. Tablets and capsules for rectal administration can be manufactured using the same pharmaceutically acceptable substance and by the same methods as for formulations for oral administration.

The invention is also directed to kits and other articles of manufacture for treating infectious diseases or neurodegenerative diseases or disorders. In one embodiment, a kit is provided that comprises a composition comprising at least one compound disclosed herein in combination with instructions. The instructions can indicate the disease state for which the composition is to be administered, storage information, dosing information and/or instructions regarding how to administer the composition. The kit can also comprise packaging materials. The packaging material can comprise a container for housing the composition. The kit can also optionally comprise additional components, such as syringes for administration of the composition. The kit can comprise the composition in single or multiple dose forms.

In another embodiment, an article of manufacture is provided that comprises a composition comprising at least one compound disclosed herein in combination with packaging materials. The packaging material can comprise a container for housing the composition. The container can optionally comprise a label indicating the disease state for which the composition is to be administered, storage information, dosing information and/or instructions regarding how to administer the composition. The kit can also optionally comprise additional components, such as syringes for administration of the composition. The kit can comprise the composition in single or multiple dose forms.

It is noted that the packaging material used in kits and articles of manufacture according to the present invention can form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets can be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or can have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds described herein can be used or administrated to a subject in combination with another compound, e.g., a pharmaceutically active agent or treatment modality for a particular indication. Exemplary pharmaceutically active compound include, but are not limited to, those found in *Harrison's Principles of Internal Medicine*, 13$^{th}$ Edition, Eds. T. R. Harrison et al. McGraw-Hill N.Y., NY; Physicians' Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

Wide variety compounds, e.g., therapeutic agents can have an additive or synergistic effect with the compounds described herein. Such compounds can additively or synergistically combine with the compounds described herein in the methods disclosed herein, e.g., to differentiate stem cells and/or treat a neurodegerative disease or disorder in a subject.

The inventors have discovered that the combination of compounds disclosed herein, e.g., 7-chloro-4-aminoquinoline compounds with forskoline unexpectedly, surprisingly shows a synergistic effect on stimulating the transcriptional activity through the ligand binding domain of Nurr1 and enhancing the contrasting dual function of Nurr1.

The term "synergistic" as used herein is defined to mean a combination of components wherein the activity of the combination is greater than the additive of the individual activities of each component of the combination. In some embodiments, the activity of the combination is at least 5%, at least 10%, at least 15%, at least 20%, at least 25%, at least 30%, at least 40%, at least 50%, at least 60%, at least 70%, at least 80%, at least 90%, at least 1-fold, at least 2-fold, at least 3-fold, at least 4-fold, at least 5-fold, at least 10-fold, at least 50-fold, at least 100-fold or greater than the additive of the individual activities of each component of the combination.

In some embodiments, a compound disclosed herein can be used in combination with a dopamine agonist. Without wishing to be bound by a theory, it is believed that the combination of a compound disclosed herein with a dopamine agonist shows a synergistic effect on stimulating the transcriptional activity through the ligand binding domain of Nurr1 and enhancing the contrasting dual function of Nurr1.

As used herein, the term "dopamine agonist" refers to compounds that activate and/or stimulate one or more dopamine receptors and/or increase levels of dopamine (such as L-dopa or drugs which inhibit dopamine metabolism) and/or stimulate a dopamine signaling pathway and/or reduce levels of norepinephrine, and/or inhibit a norepinephrine signaling pathway. The term "dopamine agonist" also includes analogs of dopamine molecules which exhibit at least some biological activity in common with native human dopamine receptors. As such, the term "dopamine agonist" encompasses dopaminergic agents. As used herein the term "dopaminergic agent" refers to compounds which mimic the action of dopamine. Accordingly, the term dopaminergic agent is intended to encompass dopamine, derivatives of dopamine, and compounds which have dopamine like actions on dopamine receptors. Exemplary analogs of dopamine include the ergolines and the aporphines such apomorphine, pergolide, bromocriptine and lisuride). Dopamine agonists are primarily used for the treatment of Parkinson's disease due to their neuroprotective effects on dopaminergic neurons.

Without wishing to be bound by a theory, a dopamine agonist can act via one of several pathways. For example, a dopamine agonist can activate or potentiate D1 dopamine receptors and/or Dj-like receptors such as D1 and D5 dopamine receptors and/or D2 dopamine receptors (e.g., D2, D2 short and D2 long receptors, D4, and D4 dopamine receptors) and/or D3 dopamine receptors and/or D4 dopamine receptors. A dopamine agonist can act by inhibiting one or more enzyme involved in biosynthesis and/or transformation and/or breakdown of dopamine.

Exemplary dopamine agonists include, but are not limited to, L-3,4-dihydroxyphenylalanine (L-Dopa); (−)-7-{[2-(4-Phenylpiperazin-1-yl)ethyl]propylamino}-5,6,7,8-tetrahydronaphthalen-2-ol; (+)-4-propyl-9-hydroxynaphthoxazine ((+)PHNO); (E)-1-aryl-3-(4-pyridinepiperazin-1-yl)propanone oximes; (R)-3-(4-Propylmorpholin-2-yl)phenol (PF-219,061); (R,R)—S32504; 2-(N-phenylethyl-N-propylamino)-5-hydroxytetralin; 2-bromo-a-ergocriptine (bromocriptine); 5,6,7,8-Tetrahydro-6-(2-propen-1-yl)-4H-thiazolo[4,5-d]azepin-2-amine (BHT-920); 5-HT uptake inhibitor; 5-HT-1A agonists (such as roxindole); 6-Br-APB; 6-methyl-8-a-(N-acyl)amino-9-ergoline; 6-methyl-8-a-(N-phenyl-acetyl)amino-9-ergoline; 6-methyl-8β-carbobenzyloxy-aminoethyl-10-a-ergoline; 7,8-Dihydroxy-5-phenyl-octahydrobenzo[h]isoquinoline; 8-acylaminoergoline; 9,10- dihydroergocomine; a2-adrenergic antagonist (such as terguride); A-412,997; A-68,930; A-77,636; A-86,929; ABT-670; ABT-724; AF-14; alaptide; amisulpride; any D-2-halo-6-alkyl-8-substituted ergoline; Aplindore; Apomorphine; Aripiprazole (Abilify in USA); benzazepine analogs; BP-897; Bromocriptine; bromocriptine mesylate; Cabergoline; cis-8-Hydroxy-3-(n-propyl)-1,2,3a,4,5,9b-hexahydro-1H- and trans-N-{4-[4-(2,3-Dichlorophenyl)-1-piperazinyl] cyclohexyl}-3-methoxybenzamide; clozapine; COMT inhibitors (such as CGP-28014, entacapone and tolcapone); CP-226,269; CP-96,345; CY-208,243; D-2-bromo-6-methyl-8-cyanomethylergoline; Dihydrexidine; dihydro-alpha-ergocriptine; dihydro-alpha-ergotoxine; dihydroergocriptine; dihydroergocryptine; dihydroergotoxine (hydergine); Dinapsoline; Dinoxyline; domperidone; Dopamine; dopamine D1 receptor agonists; dopamine D2 receptor agonists; dopamine D3 receptor agonists; dopamine D4 receptor agonists; dopamine D5 receptor agonists; dopamine uptake inhibitors (such as GBR-12909, GBR-13069, GYKI-52895, and NS-2141); doprexin; Doxanthrine; ER-230; erfotoxine; Ergocornine; ergoline derivatives; ergot alkaloid derivatives; eticlopride; etisulergine; FAUC 299; FAUC 316; Fenoldopam; Flibanserin; haloperidol; iloperidone; levodopa; Lisuride; lisuride; LSD; LU111995; mazapertine; Methylphenidate; monoamine oxidase-B inhibitors (such as selegiline, N-(2butyl)-N-methylpropargylamine, N-methyl-N-(2-pentyl) propargylamine, AGN-1133, ergot derivatives, lazabemide, LU-53439, MD-280040 and mofegiline); N-0434; Naxagolide; olanzapine; opiate receptor agonists (such as NIH-10494); PD-118,440; PD-168,077; Pergolide (such as A-68939, A-77636, dihydrexine, and SKF-38393); PIP3EA; piribedil; Piribedil; Pramipexole; Quinagolide; Quinelorane; Quinpirole; racemic trans-10,11-dihydroxy 5,6,6a, 7,8,12b-hexahydro and related benzazepine analogs; raclopride; remoxipride; risperidone; Ro10-5824; Ropinirole; Rotigotine; Salvinorin A; SDZ-HDC-912; sertindole; SKF-38,393; SKF-75,670; SKF-81,297; SKF-82,526 (fenoldopam); SKF-82,598; SKF-82,957; SKF-82,958; SKF-38,393; SKF-77,434; SKF-81,297; SKF-82,958; SKF-89,145; SKF-89,626; spiperone; spiroperidol; sulpride; sumanirole; Talipexole; Terguride; tropapride; WAY-100635; YM 09151-2; zetidoline; β-adrenergic receptor agonists; cabergoline; bromocriptine; pergolide; talipexole; ropinirole; pramipexole; and analogs, derivatives, enantiomers, metabolites, prodrugs, and pharmaceutically acceptable salts thereof.

Exemplary beta-3 adrenergic receptor agonists include, but are not limited to, DPDMS; dopexamine; AJ-9677; AZ-40140; BMS187413; BMS-194449; BMS-210285; BRL-26830A; BRL-28410; BRL-35135; BRL-37344; CGP 12177; CL-316243; CP-114271; CP-331648; CP-331679; D-7114; FR-149175; GW-2696; GW-427353; ICI-198157; L-750355; L-796568; LY-377604; N-5984; SB-226552; SR-58611A; SR-59062A; SWR0342SA; ZD-2079; and analogs, derivatives, enantiomers, metabolites, prodrugs, and pharmaceutically acceptable salts thereof.

In some embodiments, the dopamine agonist inhibits the dopamine beta-hydroxylase. Dopamine beta-hydroxylase converts dopamine to norepinephrine. Thus, by inhibiting dopamine beta-hydroxylase, intracellular dopamine is increased while norepinephrine is decreased.

Exemplary inhibitors of DBH include, but are not limited to fusaric acid; 1,1',1'',1'''-[disulfanediylbis-(carbonothioylnitrilo)]tetraethane (disulfiram); 2-Hydroxy-2,4,6-cycloheptatrien-1-one (tropolone, also referred to as 2-Hydroxytropone or Purpurocatechol); 5-(aminomethyl)-1-[(2S)-5,7-difluoro-1,2,3,4-tetrahydronaphthalen-2-yl]-1,3-dihydro-2H-imidazole-2-thione (Nepicastat, INN, or SYN117)); 1-(4-hydroxybenzyl)imidazole-2-thiol; FLA-63; diethyidithiocarbamate; betachlorophenethylamine; 4-hydroxybenzyl cyanide; 2-halo-3(p-hydroxyphenyl)-1-propene; 1-phenyl-1-propyne; 2-phenylallylamine; 2-(2-thienyl) allylamine; 2-thiophene-2(2-thienyl)allylamine; 3-phenylpropargylamine; 1-phenyl-1 (aminoethyl)ethane; N-(trifluoroacetyl)phenyl(aminoethyl) ethane; 5-picolinic acid substituted with an alkyl group containing up to 6 carbon atoms; 5-picolinic acid substituted with a halo alkyl group containing up to 6 carbon atoms; and analogs, derivatives, enantiomers, metabolites, prodrugs, and pharmaceutically acceptable salts thereof. Other inhibitors of dopamine beta-hydroxylase include, but are not limited to U.S. Pat. No. 4,487,761; No. 4,634,711; No. 4,719,223; No. 4,743,613; No. 4,749,717; No. 4,761,415; No. 4,762,850; No. 4,798,843; No. 4,810,800; No. 4,835,154; No. 4,839,371; No. 4,859,779; No. 4,876,266; No. 4,882,348; No. 4,906,668; No. 4,935,438; No. 4,963,568; No. 4,992,459; No. 5,100,912; No. 5,189,052; No. 5,597,832; No. 6,407,137; No. 6,559,186; No. 7,125,904; No. 7,576,081, content of all of which is herein incorporated by reference in their entirety.

Cabergoline (Dostinex®) is a long-acting ergot derivative agonist with a high affinity for D2 receptors. Bromocriptine (Parlodel®) is an ergot alkaloid dopamine receptor agonist. It is a strong D2 receptor agonist and a weak DI receptor antagonist. It stimulates both pre- and post-synaptic receptors. Pergolide (Permax®) is a semisynthetic, clavine ergot derivative dopamine agonist. In contrast to bromocriptine, it is a strong D2 receptor agonist and a weak D1 receptor agonist. Ropinirole (Requip®) is a potent, non-ergoline dopamine agonist. Pramipexole (Mirapex®) is a synthetic amino-benzothiazol derivative and a non-ergot D2/D3 agonist. Quinagolide (1-propylbenzo[g]quinolin-3-yl)-Norprolac®; formerly CV 205-502) is another, non-ergot, non-ergoline, benzoquinoline dopaminergic agonist that blocks prolactin release.

For in vivo methods, a compound disclosed herein can be co-adminstered with the dopamine agonist. For example, for treating neurodegerative disorders, the compound disclosed herein can be co-adminstered with the dopamine agonist.

For treating inflammation or inflammation associated disorders, a compound disclosed herein can be co-administered with an agent known in the art for treatment of inflammation or inflammation associated disorders or infections. Exemplary anti-inflammatory agents include, but are not limited to, non-steroidal anti-inflammatory drugs (NSAIDs—such as aspirin, ibuprofen, or naproxen, coricosteroids (such as presnisone), anti-malarial medication (such as hydrochloroquine), methotrexrate, sulfasalazine, leflunomide, anti-TNF medications, cyclophosphamise, mycophenolate, dexamethasone, rosiglitazone, prednisolone, corticosterone, budesonide, estrogen, estrodiol, sulfasalazine, fenfibrate, provastatin, simvastatin, proglitazone, acetylsalicylic acid, mycophenolic acid, mesalamine, and analogs, derivatives, prodrugs, and pharmaceutically acceptable salts thereof.

The term "co-administering," "co-administration," or "co-administer" refers to the administration of a compound disclosed herein and a second compound, e.g. a dopamine agonist, forskolin, or colfosin, wherein the compound disclosed herein and the second compound can be administered simultaneously, or at different times, as long as they work additively or synergistically to increase stem cell differentiation.

Without limitations, the compound disclosed herein and the second compound can be administered in the same formulation or in separate formulations. When administered in separate formulations, the compound disclosed herein and the second compound can be administered within any time of each other. For example, the compounds can be administered with in 24 hours, 12 hours, 6 hours, 5 hours, 4 hours, 3 hours, 2 hours, 1 hours, 45 minutes, 30 minute, 25 minutes, 20 minutes, 15 minutes, 10 minutes, 5 minutes or less of each other. When administered in separate formulations, either compound can be administered first.

Additionally, co-administration does not require the two compounds to be administered by the same route. As such, each can be administered independently or as a common dosage form. Further, the two compounds can be administered in any ratio to each other by weight or moles. For example, two compounds can be administered in a ratio of from about 50:1, 40:1, 30:1, 25:1, 20:1, 15:1, 10:1, 5:1, 3:1, 2:1, 1:1.75, 1.5:1, or 1.25:1 to 1:1.25, 1:1.5, 1.75, 1:2, 1:3, 1:4, 1:5, 1:10, 1:15, 1:20, 1:20, 1:30, 1:40, or 1:50. The ratio can be based on the effective amount of either compound.

In some embodiments, a compound disclosed herein can be co-adminstered with forskloin or colfosin.

In some embodiments, amodiaquine or chloroquine can be co-adminstered with forskloin or colfosin. In some other embodiments, In some embodiments, a compound disclosed herein is co-adminstered amodiaquine or chloroquine can be co-adminstered with a dopamine agonist.

Without limitation, methods comprising co-administering a compound disclosed herein can provide novel mechanism-based neuroprotective therapy that could have disease-modifying effects in (neuro)inflammatory diseases such as PD and AD as well as auto-immune diseases such as rheumatoid arthritis and lupus disease. Furthermore, since the current pharmacological treatments of PD by dopamine agonists such as L-Dopa leads to severe side effects while AQ or CQ did not induce any such side effects, their combined use will reduce or eliminate the side effects by dopamine agonists.

The invention can be defined by any of the following numbered paragraphs:

1. A compound of formula (I):

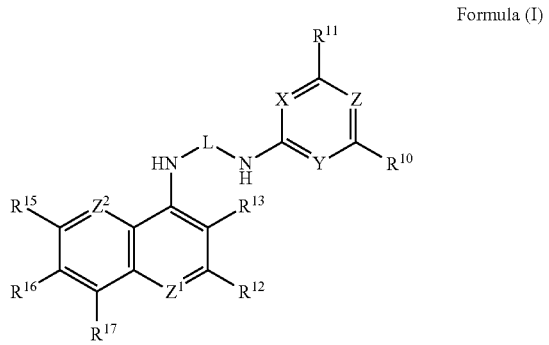

Formula (I)

wherein:
X, Y, and Z are independently $CR^{18}$, N, O, or S;
one of $Z^1$ and $Z^2$ is N and the other is $CR^{14}$;
R and $R^{10}$-$R^{18}$ independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted; and
L is a linker 2. A compound of formula (II):

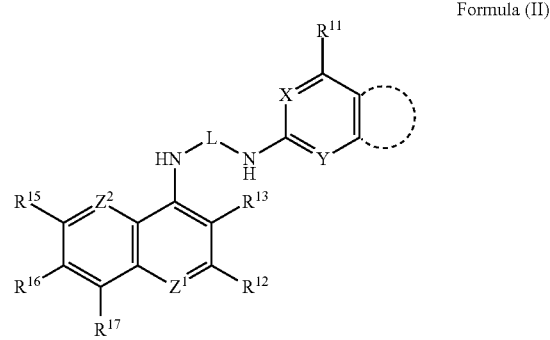

Formula (II)

wherein:
X and Y are independently $CR^{18}$, N, O, or S;
A and B are independently $CR^{18}$, N, O, or S;
one of $Z^1$ and $Z^2$ is N and the other is $CR^{14}$;
R and $R^{10}$-$R^{18}$ independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted;
----- forms a cyclyl, heterocyclyl, aryl, or heteroaryl, each of which can be optionally substituted; and
L is a linker 3. A compound of formula (III):

Formula (III)

wherein:
A and B are independently $CR^{18}$ or N;
one of $Z^1$ and $Z^2$ is N and the other is $CR^{14}$;
R and $R^{10}$-$R^{18}$ independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted; and
L is a linker 4. A compound of formula (IV):

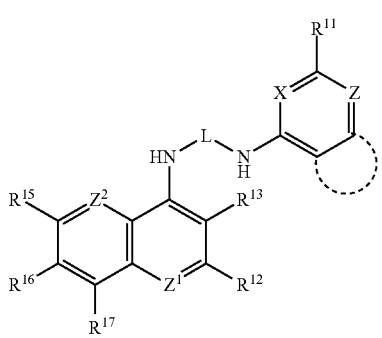

Formula (IV)

wherein:

X and Z are independently $CR^{18}$, N, O, or S;

one of $Z^1$ and $Z^2$ is N and the other is $CR^{14}$;

R and $R^{11}$-$R^{18}$ independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted;

----- forms a cyclyl, heterocyclyl, aryl, or heteroaryl, each of which can be optionally substituted; and L is a linker 5. A compound of formula (V):

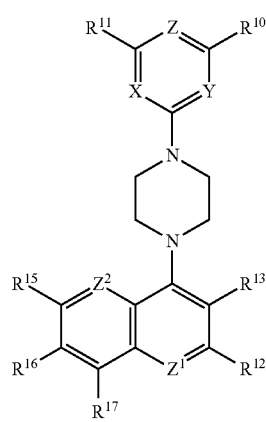

Formula (V)

wherein:

X, Y, and Z are independently $CR^{18}$, N, O, or S;

one of $Z^1$ and $Z^2$ is N and the other is $CR^{14}$;

R and $R^{10}$-$R^{18}$ independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted; and ----- forms a cyclyl, heterocyclyl, aryl, or heteroaryl, each of which can be optionally substituted.

6. A compound of formula (VI):

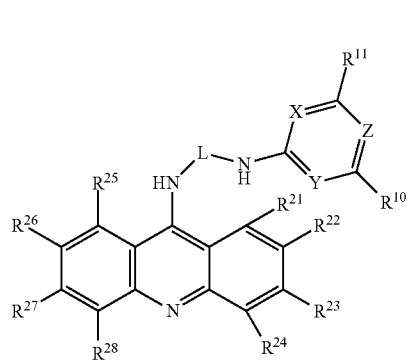

Formula (VI)

wherein:

X, Y, and Z are independently $CR^{18}$, N, O, or S;

$R^{21}$-$R^{28}$ independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted;

----- forms a cyclyl, heterocyclyl, aryl, or heteroaryl, each of which can be optionally substituted; and L is a linker 7. A compound of formula (VII):

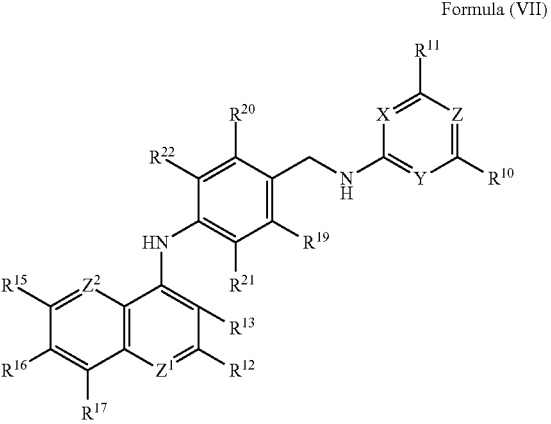

Formula (VII)

wherein:

X, Y, and Z are independently $CR^{18}$, N, O, or S;

one of $Z^1$ and $Z^2$ is N and the other is $CR^{14}$;

R and $R^{10}$-$R^{22}$ independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted.

8. A compound of formula (VIII):

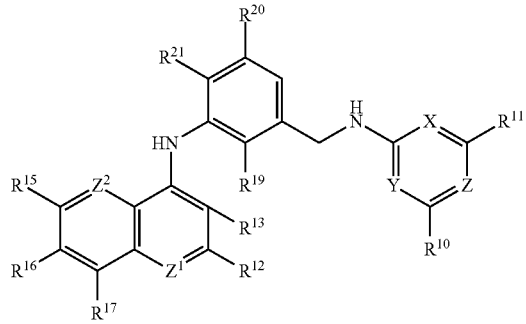

Formula (VIII)

wherein:
X, Y, and Z are independently CR$^{18}$, N, O, or S;
one of Z$^1$ and Z$^2$ is N and the other is CR$^{14}$;
R and R$^{10}$-R$^{21}$ independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted.

9. A compound of formula (IX):

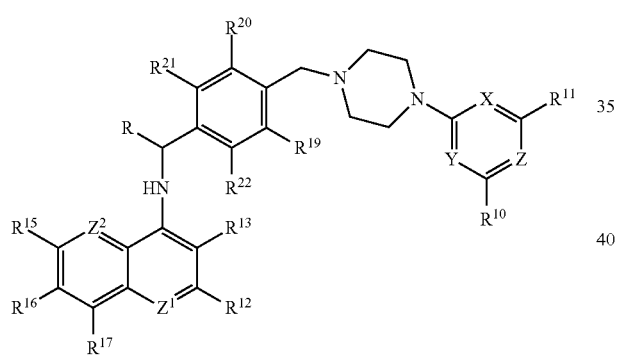

Formula (IX)

wherein:
X, Y, and Z are independently CR$^{18}$, N, O, or S;
one of Z$^1$ and Z$^2$ is N and the other is CR$^{14}$;
R and R$^{10}$-R$^{22}$ independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted.

10. A compound selected from the group consisting of

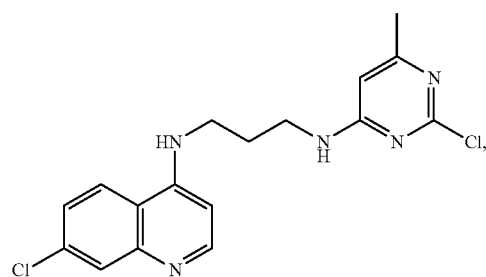

-continued

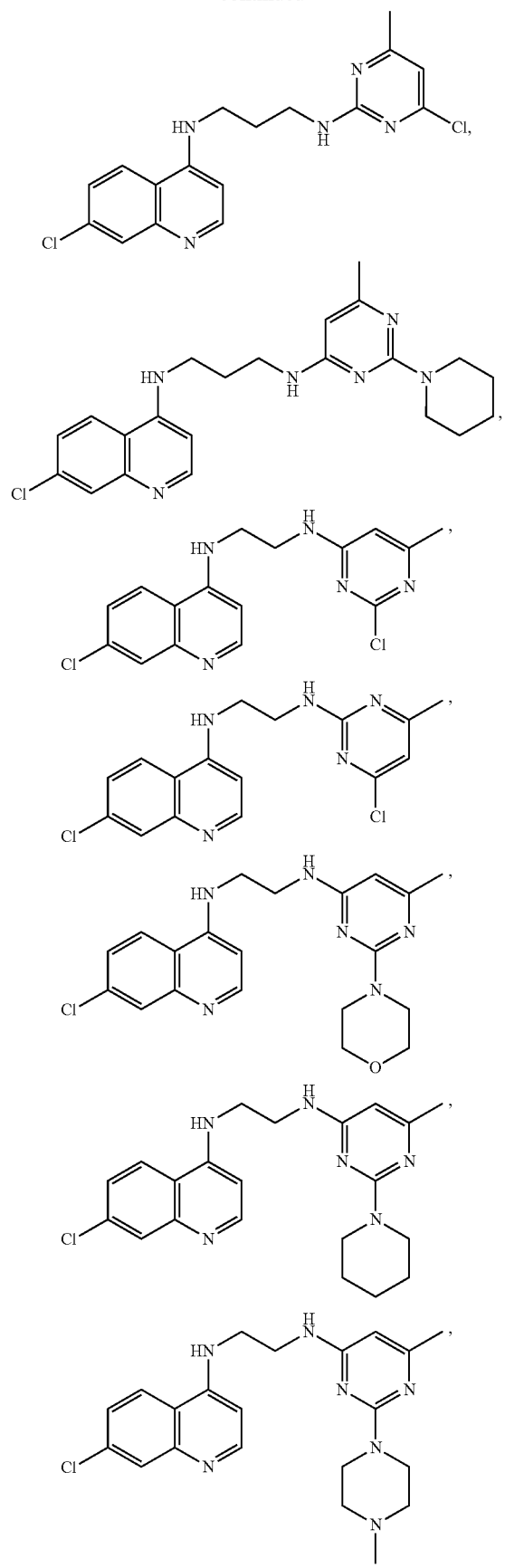

149
-continued
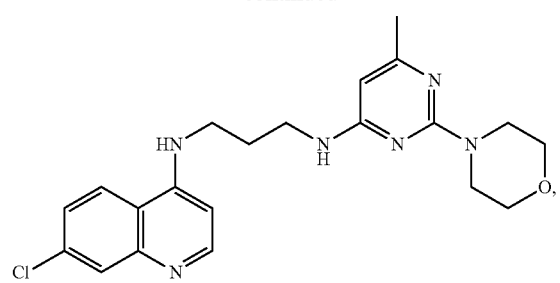
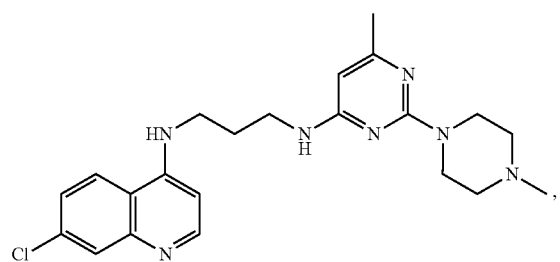
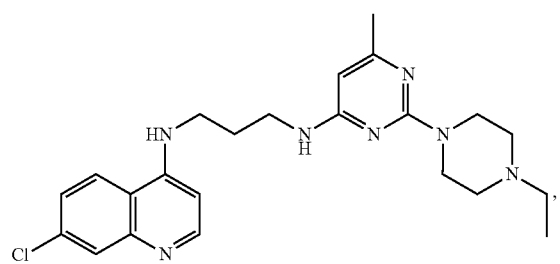
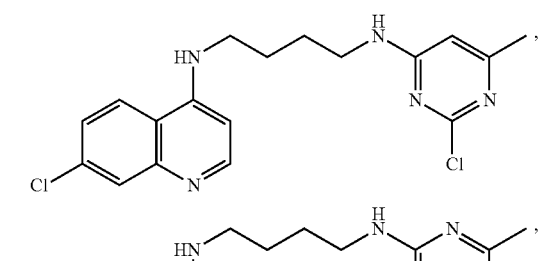
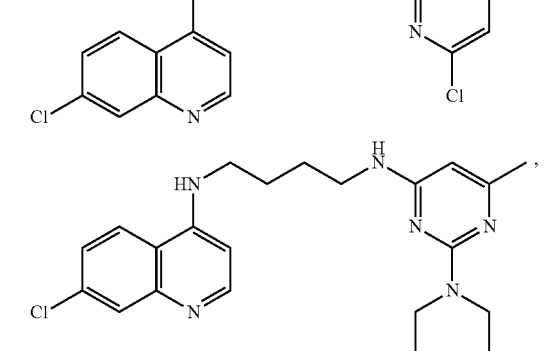
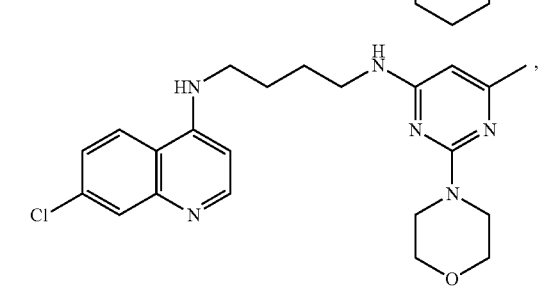
150
-continued
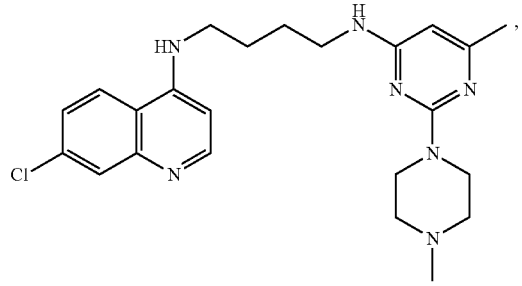
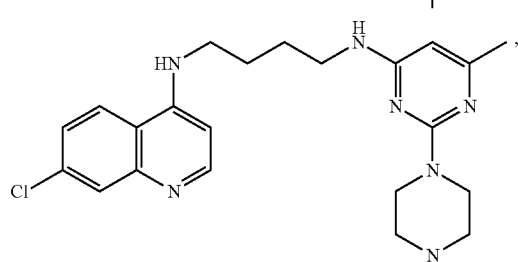
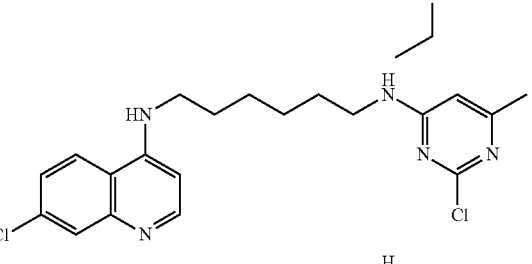
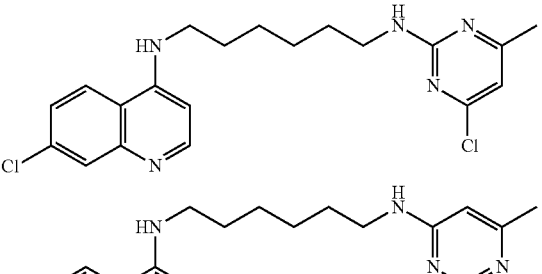
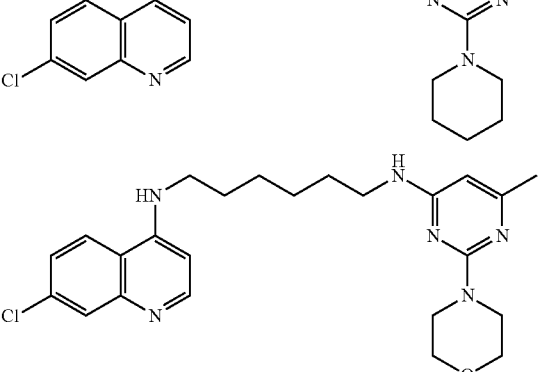
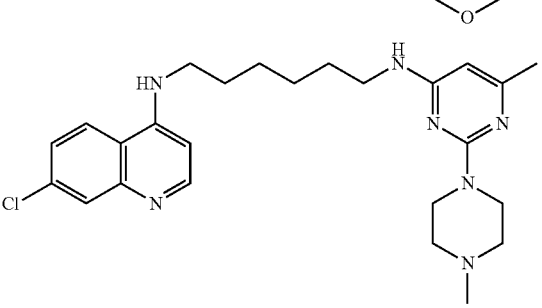

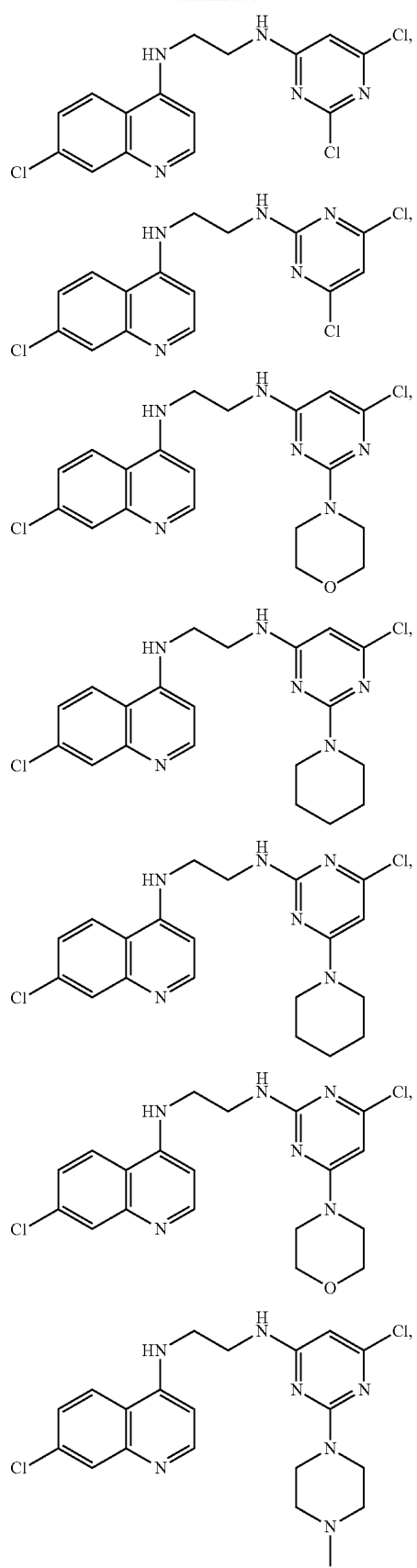
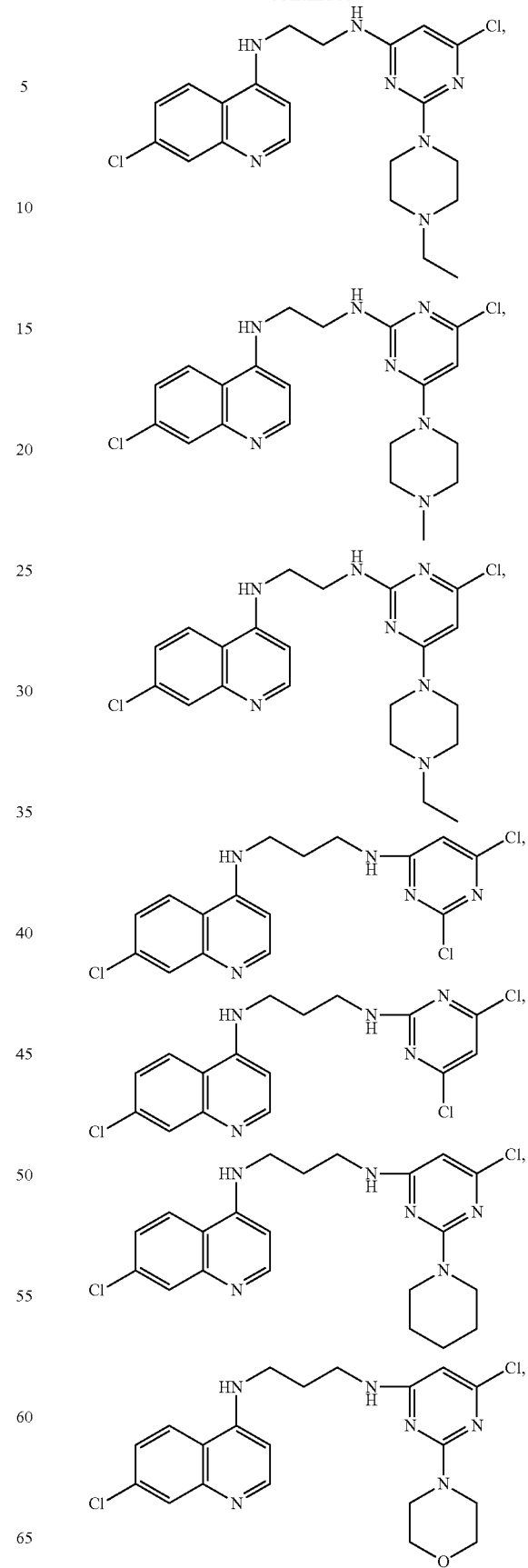

153
-continued
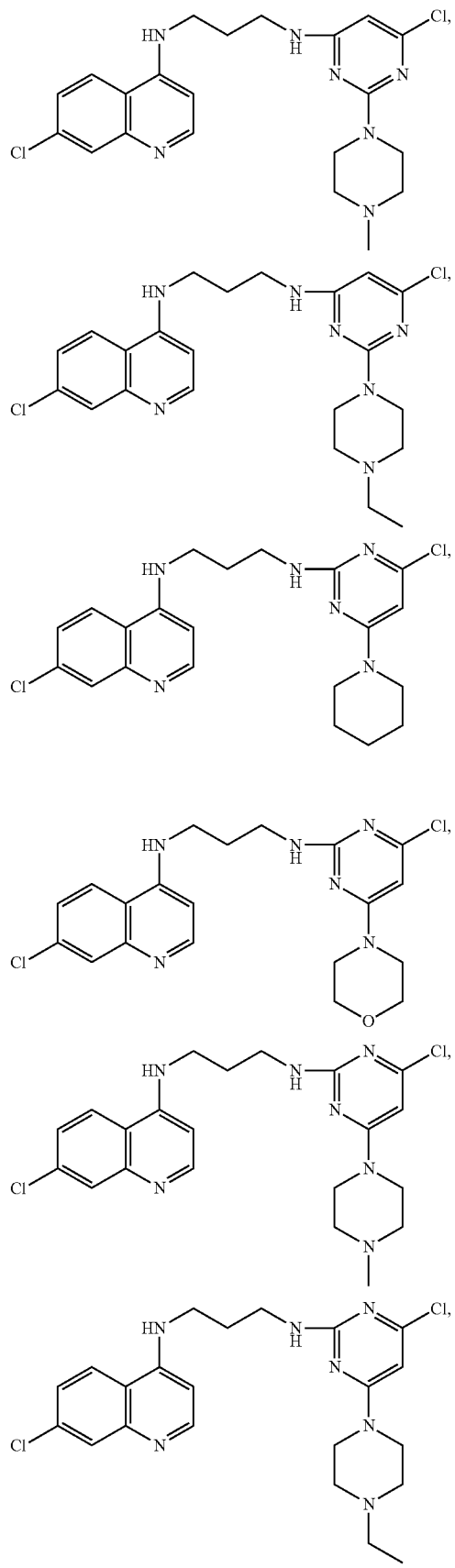
154
-continued
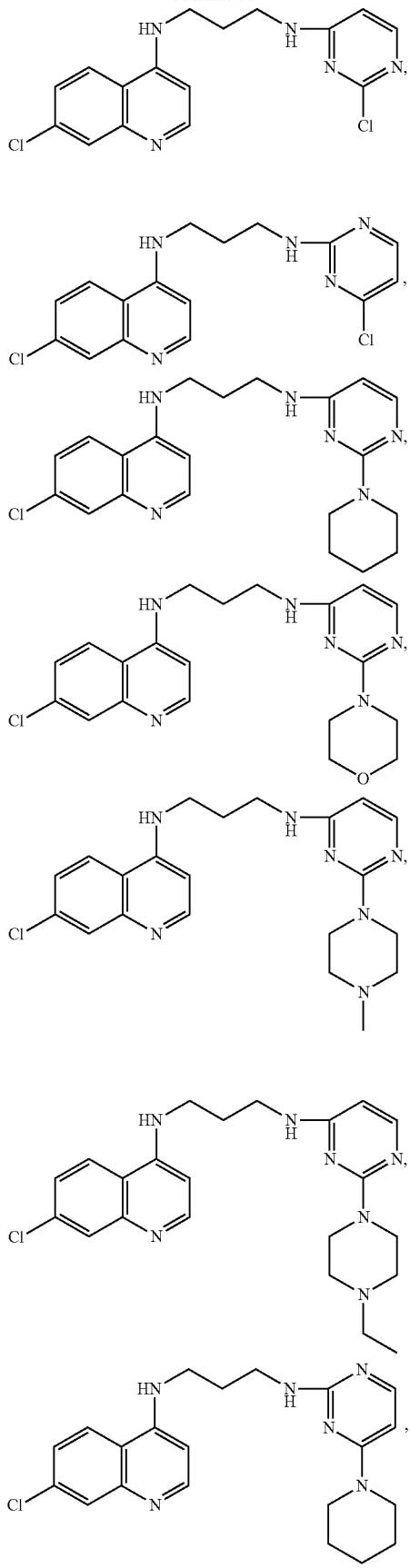

155
-continued
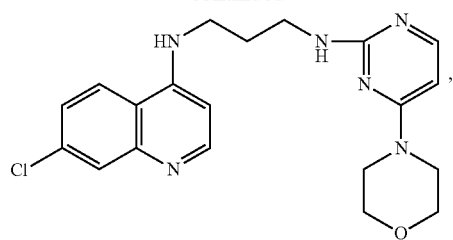
,
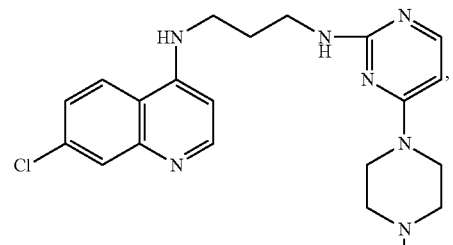
,
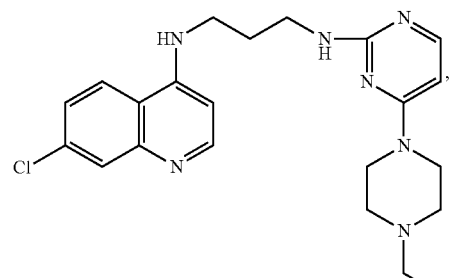
,
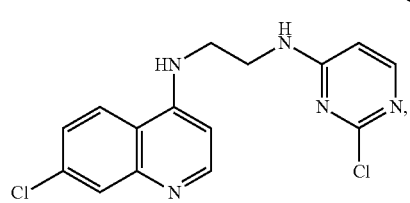
,
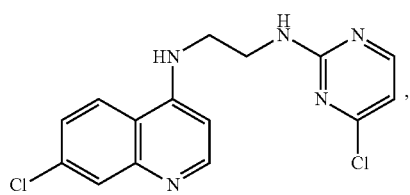
,
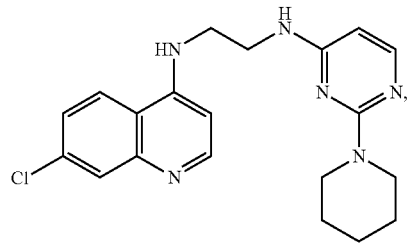
,
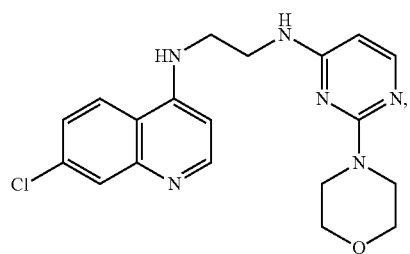
,
156
-continued
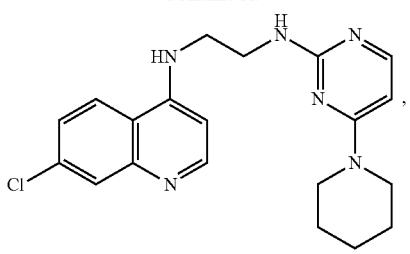
,
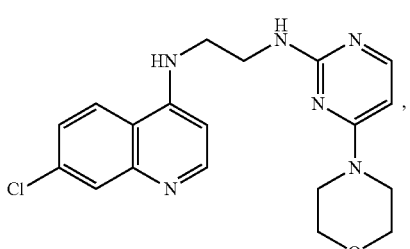
,
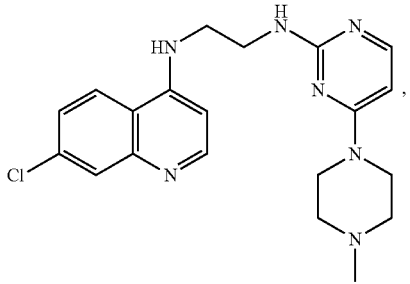
,
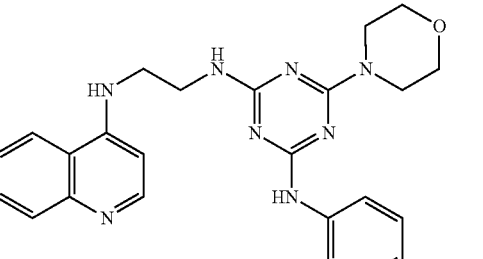
,
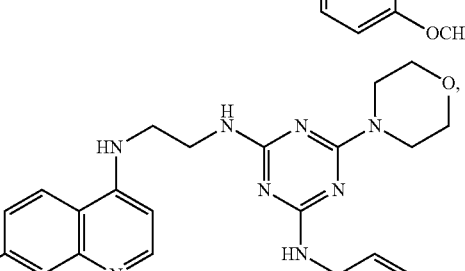
,
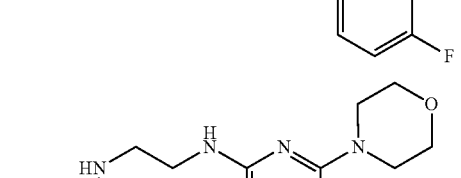
,
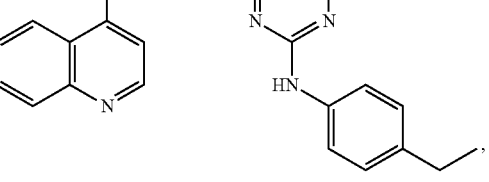
, 157
-continued
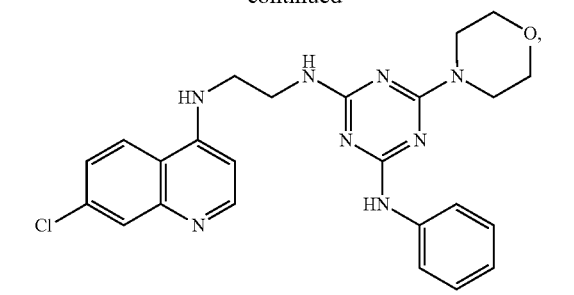
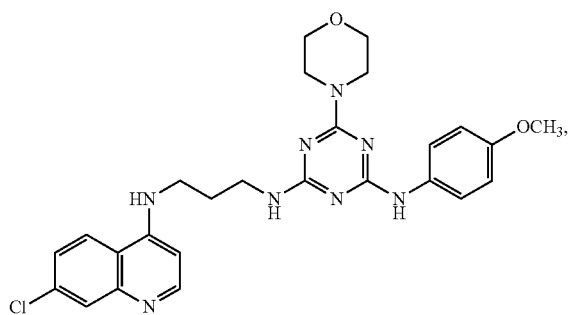
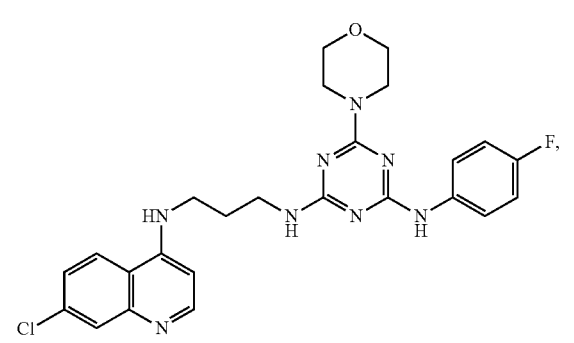
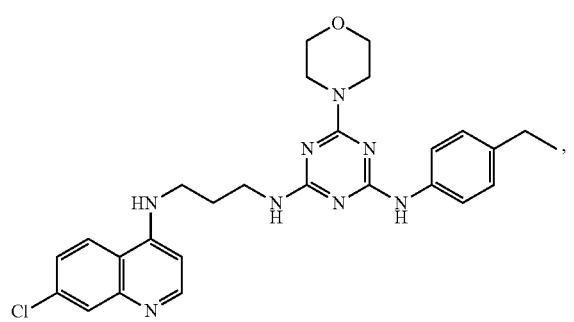
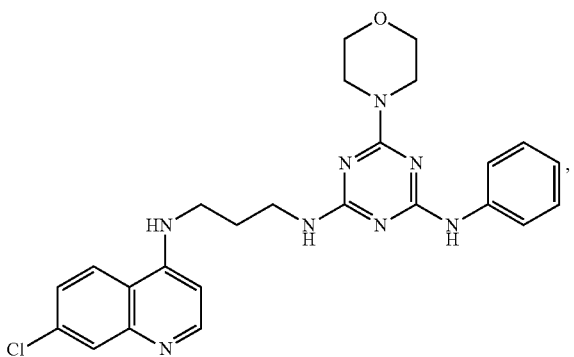
158
-continued
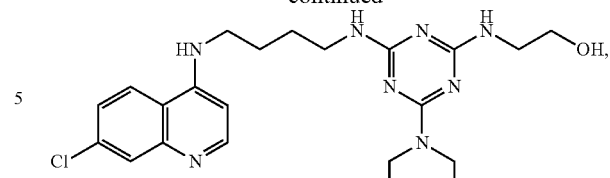
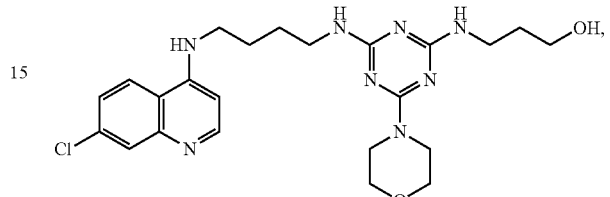
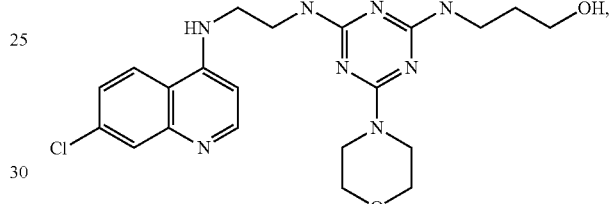
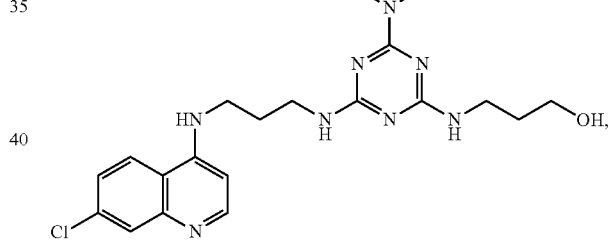
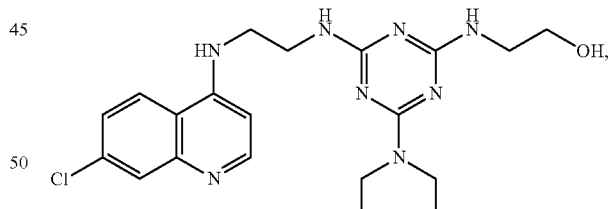
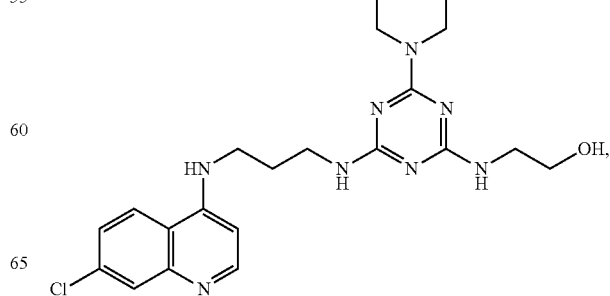

159
-continued
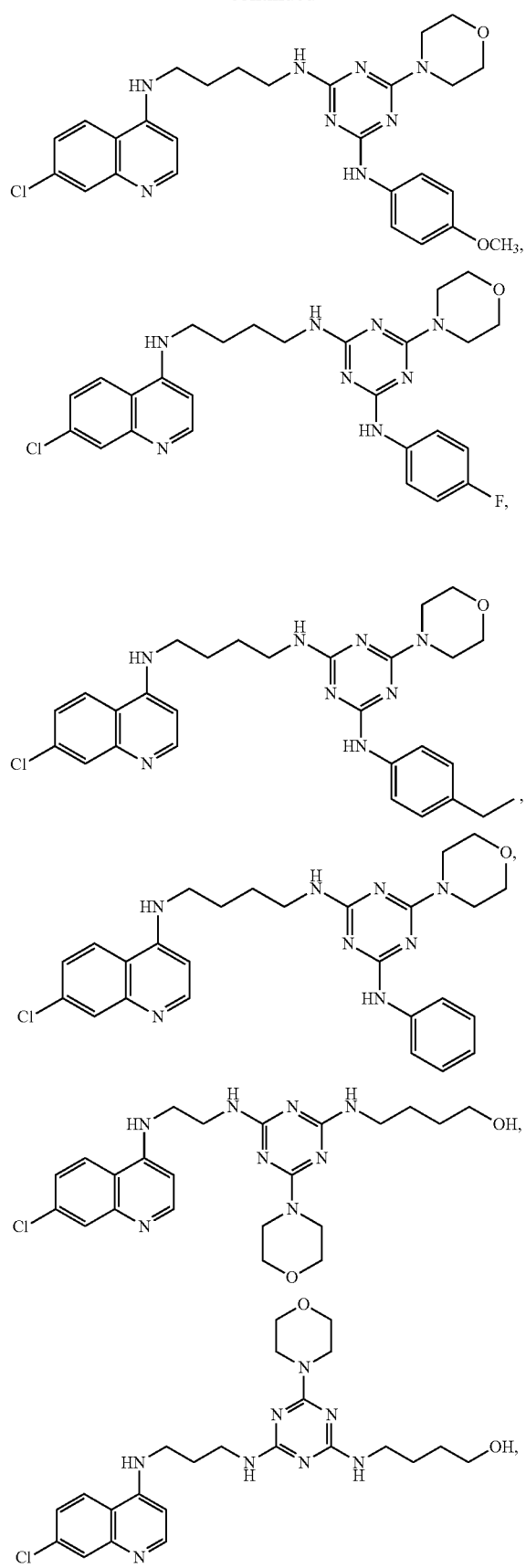
160
-continued
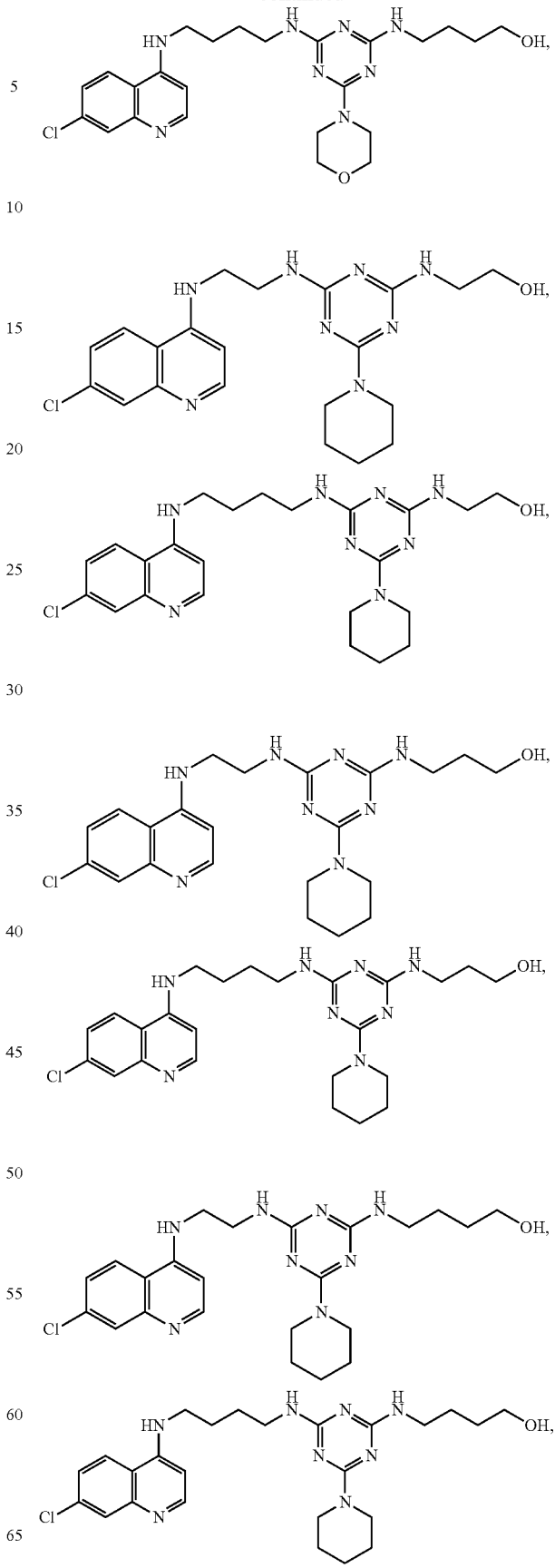

161
-continued
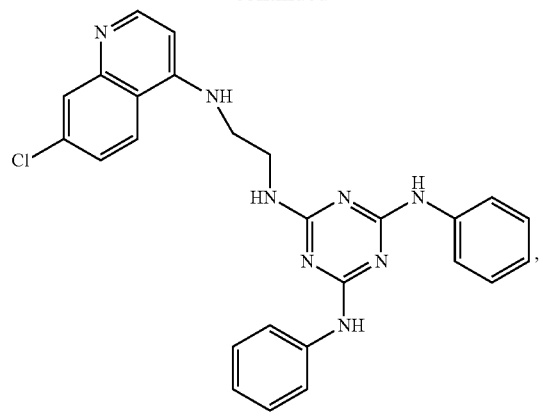
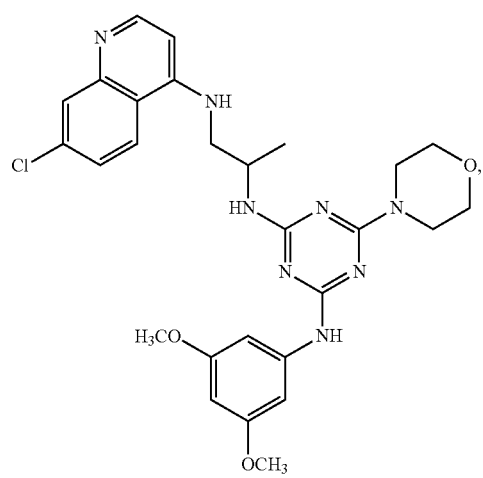
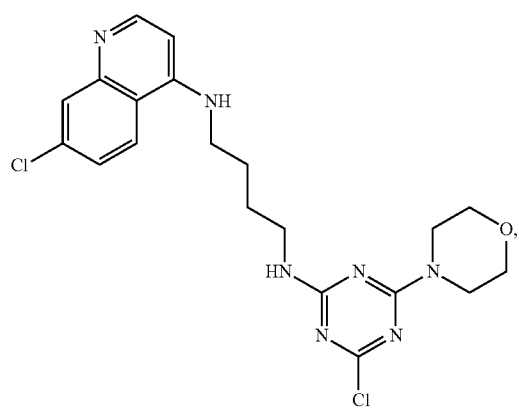
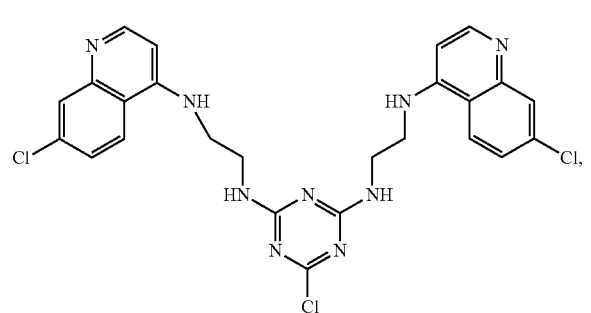
162
-continued
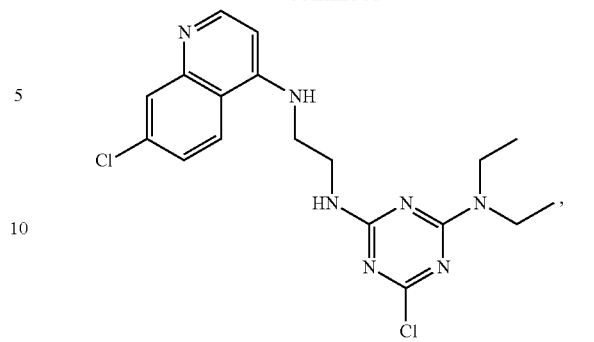
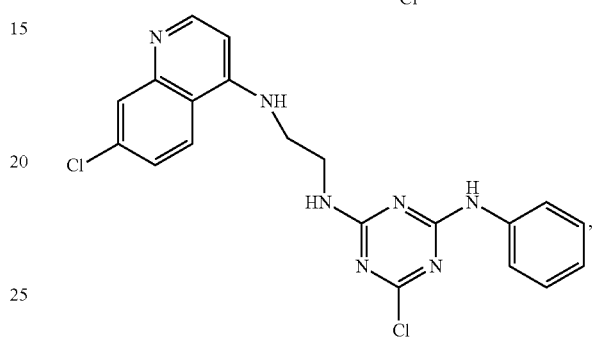
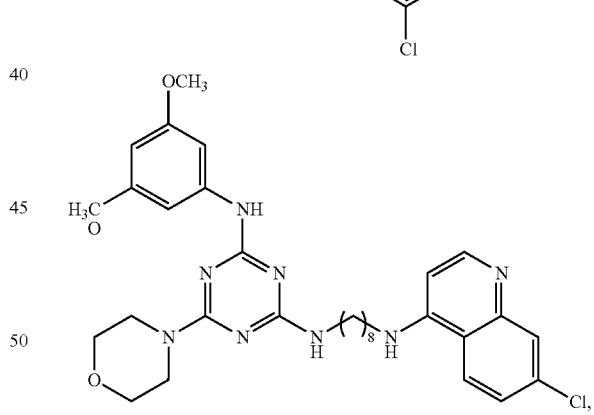
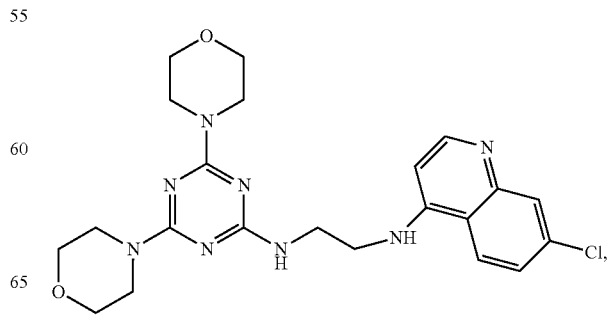

163
-continued
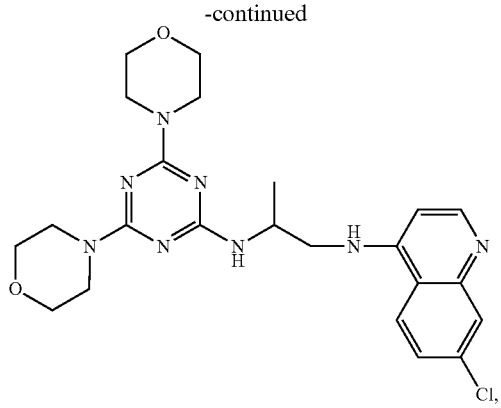
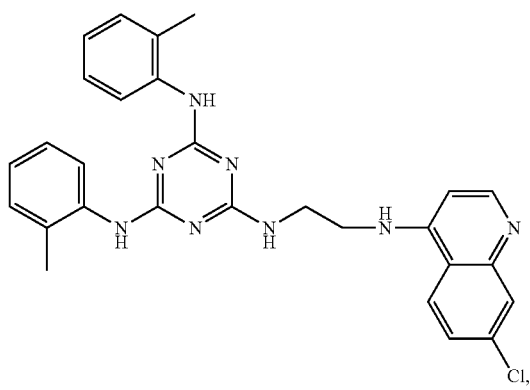
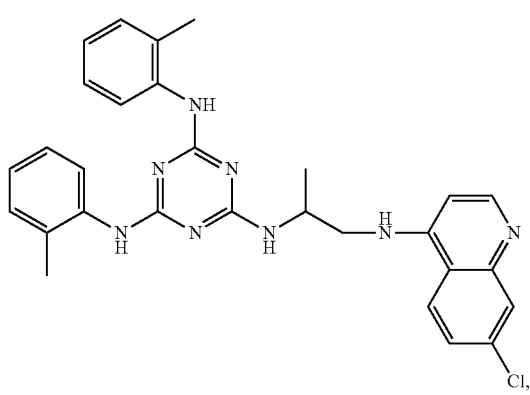
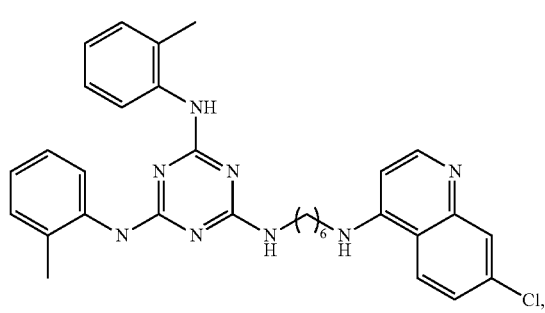
164
-continued
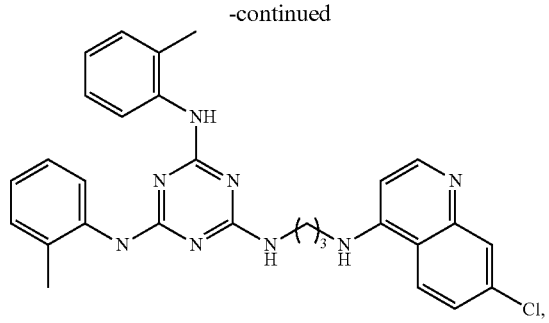
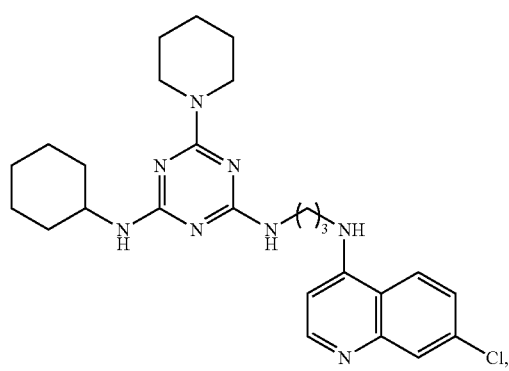
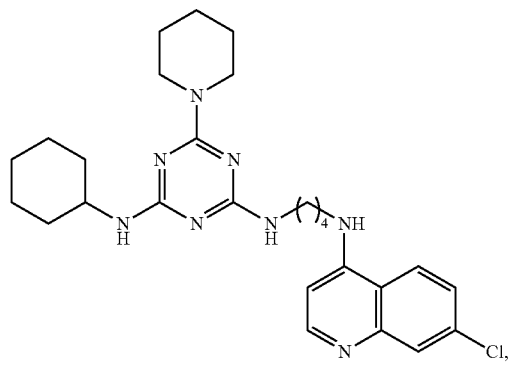
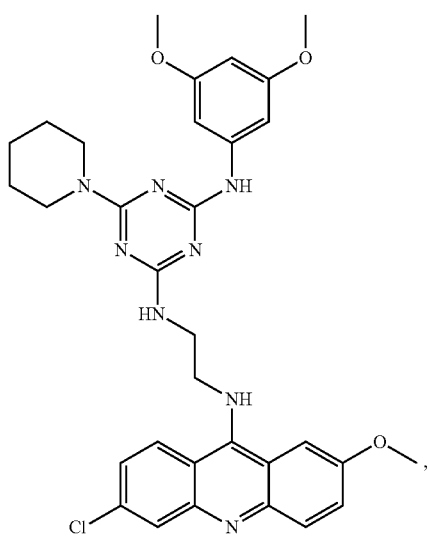

165
-continued
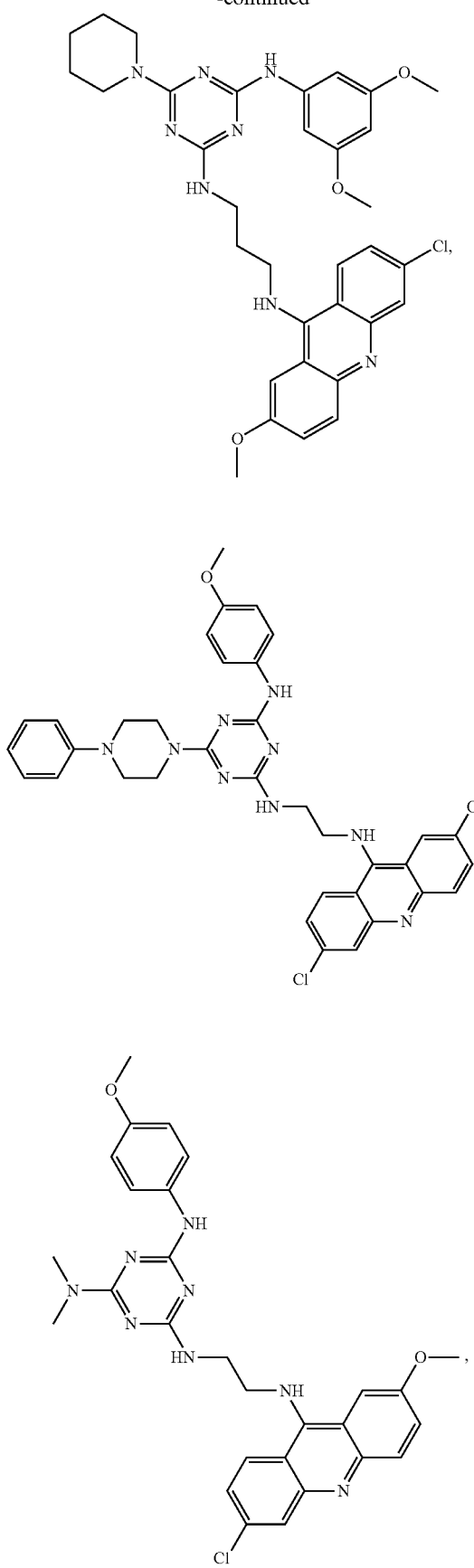
166
-continued
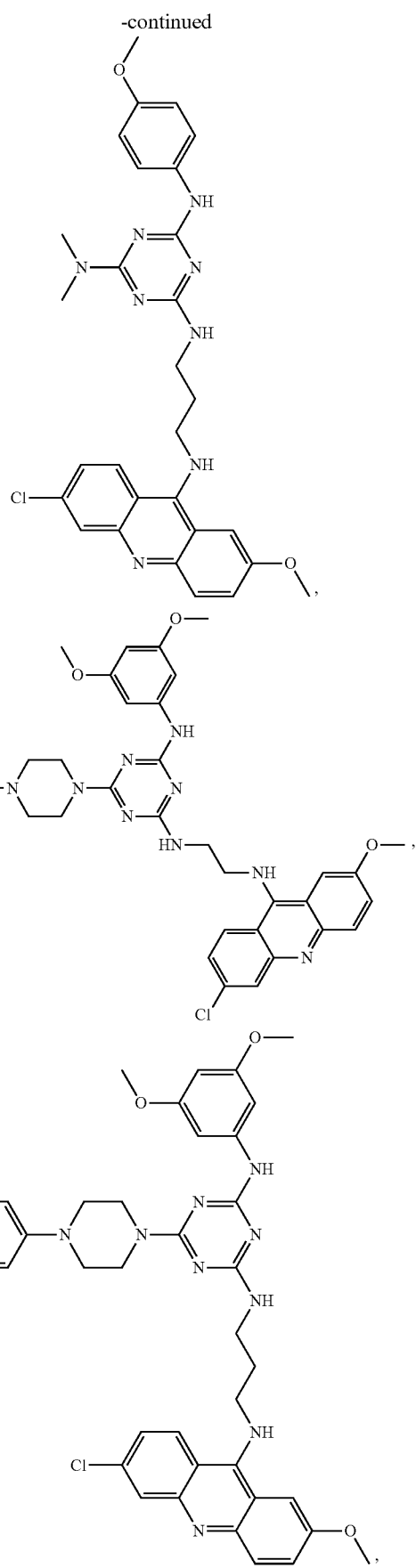

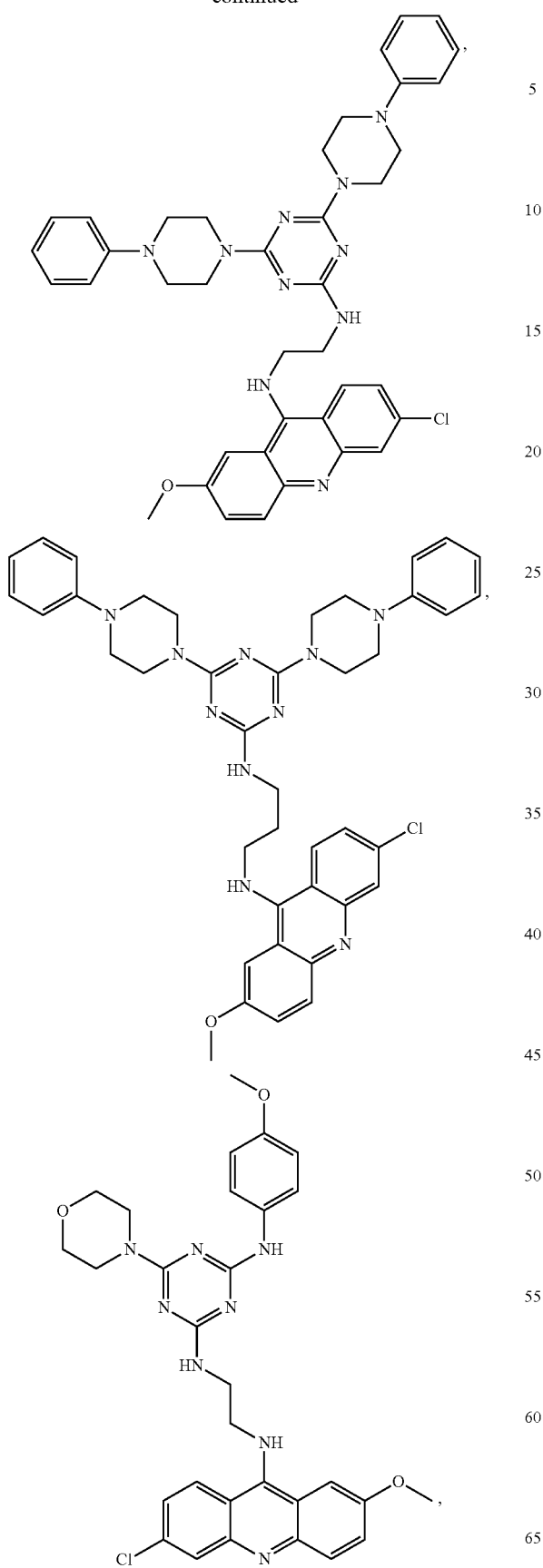

169
-continued
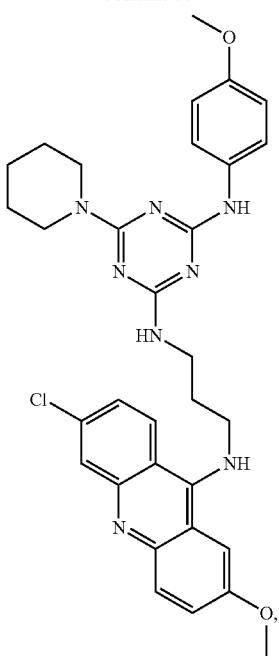
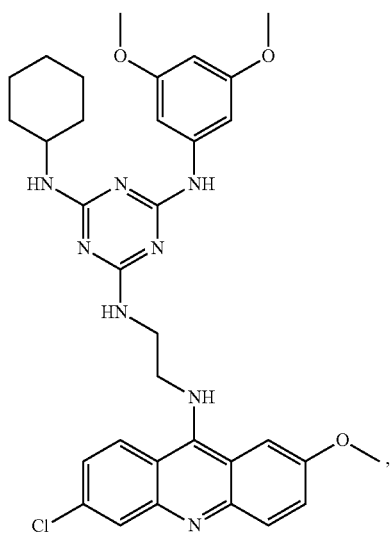
170
-continued
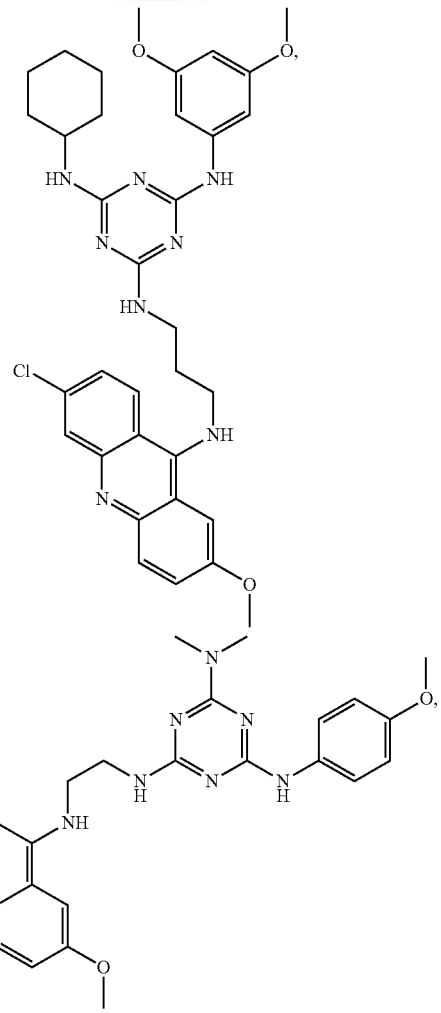

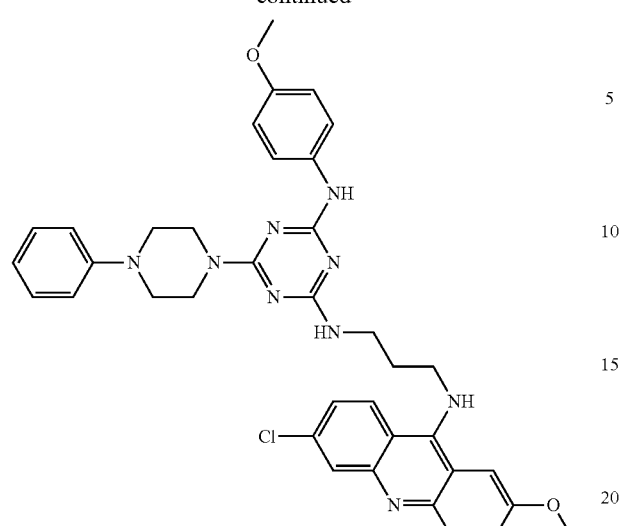
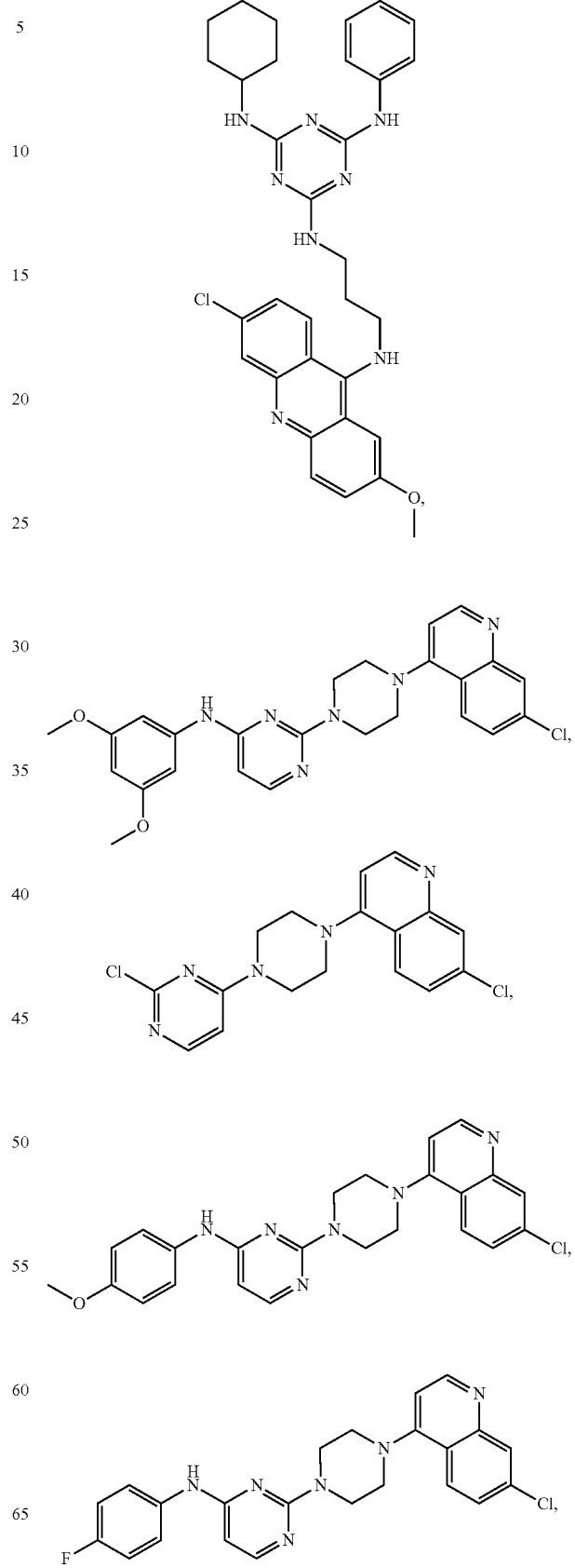

173
-continued
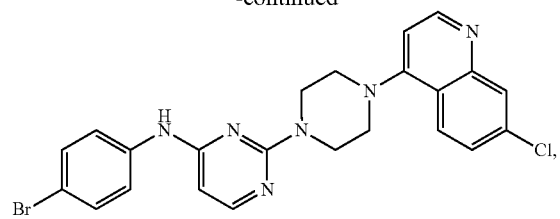
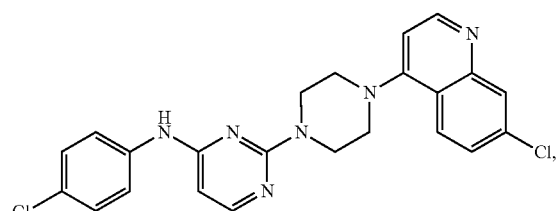
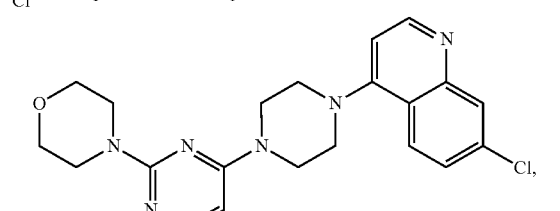
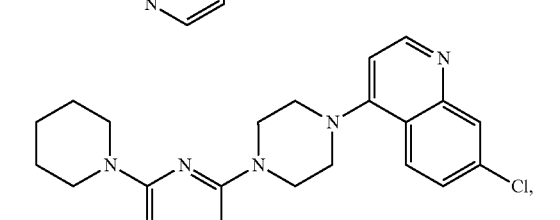
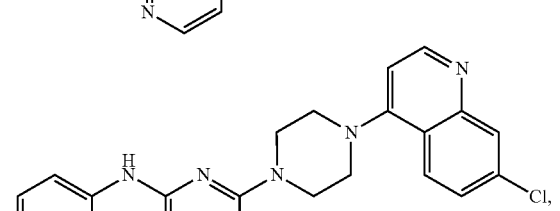
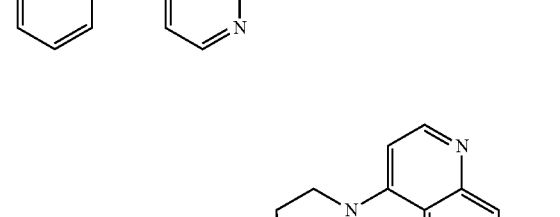
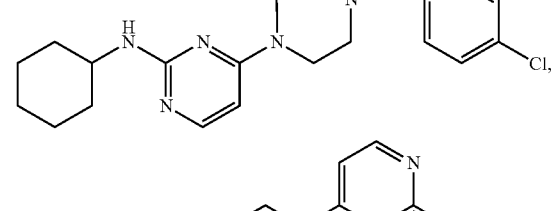
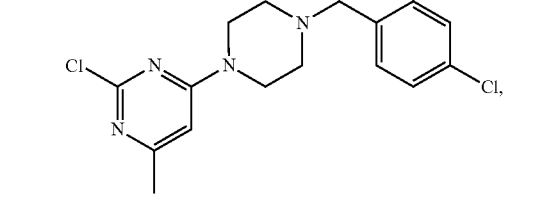
174
-continued
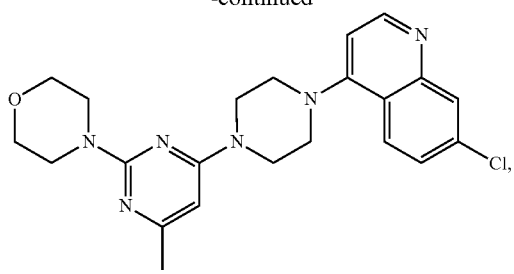
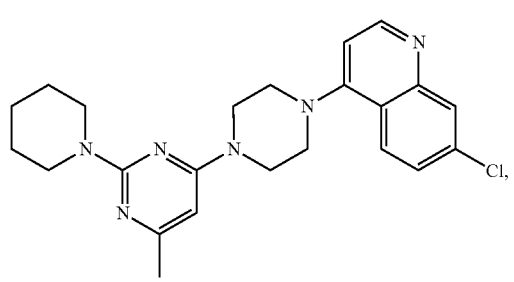
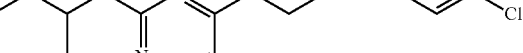

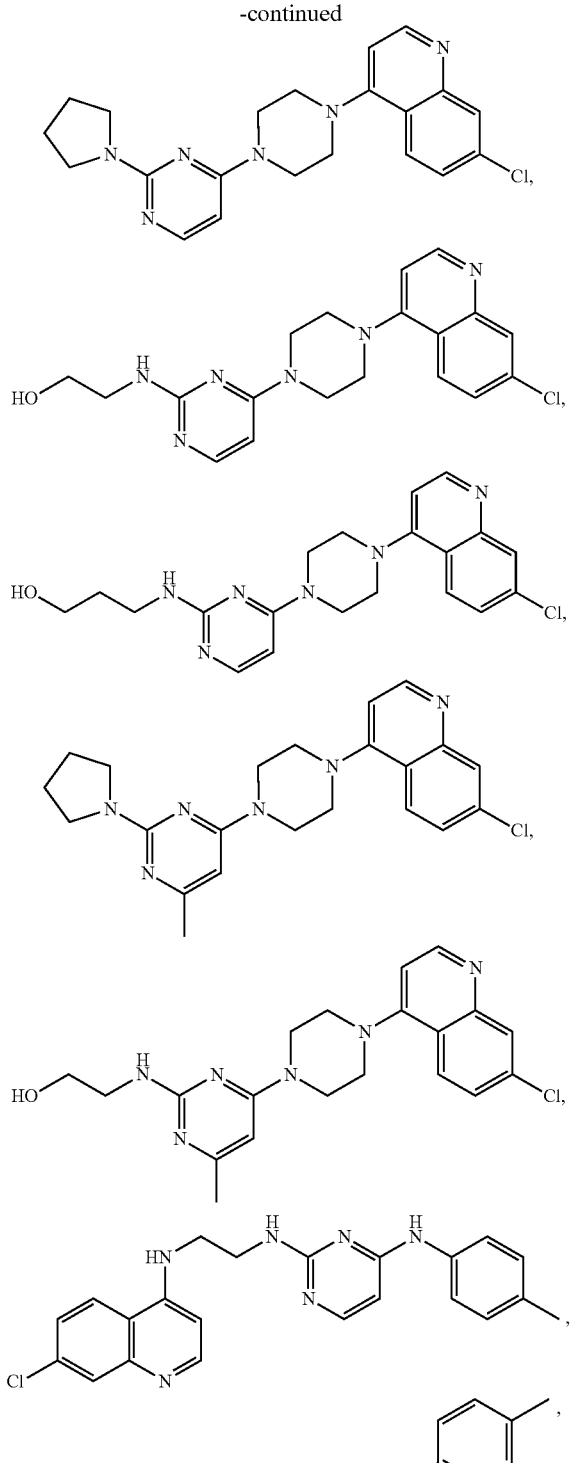
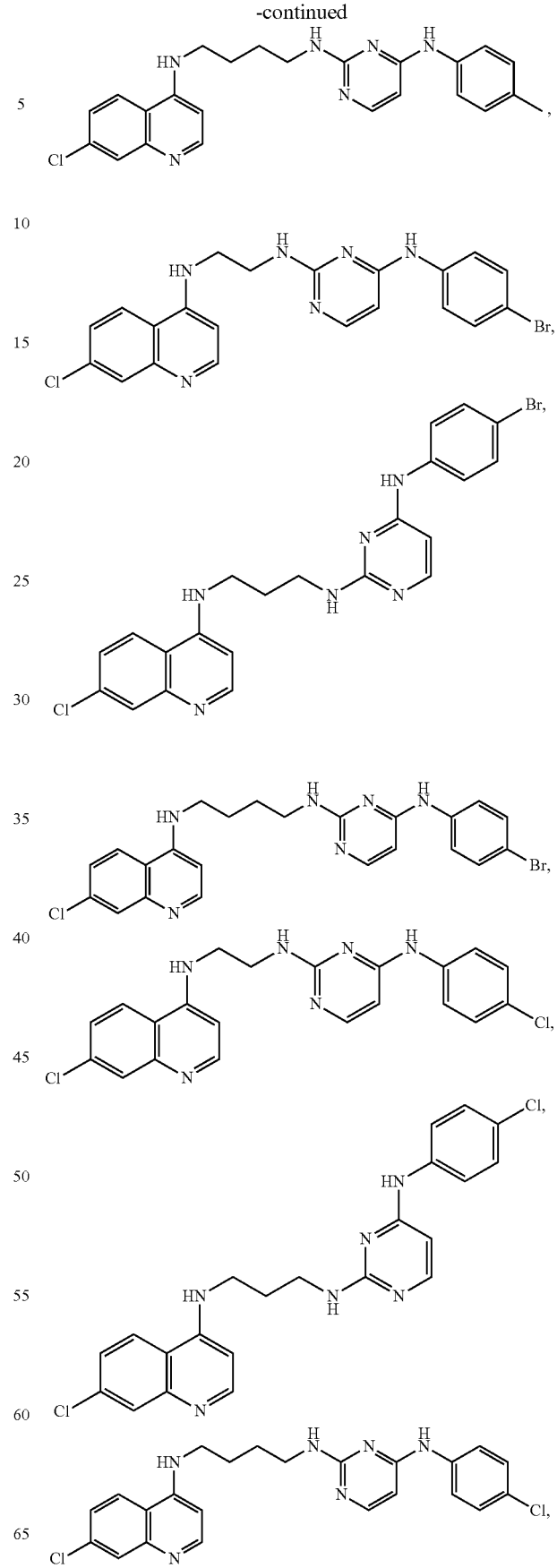

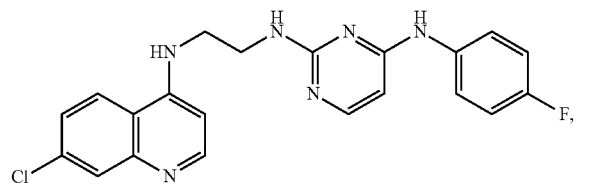
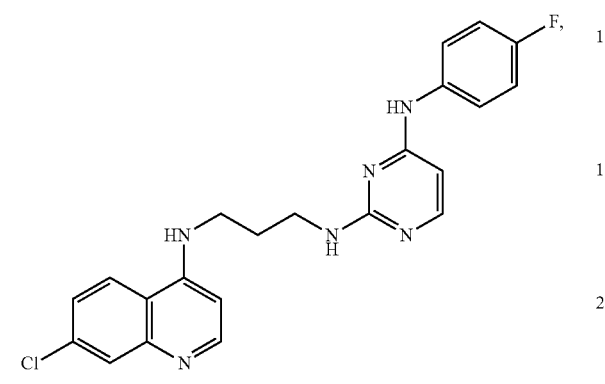
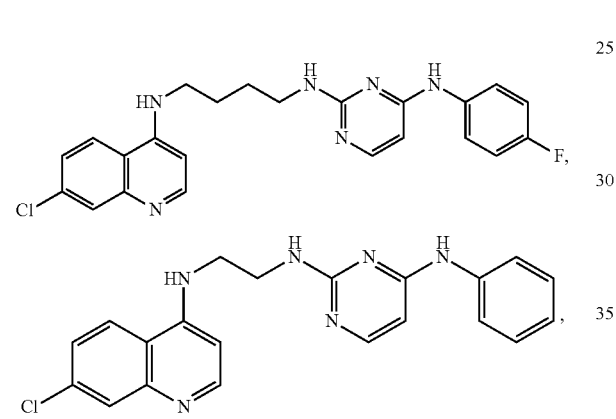
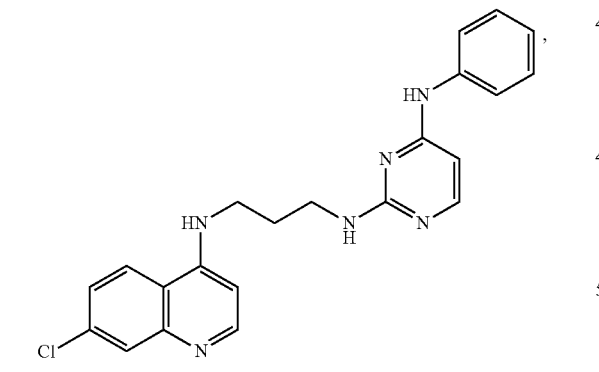
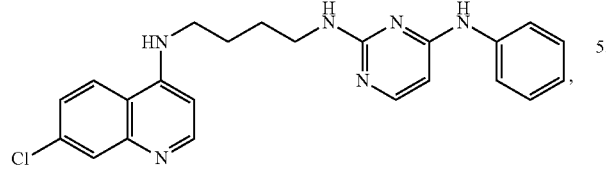
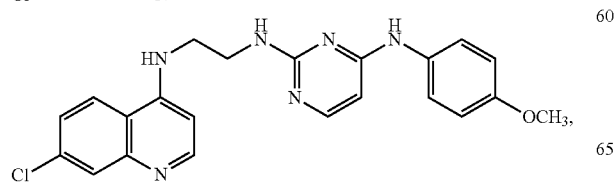
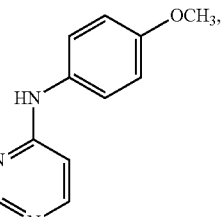
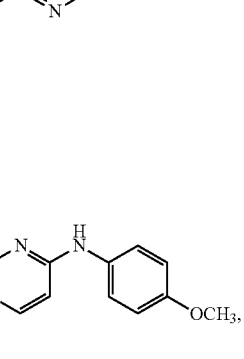
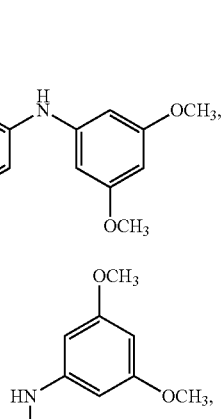
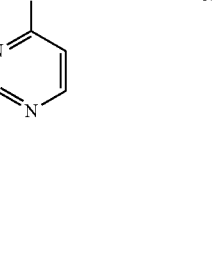
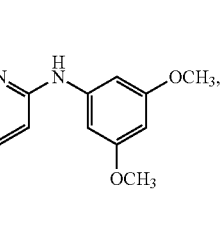
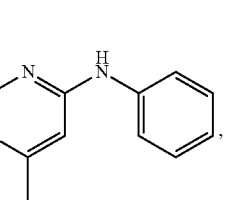

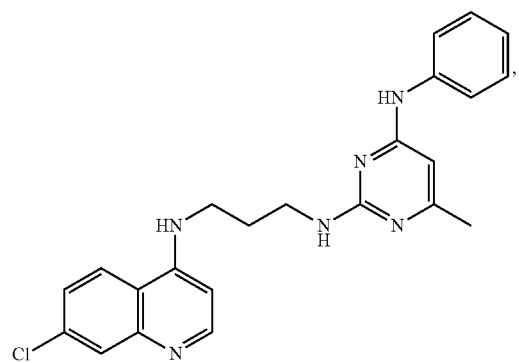
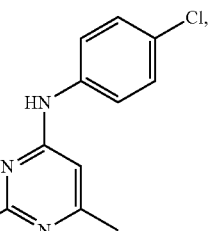
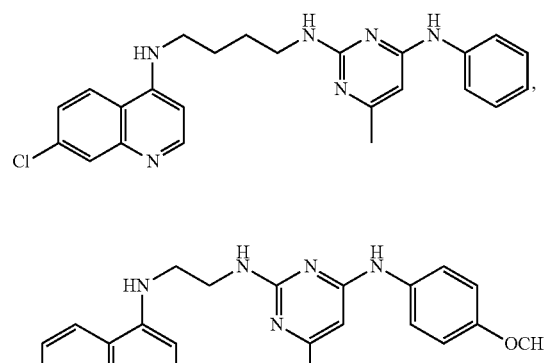
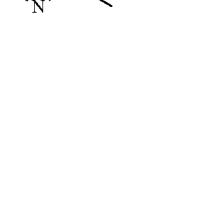
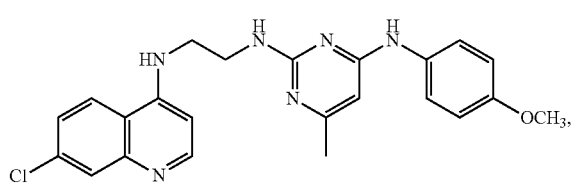
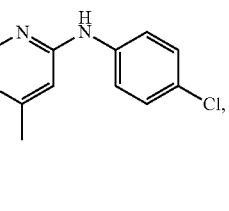
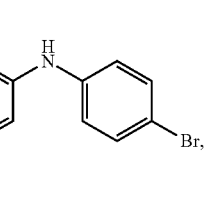
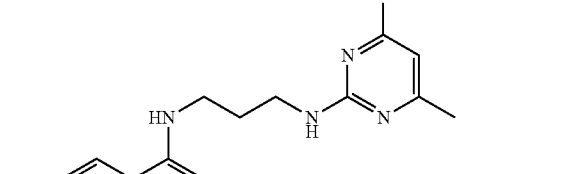
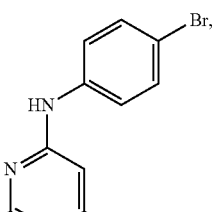
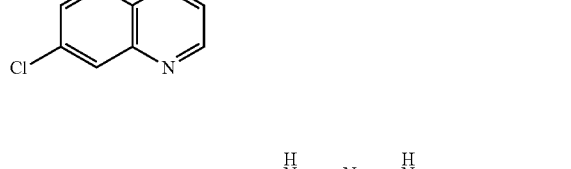
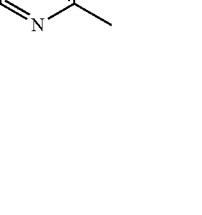

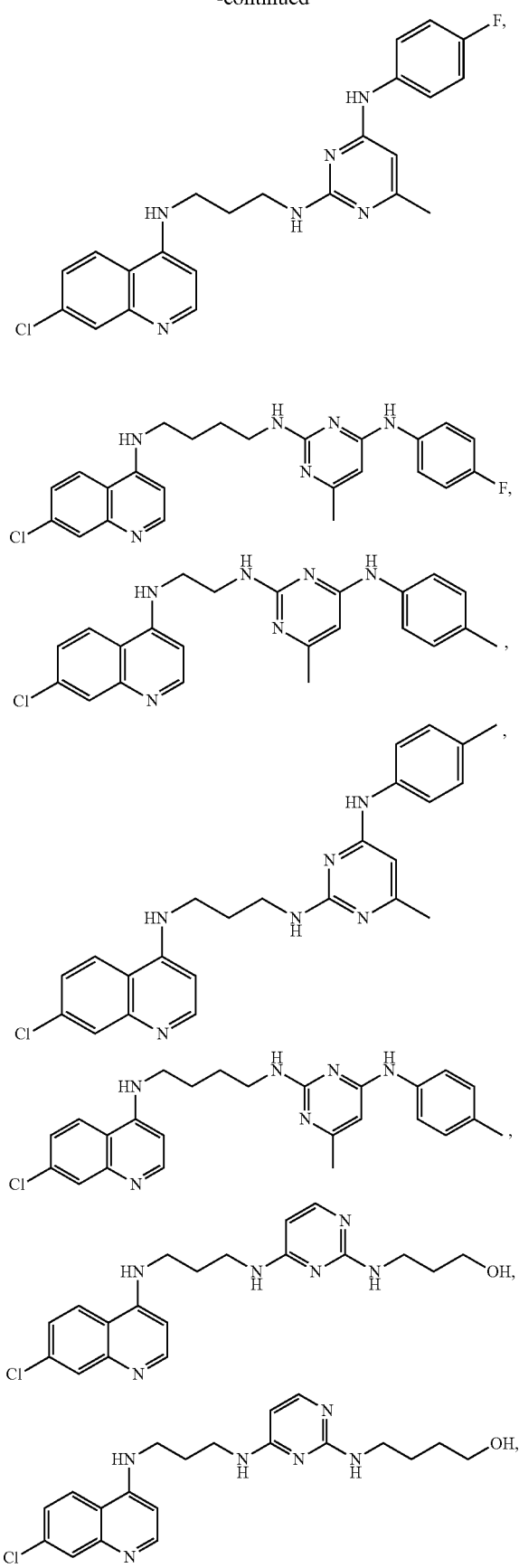
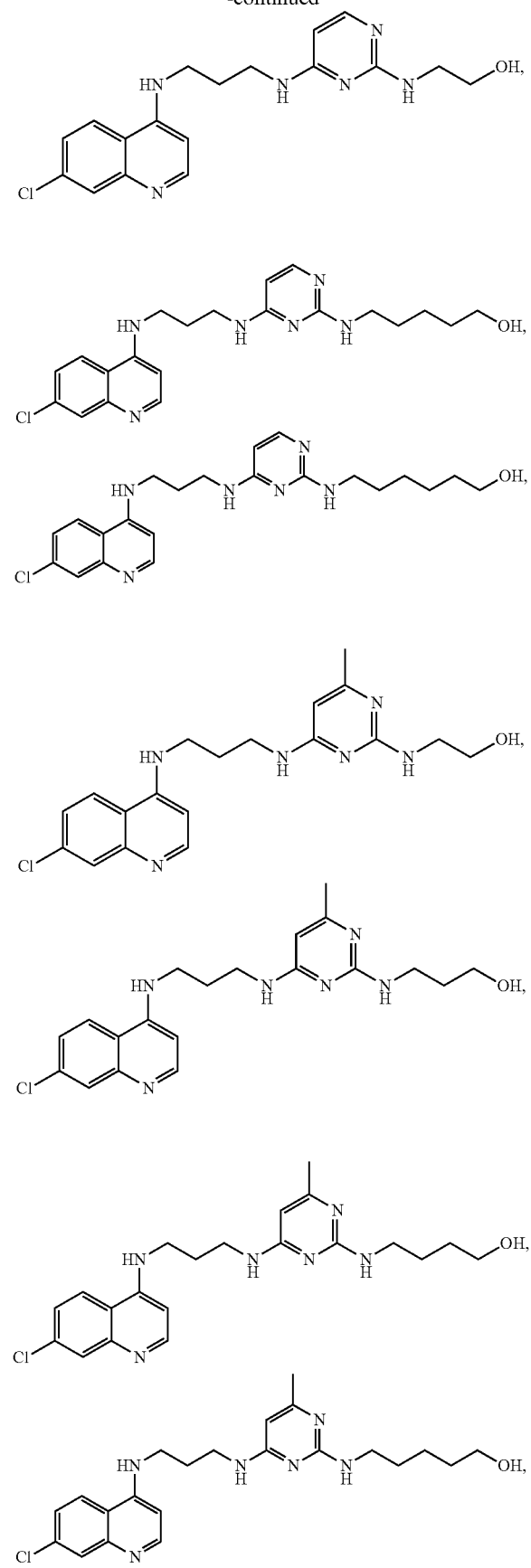

183
-continued
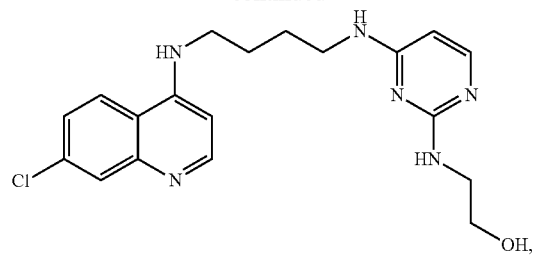
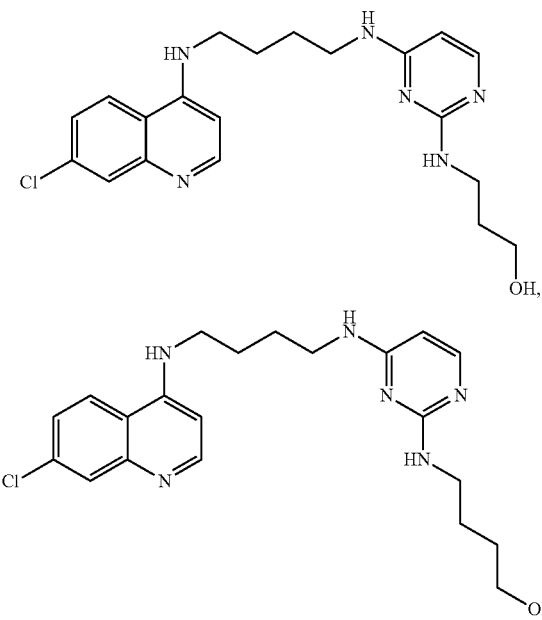
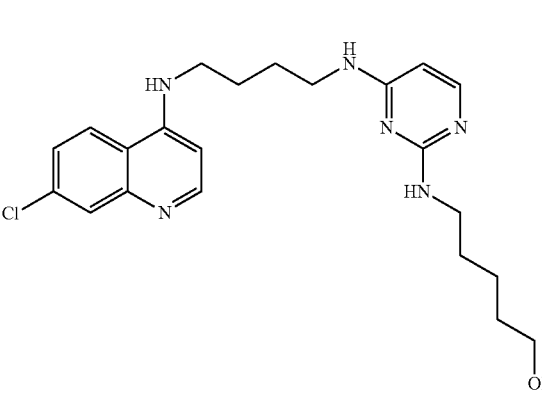
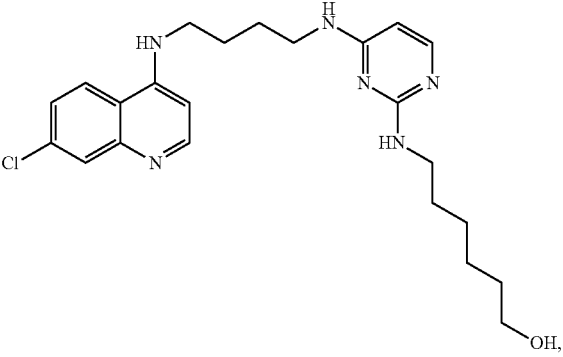
184
-continued
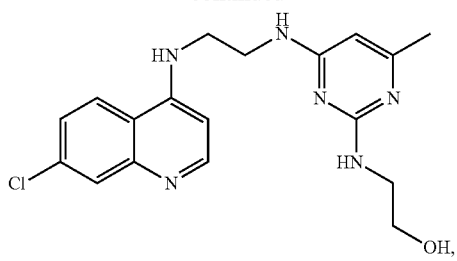
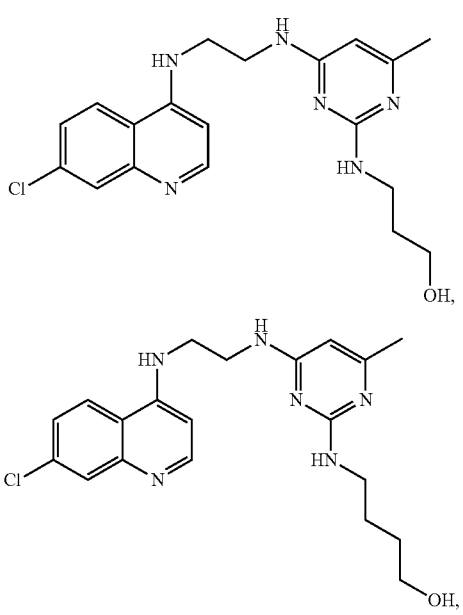
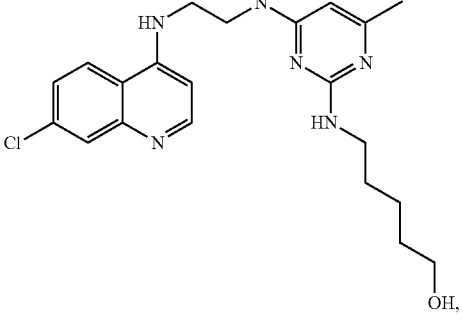
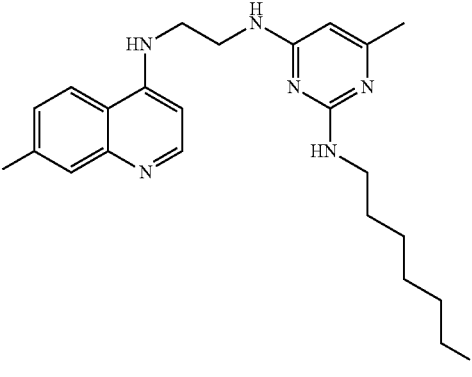

185
-continued
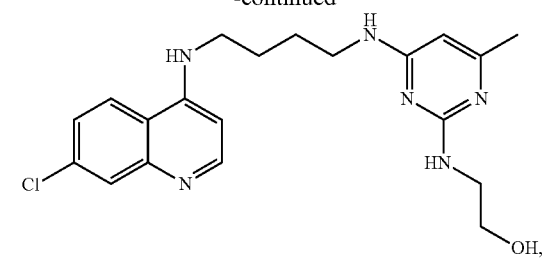
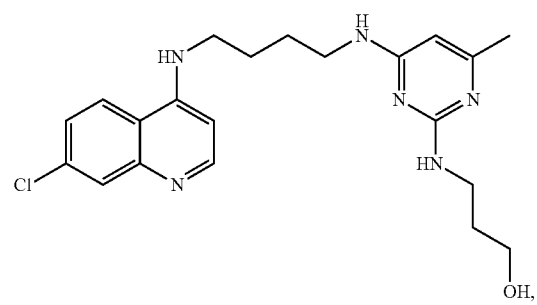
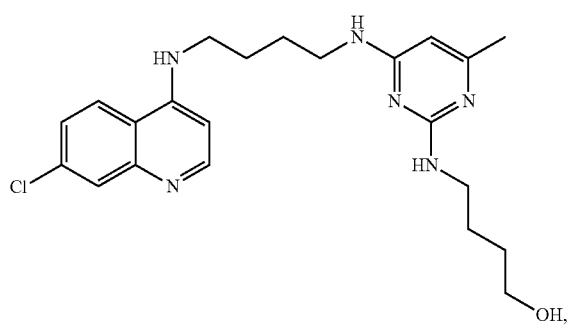
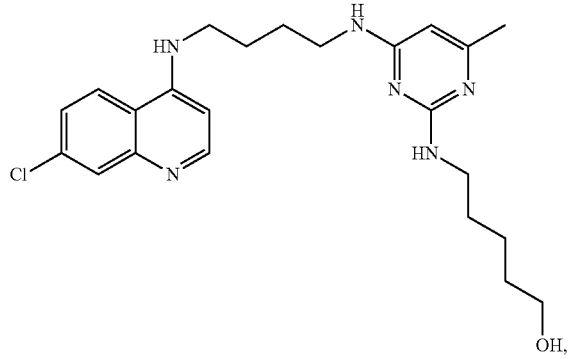
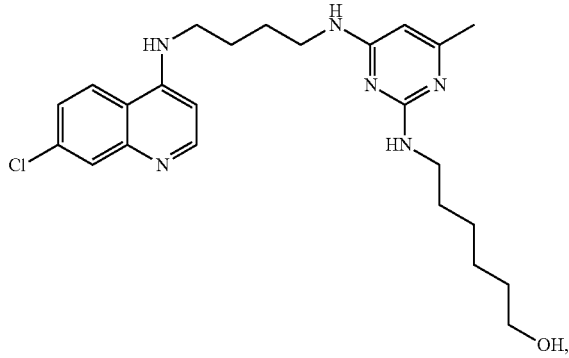
186
-continued
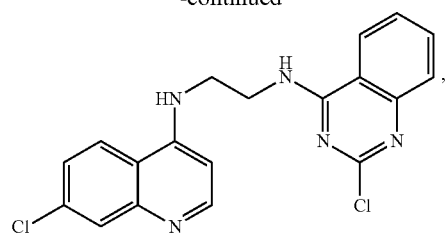
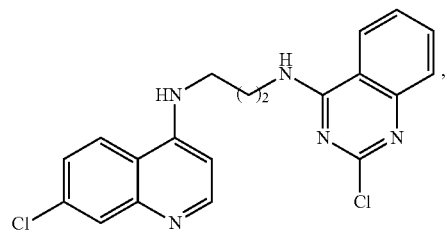
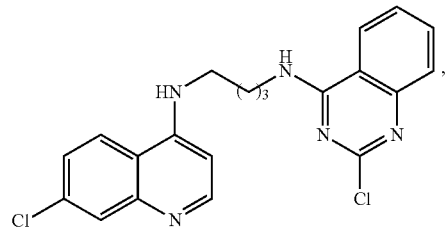
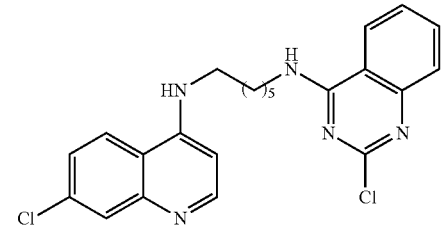
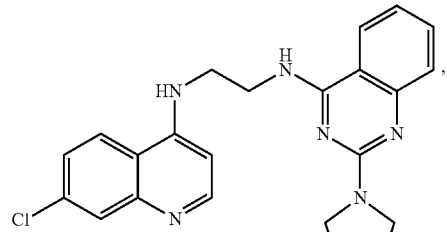
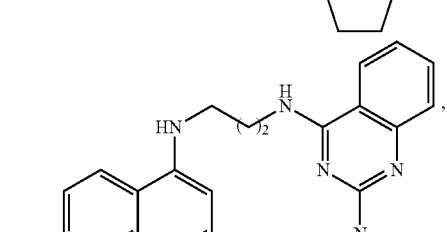
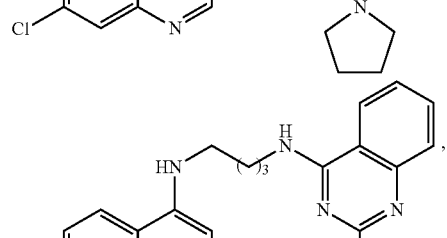
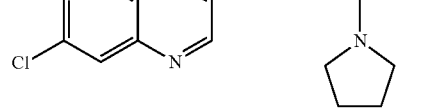

187
-continued
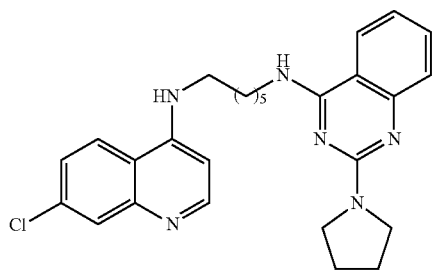
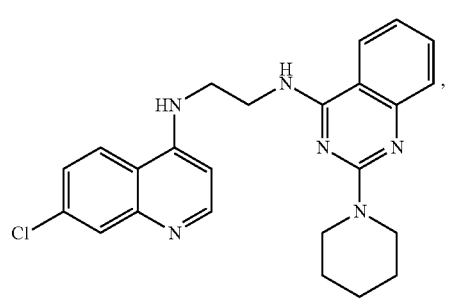
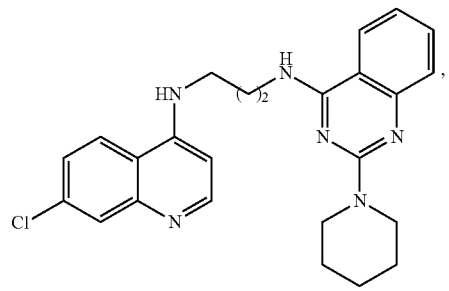
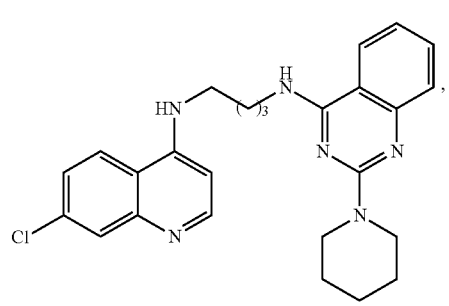
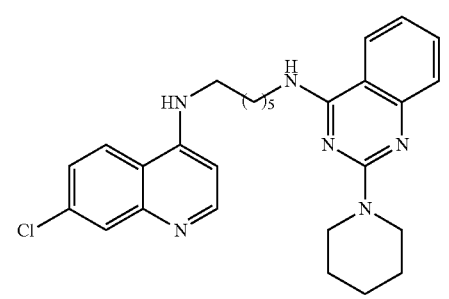
188
-continued
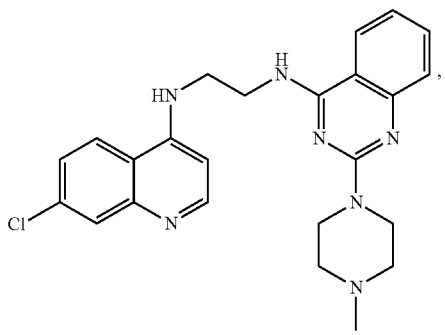
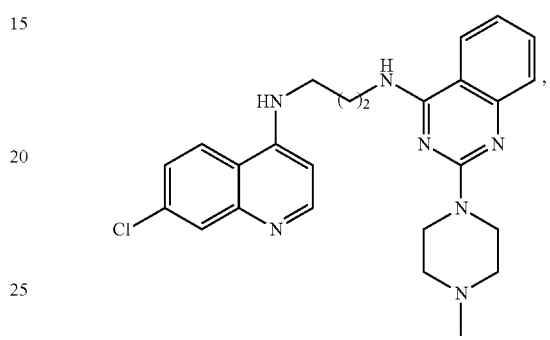
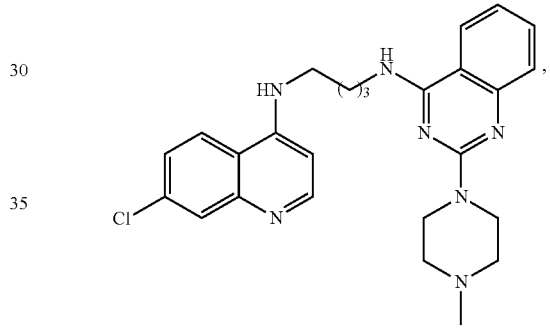
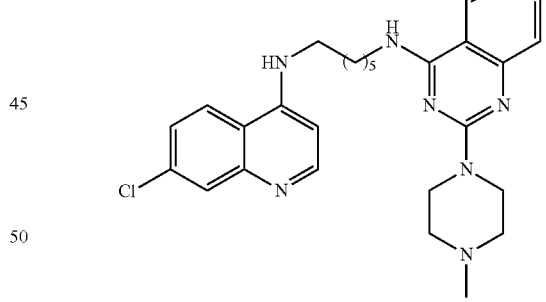
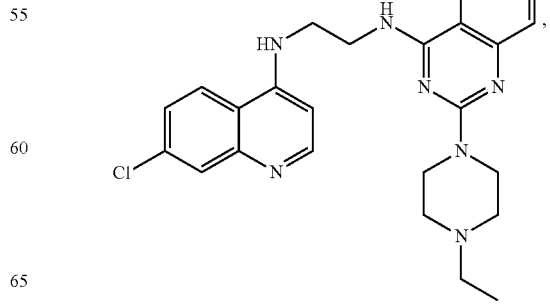

189

190

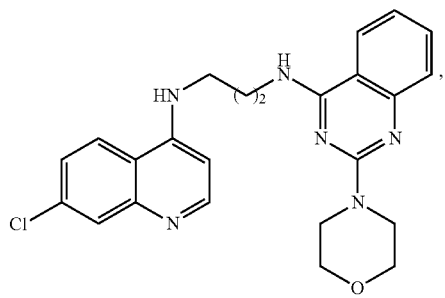
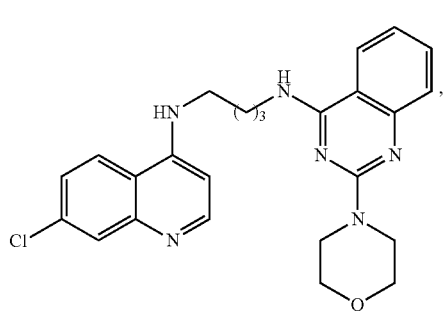
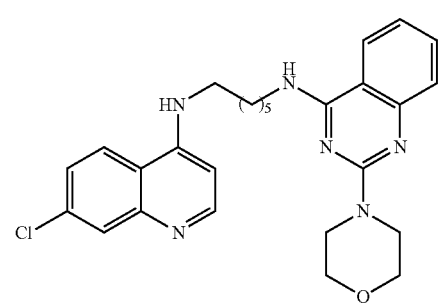
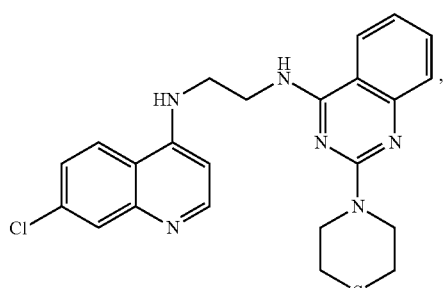
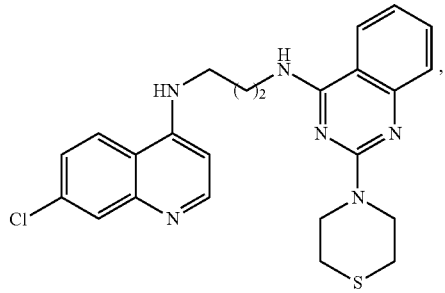
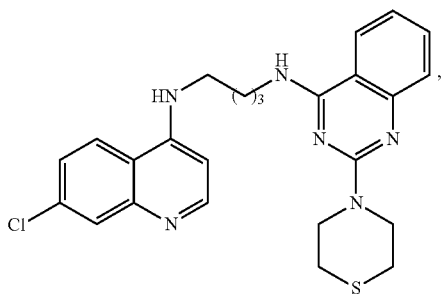
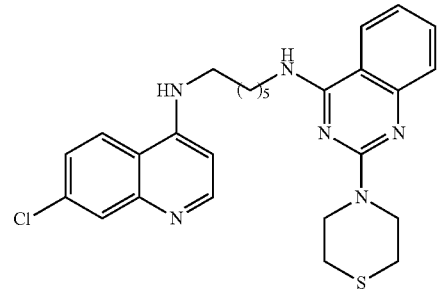
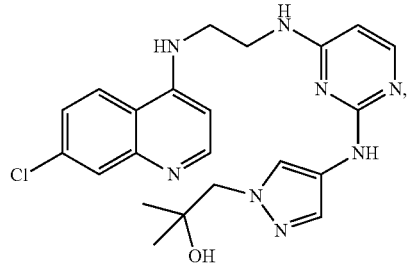
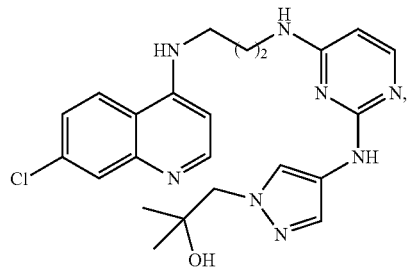
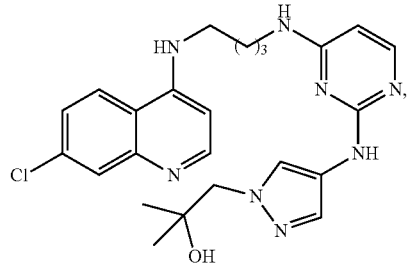
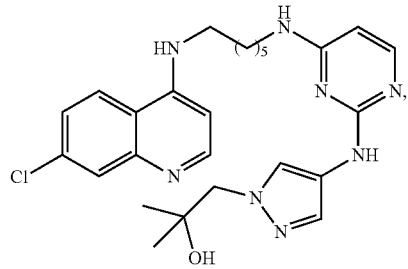

193
-continued
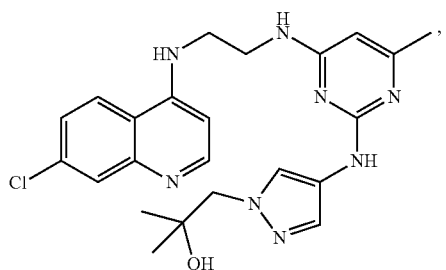
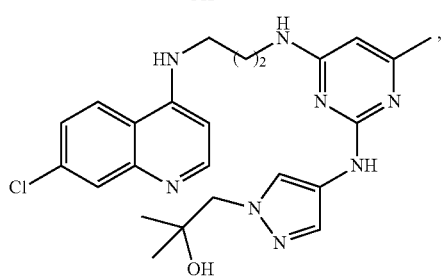
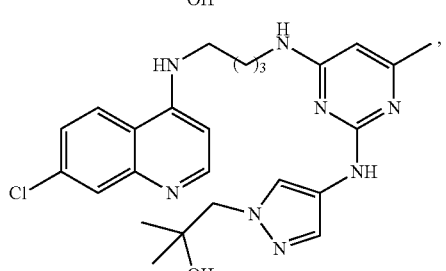
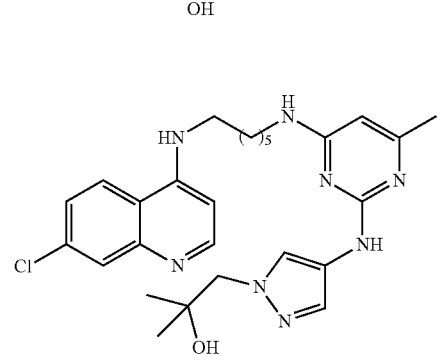
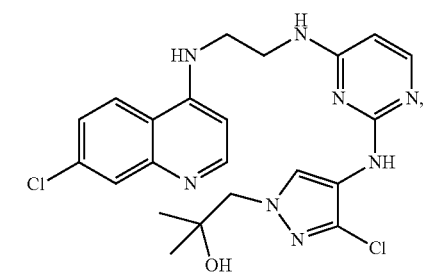
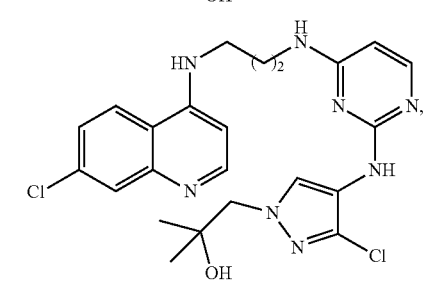
194
-continued
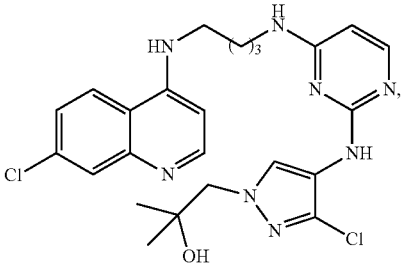
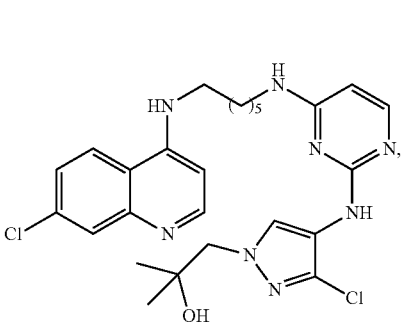
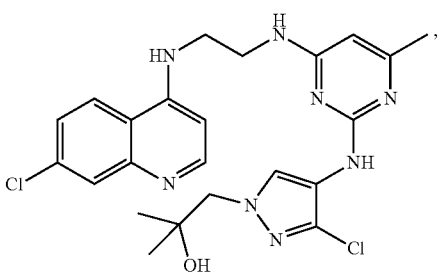
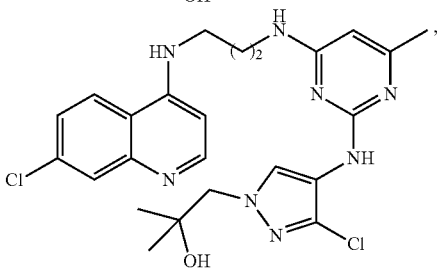
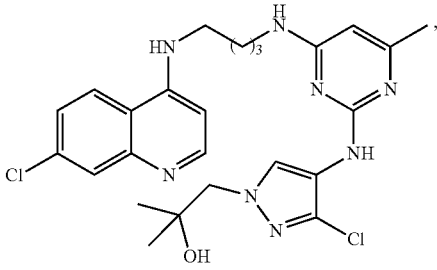
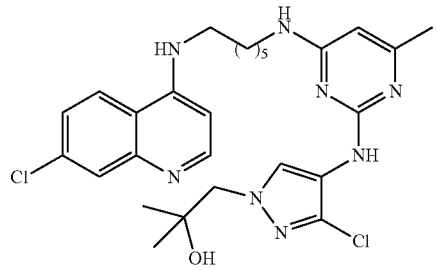

-continued
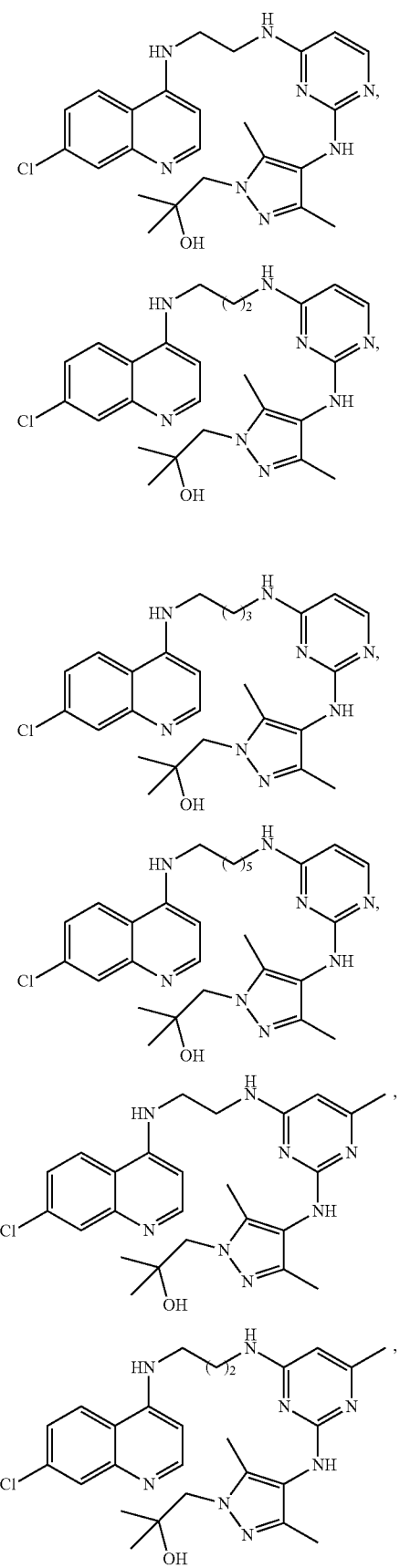
-continued
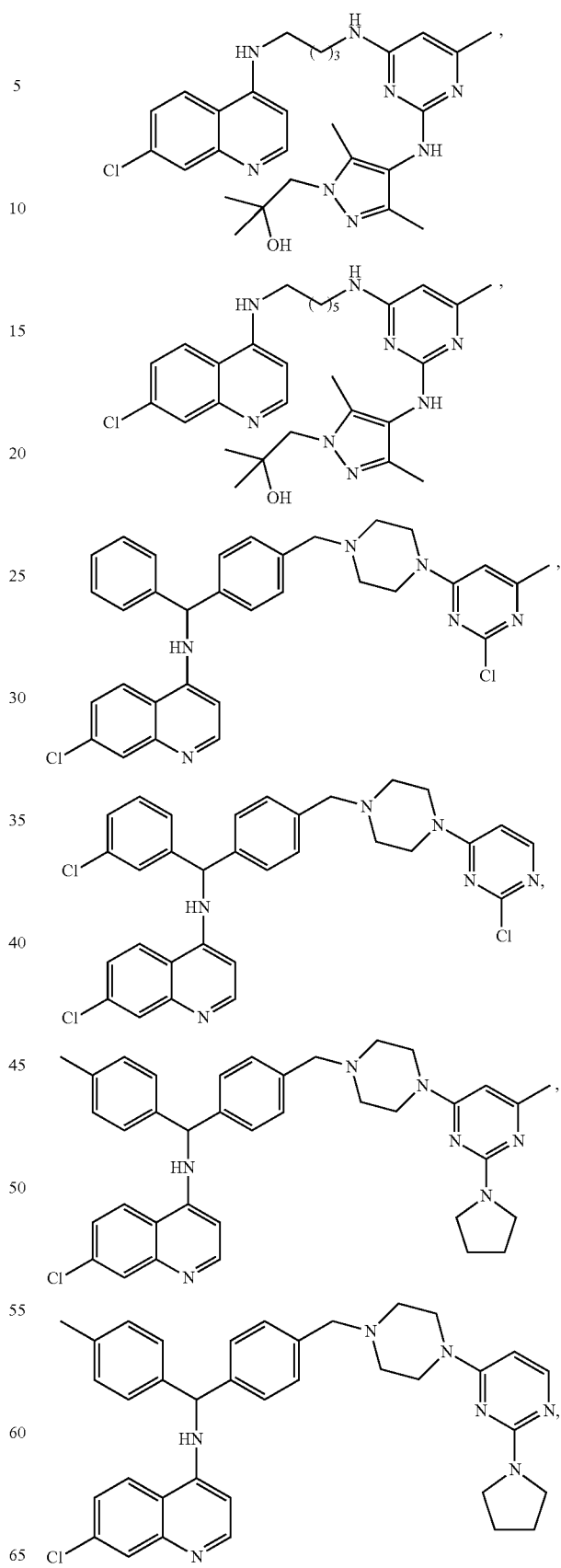

197
-continued
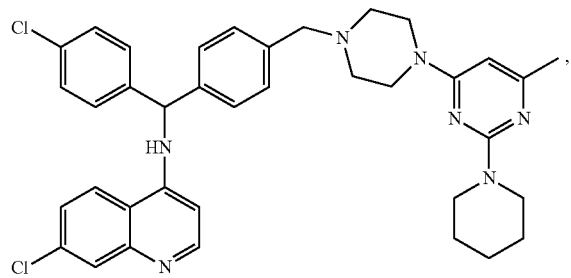
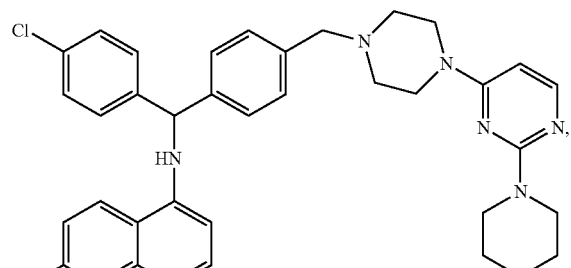
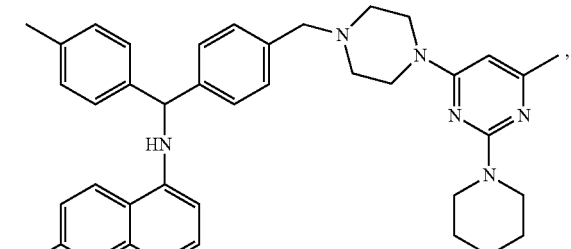
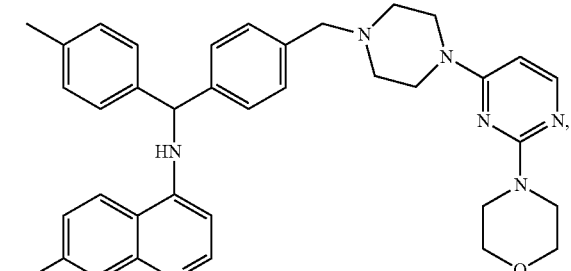
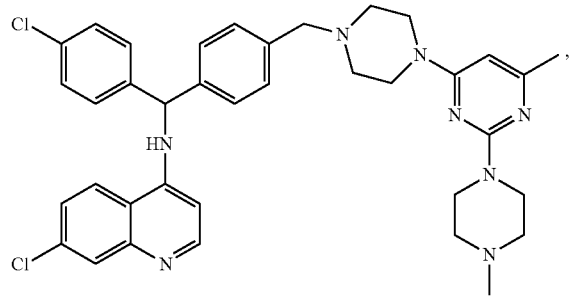
198
-continued
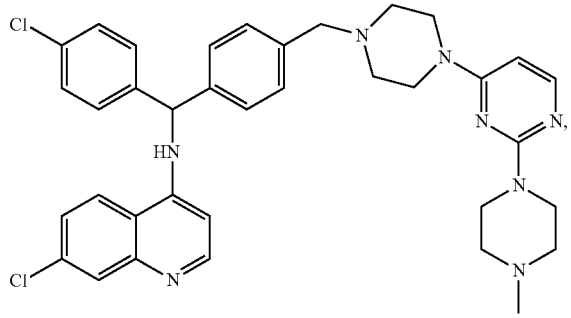
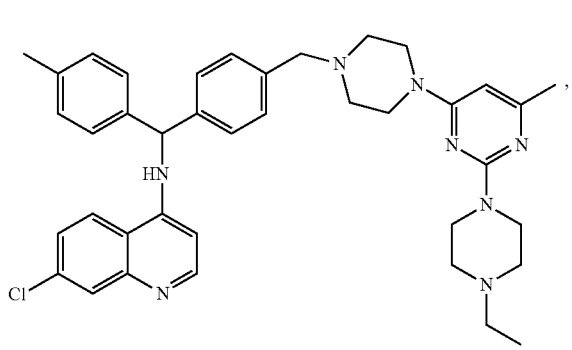
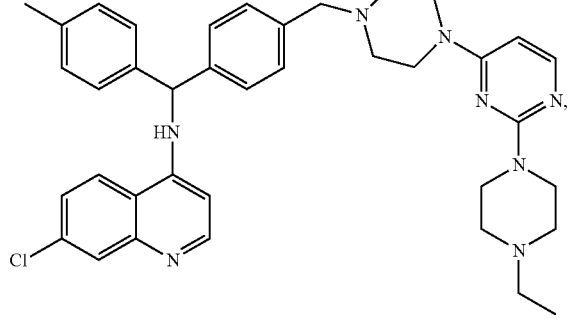
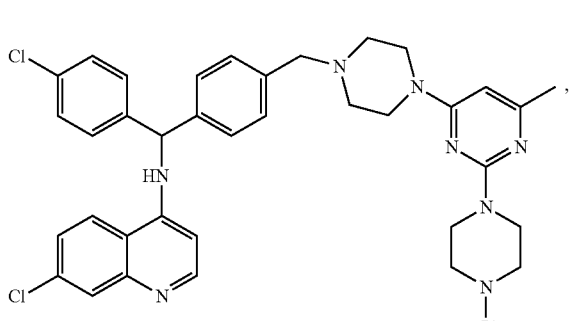
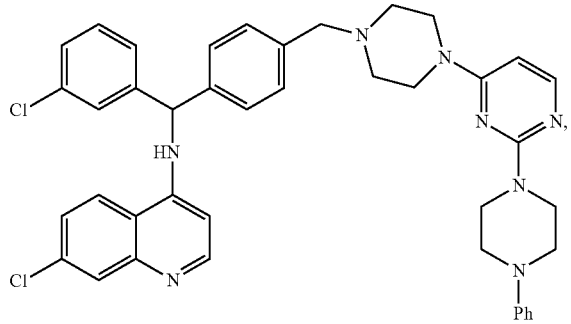

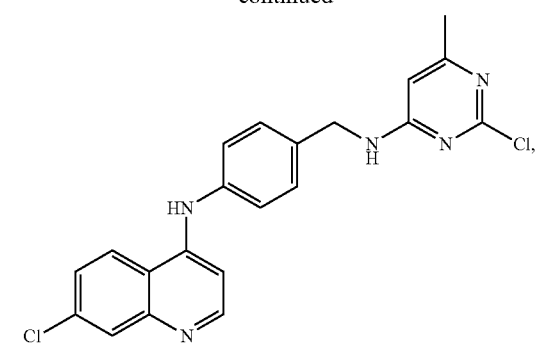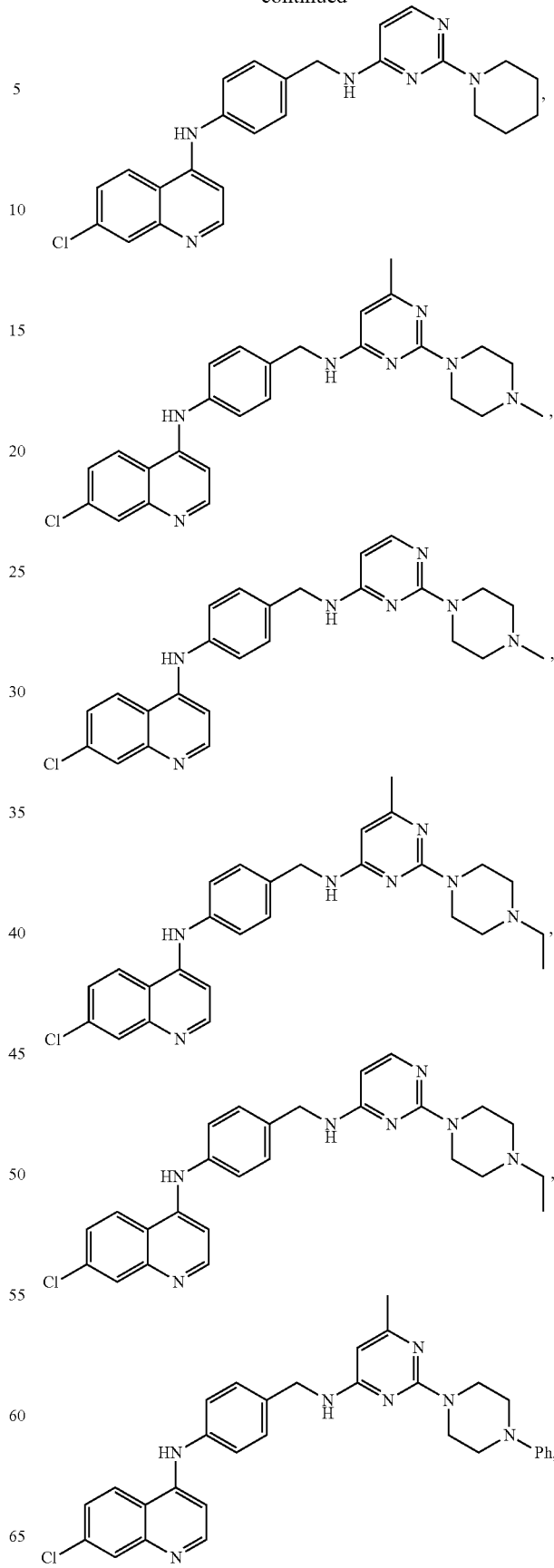

201
-continued
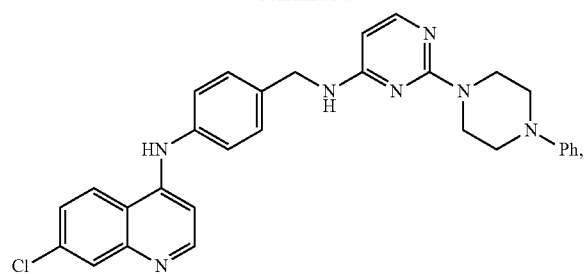
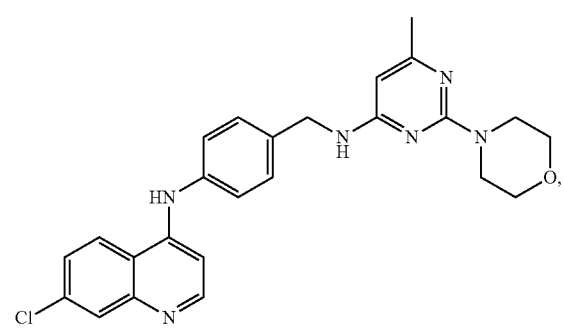
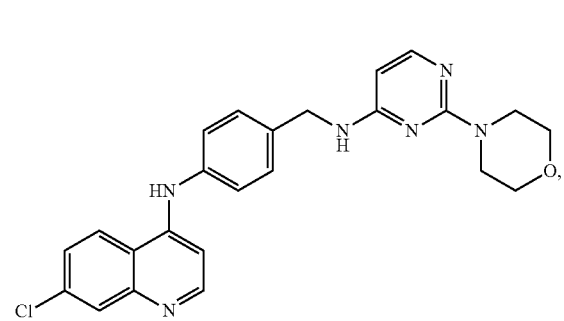
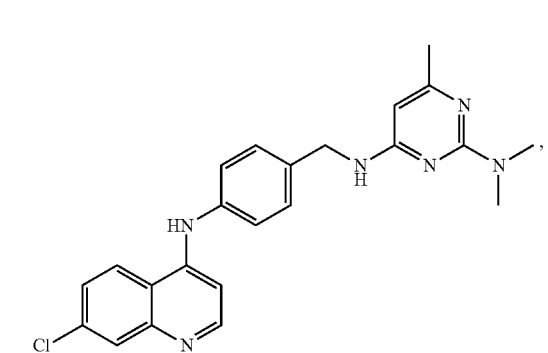
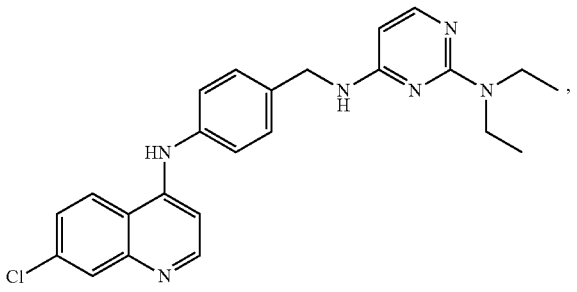
202
-continued
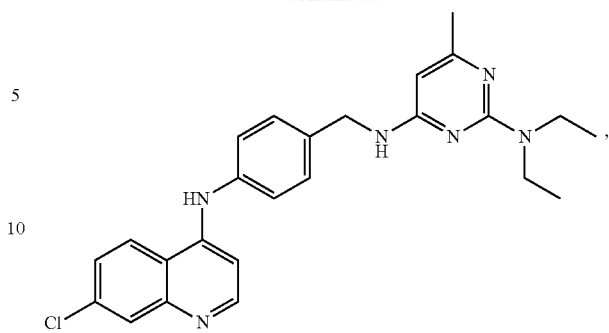
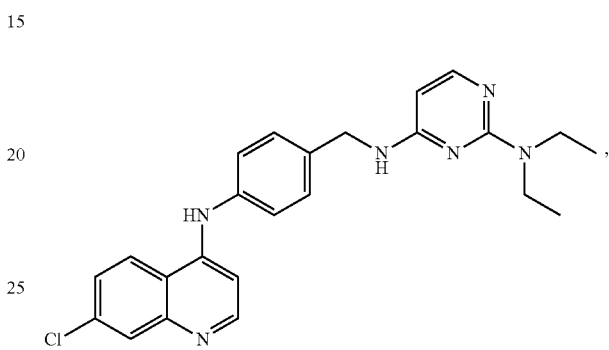
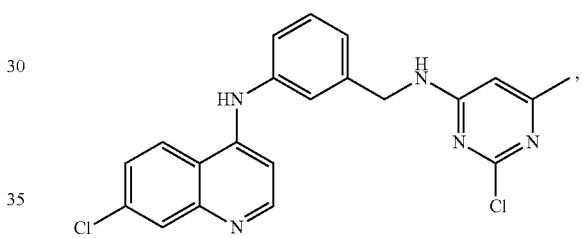
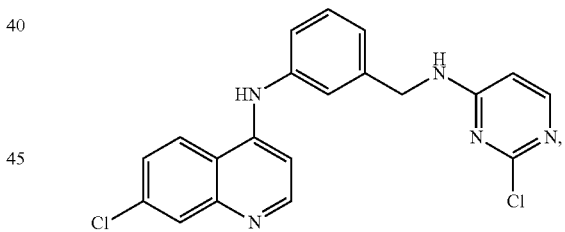
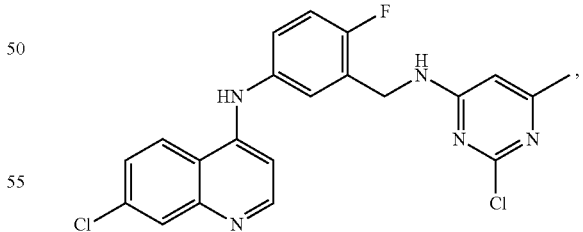
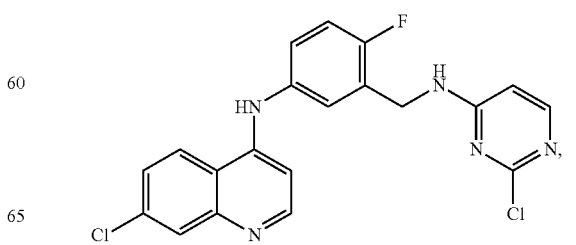

203
-continued
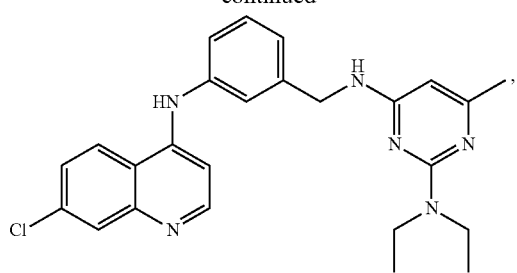
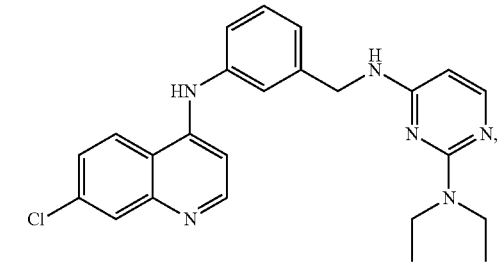
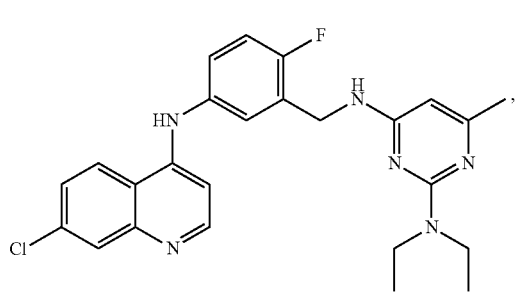
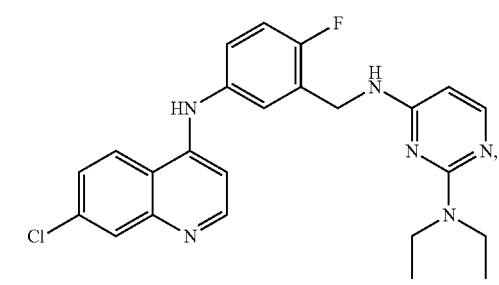
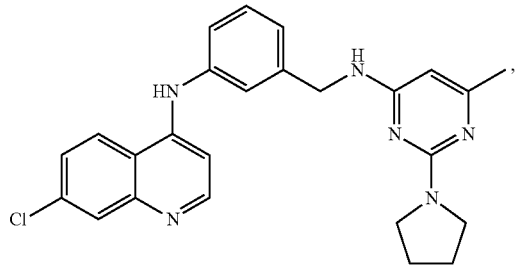
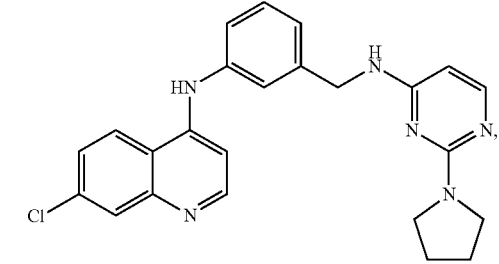
204
-continued
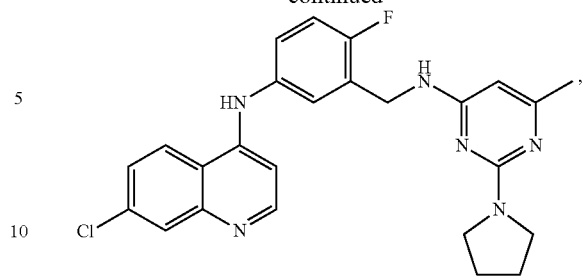
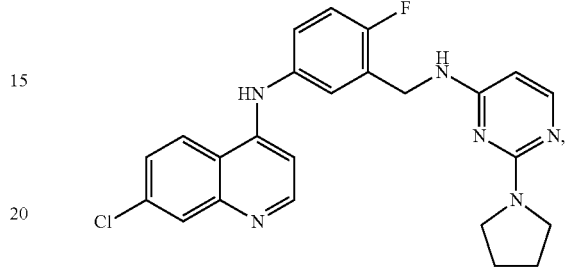
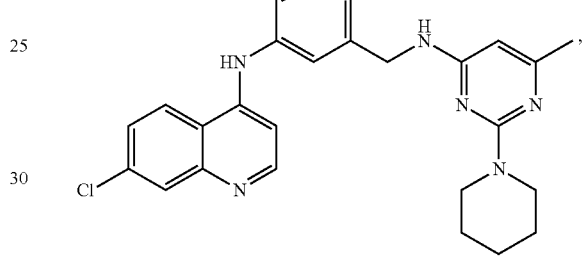
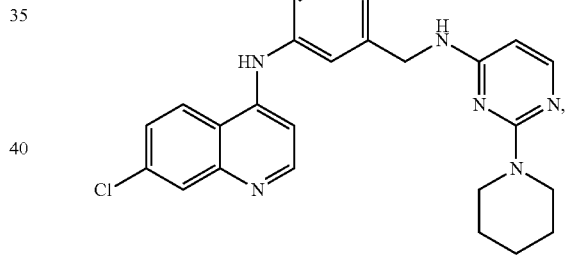
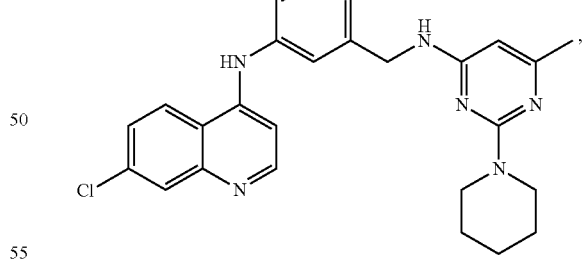
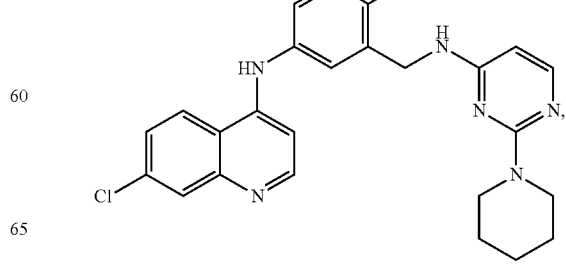

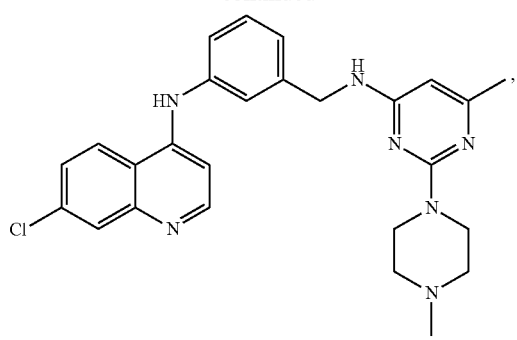
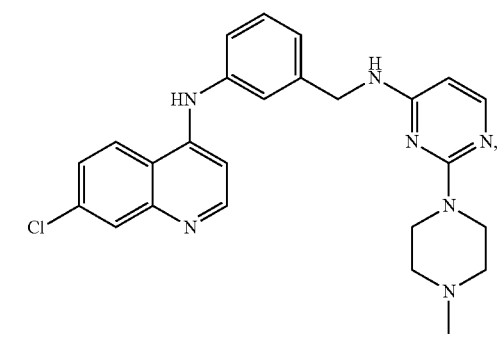
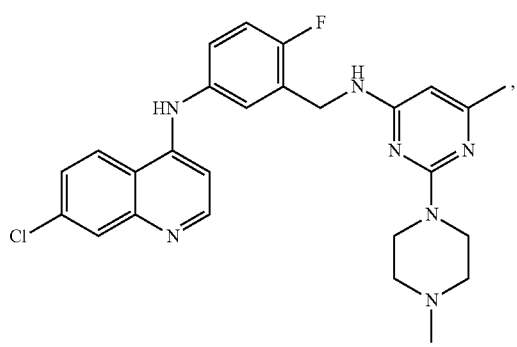
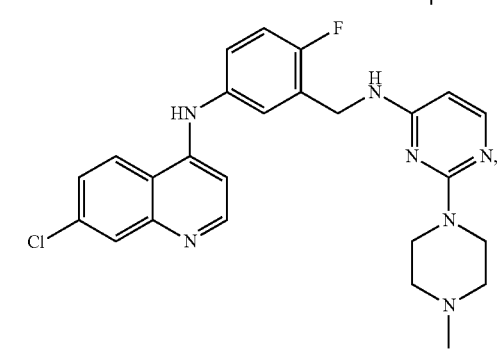
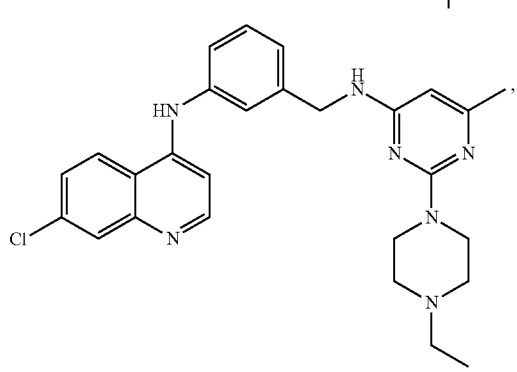
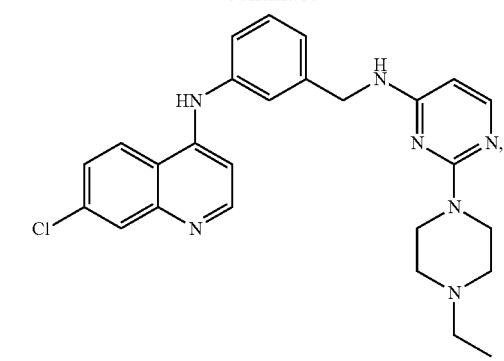
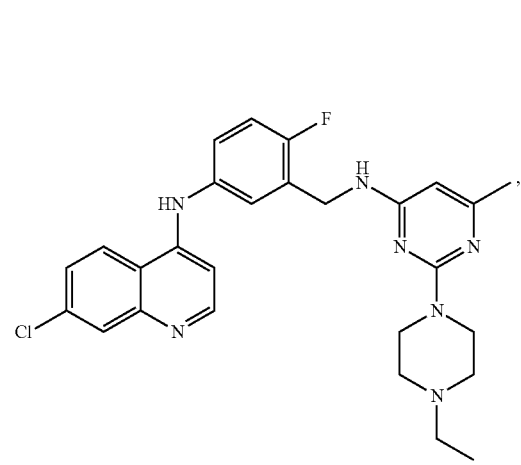
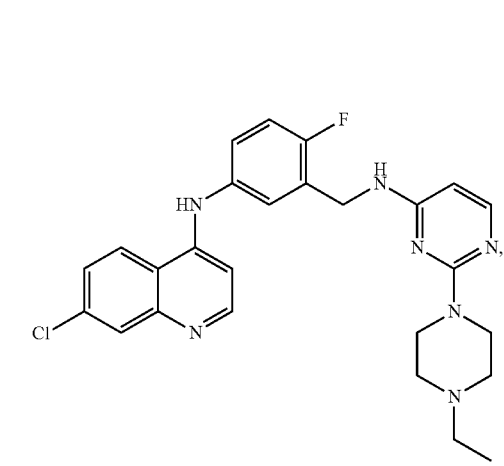
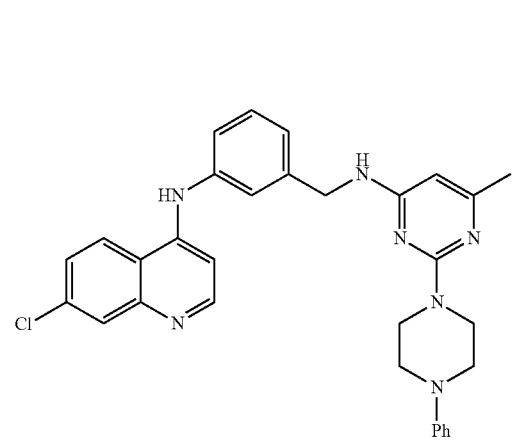

207
-continued
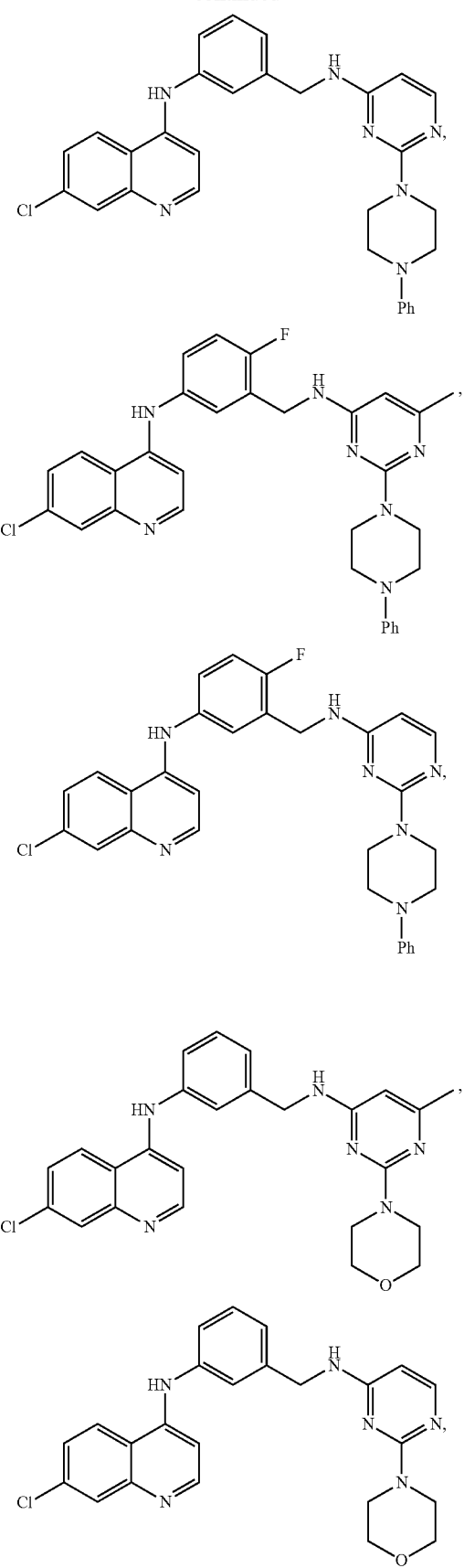
208
-continued
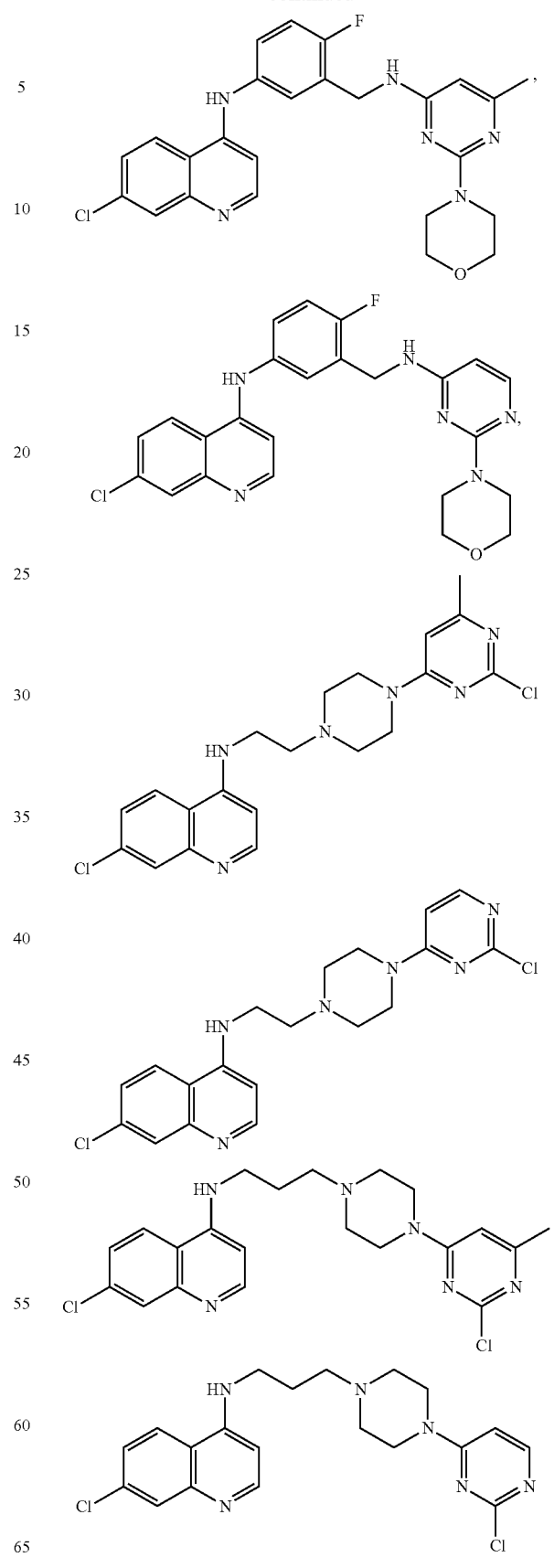

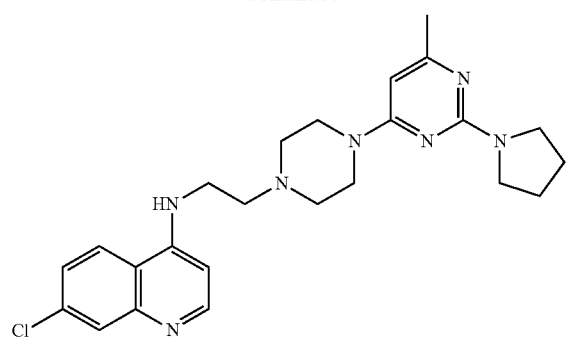
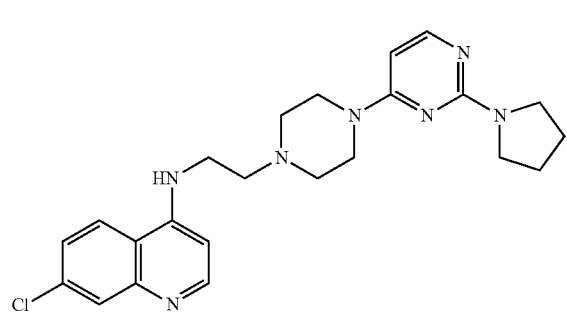
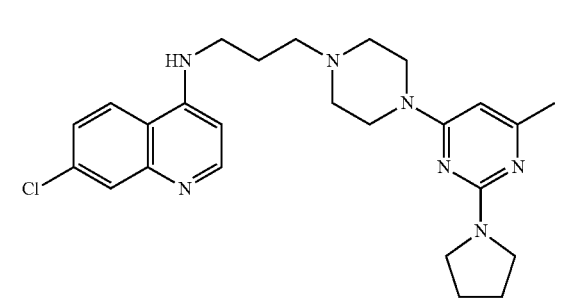
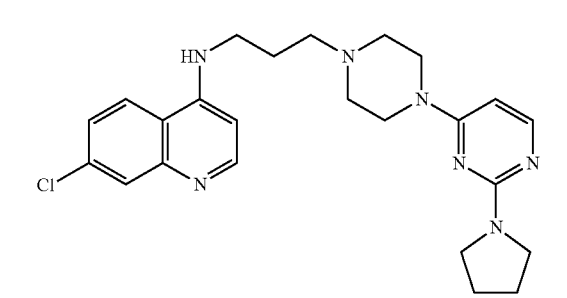
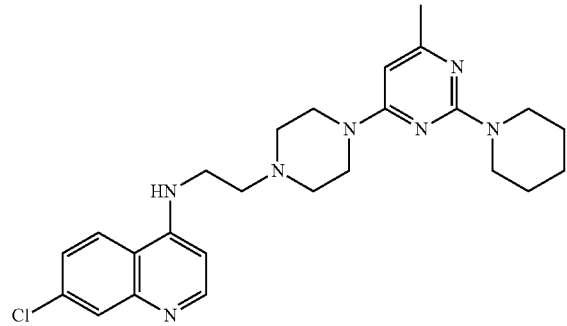
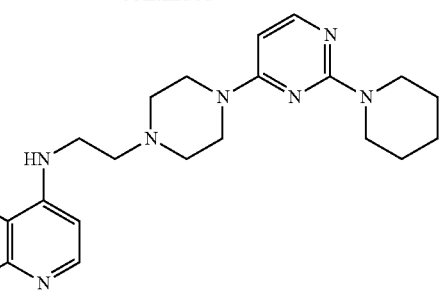
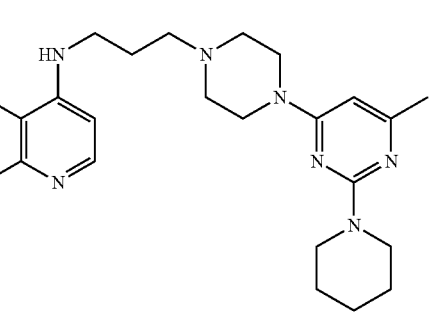
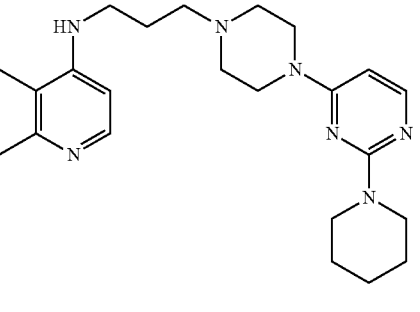
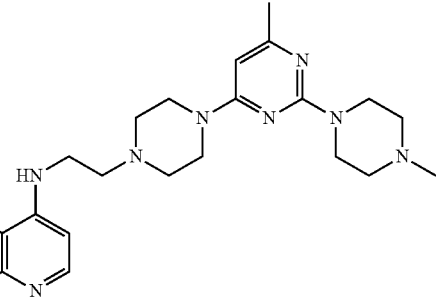
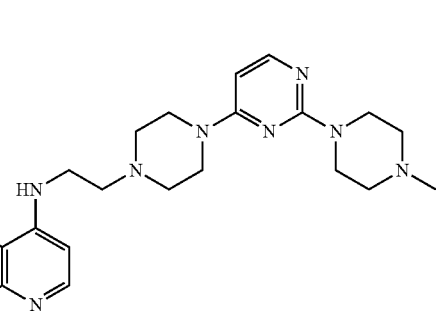

211
-continued
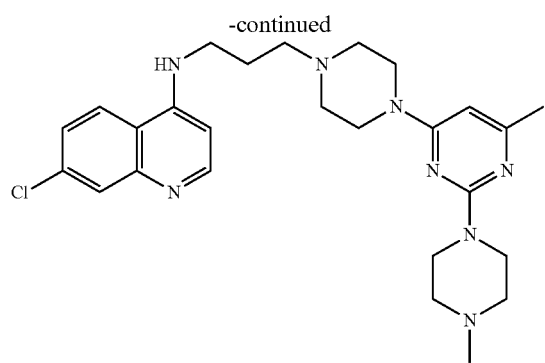
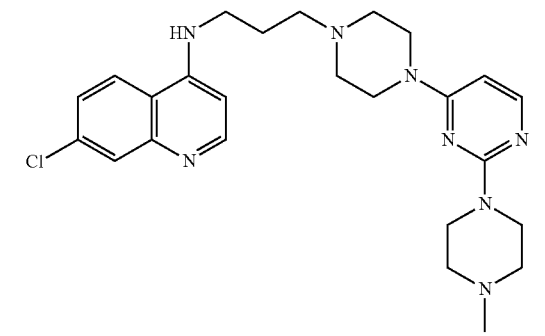
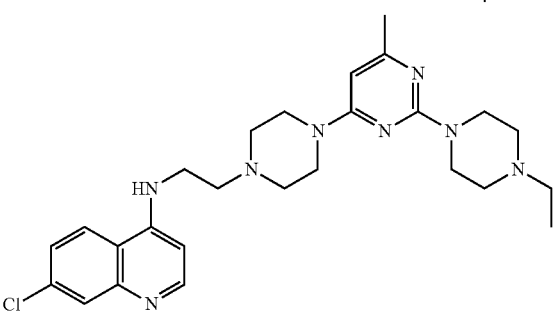
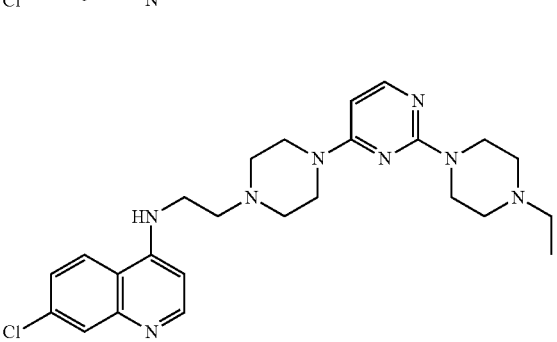
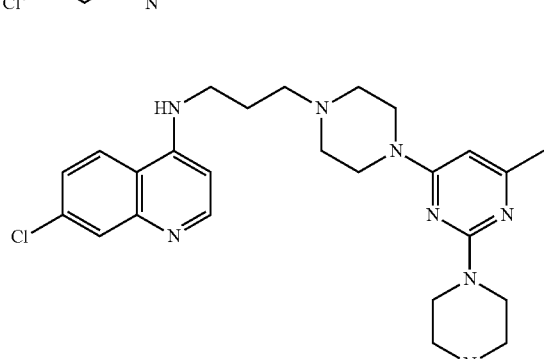
212
-continued
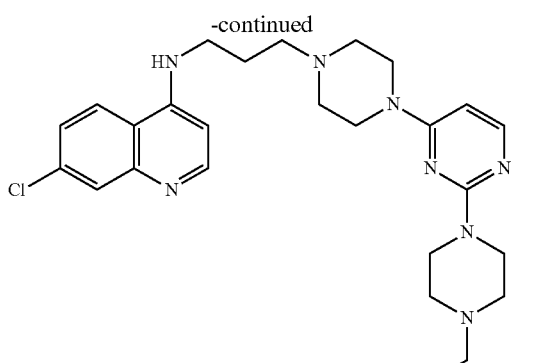
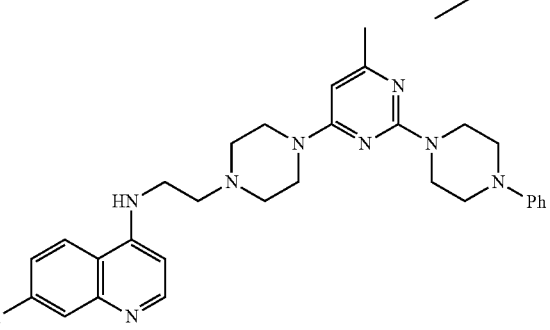
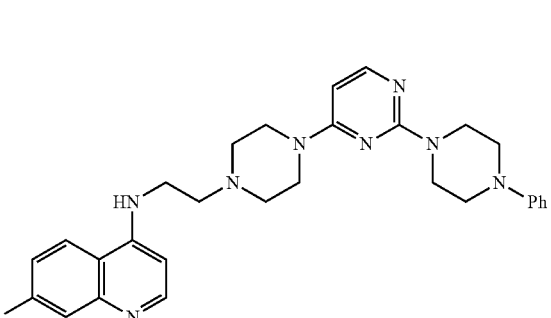
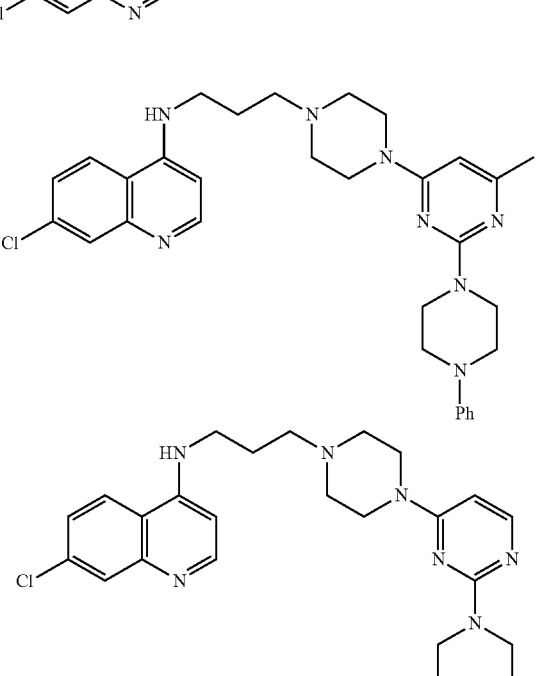

-continued

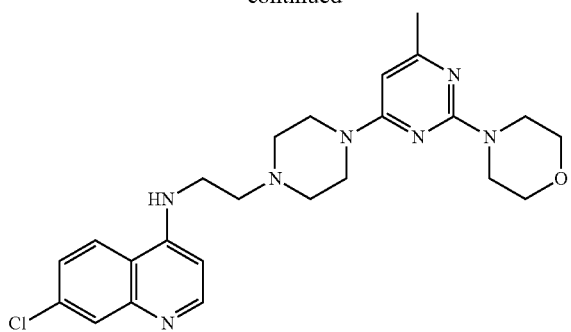
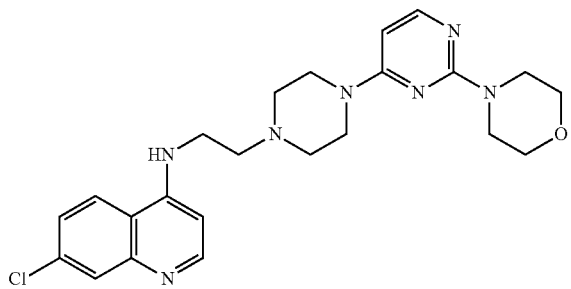
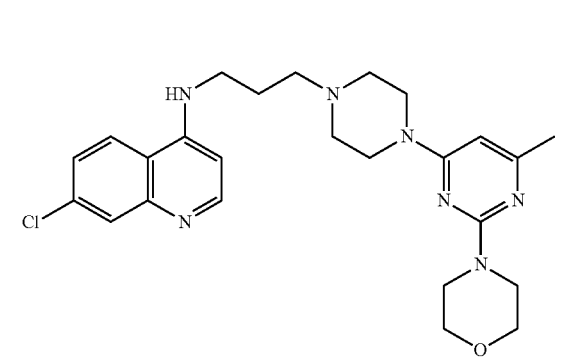
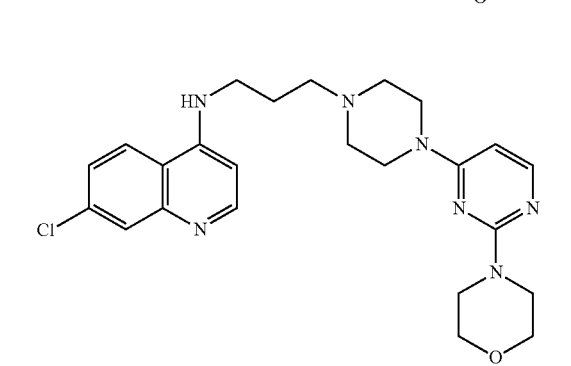
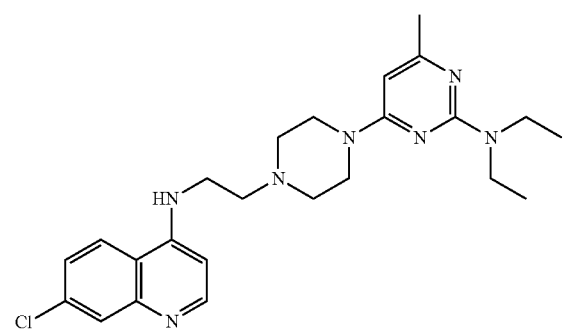

-continued

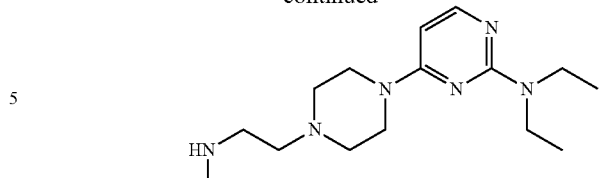
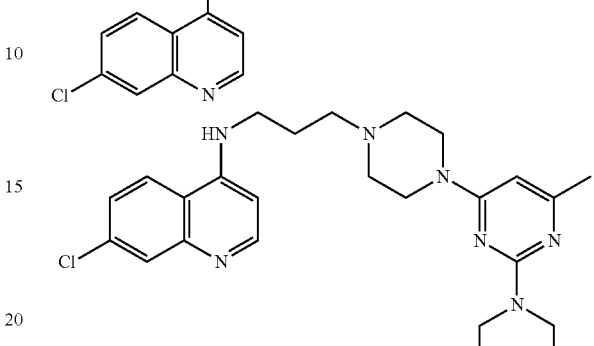
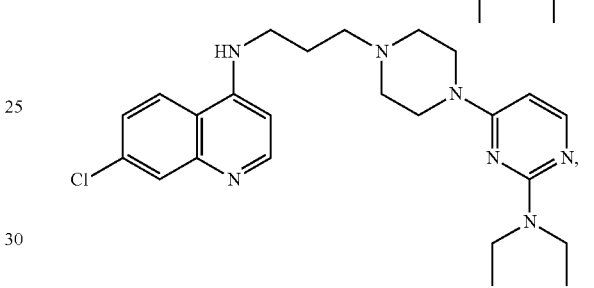

and any combinations thereof.

11. A pharmaceutical composition comprising a compound of any of paragraphs 1-10 and a pharmaceutically acceptable carrier.

12. A composition comprising a compound of any of paragraphs 1-10 and stem cells.

13. The composition of paragraph 12, wherein the stem cells are human embryonic stem cells.

14. A method of treating a disease state when a decreased Nurr1 activity contributes to the pathology or symptomology of the disease, the method comprising administering a therapeutically effective amount of a compound of any of paragraphs 1-10 to a subject in need thereof.

15. A method of treating a disease state when a Nurr1 hypoactivity contributes to the pathology or symptomology of the disease, the method comprising administering a therapeutically effective amount of a compound of any of paragraphs 1-10 to a subject in need thereof.

16. A method of treating inflammation or inflammation associated disease or disorder in a subject, the method comprising administering a therapeutically effective amount of a compound of any of paragraphs 1-10 to a subject in need thereof.

17. A method of treating a neurodegerative disease or disorder in a subject, the method comprising administering a therapeutically effective amount of a compound of any of paragraphs 1-10 to a subject in need thereof.

18. The method of paragraph 17, wherein the neurodegerative disease or disorder is Parkinson's disease.

19. The method of paragraph 17 or 18, further comprising co-administering forskolin, colforsin, or a dopamine agonist to the subject.

20. The method of paragraph 19, wherein the dopamine agonist is L-DOPA.

21. The method of any of paragraphs 14-20, wherein the therapeutically effective amount is an amount sufficient to activate Nurr1 in cells of the subject.
22. A method of inhibiting a neurodegerative disease or disorder in a subject, the method comprising co-administering: (i) a composition comprising stem cells; and (ii) a compound of any of paragraphs 1-10 in an amount sufficient to induce differentiation of the stem cells.
23. The method of paragraph 22, wherein the stem cells are human embryonic stem cells.
24. A method for inducing differentiation of a stem cell into a dopaminergic neuron, the method comprising contacting said cell with a compound of any of paragraphs 1-10 in an amount sufficient to cause differentiation of said stem cell.
25. The method of paragraph 24, wherein the stem cell is a human embryonic stem cell.
26. A kit comprising a compound of any of paragraphs 1-10 and instructions for administering said compound to a subject diagnosed with or at risk of developing a neurodegerative disease or disorder.
27. The kit of paragraph 26, further comprising a stem cell.
28. A method of treating a disease state for which a dopamine agonist is a useful treatment, the method comprising administering a therapeutically effective amount of a compound of any of paragraphs 1-10 to a subject in need thereof.
29. The method of paragraph 28, wherein the disease state is restless leg syndrome.

SOME SELECTED DEFINITIONS

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviations (2SD) away from a reference level. The term refers to statistical evidence that there is a difference. It is defined as the probability of making a decision to reject the null hypothesis when the null hypothesis is actually true.

As used herein, the term "aliphatic" means a moiety characterized by a straight or branched chain arrangement of constituent carbon atoms and can be saturated or partially unsaturated with one or more (e.g., one, two, three, four, five or more) double or triple bonds.

As used herein, the term "alicyclic" means a moiety comprising a nonaromatic ring structure. Alicyclic moieties can be saturated or partially unsaturated with one or more double or triple bonds. Alicyclic moieties can also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $C_3$-$C_8$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

As used herein, the term, "aromatic" means a moiety wherein the constituent atoms make up an unsaturated ring system, all atoms in the ring system are $sp^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

As used herein, the term "alkyl" means a straight or branched, saturated aliphatic radical having a chain of carbon atoms. $C_x$ alkyl and $C_x$-$C_y$alkyl are typically used where X and Y indicate the number of carbon atoms in the chain. For example, $C_1$-$C_6$alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$)aryl($C_0$-$C_3$)alkyl includes phenyl, benzyl, phenethyl, 1-phenylethyl 3-phenylpropyl, and the like. Backbone of the alkyl can be optionally inserted with one or more heteroatoms, such as N, O, or S.

In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, 1-propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkynls that have a chain of between 1 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

The terms "alkylene," "alkenylene," and "alkynylene" refer to divalent alkyl, alkelyne, and alkynylene" radicals. Prefixes $C_x$ and $C_x$-$C_y$ are typically used where X and Y indicate the number of carbon atoms in the chain. For example, $C_1$-$C_6$alkylene includes methylene, (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like).

As used herein, the term "alkylidene" means a straight or branched unsaturated, aliphatic, divalent radical having a general formula =CR$_a$R$_b$. $C_x$ alkylidene and $C_x$-$C_y$alkylidene are typically used where X and Y indicate the number of carbon atoms in the chain. For example, $C_2$-$C_6$alkylidene includes methylidene (=CH$_2$), ethylidene (=CHCH$_3$), isopropylidene (=C(CH$_3$)$_2$), propylidene (=CHCH$_2$CH$_3$), allylidene (=CH—CH=CH$_2$), and the like).

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

The term "aryl" refers to monocyclic, bicyclic, or tricyclic fused aromatic ring system. $C_x$ aryl and $C_x$-$C_y$aryl are typically used where X and Y indicate the number of carbon atoms in the ring system. Exemplary aryl groups include, but are not limited to, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively. $C_x$ heteroaryl and $C_x$-$C_y$heteroaryl are typically used where X and Y indicate the number of carbon atoms in the ring system. Heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$-$C_y$cylcyl are typically used where X and Y indicate the number of carbon atoms in the ring system. The cycloalkyl group additionally can be optionally substituted, e.g., with 1, 2, 3, or 4 substituents. $C_3$-$C_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF3, —CN, or the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

The terms "bicyclic" and "tricyclic" refers to fused, bridged, or joined by a single bond polycyclic ring assemblies.

The term "cyclylalkylene" means a divalent aryl, heteroaryl, cyclyl, or heterocyclyl.

As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like.

The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —NR$^N$—, —N$^+$(O$^-$)=, —O—, —S— or —S(O)$_2$—, —OS(O)$_2$—, and —SS—, wherein R$^N$ is H or a further substituent.

The term "hydroxy" means the radical —OH.

The term "imine derivative" means a derivative comprising the moiety —C(NR)—, wherein R comprises a hydrogen or carbon atom alpha to the nitrogen.

The term "nitro" means the radical —NO$_2$.

An "oxaaliphatic," "oxaalicyclic", or "oxaaromatic" mean an aliphatic, alicyclic, or aromatic, as defined herein, except where one or more oxygen atoms (—O—) are positioned between carbon atoms of the aliphatic, alicyclic, or aromatic respectively.

An "oxoaliphatic," "oxoalicyclic", or "oxoaromatic" means an aliphatic, alicyclic, or aromatic, as defined herein, substituted with a carbonyl group. The carbonyl group can be an aldehyde, ketone, ester, amide, acid, or acid halide.

As used herein, the term, "aromatic" means a moiety wherein the constituent atoms make up an unsaturated ring system, all atoms in the ring system are $sp^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, $CF_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —$SO_2$—. It is noted that the sulfonyl radical can be further substituted with a variety of substituents to form different sulfonyl groups including sulfonic acids, sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —$NH_2$. The term "alkylamino" means a nitrogen moiety having at least one straight or branched unsaturated aliphatic, cyclyl, or heterocyclyl radicals attached to the nitrogen. For example, representative amino groups include —$NH_2$, —$NHCH_3$, —$N(CH_3)_2$, —$NH(C_1$-$C_{10}$alkyl), —$N(C_1$-$C_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an ($C_2$-$C_6$) aminoalkyl refers to a chain comprising between 2 and 6 carbons and one or more nitrogen atoms positioned between the carbon atoms.

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —CH3) as well as —$CR_aR_bR_c$ where $R_a$, $R_b$, and $R_c$ can each independently be hydrogen or any other substituent where the atom alpha to the carbon is a heteroatom or cyano. Hence, $CF_3$, $CH_2OH$ and $CH_2CN$ are all $C_1$ alkyls.

The term "derivative" as used herein refers to a chemical substance related structurally to another, i.e., an "original" substance, which can be referred to as a "parent" compound. A "derivative" can be made from the structurally-related parent compound in one or more steps. In some embodiments, the general physical and chemical properties of a derivative can be similar to or different from the parent compound.

As used herein, the term "polyamine" refers to molecules comprising two or more amines. Polyamines can be aliphatic, straight-chain amines derived biosynthetically from amino acids. Several polyamines are reviewed in Marton et al. (1995) *Ann. Rev. Pharm. Toxicol.* 35:55-91, content of which is incorporated herein by reference. Polyamines cadaverine and putrescine are diamines produced by decarboxylation of lysine or ornithine, respectively. Putrescine is converted to spermidine, and spermidine to spermine, by the addition of an aminopropyl group. This group is provided by decarboxylated S-adenosyl methionine. "Polyamine analog" is defined as an organic cation structurally similar but non-identical to polyamines such as spermine and/or spermidine and their precursor, diamine putrescine. Polyamine analogs, which can be branched or unbranched, include, but are not limited to, BE-4444 [1,19bis(ethylamino)-5,10,15-triazanonadecane]; BE-333 [N1,N11-diethylnorspermine; DENSPM; 1,11-bis(efhylamino)4,8-diazaundecane; thermine; Warner-Parke-Davis]; BE-33 [N1,N7-bis(ethyl) norspermidine]; BE-34 [N1,N8-bis(ethyl) spermidine]; BE-44 [N1,N9-bis(ethyl) homospermidine]; BE-343 [N1,N12-bis (ethyl) spermine; diethylspermine-N1-N12; DESPM]; BE-373 [N,N'-bis(3-ethylamino) propyl)-1,7-heptane diamine, Merrell-Dow]; BE-444 [N1,N14-bis(ethyl) homospermine; diefhylhomospermine-N1N14]; BE-3443 [1,17-bis(ethylamino)-4,9,14-triazaheptadecane]; BE-4334 [1,17-bis(ethylamino)-5,9,13triazaheptadecane]; 1,1 2-Me2-SPM [1,12dimethylspermine]; and the various polyamine analogs disclosed in WO 98/17624; U.S. Pat. No. 5,889,061; WO 00/66175 and WO 00/66587; and O'Sullivan et al. (1997) Bioorg. Med. Chem. 5:2145-2155 and Mukhopadhyaya et al. (1995) Exp. Parasit. 81:39-46; and U.S. Pat. No. 4,935,449, content of all of which is incorporated herein by reference. Cyclic polyamine compounds and cyclic polyamine analogs are disclosed in International Patent Application WO 02/10142. In certain of these cyclic polyamine compounds, one or more of the aliphatic nitrogens form part of an amide group In some embodiments, the compounds described herein can be in the form of a prodrug. The term "prodrug" as used herein refers to compounds that can be converted via some chemical or physiological process (e.g., enzymatic processes and metabolic hydrolysis) to compound described herein. Thus, the term "prodrug" also refers to a precursor of a biologically active compound that is pharmaceutically acceptable. A prodrug can be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. For example, a compound comprising a hydroxy group can be administered as an ester that is converted by hydrolysis in vivo to the hydroxy compound. Suitable esters that can be converted in vivo into hydroxy compounds include acetates, citrates, lactates, tartrates, malonates, oxalates, salicylates, propionates, succinates, fumarates, formates, benzoates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group can be administered as an amide, e.g., acetamide, formamide and benzamide that is converted by hydrolysis in vivo to the amine compound. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl)Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which are herein incorporated by reference in its entirety.

The term "protected derivatives" means derivatives of compounds described herein in which a reactive site or sites are blocked with protecting groups. Protected derivatives are useful in the preparation of compounds or in themselves can be active. A comprehensive list of suitable protecting groups can be found in T. W. Greene, *Protecting Groups in Organic Synthesis*, 3rd edition, John Wiley & Sons, Inc. 1999.

"Isomers" mean any compound having identical molecular formulae but differing in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality. A mixture of the two enantiomeric forms is termed a "racemic mixture". A compound that has more than one chiral center has $2^{n-1}$ enantiomeric pairs, where n is the number of chiral centers. Compounds with more than one chiral center may exist as ether an individual diastereomers or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

The designations "R" and "S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses.

The designations or prefixes "(+)" and "(−)" are employed to designate the sign of rotation of plane-polarized light by the compound, with (−) meaning that the compound is levorotatory (rotates to the left). A compound prefixed with (+) is dextrorotatory (rotates to the right).

The term "racemic mixture," "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction F(+) and F(−) (where the sum of F(+) and F(−)=1). The enantiomeric excess is defined as *F(+)−F(−)* and the percent enantiomeric excess by 100× *F(+)−F(−)*. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer," "substantially resolved enantiomer" "substantially purified enantiomer preparation" are meant to indicate a preparation (e.g. derived from non-optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer," "resolved enantiomer" and "purified enantiomer preparation" are meant to indicate a preparation (e.g. derived from non-optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereo-preferred procedure, followed by separation steps, or a purified enantiomer may be derived from a racemic mixture.

The term "enantioselectivity," also called the enantiomeric ratio indicated by the symbol "E," refers to the selective capacity of an enzyme to generate from a racemic substrate one enantiomer relative to the other in a product racemic mixture; in other words, it is a measure of the ability of the enzyme to distinguish between enantiomers. A non-selective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects. The compounds described herein are effective in treating various types of cancer.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount, for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of human diseases and disorders. In addition, compounds, compositions and methods described herein can be used to treat domesticated animals and/or pets.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

The phrase "therapeutically-effective amount" as used herein means that amount of a compound, material, or composition comprising a compound described herein which is effective for producing some desired therapeutic effect in at least a sub-population of cells in a subject at a reasonable benefit/risk ratio applicable to any medical treatment. Thus, "therapeutically effective amount" means that amount which, when administered to a subject for treating a disease, is sufficient to effect such treatment for the disease.

Determination of an effective amount is well within the capability of those skilled in the art. Generally, the actual effective amount can vary with the specific compound, the use or application technique, the desired effect, the duration of the effect and side effects, the subject's history, age, condition, sex, as well as the severity and type of the medical condition in the subject, and administration of other pharmaceutically active agents. Accordingly, an effective dose of compound described herein is an amount sufficient to produce at least some desired therapeutic effect in a subject.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of use or administration utilized.

The effective dose can be estimated initially from cell culture assays. A dose can be formulated in animal models to achieve a circulating plasma concentration range that includes the $IC_{50}$ (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay. The effective plasma concentration for a compound as disclosed herein can be about 0.01 µM to about 10 µM, about 0.2 µM to about 5 µM, or about 0.8 to about 3 µM in a subject, such as a rat, dog, or human.

Generally, the compositions are administered so that a compound of the disclosure herein is used or given at a dose from 1 µg/kg to 1000 mg/kg; 1 µg/kg to 500 mg/kg; 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. Further contemplated is a dose (either as a bolus or continuous infusion) of about 0.1 mg/kg to about 10 mg/kg, about 0.3 mg/kg to about 5 mg/kg, or 0.5 mg/kg to about 3 mg/kg. It is to be further understood that the ranges intermediate to those given above are also within the scope of this disclosure, for example, in the range 1 mg/kg to 10 mg/kg, for example use or dose ranges such as 2 mg/kg to 8 mg/kg, 3 mg/kg to 7 mg/kg, 4 mg/kg to 6 mg/kg, and the like.

The compounds described herein can be administered at once, or can be divided into a number of smaller doses to be administered at intervals of time. It is understood that the precise dosage and duration of treatment will be a function of the location of where the composition is parenterally administered, the carrier and other variables that can be determined empirically using known testing protocols or by extrapolation from in vivo or in vitro test data. It is to be noted that concentrations and dosage values can also vary with the age of the individual treated. It is to be further understood that for any particular subject, specific dosage regimens can need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The compound can be administered as a single bolus or multiple boluses, as a continuous infusion, or a combination thereof. For example, the compound can be administered as a single bolus initially, and then administered as a continuous infusion following the bolus. The rate of the infusion can be any rate sufficient to maintain effective plasma concentration. Some contemplated infusion rates include from 1 µg/kg/min to 100 mg/kg/min, or from 1 µg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min. It will be appreciated that the rate of infusion can be determined based upon the dose necessary to maintain effective plasma concentration and the rate of elimination of the compound, such that the compound is administered via infusion at a rate sufficient to safely maintain a sufficient effective plasma concentration of compound in the bloodstream.

The terms "co-administration" or the like, as used herein, are meant to encompass administration of the selected therapeutic agents to a single patient, and are intended to include treatment regimens in which the agents are administered by the same or different route of administration or at the same or different time.

Generally, the term "treatment" or "treating" is defined as the application or administration of a therapeutic agent to a patient, or application or administration of a therapeutic agent to an isolated tissue or cell line from a patient, said patient having a disease, a symptom of disease or a predisposition toward a disease, with the purpose to cure, heal, alleviate, relieve, alter, remedy, ameliorate, improve or affect the disease, the symptoms of disease or the predisposition toward disease. Thus, treating can include suppressing, inhibiting, preventing, treating, or a combination thereof. Treating refers, inter alia, to increasing time to sustained progression, expediting remission, inducing remission, augmenting remission, speeding recovery, increasing efficacy of or decreasing resistance to alternative therapeutics, or a combination thereof. "Suppressing" or "inhibiting", refers, inter alia, to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. In one embodiment the symptoms are primary, while in another embodiment symptoms are secondary. "Primary" refers to a symptom that is a direct result of a disorder, e.g., diabetes, while, secondary refers to a symptom that is derived from or consequent to a primary cause. Symptoms may be any manifestation of a disease or pathological condition.

Accordingly, as used herein, the term "treatment" or "treating" includes any administration of a compound described herein and includes: (i) preventing the disease from occurring in a subject which may be predisposed to the disease but does not yet experience or display the pathology or symptomatology of the disease; (ii) inhibiting the disease in an subject that is experiencing or displaying the pathology or symptomatology of the diseased (i.e., arresting further development of the pathology and/or symptomatology); or (iii) ameliorating the disease in a subject that is experiencing or displaying the pathology or symptomatology of the diseased (i.e., reversing the pathology and/or symptomatology).

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

Specifically, by "treatment, prevention or amelioration of neurodegenerative disorder" is meant delaying or preventing the onset of such a disorder (e.g. death of motor neurons), at reversing, alleviating, ameliorating, inhibiting, slowing down or stopping the progression, aggravation or deterioration the progression or severity of such a condition. In one embodiment, the symptom of a neurodegenerative disorder is alleviated by at least 20%, at least 30%, at least 40%, or at least 50%. In one embodiment, the symptom of a neurodegenerative disease is alleviated by more than 50%. In one embodiment, the symptom of a neurodegenerative disorder is alleviated by 80%, 90%, or greater.

Efficacy of treatment is determined in association with any known method for diagnosing the disorder. Alleviation of one or more symptoms of the disorder indicates that the compound confers a clinical benefit. Any of the therapeutic methods described to above can be applied to any suitable subject including, for example, mammals such as dogs, cats, cows, horses, rabbits, monkeys, and most preferably, humans.

By "embryonic stem cell" is meant a cell, derived from an embryo at the blastocyst stage, or before substantial differentiation of the cell into the three germ layers, that can selfrenew and displays morphological characteristics of undifferentiated cells, distinguishing them from differentiated cells of embryonic or adult origin. Exemplary morphological characteristics include high nuclear/cytoplasmic ratios and prominent nucleoli under a microscope. Under appropriate conditions known to the skilled artisan, embryonic stem cells can differentiate into cells or tissues of the three germ layers: endoderm, mesoderm, and ectoderm. Assays for identification of an embryonic stem cell include the ability to form a teratoma in a suitable host or to be stained for markers of an undifferentiated cell such as Oct-4.

By "an amount sufficient to treat" is meant the amount of a compound required to improve, inhibit, or ameliorate a condition of a subject, or a symptom of a disease, in a clinically relevant manner. Any improvement in the subject is considered sufficient to achieve treatment.

By "Nurr1 biological activity" is meant any activity known to be caused in vitro, in vivo or ex vivo by a Nurr1 polypeptide. For example, such activity could include activating transcription of tyrosine hydroxylase.

"Nurr1 nucleic acid" and "Nurr1 gene" are used interchangeably herein and refer to a nucleic acid that encodes all or a portion of a Nurr1 polypeptide, or is substantially identical to all or a portion of the nucleic acid sequence of Genbank Accession No. ABO1 7586 (Ichinose et al., Gene 230:233-239, 1999), or analog thereof. By "Nurr1 polypeptide" is meant a polypeptide substantially identical to all or a portion of the polypeptide sequence of Genbank Accession No. BAA75666, or analog thereof, and having Nurr1 biological activity.

EXAMPLES

Example 1

Synthetic Protocol

Representative Examples

Among the prototype structures of FIG. 1, synthesis of 4-aminoquinoline-pyrimidine hybrids is described here. Similarly, other compounds as depicted in FIG. 1 were also synthesized. The 4-aminoquinoline-pyrimidine conjugates were synthesized using three step procedure as outlined in Scheme 1. The commercially available starting material 4,7-dichloroquinoline (8) was reacted with an excess of aliphatic linear chain diaminoalkanes via SNAr type of reaction in neat conditions as reported in literature to afford substituted 4-aminoquinolines (9a-d) with free terminal amino group in goodto excellent yield [Roepe, P. D. J. Med. Chem. 2008, 51, 3466]. These intermediates (9a-d) on reaction with commercially available 2,4-dichloro-6-methyl-pyrimidine yielded two regioisomersviz 10a-d in major and 11a-d in minor yield. The major regioisomers 10a-d was subjected to nucleophilic substitution with different cyclic secondary amines at an elevated temperature in DMF as solvent, to yield 4-aminoquinoline-pyrimidine conjugates (12a-n) in excellent yield.

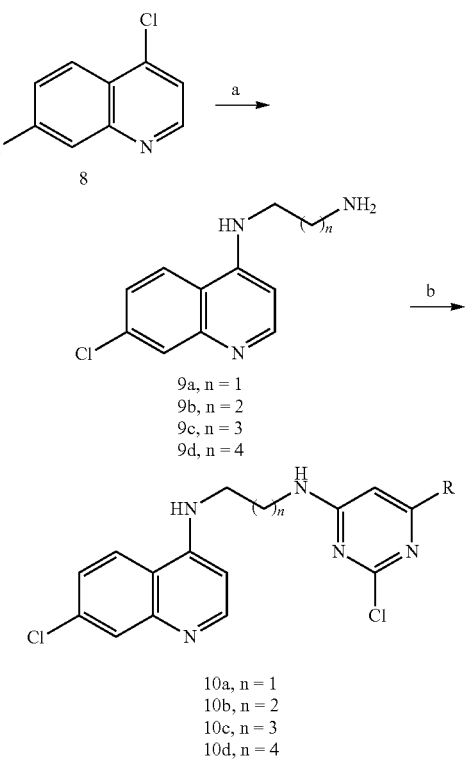

Scheme 1

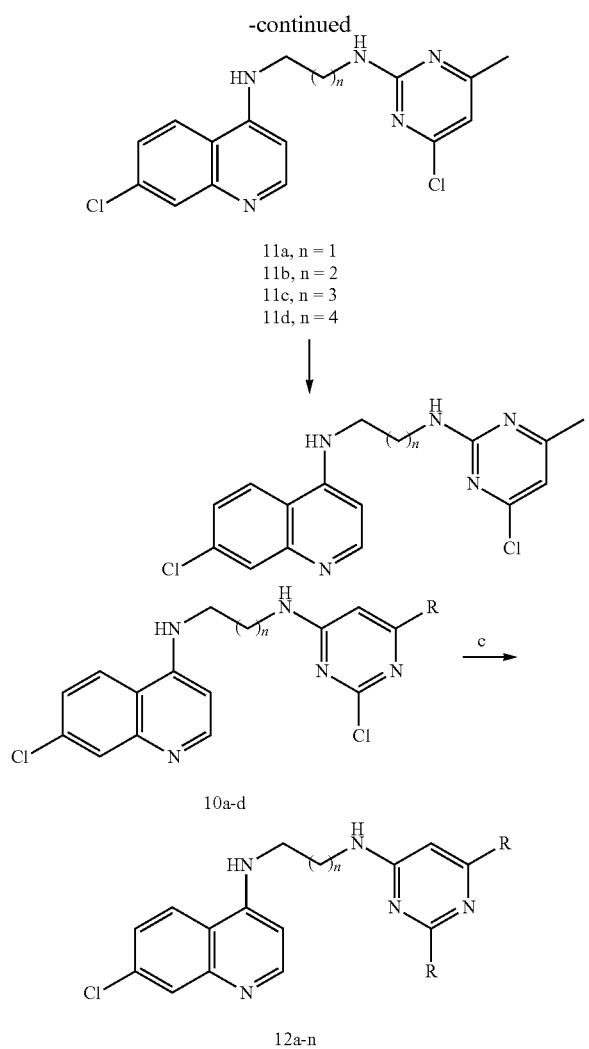

11a, n = 1
11b, n = 2
11c, n = 3
11d, n = 4

10a-d 12a-n a) diaminoalkanes, neat, 120-130° C., 6-8 h, 80-90%; b) 2,4-dichloro-6-methyl-pyrimidine, TEA, EtOH, RT, overnight, (10a-d, 70-80% and 11a-d, 15-25%); c) R = secondary amines, DMF, 100-120° C., 10-12 h, 80-85%.

In vitro antimalarial activity of all the conjugates was studied against both CQ-sensitive (D6 clone) and CQ-resistant (W2 clone) strains of *P. falciparum* while mammalian cell cytotoxicity was determined against Vero, LLC-PK-1, HepG2 cells (Table 6) using procedure as described earlier [Jain, R. Bioorg. Med. Chem. 2005, 13, 4458; Khan, I. A. Lipids 2004, 37, 169]. Most of the compounds have shown very promising antimalarial activity. Out of these, eleven compounds (12b-c, 12e-f, 12h-n) have displayed better antimalarial activity (IC50=0.006 μM to 0.041 μM) against CQ-sensitive strain, while thirteen compounds (10a, 12b-f, 12h-n) have displayed better antimalarial activity (IC50=0.016 μM to 0.34 μM) against CQ-resistant strains of *P. falciparum*. The selectivity index of antimalarial activity (calculated as a ratio of IC50 for cytotoxicity to Vero cells and IC50 for antimalarial activity) was very high for most of these compounds as compared to standard drug chloroquine (CQ). The activity of (12i, 12j, 12l and 12m) was 7-8 fold higher than CQ and 2 fold higher than artemisinin in CQ-sensitive strain revealing their strong potency. The comparison of antimalarial activity of 10a-d with 12a-n clearly showed that substitution of Cl from compounds 10a-d (IC50=0.15 μM to 0.46 μM for CQ-sensitive and 0.34 μM to 0.74 μM for CQ-resistant) with secondary amines (12b-f and 12h-n, IC50=0.006 μM to 0.066 μM for CQ-sensitive and 0.016 μM to 0.211 μM for CQ-resistant) improves antimalarial activity of these compounds. The comparison of antimalarial activity of two groups of regioisomers 10a-d (IC50=0.15 μM to 0.46 μM for CQ-sensitive and 0.34 μM to 0.74 μM for CQ-resistant) and 11a-d (IC50=0.16 μM to 0.27 μM for CQ-sensitive and 0.56 μM to 0.1.24 μM for CQ-resistant) clearly indicates that both the regioisomers displayed more or less similar potency against both the strains of *P. falciparum*. These results indicate that the point of attachment of the spacer to the pyrimidine nucleus may not have a great impact on activity profile. For a particular amino substituted 4-aminoquinoline-pyrimidine hybrids (12a-d or 12e-h or 12i-1), structure activity relationship (SAR) study demonstrated no obvious trend of activity with increasing or decreasing carbon spacer from C2 to C6 but changing the amino groups for a particular C2 (12e, 12i), C3 (12b, 12f, 12j, 12m), C4 (12c, 12k, 12n) or C6 (12d, 12h, 12l) spacer changes the activity significantly in a decreasing order of 4-ethyl piperazine>4-methyl piperazine>morpholine>piperidine.

Among the most active compounds (12b-12f, 12h-12n), although 12d, 12h, and 12l showed toxicity to all the three cell lines (VERO, LLC-PK-1, and HepG2) but their selectivity index of antimalarial activity was considerably high (Table 7). In general, the cytotoxicity of the most of the conjugates was at much higher concentrations than the concentrations responsible for their antimalarial activity. Some of the hybrids were not cytotoxic at all up to the highest tested concentration of 60 μM indicating their high selectivity index of antimalarial activity versus cytotoxicity to mammalian cells.

TABLE 6

| | In-vitro antimalarial activity of 4-aminoquinoline-pyrimidine hybrids | | | | |
|---|---|---|---|---|---|
| Comp. | | | *P. falciparum* (D6 Clone) | | *P. falciparum* (W2 Clone) |
| No | Structure | | IC50 (μM) | S.I. | IC50 (μM) | S.I. |
| 10a | 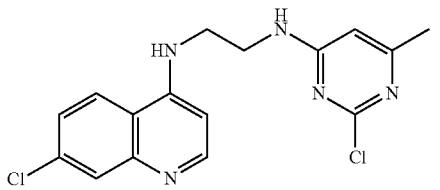 | | 0.21 | (>285) | 0.34 | (>176) |

TABLE 6-continued

In-vitro antimalarial activity of 4-aminoquinoline-pyrimidine hybrids

| Comp. No | Structure | P. falciparum (D6 Clone) IC50 (µM) | S.I. | P. falciparum (W2 Clone) IC50 (µM) | S.I. |
|---|---|---|---|---|---|
| 10b | 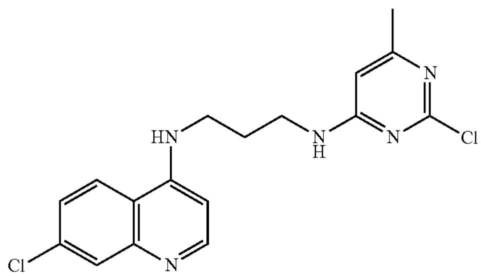 [SMILES: Cc1cc(NCCCNc2ccnc3cc(Cl)ccc23)nc(Cl)n1] | 0.35 | (>170) | 0.74 | (>80) |
| 10c | 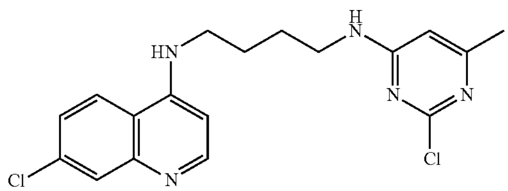 [SMILES: Cc1cc(NCCCCNc2ccnc3cc(Cl)ccc23)nc(Cl)n1] | 0.151 | (>398) | 0.690 | (>87) |
| 10d | 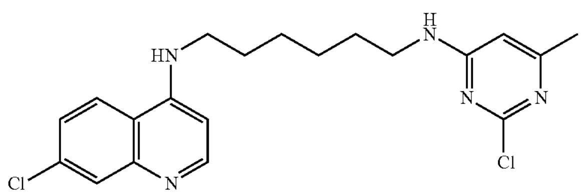 [SMILES: Cc1cc(NCCCCCCNc2ccnc3cc(Cl)ccc23)nc(Cl)n1] | 0.469 | 73.7 | 0.544 | 27.2 |
| 11a | 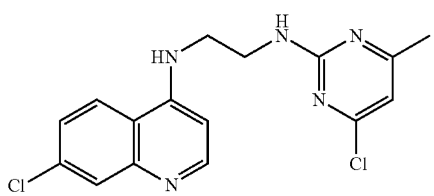 [SMILES: Cc1cc(Cl)nc(NCCNc2ccnc3cc(Cl)ccc23)n1] | 0.27 | 159.2 | 0.91 | 47.2 |
| 11b | 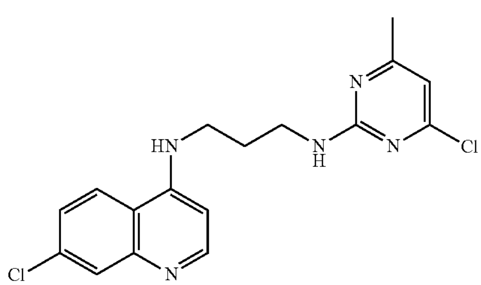 [SMILES: Cc1cc(Cl)nc(NCCCNc2ccnc3cc(Cl)ccc23)n1] | 0.27 | (>222) | 1.24 | (>48) |
| 11c | 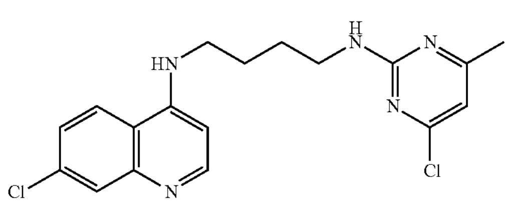 [SMILES: Cc1cc(Cl)nc(NCCCCNc2ccnc3cc(Cl)ccc23)n1] | 0.196 | (>306) | 0.664 | (>90) |

TABLE 6-continued

In-vitro antimalarial activity of 4-aminoquinoline-pyrimidine hybrids

| Comp. No | Structure | P. falciparum (D6 Clone) IC50 (µM) | S.I. | P. falciparum (W2 Clone) IC50 (µM) | S.I. |
|---|---|---|---|---|---|
| 11d | | 0.165 | 336.9 | 0.568 | 97.8 |
| 12a | | ND | ND | ND | ND |
| 12b | | 0.026 | (>2300) | 0.211 | (>284) |
| 12c | | 0.021 | (>2857) | 0.082 | (>730) |
| 12d | | 0.066 | 142.4 | 0.128 | 73.4 |
| 12e | | 0.025 | (>2400) | 0.12 | (>500) |

TABLE 6-continued
In-vitro antimalarial activity of 4-aminoquinoline-pyrimidine hybrids
| Comp. No | Structure | P. falciparum (D6 Clone) IC50 (μM) | S.I. | P. falciparum (W2 Clone) IC50 (μM) | S.I. |
|---|---|---|---|---|---|
| 12f | 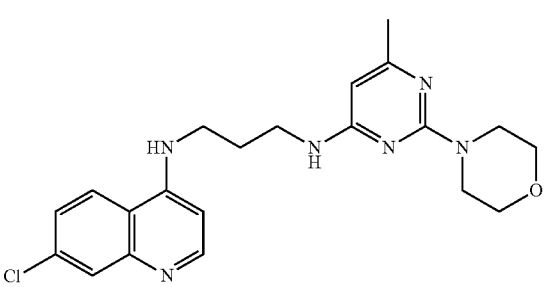 [SMILES: Cc1cc(NCCCNc2ccnc3cc(Cl)ccc23)nc(N2CCOCC2)n1] | 0.022 | (>2727) | 0.058 | (>1034) |
| 12g | 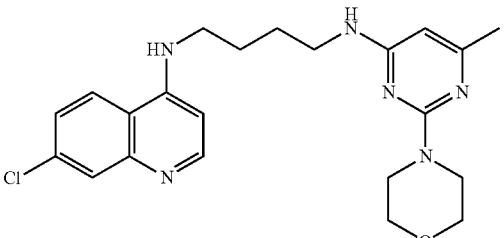 | ND | ND | ND | ND |
| 12h | 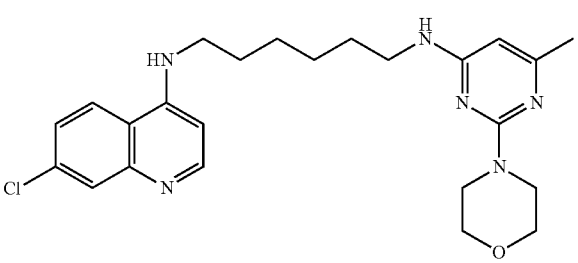 [SMILES: Cc1cc(NCCCCCCNc2ccnc3cc(Cl)ccc23)nc(N2CCOCC2)n1] | 0.041 | 417.0 | 0.120 | 142.5 |
| 12i | 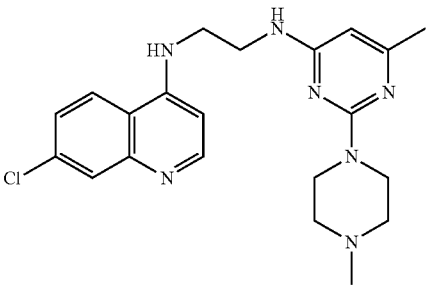 [SMILES: Cc1cc(NCCNc2ccnc3cc(Cl)ccc23)nc(N2CCN(C)CC2)n1] | 0.006 | (>10000) | 0.046 | (>1304) |
| 12j | 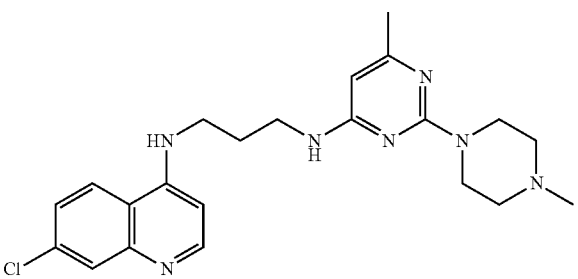 [SMILES: Cc1cc(NCCCNc2ccnc3cc(Cl)ccc23)nc(N2CCN(C)CC2)n1] | 0.007 | (>8571) | 0.063 | (>952) |

TABLE 6-continued

In-vitro antimalarial activity of 4-aminoquinoline-pyrimidine hybrids

| Comp. No | Structure | P. falciparum (D6 Clone) | | P. falciparum (W2 Clone) | |
|---|---|---|---|---|---|
| | | IC50 (μM) | S.I. | IC50 (μM) | S.I. |
| 12k | 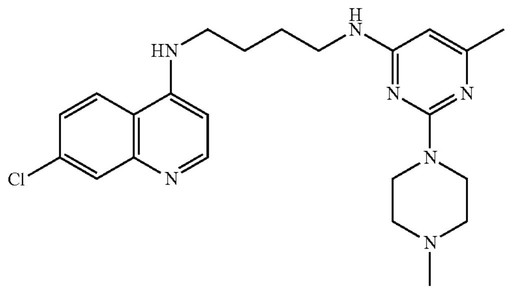 [SMILES: Cc1cc(NCCCCNc2ccnc3cc(Cl)ccc23)nc(N2CCN(C)CC2)n1] | 0.022 | (>2727) | 0.021 | (>2857) |
| 12l | 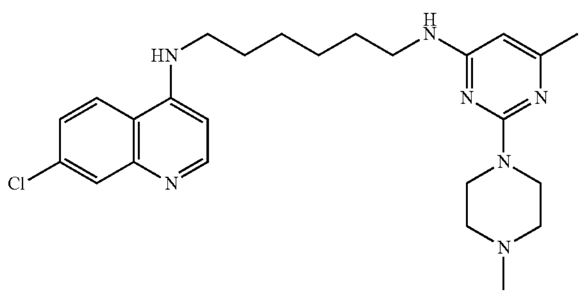 [SMILES: Cc1cc(NCCCCCCNc2ccnc3cc(Cl)ccc23)nc(N2CCN(C)CC2)n1] | 0.007 | (>1457) | 0.016 | (>637) |
| 12m | 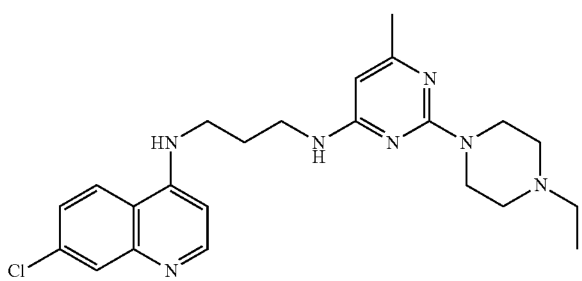 [SMILES: CCN1CCN(c2nc(C)cc(NCCCNc3ccnc4cc(Cl)ccc34)n2)CC1] | 0.006 | (>10000) | 0.061 | (>983) |
| 12n | 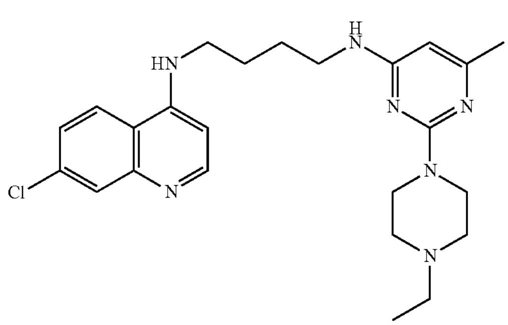 [SMILES: CCN1CCN(c2nc(C)cc(NCCCCNc3ccnc4cc(Cl)ccc34)n2)CC1] | 0.019 | 1678.9 | 0.018 | 1772.2 |
| Chloroquine | | 0.048 | 1250 | 0.43 | 140 |
| Artemisinine | | 0.012 | 5000 | 0.012 | 5000 |

TABLE 7

In vitro cytotoxicity of 4-aminoquinoline-pyrimidine hybrids to mammalian cells.

| Comp. No | IC50 (μM) | | |
|---|---|---|---|
| | VERO | LLC-PK-1 | HepG2 |
| 10a | NC | NC | NC |
| 10b | NC | NC | NC |
| 10c | NC | NC | NC |
| 10d | 34.6 | 14.8 | 9.3 |
| 11a | 43.0 | 41.6 | 43.0 |
| 11b | NC | NC | NC |
| 11c | NC | NC | 39.8 |
| 11d | 55.6 | 23.4 | 8.1 |
| 12a | ND | ND | ND |
| 12b | NC | NC | NC |
| 12c | NC | NC | >60 |
| 12d | 9.4 | <6.7 | <6.7 |
| 12e | NC | NC | NC |
| 12f | NC | 35.1 | 26.1 |
| 12g | ND | ND | ND |
| 12h | 17.1 | 9.8 | <6.7 |
| 12i | NC | NC | NC |
| 12j | NC | 35.2 | 25.8 |
| 12k | NC | 34.0 | 27.2 |
| 12l | 10.2 | 7.4 | <6.7 |
| 12m | NC | NC | NC |
| 12n | 31.9 | 10.5 | 14.9 |
| Doxorubicin | 8.2 | 1.0 | <1.0 |

Considering the excellent in-vitro activity of these compounds, two of the hybrids 12i and 12m (Table 8) were subjected to in-vivo antimalarial activity evaluation. The results showed 100% parasitemia suppression on day 5 for both the compounds (12i and 12m) with the survival rate of 5/5 and 4/5 respectively on day 28 when the mice's are given a dose of 30 mg/kg for 3 days post infection. No apparent toxicity is also observed for these compounds. These results are found to be better than the standard drug (Chloroquine) which gives 100% parasitemia suppression on day 5 when a 100 mg/kg dose was given for 3 days post infection.

These excellent results on animal models clearly depicted the potency of these compounds and give an insight about considering them for future drug candidates.

General Procedure for the Synthesis of Selected Compounds (10a-d and 11a-d):

To a well stirred solution of 2,4-dichloro-6-methyl-pyrimidine (2.0 g, 12.2 mmol) and triethylamine (2.48 g, 24.5 mmol) in ethanol (50 ml) at room temperature was added diamines 9a-d (12.2 mmol). The reaction mixture was allowed to stir overnight at room temperature. After completion of reaction as evident by TLC, reaction mixture was poured into ice cold water (250 ml) and precipitate thus formed was filtered and washed with excess of water at vacuum pump. The crude precipitate was then dried, dissolved in 100 ml of CHCl3 and extracted with water (2×500 ml) and finally with brine. Excess of solvent was evaporated to dryness under vacuum and the crude product thus obtained was purified by SiO2 column using MeOH/CHCl3 as eluent to yield respective compounds 13a-d and 14a-d.

General Procedure for the Synthesis of Selected Compounds (12a-n)

In a 100 ml round bottom flask, compound 10a-d (1 eq.) was taken and dissolved in 10 ml of DMF. To this, a solution of respective amine (3 eq.) in DMF (5 ml) was added dropwise. Reaction mixture was allowed to stir at 100-120° C. for 10 hours monitored by TLC. After completion, water (50 ml) was added to reaction mixture and it was extracted with EtOAc (2×25 ml). Organic layer was then collected, washed with water (2×100 ml) and brine, dried over Na2SO4 and finally excess of solvent was evaporated under vacuum. The crude residue thus obtained was purified by SiO2 column using MeOH/CHCl3 as eluent to afford respective compounds 15a-n.

Spectral Data of Selected Compounds:

N-(7-chloro-quinolin-4-yl)-N'-(6-methyl-2-piperidin-1-yl-pyrimidin-4-yl)-ethane-1,2-diamine (12a): White solid. Yield: 85%; mp 177-179° C.; IR (cm-1, KBr): 3385, 3344, 2941, 1580, 1447, 1331, 1237, 1141, 790; 1H NMR (400 MHz, DMSO-d6): 1.36-1.49 (m, 6H), 2.02 (s, 3H), 3.31-3.41 (m, 8H), 5.85 (s, 1H), 6.56-6.72 (m, 2H), 7.34 (dd, 1H, J=11.0 Hz, 2.0 Hz), 7.41 (brs, 1H), 7.68 (d, 1H, J=2.3 Hz); 8.07 (d, 1H, J=8.7 Hz), 8.28 (d, 1H, J=5.5 Hz); ESI-MS (m/z): 397.22 (M+H)+; Anal. Calcd for C21H25ClN6: C, 63.55; H, 6.35; N, 21.17. Found: C, 63.53; H, 6.39; N, 21.26.

TABLE 8

In-vivo antimalarial activity of 4-aminoquinoline-pyrimidine hybrids 12i and 12m.

| Cage | Treatment | Dose (mg/kg × no. of days post-infection) | % Parasitemia suppression[1] | | Survival[2] | Day of Death | MST[3] | Cure[4] | Remarks |
|---|---|---|---|---|---|---|---|---|---|
| | | | Day 5 | Day 7 | | | | | |
| 1 | Vehicle PO | NA × 4 | — | — | 0/5 | 11/11/12/21/21 | 15.2 | | 0/5 |
| 2 | Chloroquine PO | 100 × 3 | 100.00 | 100.00 | 5/5 | 28/28/88/28/28 | 28 | | 0/5 |
| 3 | 12i PO | 3.3 × 3 | 23.52 | 35.21 | 1/5 | 21/28/21/13/13 | 19.2 | No apparent Toxicity | 0/5 |
| 4 | 12i PO | 10 × 3 | 97.03 | 2.03 | 0/5 | 21/22/22/21/21 | 21.4 | No apparent Toxicity | 0/5 |
| 5 | 12i PO | 30 × 3 | 100.00 | 100.00 | 5/5 | 28/28/28/28/28 | 28 | No apparent Toxicity | 4/5 |
| 6 | 12m PO | 3.3 × 3 | 20.12 | 19.09 | 0/5 | 17/21/21/21/21 | 20.2 | No apparent Toxicity | 0/5 |
| 7 | 12m PO | 10 × 3 | 73.89 | 27.14 | 0/5 | 7/21/20/7/21 | 15.2 | No apparent Toxicity | 0/5 |
| 8 | 12m PO | 30 × 3 | 100.00 | 100.00 | 4/5 | 28/28/28/28/24 | 27.2 | No apparent Toxicity | 1/5 |

[1]1% suppression in parasitemia is calculated by considering the mean marasitemia in the vehical control as 100%. Parasitemia suppression <80% is considered as non-significant.
[2]Number of animals that survived day 28/total animals in group (the day of the death-post-infection).
[3]MST—mean survival time (days).
[4]Number of mice without parasitemia (cured) till day 28 post-infection.
*Not included in analysis N-(7-Chloro-quinolin-4-yl)-N'-(6-methyl-2-piperidin-1-yl-pyrimidin-4-yl)-propane-1,3-diamine (12b): Pale yellow solid; Yield: 82%; mp 194-196° C.; IR (cm-1, KBr): 3241, 3079, 1940, 1615, 1587, 1361, 1208, 1001, 804; 1H NMR (400 MHz, CDCl3): 1.46-1.56 (m, 6H), 1.87 (quin, 2H), 2.16 (s, 3H), 3.36 (q, 2H), 4.45 (t, 4H), 3.49 (q, 2H), 4.86 (brs, 1H), 5.72 (s, 1H), 5.92 (brs, 1H), 6.32 (d, 1H, J=5.4 Hz), 7.22 (dd, 1H, J=11.0 Hz, 2.0 Hz), 7.66 (d, 1H, J=8.7 Hz), 7.85 (d, 1H, J=2.3 Hz), 8.41 (d, 1H, J=5.5 Hz); 13C NMR (100 MHz, CDCl3): 24.36, 24.67, 25.45, 29.06, 38.55, 40.34, 44.89, 92.36, 98.86, 117.43, 121.55, 124.83, 128.53, 134.63, 149.18, 149.91, 151.96, 162.42, 162.84, 165.62; ESI-MS (m/z): 411.23 (M+H)+; Anal. Calcd for C22H27ClN6: C, 64.30; H, 6.62; N, 20.45. Found: C, 64.42; H, 6.68; N, 20.41.

N-(7-Chloro-quinolin-4-yl)-N'-(6-methyl-2-piperidin-1-yl-pyrimidin-4-yl)-butane-1,4-diamine (12c): White solid; Yield: 88%; mp 187-189° C.; IR (cm-1, KBr): 3247, 3067, 2935, 1581, 1364, 1210, 1079, 848; 1H NMR (400 MHz, CDCl3): 1.49-1.65 (m, 6H), 1.73-1.79 (m, 2H), 1.83-1.89 (m, 2H), 2.17 (s, 3H), 3.35 (q, 2H), 3.45-3.52 (m, 6H), 4.79 (brs, 1H), 5.25 (brs, 1H), 5.76 (s, 1H), 6.38 (d, 1H, J=5.5 Hz), 7.31 (dd, 1H, J=11.0 Hz, 2.0 Hz), 7.63 (d, 1H, J=8.7 Hz), 7.93 (d, 1H, J=2.3 Hz), 8.50 (d, 1H, J=5.5 Hz); 13C NMR (100 MHz, CDCl3): 24.09, 24.67, 25.43, 25.75, 27.64, 40.64, 43.02, 44.87, 91.91, 98.92, 117.14, 121.21, 125.04, 128.56, 134.66, 149.05, 149.76, 151.93, 162.17, 162.90, 165.67; ESI-MS (m/z): 425.28 (M+H)+; Anal. Calcd for C23H29ClN6: C, 65.00; H, 6.88; N, 19.78. Found: C, 64.98; H, 6.90; N, 19.81.

N-(7-Chloro-quinolin-4-yl)-N'-(6-methyl-2-piperidin-1-yl-pyrimidin-4-yl)-hexane-1,6-diamine (12d): Light brown solid; Yield: 82%; mp 97-99° C.; IR (cm-1, KBr): 3314, 2933, 1579, 1368, 1232, 1134, 983, 853, 789; 1H NMR (400 MHz, CDCl3): 1.47-1.64 (m, 12H), 1.72-1.79 (m, 2H), 2.17 (s, 3H), 3.29 (q, 2H), 3.39 (q, 2H), 3.54 (t, 4H), 4.76 (brs, 1H), 5.07 (brs, 1H), 5.74 (s, 1H), 6.39 (d, 1H, J=5.5 Hz), 7.34 (dd, 1H, J=11.0 Hz, 2.0 Hz), 7.67 (d, 1H, J=8.7 Hz), 7.95 (d, 1H, J=2.3 Hz), 8.51 (d, 1H, J=5.5 Hz); ESI-MS (m/z): 453.12 (M+H)+; Anal. Calcd for C25H33ClN6: C, 66.28; H, 7.34; N, 18.55. Found: C, 66.32; H, 7.35; N, 18.49.

N-(7-Chloro-quinolin-4-yl)-N'-(6-methyl-2-morpholin-4-yl-pyrimidin-4-yl)-ethane-1,2-diamine (12e): Pale yellow solid; Yield: 86%; mp 165-167° C.; IR (cm-1, KBr): 3391, 3245, 2954, 1585, 1438, 1228, 1110, 993; 1H NMR (400 MHz, DMSO-d6): 2.09 (s, 3H), 3.35-3.48 (m, 8H), 3.57 (t, 4H), 5.91 (s, 1H), 6.62-6.70 (m, 2H), 7.41 (dd, 1H, J=11.0 Hz, 2.0 Hz), 7.44 (brs, 1H), 7.74 (d, 1H, J=2.3 Hz), 8.14 (d, 1H, J=9.1 Hz), 8.35 (d, 1H, J=5.5 Hz); ESI-MS (m/z): 399.20 (M+H)+; Anal. Calcd for C20H23ClN6O: C, 60.22; H, 5.81; N, 21.07. Found: C, 60.34; H, 5.79; N, 21.09.

N-(7-Chloro-quinolin-4-yl)-N'-(6-methyl-2-morpholin-4-yl-pyrimidin-4-yl)-propane-1,3-diamine (12f): White solid; Yield: 82%; mp 165-167° C.; IR (cm-1, KBr): 3233, 3063, 2954, 1576, 1366, 1247, 1123, 791; 1H NMR (400 MHz, CDCl3): 1.92 (quin, 2H), 2.20 (s, 3H), 3.39 (q, 2H), 3.47 (t, 4H), 3.52 (q, 2H), 3.66 (t, 4H), 5.22 (brs, 1H), 5.71 (s, 1H), 5.95 (brs, 1H), 6.34 (d, 1H, J=5.4 Hz), 7.25 (dd, 1H, J=11.0 Hz, 2.2 Hz), 7.72 (d, 1H, J=8.7 Hz), 7.89 (d, 1H, J=2.3 Hz), 8.44 (d, 1H, J=5.5 Hz); 13C NMR (100 MHz, CDCl3): 24.10, 28.85, 38.56, 40.34, 44.09, 66.46, 92.27, 98.85, 117.35, 121.52, 124.93, 128.46, 134.73, 149.06, 149.90, 151.83, 161.87, 163.27, 165.70; ESI-MS (m/z): 413.21 (M+H)+; Anal. Calcd for C21H25ClN6O: C, 61.08; H, 6.10; N, 20.35. Found: C, 61.12; H, 6.17; N, 20.40.

N-(7-Chloro-quinolin-4-yl)-N'-(6-methyl-2-morpholin-4-yl-pyrimidin-4-yl)-butane-1,4-diamine (12g): White solid; Yield: 80%; mp 214-216° C.; IR (cm-1, KBr): 3256, 3066, 2964, 1583, 1367, 1245, 1122, 994, 790; 1H NMR (400 MHz, CDCl3): 1.72-1.80 (m, 2H), 1.83-1.91 (m, 2H), 2.20 (s, 3H), 3.36 (q, 2H), 3.48 (q, 2H), 3.52 (t, 4H), 3.71 (t, 4H), 4.83 (brs, 1H), 5.19 (brs, 1H), 5.75 (s, 1H), 6.40 (d, 1H, J=5.5 Hz), 7.32 (dd, 1H, J=11.0 Hz, 2.0 Hz), 7.63 (d, 1H, J=8.7 Hz), 7.95 (d, 1H, J=2.3 Hz), 8.51 (d, 1H, J=5.5 Hz); 13C NMR (100 MHz, CDCl3): 22.75, 24.18, 25.83, 41.39, 42.69, 64.93, 89.96, 97.19, 122.10, 122.28, 122.80, 126.34, 132.68, 147.77, 149.11, 150.43, 160.69, 161.99, 164.64; ESI-MS (m/z): 427.12 (M+H)+; Anal. Calcd for C22H27ClN6O: C, 61.89; H, 6.37; N, 19.68. Found: C, 61.99; H, 6.45; N, 19.70.

N-(7-Chloro-quinolin-4-yl)-N'-(6-methyl-2-morpholin-4-yl-pyrimidin-4-yl)-hexane-1,6-diamine (12h): Pale yellow solid; Yield: 90%; mp 107-109° C.; IR (cm-1, KBr): 3245, 2935, 2855, 1579, 1366, 1220, 1123, 994, 789; 1H NMR (400 MHz, CDCl3): 1.44-1.46 (m, 4H), 1.55-1.62 (m, 2H), 1.69-1.74 (m, 2H), 3.27 (q, 2H), 3.36 (q, 2H), 3.54 (t, 4H), 3.78 (t, 4H), 4.88 (brs, 1H), 5.26 (brs, 1H), 5.73 (s, 1H), 6.37 (d, 1H, J=5.1 Hz), 7.31 (dd, 1H, J=11.0 Hz, 2.0 Hz), 7.70 (d, 1H, J=8.7 Hz), 7.93 (d, 1H, J=2.2 Hz), 8.50 (d, 1H, J=5.1 Hz); 13C NMR (100 MHz, CDCl3): 24.13, 26.62, 26.82, 28.66, 29.60, 41.04, 43.06, 44.09, 66.53, 91.58, 98.93, 117.07, 121.00, 125.08, 128.62, 134.67, 149.04, 149.68, 151.94, 162.00, 163.45, 166.31; ESI-MS (m/z): 456.21 (M+H)+; Anal. Calcd for C24H31ClN6O: C, 63.35; H, 6.87; N, 18.47. Found: C, 63.29; H, 6.91; N, 18.46.

N-(7-Chloro-quinolin-4-yl)-N'-[6-methyl-2-(4-methyl-piperazin-1-yl)-pyrimidin-4-yl]-ethane-1,2-diamine (12i): White solid 83%; Yield: mp 134-136° C.; IR (cm-1, KBr): 3385, 3066, 2940, 1581, 1445, 1305, 1139, 997, 793; 1H NMR (400 MHz, CDCl3): 2.29 (s, 3H), 2.30 (s, 3H), 2.42 (t, 4H), 3.41 (q, 2H), 3.62 (t, 4H), 3.84 (q, 2H), 5.51 (brs, 1H), 5.87 (s, 1H), 6.30 (d, 1H, J=5.5 Hz), 6.90 (brs, 1H), 7.21 (dd, 1H, J=11.0 Hz, 2.0 Hz), 7.55 (d, 1H, J=8.7 Hz), 7.89 (d, 1H, J=2.3 Hz), 8.46 (d, 1H, J=5.5 Hz); ESI-MS (m/z): 412.26 (M+H)+; Anal. Calcd for C21H26ClN7: C, 61.23; H, 6.36; N, 23.80. Found: C, 61.18; H, 6.51; N, 23.85.

N-(7-Chloro-quinolin-4-yl)-N'-[6-methyl-2-(4-methyl-piperazin-1-yl)-pyrimidin-4-yl]-propane-1,3-diamine (12j): Off white solid; Yield: 80%; mp 176-178° C.; IR (cm-1, KBr): 3257, 3065, 2938, 1580, 1369, 1236, 1142, 1001, 789; 1H NMR (400 MHz, CDCl3): 1.94 (quin, 2H), 2.21 (s, 3H), 2.28 (s, 3H), 2.36 (t, 4H), 3.42 (q, 2H), 3.52-3.56 (m, 6H), 5.32 (brs, 1H), 5.74 (s, 1H), 6.01 (brs, 1H), 6.37 (d, 1H, J=5.4 Hz), 7.27 (dd, 1H, J=11.0 Hz, 2.0 Hz), 7.75 (d, 1H, J=8.7 Hz), 7.91 (d, 1H, J=2.3 Hz), 8.46 (d, 1H, J=5.5 Hz); ESI-MS (m/z): 426.32 (M+H)+; Anal. Calcd for C22H28ClN7: C, 62.03; H, 6.63; N, 23.02. Found: C, 62.11; H, 6.68; N, 22.95.

N-(7-Chloro-quinolin-4-yl)-N'-[6-methyl-2-(4-methyl-piperazin-1-yl)-pyrimidin-4-yl]-butane-1,4-diamine (12k): White solid; Yield: 87%; mp 183-185° C.; IR (cm-1, KBr): 3248, 3072, 2927, 1581, 1367, 1280, 1139, 997, 790; 1H NMR (400 MHz, CDCl3): 1.75-1.91 (m, 4H), 2.19 (s, 3H), 2.29 (s, 3H), 2.39 (t, 4H), 3.36 (q, 2H), 3.48 (q, 2H), 3.56 (t, 4H), 4.86 (brs, 1H), 5.23 (brs, 1H), 5.77 (s, 1H), 6.39 (d, 1H, J=5.5 Hz), 7.32 (dd, 1H, J=11.0 Hz, 2.0 Hz), 7.64 (d, 1H, J=8.7 Hz), 7.94 (d, 1H, J=2.3 Hz), 8.51 (d, 1H, J=5.5 Hz); 13C NMR (100 MHz, CDCl3): 24.15, 25.79, 27.65, 40.65, 43.04, 43.64, 46.10, 54.61, 92.00, 98.97, 117.12, 121.09, 125.09, 128.69, 134.67, 149.11, 149.68, 151.99, 162.13, 163.16, 166.16; ESI-MS (m/z): 440.19 (M+H)+; Anal. Calcd for C23H30ClN7: C, 62.79; H, 6.87; N, 22.28. Found: C, 62.80; H, 6.85; N, 22.30.

N-(7-Chloro-quinolin-4-yl)-N'-[6-methyl-2-(4-methyl-piperazin-1-yl)-pyrimidin-4-yl]-hexane-1,6-diamine (12l): Light brown solid; Yield: 85%; mp 152-154° C.; IR (cm-1, KBr): 3266, 3068, 2931, 1580, 1367, 1279, 1164, 993, 789; 1H NMR (400 MHz, CDCl3): 1.46-1.55 (m, 4H), 1.59-1.61 (m, 2H), 1.74-1.77 (m, 2H), 2.19 (s, 3H), 2.30 (s, 3H), 2.42-2.44 (m, 4H), 3.29 (q, 2H), 3.38 (q, 2H), 3.60 (t, 4H), 4.77 (brs, 1H), 5.02 (brs, 1H), 5.75 (s, 1H), 6.40 (d, 1H, J=5.5 Hz), 7.35 (dd, 1H, J=11.0 Hz, 2.1 Hz), 7.66 (d, 1H, J=8.7 Hz), 7.95 (d, 1H, J=2.3 Hz), 8.51 (d, 1H, J=5.5 Hz); 13C NMR (100 MHz, CDCl3): 24.14, 26.62, 26.82, 28.70, 29.63, 41.05, 43.10, 43.64, 46.12, 54.67, 91.72, 98.98, 117.08, 120.96, 125.14, 128.70, 134.71, 149.07, 149.67, 151.98, 162.05, 163.21, 166.09; ESI-MS (m/z): 468.32 (M+H)+; Anal. Calcd for C25H34ClN7: C, 64.15; H, 7.32; N, 20.95. Found: C, 64.09; H, 7.31; N, 20.98.

N-(7-Chloro-quinolin-4-yl)-N'-[2-(4-ethyl-piperazin-1-yl)-6-methyl-pyrimidin-4-yl]-propane-1,3-diamine (12m): White solid; Yield: 82%; mp 184-186° C.; IR (cm-1, KBr): 3233, 2967, 2812, 1579, 1366, 1250, 1132, 998; 1H NMR (400 MHz, CDCl3): 1.10 (t, 3H), 1.95 (quin, 2H), 2.24 (s, 3H), 2.40-2.44 (m, 6H), 3.43 (q, 2H), 3.55-3.59 (m, 6H), 4.94 (brs, 1H), 5.78 (s, 1H), 5.92 (brs, 1H), 6.40 (d, 1H, J=5.4 Hz), 7.30 (dd, 1H, J=11.0 Hz, 2.0 Hz), 7.73 (d, 1H, J=8.7 Hz), 7.93 (d, 1H, J=2.3 Hz), 8.49 (d, 1H, J=5.4 Hz); 13C NMR (100 MHz, CDCl3): 11.86, 24.38, 29.05, 38.50, 40.31, 43.64, 52.26, 52.34, 92.35, 98.85, 117.38, 121.47, 124.84, 128.53, 134.61, 149.15, 149.84, 151.94, 162.34, 163.04, 166.03; ESI-MS (m/z): 440.16 (M+H)+; Anal. Calcd for C23H30ClN7: C, 62.79; H, 6.87; N, 22.28. Found: C, 62.75; H, 6.89; N, 22.20.

N-(7-Chloro-quinolin-4-yl)-N'-[2-(4-ethyl-piperazin-1-yl)-6-methyl-pyrimidin-4-yl]-butane-1,4-diamine (12n): White solid; Yield: 86%; mp 101-103° C.; IR (cm-1, KBr): 3255, 2939, 2813, 1583, 1372, 1249, 1127, 994, 791; 1H NMR (400 MHz, CDCl3): 1.09 (t, 3H), 1.73-1.80 (m, 2H), 1.84-1.91 (m, 2H), 2.19 (s, 3H), 2.38-2.43 (m, 6H), 3.35 (q, 2H), 3.48 (q, 2H), 3.57 (t, 4H), 4.83 (brs, 1H), 5.23 (brs, 1H), 5.77 (s, 1H), 6.39 (d, 1H, J=5.5 Hz), 7.31 (dd, 1H, J=11.0 Hz, 2.0 Hz), 7.64 (d, 1H, J=8.7 Hz), 7.94 (d, 1H, J=2.3 Hz), 8.51 (d, 1H, J=5.5 Hz); ESI-MS (m/z): 454.11 (M+H)+; Anal. Calcd for C24H32ClN7: C, 63.49; H, 7.10; N, 21.60. Found: C, 63.59; H, 7.18; N, 21.63.

Example 2

Agonists for Orphan Nuclear Receptor Nurr1 Exert Neuroprotective Effects and Rescue Behavioral Deficits in Animal Models of Parkinson's Disease Materials and Methods Chemical Library.

The 960 compounds from The Genesis Plus Collection (MicroSource Discovery Systems) were used to identify the Nurr1 activator. The compounds in this library are primarily U.S. Food and Drug Administration-approved compounds. The 720 compounds containing pure natural products and their derivatives (Microsource Discovery Systems) were also tested.

Plasmid Constructs.

The pTH2600LUC reporter construct contains the 2.6 kb upstream sequences of the rat tyrosine hydroxylase gene in front of a firefly luciferase gene in pGL3-basic vector. A Nurr1-expression plasmid, pSV40Nurr1, was kindly provided by Dr Orla M. Conneely at Baylor College of Medicine (Houston, Tex., USA). Full-length mouse Nurr1cDNA was amplified by RT-PCR from pSV40Nurr1 using forward 5'-GCTTTCAAGCTTATGCCTTGTGTTCAGGCGCAG-TATGG-3' (SEQ ID NO: 1) and reverse 5'-GTCAATCTC-GAGGAAAGGTAAGGTGTCCAGGAAAAG-3' (SEQ ID NO: 2) oligonucleotides. The amplified PCR fragment was cut with Hind III and Xho I and then cloned into the plasmid pCDNA3.1/myc-His (Invitrogen), resulted in the expression of a C-terminal myc-tagged fusion protein and named with pCMVNurr1-myc. The NM 1 LBD fragment from amino acid position 328 to amino acid position 598 was PCR-amplified and subcloned into pZeoSV (Invitrogen) containing the GAL4 DNA binding domain. The Nur77 LBD (aa 354-598), glucocorticoid receptor-a (GRα) LBD (aa 522-777), liver X receptor-a (LXRα) LBD (aa 207-447), retinoid X receptor (RXR) LBD (aa 223-462), peroxisome proliferator-activated receptor-a (PPARα) LBD (aa 201-467), peroxisome proliferator-activated receptor-g(PPARγ) LBD (aa 209-476) were amplified by PCR and subcloned to pZeoSV GAL containing the GAL4 DNA binding domain. The reporter plasmid, p8xGAL-Luc, was constructed by cloning synthetic oligonucleotides to generate 8 tandem repeat GAL4 binding sites (5'-CTCGGAGGACAG-TACTCCG-3' (SEQ ID NO: 3))[1] upstream of the luciferase in pGV-B2 (Toyo Ink) plasmid. 4 copies of NL3 (5'-GATCGAAAACAAAAGGTCACTTAC-3' (SEQ ID NO: 4); bold indicates a consensus NBRE motif)[2] were inserted into upstream of the minimal promoter of TATA-Luciferase, resulting in p4x(NL3)-Luc. Mouse SRC-1 and human SRC-3 cDNAs were amplified by PCR using pYX-mSRC1 (Open Biosystem, MMM1013-9498102) and pCR-TOPO hSRC3 (Open Biosystem, MHS4426-99625636) as a template, respectively. Amplified cDNAs were subcloned into pCMV 2B (Stratagene) and resulted in the expression of an NH2-terminal flag-tagged fusion protein. The VP16/SRC1 and VP16/SRC3 hybrid were constructed by inserting the transactivation domain of the VP16 protein upstream of SRC1 and SRC3, respectively. Nurr1-LBD, RXR-LBD, and Nur77-LBD were amplified by PCR using 5'-AAA AAACATATGGTTAAAGAAGTGGTTCG-3' (SEQ ID NO: 5) and 5'-GTCAATCTCGAGTTAGAAAGG-TAAGGTGTCCAGGAAAAG-3' (SEQ ID NO: 6) for Nurr1 LBD, 5'-GAG GTG CAT ATG ACC AGC AGC GCC AAC GAG GAC ATG-3' (SEQ ID NO: 7) and 5'-AAA AAA CTC GAG CTA AGT CAT TTG GTG CGG CGC CTC-3' (SEQ ID NO: 8) for RXR LBD, and 5'-AAA CCC CAT ATG AAG CAG CCC CCA GAT GCC-3' (SEQ ID NO: 9) and 5'-AAA AAA CTC GAG TCA GAA GGG CAG CGT-3' (SEQ ID NO: 10) for Nur77 LBD (bold letters indicate the restriction enzyme site) and then subcloned into vector pET15b to express the His-tagged fusion protein. The recombinant proteins were purified by Ni-NTA column chromatography (Qiagen) according to the manufacturer's instruction. The integrity of all sequences was verified by DNA sequence analyses.

Transfection and Compound Screening.

Human neuroblastoma SK-N-BE(2)C cells were maintained in Dulbecco's modified Eagle's medium (DMEM) supplemented with 10% fetal bovine serum. All culture media contained 100 units/ml penicillin and 100 μg/ml streptomycin. For transfection, cells were plated at $1.5 \times 10^5$ cells/well in the DMEM media without antibiotic into 24-well plates 1 day prior to transfection. Transfections were carried out by the Lipofectamine plus (Invitrogen) according to the manufacture's protocol. Total DNA amount was 0.5 μg per well with 0.1 μg of pRSV-β-gal as an internal control. 6 hours after transfection, compounds in the DMEM media with 1% charcoal-stripped fetal calf serum was added and incubated overnight. Cells from each well were lysed with 100 µl of lysis buffer, which contains 25 mM Tris-phosphate (pH 7.8), 2 mM DTT, 2 mM CDTA (1,2-diaminocyclohexane-N,N,N',N'-tetraacetic acid), 10% glycerol, and 1% Triton X-100. Then equal volume of firefly luciferase substrate was added and the luciferase activity was measured using a Luminometer plate reader and normalized for beta-galactosidase activity.

Western Blotting.

Cells were washed twice with phosphate-buffered saline (PBS) and harvested in a solution containing 1% Triton X-100, 20 mM Tris (pH7.6), 150 mM sodium chloride, 1 mM phenylmethylsulfonylfluride (PMSF). The cell suspension was sonicated and boiled in an equal volume of SDS-sample buffer. Samples were subjected to SDS-polyacrylamide gel electrophoresis (PAGE) and transferred to a nitrocellulose membrane (Hybond-ECL, Amersham). After blocking, the membrane was incubated with primary antibodies diluted in PBS containing 0.1% BSA. The following primary antibodies were used: rabbitanti-Nurr1 (Santa Cruz; 1:3000), mouse anti-myc (Roche; 1:3000), mouse anti-flag (Roche 1:3000), rabbit anti-caspase3 (Cell Signalling; 1:1000), and mouse anti-actin (Sigma 1:5000). The membrane was incubated with 1:3000-dilution of horseradish peroxidase-conjugated anti-mouse or anti-rabbit immunoglobulin G (IgG) antibody (Amersham). Detection was achieved using an enhanced-chemiluminescent substrate (Amersham).

Immunoprecipitation Analysis.

Cells were disrupted in lysis buffer containing 20 mM Tris (pH7.6), 100 mM sodium chloride, 0.5% NP-40, 0.5 mM EDTA, 0.5 mM PMSF, 1× protease inhibitor cocktail (Roche). One µg of anti-flag previously absorbed for 4 hours with protein-Aagarose (Upstate) were added to media and cell lysates, and incubated for 16 hours at 4° C. Pellets were collected by centrifugation for 5 minutes and washed 3 times with lysis buffer. The immunoprecipitated proteins were released from protein-A by boiling 5 minutes in SDS-sample buffer. Samples were analyzed by 10% SDS-PAGE and subjected to western blotting assay using mouse anti-myc antibodies.

BIAcore Analysis.

Binding experiments were performed with the surface Plasmon Resonance-based biosensor instrument BIAcore 3000 (BIAcore AB, Uppsala). Immobilization of the purified proteins on the sensor surface was performed following the standard amine coupling procedure according to manufacturer's instructions. The final immobilization response of each protein was 6000 resonance units. A reference surface was generated simultaneously under the same conditions with BSA and used as a blank to correct for instrument and buffer artifacts. AQ and kanamycin were injected at variable concentrations at 20 µl/min flow rate, and binding to the protein immobilized on the chip was monitored in real-time. Each sensorgram consists of an association phase (60-160 sec), reflecting binding of the injected AQ to the protein, followed by a dissociation phase (after 160 sec), during which the running buffer is passed over the chip and the bound AQ is being washed off the protein surface. Binding data were analyzed using the BIAcore 3000 CONTROL® software and the BIAEVALUATION® software.

Fluorescence Quenching Assay.

Fluorescence spectra were measured using a SHIMADZU fluorescence spectrophotometer (model RF-5310PC, SHIMADZU). The proteins (15 ng/µl) were incubated with different concentrations of AQ or kanamycin (0.1 nM, 1 nM, 10 nM, 100 nM and 1 µM in PBS buffer, pH7.0). Protein quenching was monitored at 25° C. by using 5 nm of excitation and 5 nm of emission slit-width. The excitation wavelength was 280 nm, and the emission spectra were measured between 290 and 430 nm.

Filter binding assay. Aliquots (100 µl) of an assay mixture containing 0.32 µM Nurr-LBD and 3.9-1000 nM [$^3$H]-CQ (Moravek Biochemicals, CA) in binding buffer (25 mM sodium acetate buffer (pH 5.2)) were incubated at 4° C. for overnight. Non-specific binding was determined in parallel in the presence of a 1000-fold molar excess of unlabeled CQ. GF/C filters were wet with in binding buffer and placed on a 48-place filter manifold. 100 µl of assay mixture containing the [$^3$H]-CQ and Nurr1-LBD was applied on the surface of the filter. Filters were washed with 4×100 ml binding buffer, dried, and mixed with 5 ml Scintiverse BD (Fisher) and radioactivity was determined in a Beckman LS6000SC liquid scintillation counter. For competition assay, reactions containing 0.32 µM Nurr-LBD, 500 nM [$^3$H]-CQ and various concentrations of the competitor were incubated at 4° C. for overnight. The mixture was applied to GF/C filter and filter was washed and counted as described above.

Dopamine-Uptake Assay.

For measuring [$^3$H]Dopamine uptake following 6-OHDA treatment in the presence or absence of AQ, DA neurons were rinsed with Krebs Ringers solution, incubated in Krebs Ringers solution containing 1 mM ascorbate, 2 mM β-alanine, 100 µM pargyline at 37° C. for 5 min in a humidified 5% $CO_2$ atmosphere, and further incubated with 25 nM [$^3$H]Dopamine (45 Ci/mmol; Amersham Pharmacia) for 15 min. Control DA neurons were treated with the above medium in the presence of a dopamine uptake blocker, 10 µM mazindol (Sigma). Cells were then washed with ice-cold Krebs Ringers solution and lysed with 0.5 M NaOH. Radioactivity was quantified by a liquid scintillation counter (Beckman, Fullerton, Calif.).

Cell Culture and Drug Treatments.

PC12 cells were initially incubated at a density of 2×10$^5$ cells in poly-D-lysine-coated 24-well dishes and subsequently switched to serum-free N-2-defined medium containing 6-OHDA with or without AQ. Cell viabilities were determined by the conventional MTT reduction assay. After incubation for indicated times, cells were treated with the MTT solution (final concentration, 1 mg/ml, Sigma) for 1 h. Formazan grains formed in intact cells were solubilized with MTT Solubilization. Solution containing 10% Triton X-100 plus 0.1 N HCl in anhydrous isopropanol for 24 h and then absorbance at 570 nm was measured with a microplate reader (Molecular Devices, Menlo Park, Calif.).

To prepare primary cultures of DA neurons, the ventral mesencephalon was removed from 14 day gestation Sprague Dawley rat embryo (Charles River, Cambridge, Mass.). Tissues were incubated with 0.01% trypsin in MEM (MEM, Invitrogen) for 10 min at 37° C. and triturated using a constricted Pasteur pipette. DA neurons were plated at 1.0×10$^5$ cells per 9 mm diameter glass cover slip precoated with 100 µg/ml poly-D-lysine (Sigma, St. Louis, Mo.) and 4 µg/ml laminin (Invitrogen). DA neurons were maintained at 37° C. in a humidified 5% $CO_2$ atmosphere in minimum essential medium supplemented with 10% FBS (Hyclone), 2 mM glutamine and 6.0 g/l glucose. At 5 or 6 days in vitro, DA neurons were washed with MEM and treated with various experimental reagents for the time periods indicated. Reagents used were 6-OHDA (Sigma), N-acetyl-cysteine, N-benzyloxycarbonyl-Val-Ala-Asp-fluoromethylketone (Z-VAD-fmk; Enzyme Systems Products, Livermore, Calif.). BV-2 cells, a microglial-like mouse cell line, were thawed and passaged until logarithmic growth was achieved.

Cell cultures were maintained in 6-well culture plate (Corning Costar, Corning, N.Y.) at a concentration of $1.0 \times 10^5$ cells per well, in the growth medium consisting of DMEM (Sigma, St. Louis, Mo.), supplemented with 10% fetal bovine serum (FBS; Hyclone) heat inactivated at 56° C. for 30 min, 2 mM L-glutamine (Sigma) and 1× Pen-Strep (Invitrogen). To begin the experiment, BV-2 cells were washed with DMEM and treated with LPS (Sigma) in the presence or absence of AQ (Sigma). The plates were at 37° C. in an atmosphere of 5% $CO_2$/95% air for the listed period of time. Cells from each single well were withdrawn for RNA extraction.

Neural precursor cells (NPCs) from dissection of rat embryos days 14 cortices (E14) were proliferated in N2 medium supplemented with 20 ng/mL basic fibroblast growth factor (bFGF; R&D Systems, Minneapolis, Minn., USA). Following 3-4 days of bFGF-expansion, NPCs were dissociated in $Ca^{2+}/Mg^{2+}$-free Hank's balanced salt solution (CMF-HBSS, Invitrogen, Carlsbad, Calif.) and re-plated onto coverslips (12 mm diameter; Carolina Biological Supply Company, Burlington, N.C.) at 32,000 cells/coverslip pre-coated with poly-L-ornithine (PLO; 15 mg/ml, Sigma, St Louis, Mo.) at 37° C. overnight followed by fibronectin (FN; 1 mg/ml, Sigma) overnight. Prior to drug treatment, NPCs were transduced with Nurr1-expressing retrovirus of MOI 5 in the presence of polybrene (1 µg/ml, Sigma), cultured overnight in N2, and then differentiated. Getting started chemical treatment (every day for 2 hours), bFGF was not added anymore[3].

Immunocytochemistry and Immunohistochemistry.

Cells were fixed in 4% papraformaldehyde (PFA) for 20 min, washed and then incubated with blocking buffer [PBS, 10% goat serum (Invitrogen), 0.3% Triton X-100 (Sigma)] for 1 hour. Cells were then incubated overnight at 4° C. with primary antibodies with the primary antibody in PBS containing 1% normal goat serum and 0.1% Triton X-100. A rabbit polyclonal anti-TH antibody (1:500; Pel-Freez, Rogers, Ark.) was used as a primary antibody. Following washes with PBS, appropriate fluorescence-tagged secondary antibodies (Jackson Immunoresearch Laboratories, West Grove, Pa.) were used for visualization. Stained samples were mounted in VECTASHIELD with DAPI mounting solution (Vector Laboratories INC., Burlingame, Calif.) and photographed using epifluorescence microscope (Leica). The animals were euthanized by anesthesia with pentobarbital (3 ml/kg), and then transcardially perfused with 4% PFA in a 0.05M phosphate buffer (PB). Immunohistochemistry and immunofluorescence assay were performed as previously described[4], on free-floating cryomicrotome-cut sections (40 µm thick) that encompassed the entire brain. After their incubation with 3% $H_2O_2$ in 0.05M PBS, followed by 0.3% Triton X-100 and 3% bovine serum albumin (BSA) in 0.05M PBS, the sections were stained overnight at 4° C. with a primary antibody. The ABC kit (Vector Laboratories, Burlingame, Calif., USA) was used as a secondary antibody. After the tissue was washed three times in 0.05M PBS, followed by 0.3% Triton X-100 and 1% BSA in 0.05M PBS, the sections were stained overnight at 4° C. with primary antibodies. The following primary antibodies were used: mouse anti-Iba-1 (Abcam; 1:500), goat anti-FoxA2 (SCBT; 1:200), sheep anti-tyrosine hydroxylase (TH) (Pel-Freez; 1:200), rabbit anti-TH (Pel-Freez 1:200), goat anti-FoxA2 (Millipore; 1:200), and sheep anti-AADC (Millipore; 1:500). The tissues were washed three times in PBS and incubated for 2 h with the secondary fluorescence-conjugated goat anti-mouse and rabbit antibody (DAKO, Denmark, Cy3, FITC, both dilutions at 1:1,000) and tissues were washed and mounted in Vectorshield. All tissue samples were additionally counterstained with DAPI. Tissues were visualized using fluorescence microscopy. Every $6^{th}$ section of rat brains was assayed to count immunoreactive cells using the Image J (version 1.42q, National Institutes of Health, USA) and Stereo Investigator and software (Microbright Field, Williston, Vt.). The protection percentage of total $TH^+$ cells in the lesioned hemisphere of each rat brain was calculated by dividing total $TH^+$ cells in the intact hemisphere of each rat brain and multiplying $100^5$.

Semi-quantitative and quantitative RT-PCR analyses. Total RNA was extracted by single step preparation using Trizol reagent (Invitrogen) following the manufacturer's instructions. Total RNA from each single well was reverse transcribed into cDNA using SuperscriptII Reverse Transcriptase and oligo(dT)18 primer (SEQ ID NO: 35) (Invitrogen). Real-time PCR analysis was performed using the ABI-Prism7700 sequence detection system (Applied Biosystems). Briefly, it was performed in a 0.5 ml tubes (Applied Biosystems) on cDNA equivalent to 50 ng of DNase-digested RNA in a volume of 25 µl, containing 12.5 µl of SyBR green Universal Master mix, forward and reverse primers (IL-1β; forward 5'-GCA ACT GTT CCT GAA CTC AAC T-3' (SEQ ID NO: 11), reverse 5'-ATC TTT TGG GGT CCG TCA ACT-3' (SEQ ID NO: 12), IL-6; forward 5'-TAG TCC TTC CTA CCC CAA TTT CC-3' (SEQ ID NO: 13), reverse 5'-TTG GTC CTT AGC CAC TCC TTC-3' (SEQ ID NO: 14) iNOS; forward 5'-ACA TCG ACC CGT CCA CAG TAT-3' (SEQ ID NO: 15), reverse 5'-CAG AGG GGT AGG CTT GTC TC-3' (SEQ ID NO: 16), TNF-α; forward 5'-ATG TCG GCT CCA GGA CCT TA-3' (SEQ ID NO: 17), reverse 5'-GGT AGT AAC TGT TGA CAC CCA CT-3' (SEQ ID NO: 18), mouse GAPDH; forward 5'-AGG TCG GTG TGA ACG GAT TTG-3' (SEQ ID NO: 19), reverse 5'-TGT AGA CCA TGT AGT TGA GGT CA-3' (SEQ ID NO: (20), TH; forward 5'-AGC CCC CAC CTG GAGTAT TTT G-3' (SEQ ID NO: 21), reverse 5'-AGC AAT CTC TTC CGC TGT GTA TTC-3' 22), AADC; forward 5'-GCC TTT ATC TGT CCT GAG TTC CG-3' (SEQ ID NO: 23), reverse 5'-TGA TGA GTC CTG AGT CCT GGT GAC-3' (SEQ ID NO: 24), DAT; forward 5'-GCT GGC ACA TCT ATC CTC TTT GG-3' (SEQ ID NO: 25), reverse 5'-CAA TGC TGA CCA CGA CCA CAT AC-3' (SEQ ID NO: 26), VMAT; forward 5'-GCA CAC AAA ATG GGA AGG TGG C-3' (SEQ ID NO: 27), reverse 5'-CAT TTT TTC CTC CTT AGC AGG TGG-3' (SEQ ID NO: 28), rat GAPDH; forward 5'-TGA CAT CAA GAA GGT GGT GAA GC-3' (SEQ ID NO: 29), reverse 5'-GGA AGA ATG GGA GTT GCT GTT G-3' (SEQ ID NO: 30)) following manufacturer's protocol. Gene expression values were normalized to those of GAPDH.

Chromatin Immunoprecipitation

PC12 cells were grown in 150 mm dishes in the absence or presence of 20 µM AQ or 75 µM CQ for 15 hrs. Cells were washed with PBS, fixed with 1% formaldehyde, lysed, and sonicated according to the manufacturer's instruction (Active Motif). 25 µg of soluble chromatin DNA were co-immunoprecipitated 1 µg of Nurr1 specific antibody (E-20, Santa Cruz) or control antibody (rabbit IgG, santa Cruz). 2 µl ChIP DNA was subjected to quantitative real-time PCR using the following primer pairs: NL1: 5'-GCG TGG AGA GGA TGC GCA GG-3' (SEQ ID NO: 31) and 5'-AGT GCA AGC TGG TGG TCC CG-3' (SEQ ID NO: 32); NL3: 5'-TCC TTA GAG ATC CTG TTT CC-3' (SEQ ID NO: 33) and 5'-TCA GCT GGT CCC CAT GTA AG-3' (SEQ ID NO: 34). Values are shown as fold induction compared to mock treated control cells.

6-OHDA-Lesioned Rat Model of PD.

To assess the potential neuro-protective effects of AQ/CQ, we generated intrastriatal 6-OHDA-lesioned rats[6-8] using male Sprague-Dawley rats weighing 240-300 g at the beginning of experiments. The rats were anesthetized with Ketamine[4.5 mg/kg, intraperitoneal (i.p.)] mixed with Rumpun (1.5 mg/kg, i.p.) and given a unilateral stereotaxic injection of 6-OHDA (20 μg/5 μl with 0.2 mg/ml L-ascorbic acid; Sigma, St. Louis, Mo., USA) or the same volume of the vehicle (L-ascorbic acid) into their right striatum using coordinates relative to the bregma and dura (A/P, 0.7; L/M, −2.6; D/V, −4.5) according to the atlas of Paximos and Watson[9] at the rate of 1 μl/min using a 26-gauge Hamilton microsyringe. Following infusion, the cannula was kept in place for 5 min to minimize backflow before being slowly retracted. The use of animals was in accordance with McLean's Institutional Animal Care and Use Committee and followed National Institutes of Health guide lines. In our preliminary experiments, we tested different doses (1, 5, and 20 mg/kg) of both AQ and CQ and found that AQ at 20 mg/kg exhibited most prominent effects. Thus, we used this condition for more systematic in vivo experiments.

Assay for the Neuroprotective Effects of AQ in the 6-OHDA-Lesioned Rat Model.

One day before modeling PD, rats were randomly assigned to two groups: saline group (n=6) and AQ-treatment group (n=8). AQ-treatment group received an i.p. injection of 20 mg/kg of AQ twice one day before 6-OHDA injection. After 6-OHDA injection, animals were given either AQ or saline twice per day for 13 days (in total, 2 weeks of AQ injection including one day of AQ injection before the PD modeling). For the behavioral functional assay, rotation behavior was measured for 90 min following intraperitoneal injection of 5 mg/kg amphetamine (Sigma-Aldrich, St. Louis, Mo.), using automatized rotameter system (Med Associate Inc., St. Albans, Vt., USA)[6,7]. Ipsilateral rotations were measured at 4 and 6 weeks post 6-OHDA letioning.

Abnormal Involuntary Movements (AIMs) Behavior in 6-OHDA-Lesioned Rats.

To test dyskinesia-like involuntary behaviors, AIMs test was performed at the two time points, immediately after two weeks of drug injection (2 weeks post 6-OHDA lesion; n=6), and one month after two weeks of drug injection (6 weeks post 6-OHDA lesion; n=6) Saline- and L-DOPA (8 mg/kg for two weeks; n=6) treatment was used as negative and positive control of AIMs behavior, respectively. The following behavioral tests were all videotaped and scored at a later date by two investigators blind to the animals' treatment. Rats were monitored for four types of AIMs[10]; Axial (dystonic posturing of neck and torso twisted toward the side of the body contralateral to the lesion), Forelimb (contralateral forelimb movements that are "rapid" and "purposeless"), Orolingual (repetitive jaw openings and tongue protrusions), and Locomoter (walking in a contralateral circular motion) AIMs. Rats were observed for 2 minutes at every 20 minute mark within a 2 hour period. During the 1st minute, each AIMs behavior was monitored and scored with 0-4 scale (0: no abnormal behavior at all; 1: present for less than 50% of observation time; 2: present for over 50% of observation time; 3: present for the entire observation period but interrupted by external stimulus; 4: present for the entire observation period and not interrupted by external stimulus). The AIMs scores for the 2 hour period in each category were summed (maximum score is 24).

Behavioral Studies in ak/ak Mice.

Either 20 mg/kg of AQ (AQ group) or saline (Saline group) was intraperitoneally injected (I.P.) twice per day for two weeks. 8 mg/kg of L-DOPA (L-DOPA group) in 0.5% DMSO was injected (I.P.) once per day for two weeks. The L-DOPA group was given 12.5 mg/kg benserazide 20 min prior to administration of L-DOPA.

Behavioral Experimental Groups and Behavioral Testing Design:

Each ak mouse was randomly assigned into one of three experiment groups, (1) saline group (negative control; n=8), (2) L-DOPA group (positive control; n=8), (3) AQ group (n=10). Each WT or rdl mouse was randomly divided into two groups, (1) saline group (n=8) and (2) AQ group (n=10). Pole Test, Challenging Beam Traversal Test, and Cylinder Test were performed at two time points, immediately and one month after two weeks of either AQ or saline injection. Each mouse ran each task twice. Rota rod test was performed immediately after two weeks of either drug or saline injection. Acclimation and data recording process were identical to the rat study described above. All tasks were performed as described previously[11] and the short description of each task is as follows.

Pole Test:

A vertical wooden pole 50 cm in length and 1 cm in diameter was used for Pole Test. Each mouse was gently placed head upwards on top of the pole which is placed on each animal's home cage. Each mouse ran tree trials per session during 2 training sessions. On the testing day, mice ran three trials. Two parameters (the meantime to orient downward and the total travel mean time) were used for the statistical analysis.

Challenging Beam Traversal Test:

A 1 m length of plastic beam was used for Challenging Beam Traversal Test. The starting width of the beam was 3.5 cm and it gradually narrowed in 1 c increments to 0.5 cm at the other end site of the beam Animals were trained to walk from the wide end to the other end for 2 sessions, three trials per session before testing. A mesh grid was removed during the training period. On the testing day, a mesh grid (1 cm square) covering the beam surface was equipped leaving a −1 cm room between the grid and the beam surface. On the testing day, mice ran three trials. Two parameters (the mean number of steps taken by each animal and the mean time to traverse across three trials) were collected and used for statistical analysis.

Cylinder Test:

A small transparent cylinder (height, 15.5 cm; diameter, 12.7 cm) was used to evaluate somatosensory motor function. Mice were placed in the cylinder and their rears were counted for 5 minutes. The forelimb touching the Plexiglas wall (a vertical movement) is defined as a full rear. The mean number of forelimb use was calculated for the statistical analysis. Each mouse ran Cylinder task for one session and no training sessions were necessary.

Rota Rod Test:

The Rota rod equipment (Med-Associates, Inc, Albans, Vt., USA) was used to measure motor coordination. The Rota rod is accelerated from 4 to 40 revolutions per minute (R$^P$Ms) over 4 min. The mean latency to fall off from the Rota rod was measured for the statistical analysis. Each mouse runs 3 consecutive trials daily with 10 min interval between trials for 3 consecutive sessions.

Statistical Methods

Statistical analyses were conducted using the statistical Analysis System (Version 9.1; SAS institute, Cary, N.C.). Performance measures of in vitro outcomes, cell counting, and behavioral outcomes were analyzed using the PROC TTEST, ANOVA, MIXED or GLIMMIX program, a generalized linear mixed models procedure for conducting repeated measures analyses followed by LSD (Fisher's least significant difference) post-hoc tests (LSD is a default post-hoc test provided in SAS). Means were calculated for each animal for each testing condition, defined by the following variables (where appropriate): Treatment (AQ, L-Dopa, or saline) and Time (2, 4, or 6 weeks after 6-OHDA lesion).

REFERENCES

1. Webster, N., Jin, J. R., Green, S., Hollis, M. & Chambon, P. The yeast UASG is a transcriptional enhancer in human HeLa cells in the presence of the GAL4 trans-activator. *Cell* 52, 169-78 (1988).
2. Kim, K. S. et al. Orphan nuclear receptor Nurr1 directly transactivates the promoter activity of the tyrosine hydroxylase gene in a cell-specific manner. *J Neurochem* 85, 622-34 (2003).
3. Park, C. H. et al. Proneural bHLH neurogenin 2 differentially regulates Nurr1-induced dopamine neuron differentiation in rat and mouse neural precursor cells in vitro. *FEBS Lett* 582, 537-42 (2008).
4. Chung, S. et al. ES cell-derived renewable and functional midbrain dopaminergic progenitors. *Proc Natl Acad Sci USA* 108, 9703-8 (2011).
5. Park, H. J. et al. Acupuncture prevents 6-hydroxydopamine-induced neuronal death in the nigrostriatal dopaminergic system in the rat Parkinson's disease model. *Exp Neurol* 180, 93-8 (2003).
6. Voutilainen, M. H. et al. Mesencephalic astrocyte-derived neurotrophic factor is neurorestorative in rat model of Parkinson's disease. *J Neurosci* 29, 9651-9 (2009).
7. Espino, A. et al. Chronic effects of single intrastriatal injections of 6-hydroxydopamine or 1-methyl-4-phenylpyridinium studied by microdialysis in freely moving rats. *Brain Res* 695, 151-7 (1995).
8. Blandini, F., Levandis, G., Bazzini, E., Nappi, G. & Armentero, M. T. Time-course of nigrostriatal damage, basal ganglia metabolic changes and behavioural alterations following intrastriatal injection of 6-hydroxydopamine in the rat: new clues from an old model. *Eur J Neurosci* 25, 397-405 (2007).
9. Paxinos, E. and Watson, C. The rat brain in stereotaxic coordinates. San Diego, Calif.: Academic Press (1997).
10. Dekundy, A., Lundblad, M., Danysz, W. & Cenci, M. A. Modulation of L-DOPA-induced abnormal involuntary movements by clinically tested compounds: further validation of the rat dyskinesia model. *Behav Brain Res* 179, 76-89 (2007).
11. Hwang, D. Y., et al. 3,4-dihydroxyphenylalanine reverses the motor deficits in Pitx3-deficient aphakia mice: behavioral characterization of a novel genetic model of Parkinson's disease. *J Neurosci* 25, 2132-2137 (2005).

Results and Discussion

Based on its unique dual role for development/maintenance of midbrain dopamine neurons and for their protection from inflammation-induced death, Nurr1 is a potential target for Parkinson's disease (PD). Here we show successful identification of Nurr1 agonists that share an identical chemical scaffold and stimulate the transcriptional activity through binding to the ligand-binding domain. Remarkably, they also enhanced the contrasting dual functions of Nurr1 and improved behavioral deficits in animal models of PD.

Figure 13A:
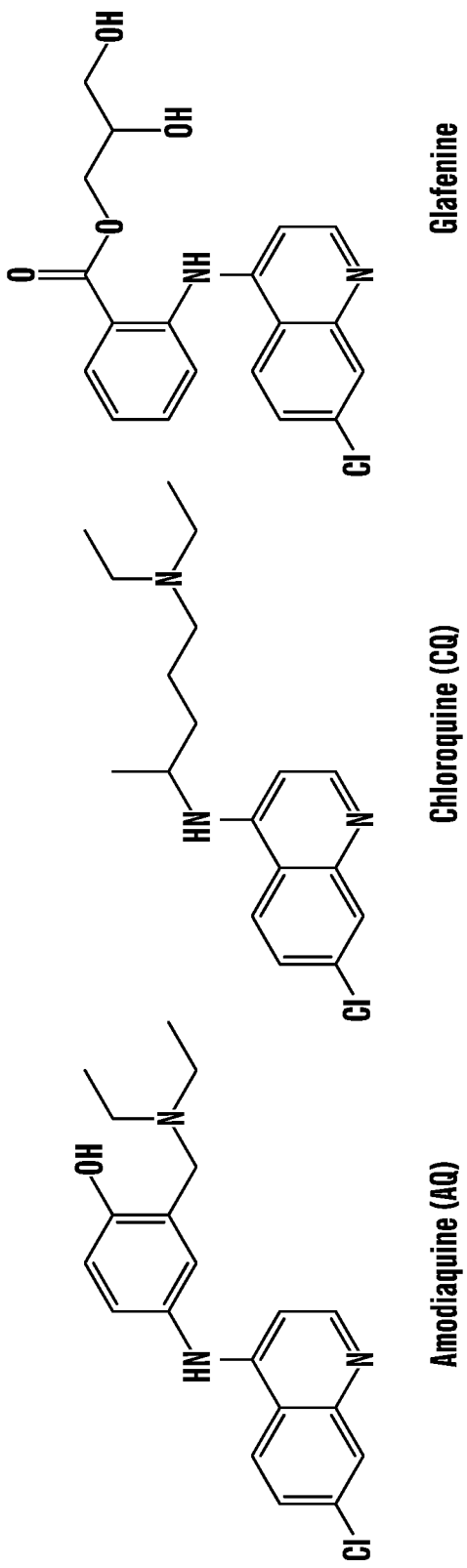
Figure 13B:
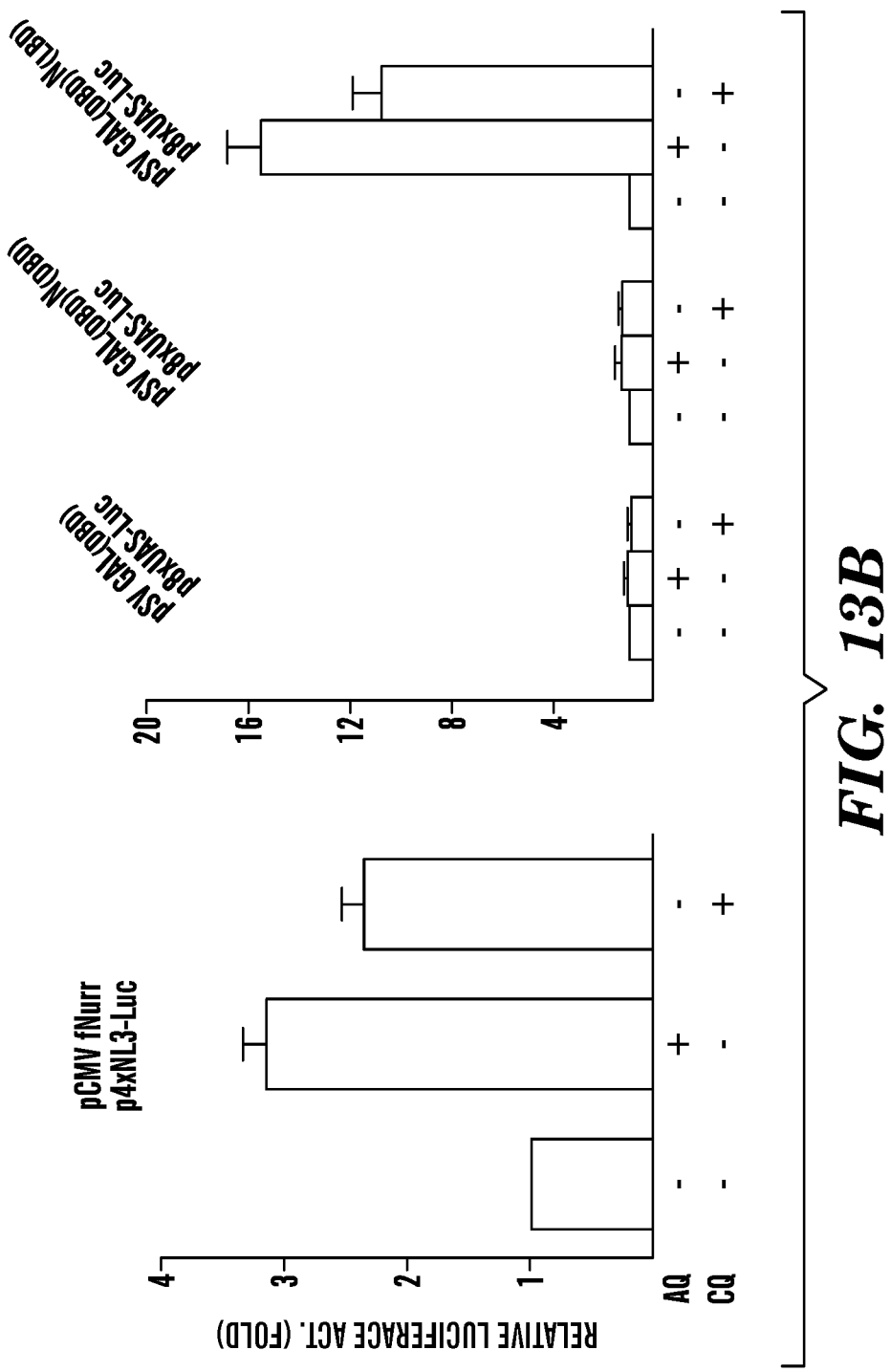

PD, primarily caused by selective degeneration of midbrain dopamine (mDA) neurons, is the most prevalent movement disorder, affecting 1-2% of the global population over the age of 65[1-3]. Currently available pharmacological treatments (e.g., L-DOPA) are largely symptomatic and lose their efficacy over time, with accompanying severe side effects such as dyskinesia. Thus, there is an unmet clinical need to develop mechanism-based and/or disease-modifying treatments[2,3]. The orphan nuclear receptor Nurr1 (also known as NR4A2) is essential not only for development and maintenance of mDA neurons[4-7] but also for their protection from inflammation-induced death[8]. Furthermore, previous studies showed decreased Nurr1 expression in postmortem brains of PD patients[9] and functional mutant forms in rare familial PD cases[10], strongly suggesting that Nurr1 is a promising target for the development of novel disease-modifying therapeutics for PD[11]. To address this possibility, we established efficient high-throughput assay systems based on Nurr1's ability to directly activate TH promoter function[12]. Using these cell-based assay systems, we screened a library composed of 960 FDA-approved drugs and successfully identified three hit compounds, i.e., two antimalarial drugs amodiaquine (AQ) and chloroquine (CQ) and the pain drug glafenine. Surprisingly, all three compounds share an identical chemical scaffold, 4-amino-7-chloroquinoline, suggesting a structure-activity relationship (SAR) (FIG. 13a).

Figure 3:
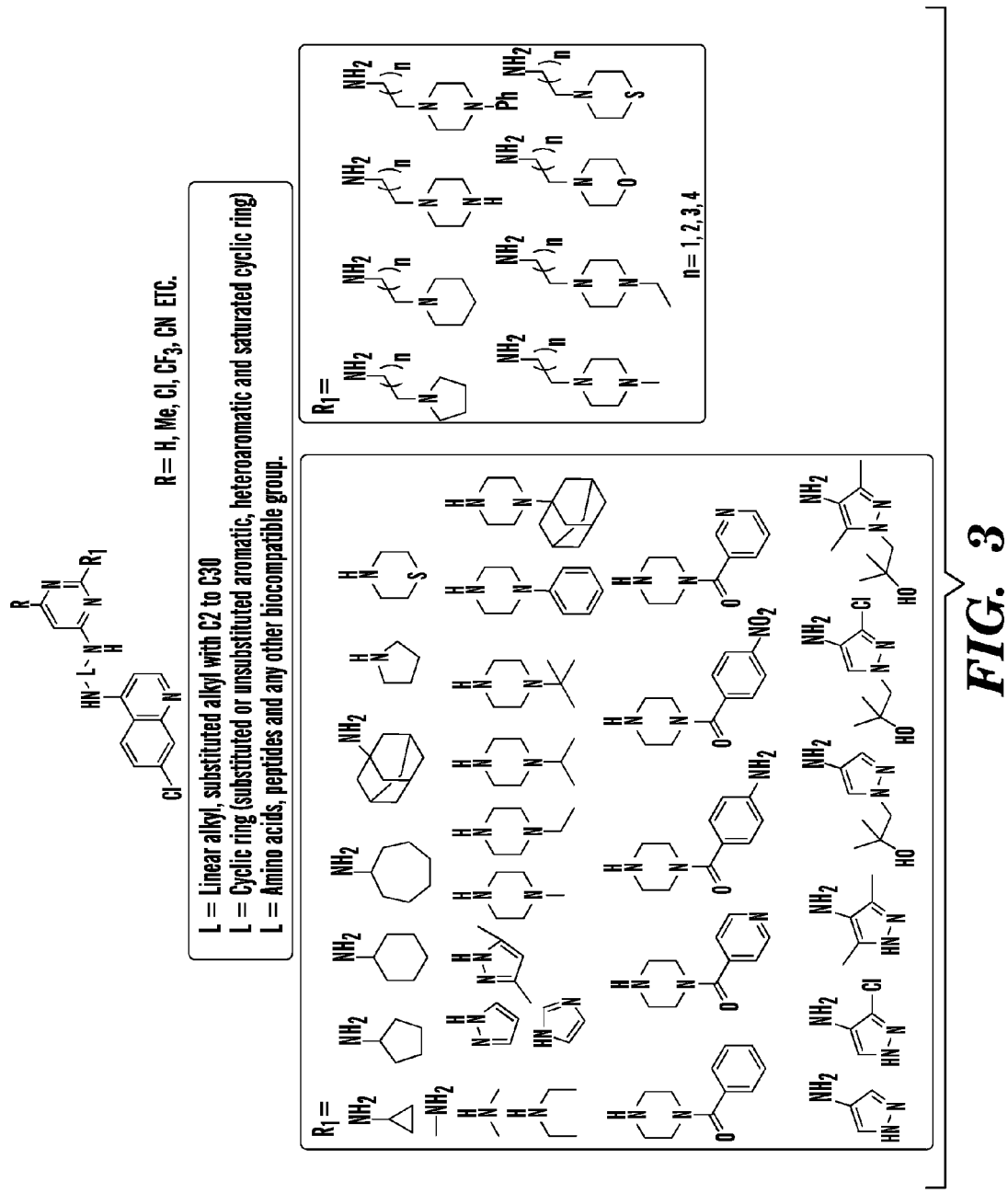
FIGS. 3-12 show exemplary embodiments of the compounds of the invention.
Figure 4:
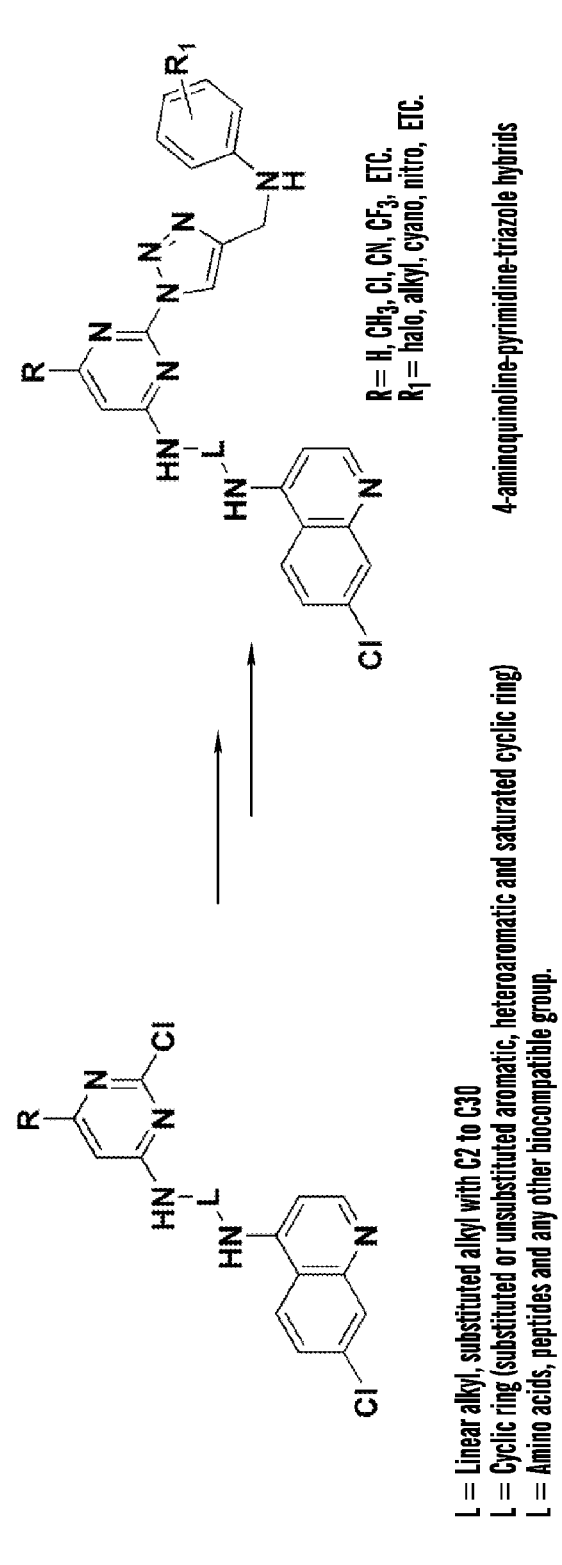
Figure 5:
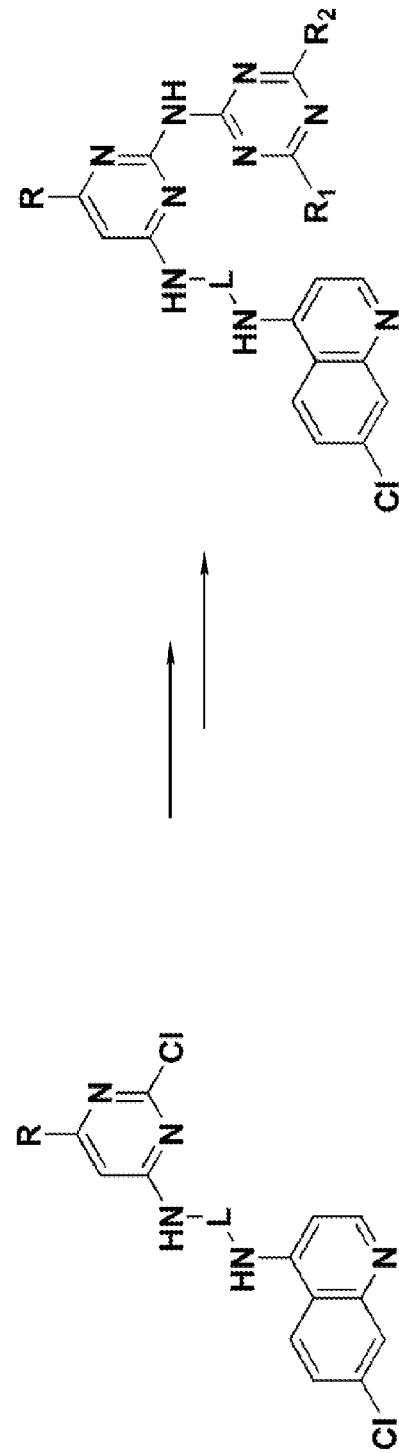
Figure 6:
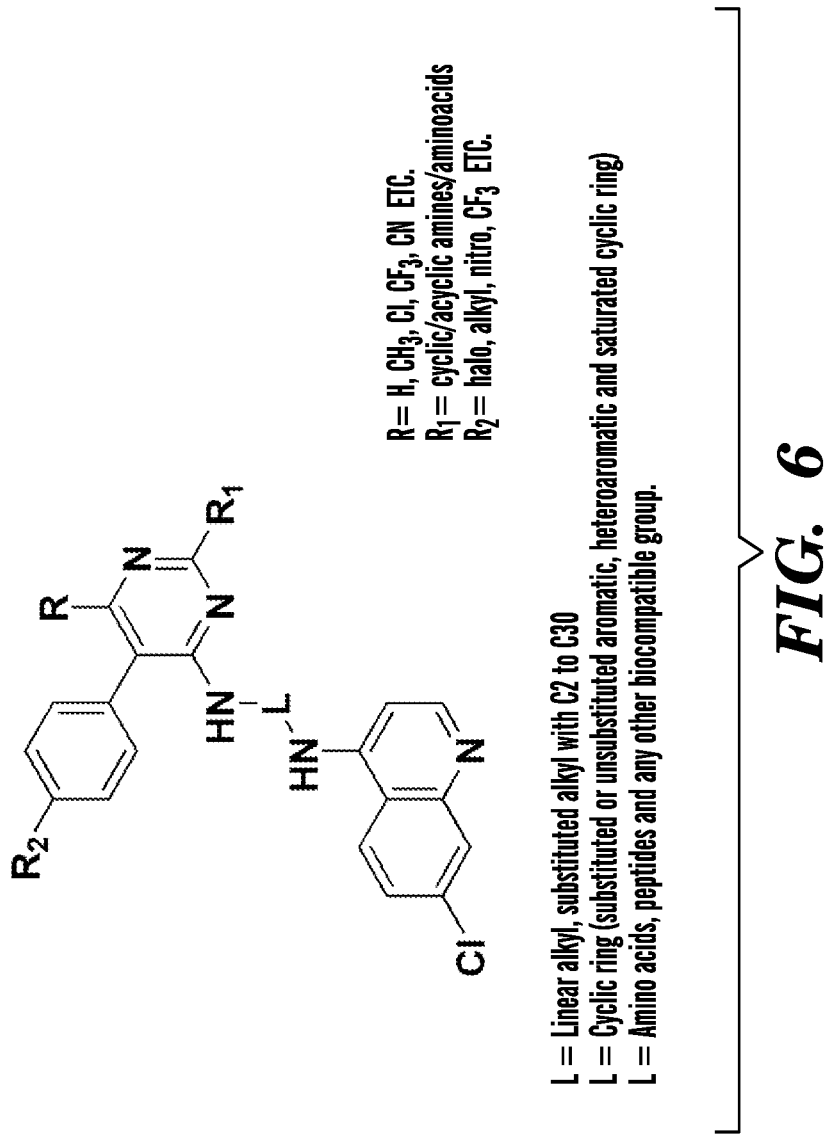
Figure 7:
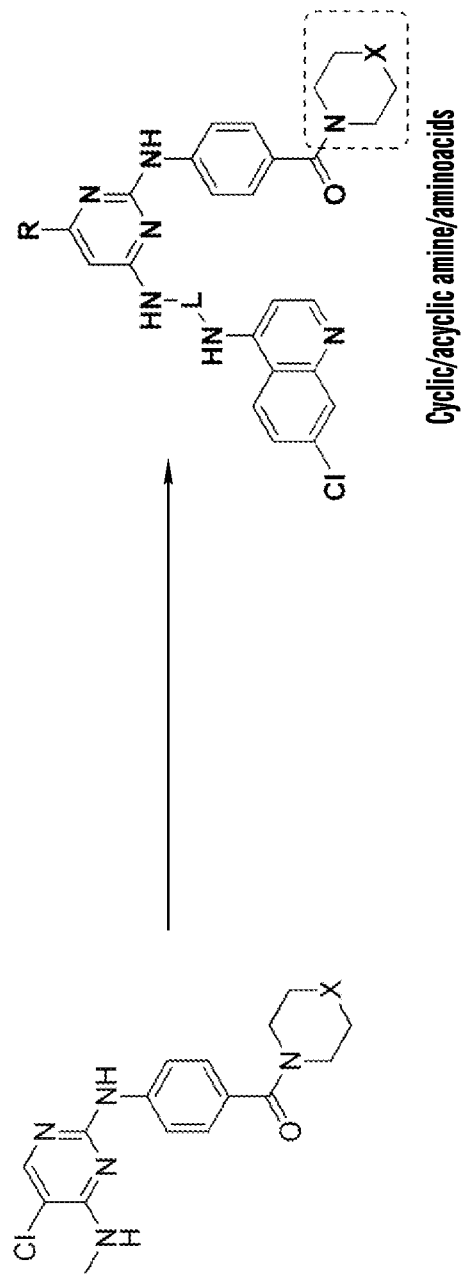
Figure 8:
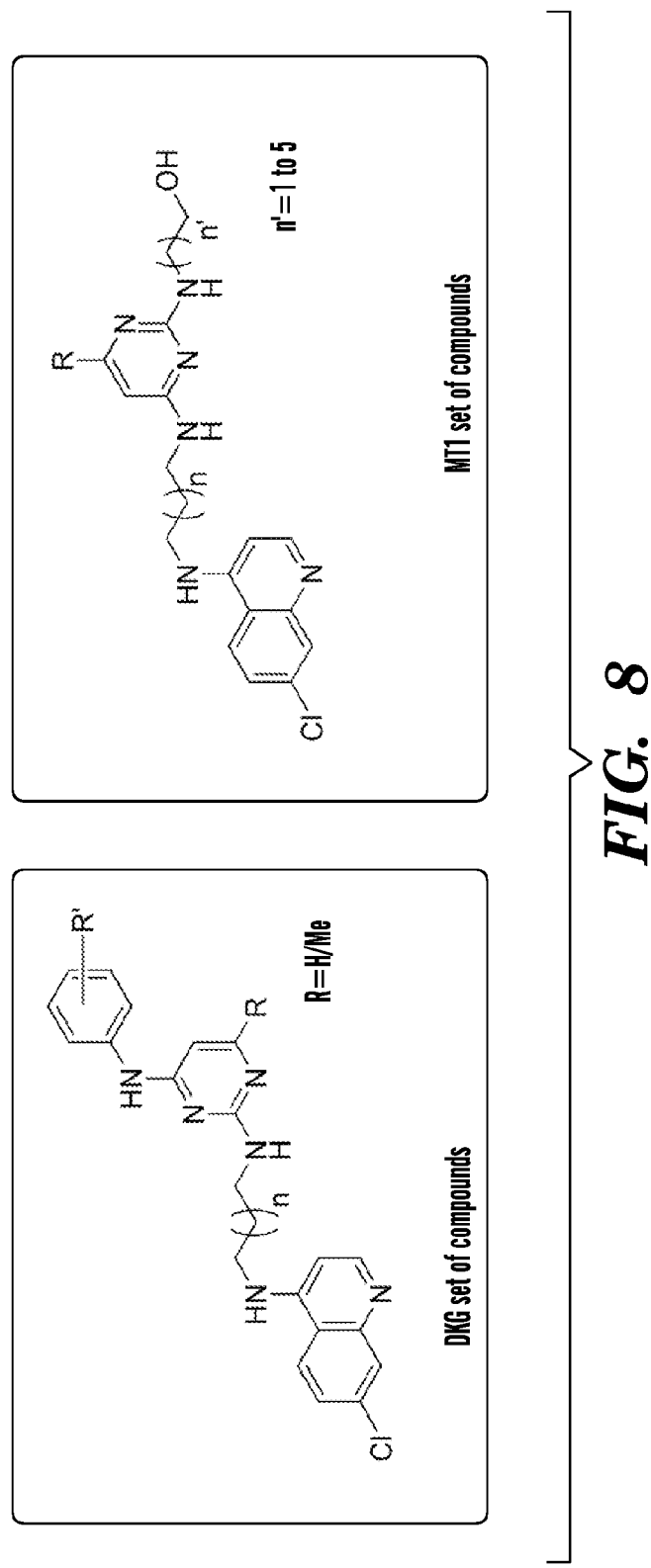
Figure 9:
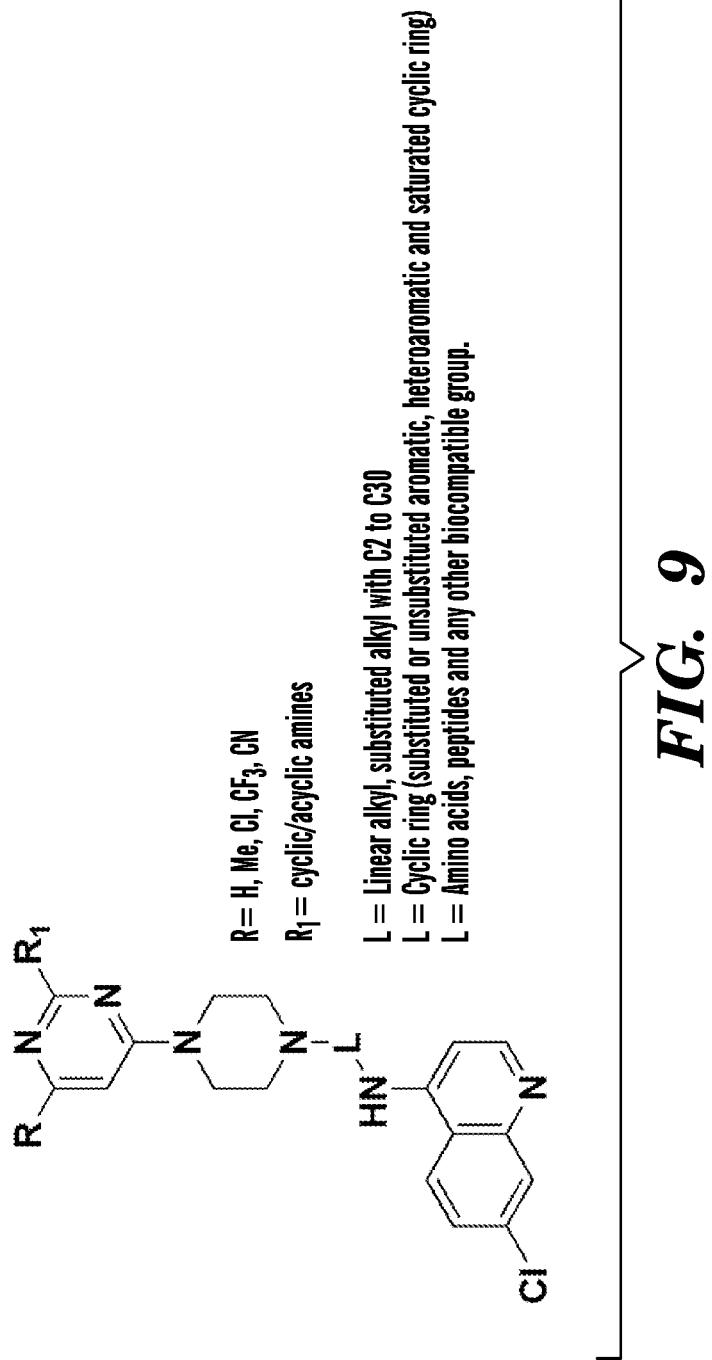
Figure 10:
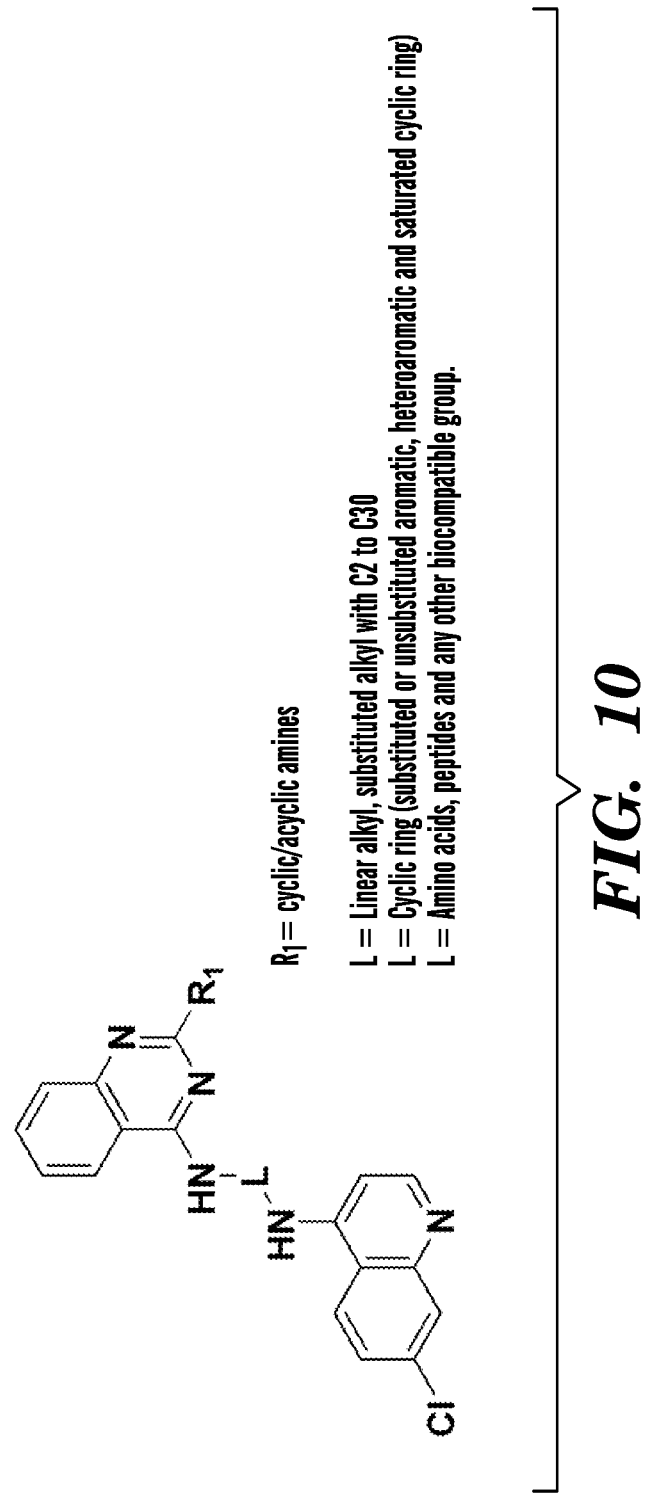
Figure 11:
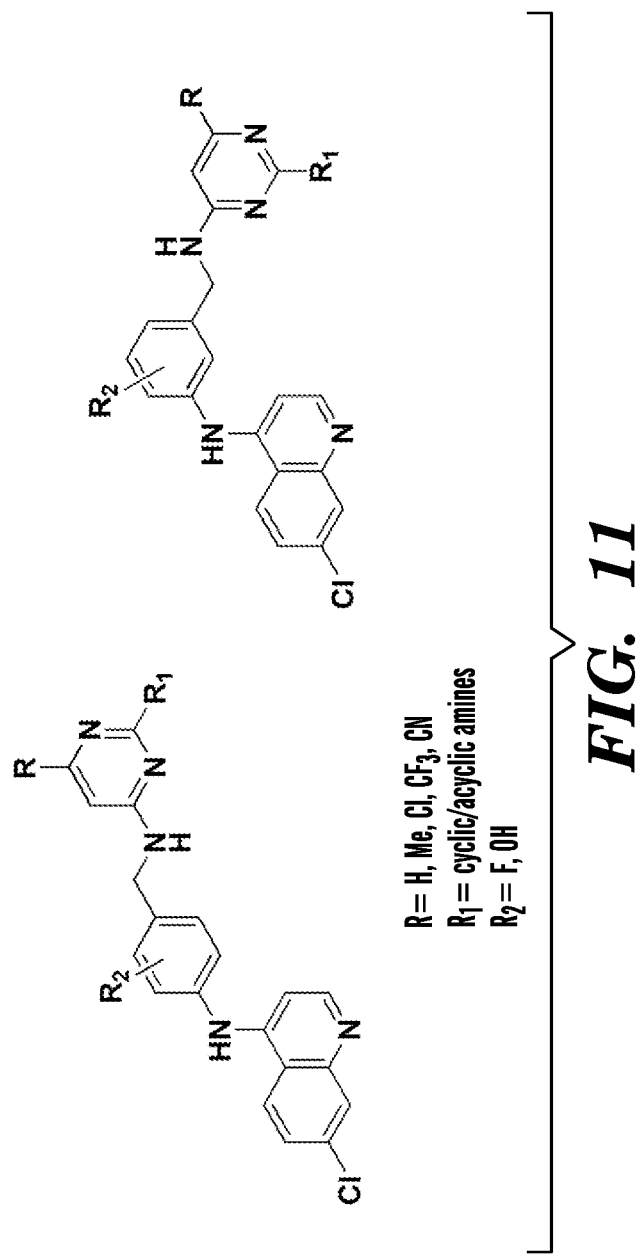
Figure 12:
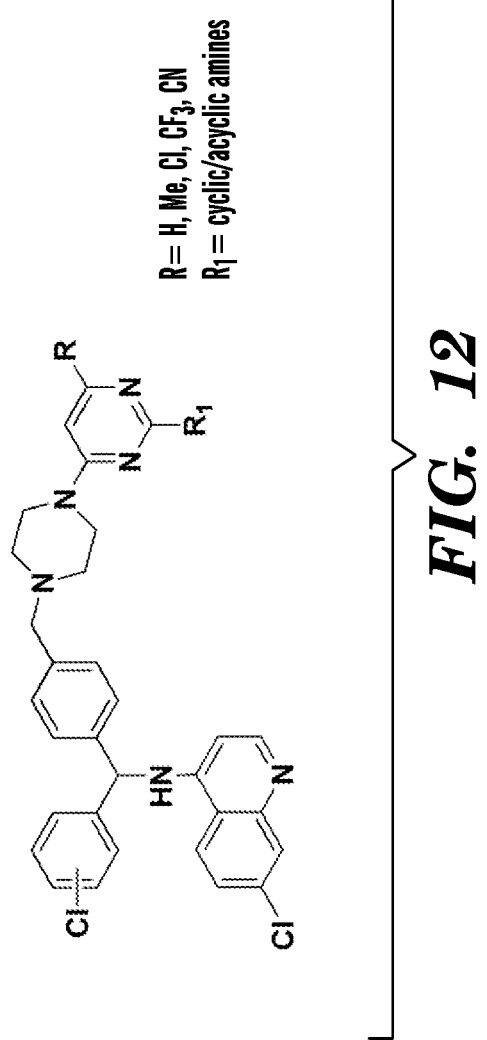
Figure 15A:
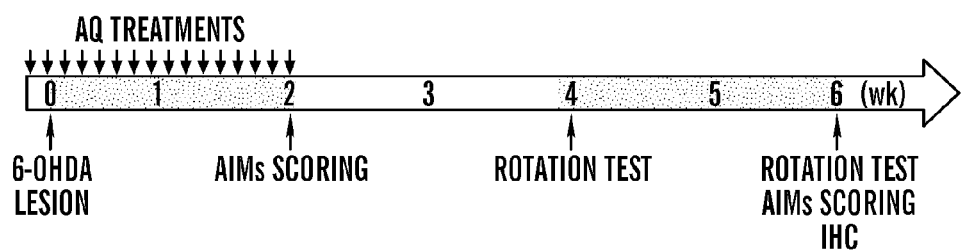
Figure 16A:
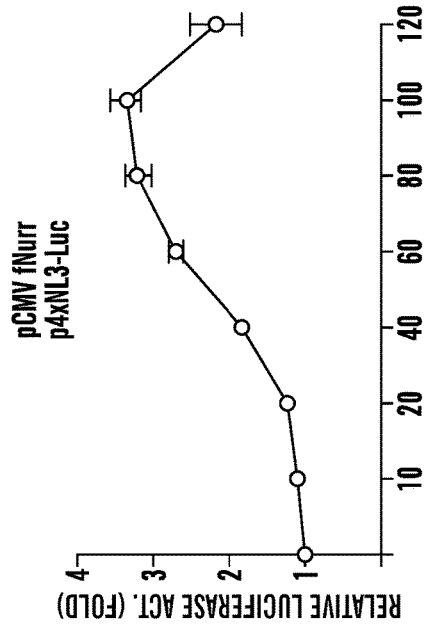
FIGS. 16A-16D show that AQ and CQ activate the transcriptional activity of full-length Nurr1 (FIGS. 16A and 16B) and Nurr1 LBD (FIGS. 16C and 16D in a dose-dependent manner.
Figure 16B:
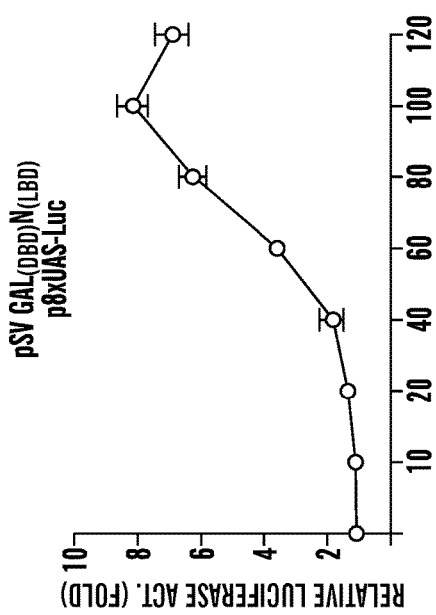
Figure 16C:
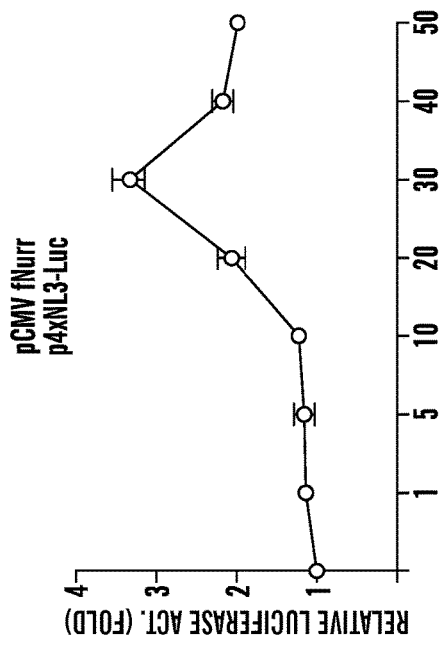
Figure 16D:
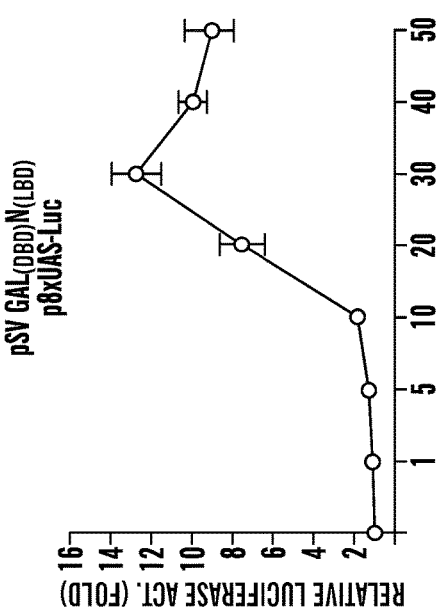

In inventors' previously reported assays using the reporter construct p4xNL3-Luc, containing four copies of the NBRE-like NL3 motif residing in the TH promoter[12], AQ and CQ activated luciferase reporter activity up to approximately 3-fold in a dose-dependent manner (FIGS. 3B, 15A, and 16B). In the present study the inventors focused on AQ and CQ since glafenine showed a weaker activity (approximately 1.6-fold). To investigate whether AQ and CQ activate Nurr1 function through its ligand binding domain (LBD) or DNA binding domain (DBD), the inventors next generated additional reporter constructs in which the yeast transcription factor GAL4's DBD is fused to either Nurr1 LBD or DBD (pSVGAL$_{(DBD)}$-N$_{(LBD)}$ and pSVGAL$_{(DBD)}$-N$_{(DBD)}$). Notably, AQ and CQ stimulated Nurr1's transcriptional activity through its LBD (FIG. 3B), while no response was observed when GAL4 or GAL4-Nurr1 DBD was used. AQ and CQ induced Nurr1 LBD-based reporter activity up-to 15- and 10-fold with an EC$_{50}$ of approximately 20 and 50 µM, respectively (FIGS. 3B, 16C, and 16D).

Figure 17:
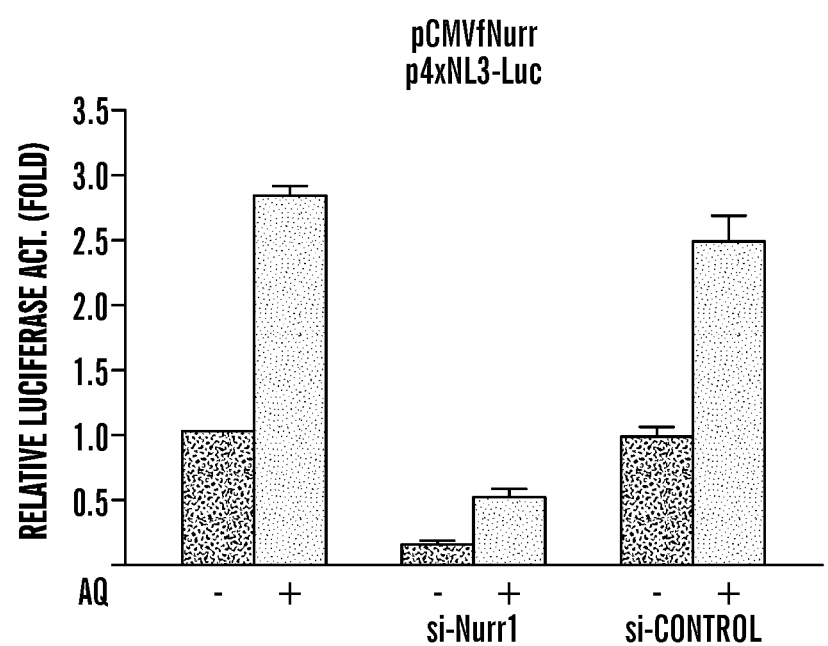
FIG. 17 shows the effect of Nurr1-specific siRNA on the transcriptional activity of full-length NM 1.
Figure 18:
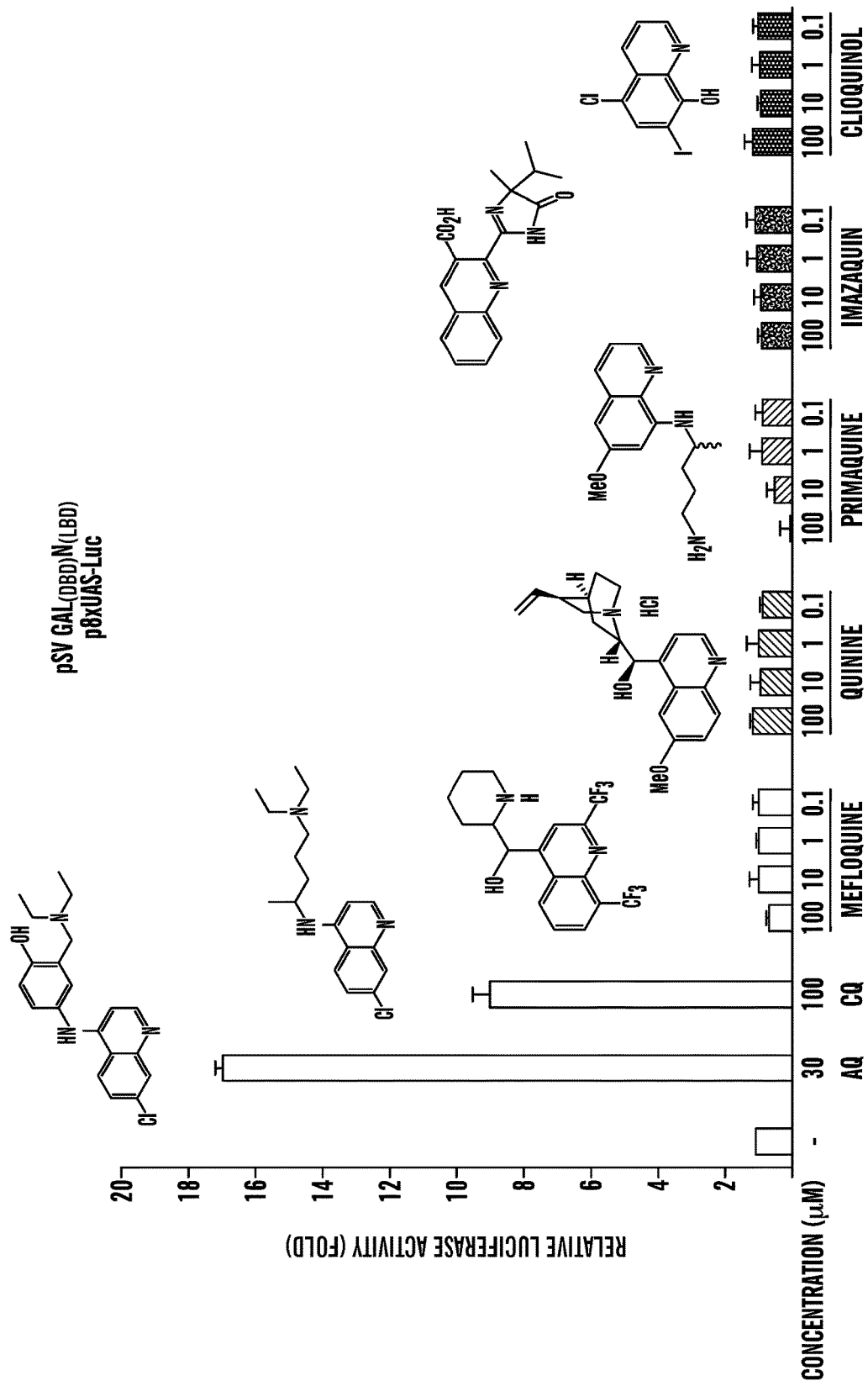
FIG. 18 show that structure activity relationship (SAR) analysis indicates that 4-amino-7-chloroquinoline can be an essential feature for transactivation function of Nurr1. The inventors examined the function of related quinoline compounds for potential activation of Nurr1. None of the quinoline compounds (without 4-amino-7-chloroquinoline) tested here exhibited any detectable transactivation of the Nurr1 LBD over a wide range of concentrations. Bars represent means±SEM from three independent experiments.
Figure 19:
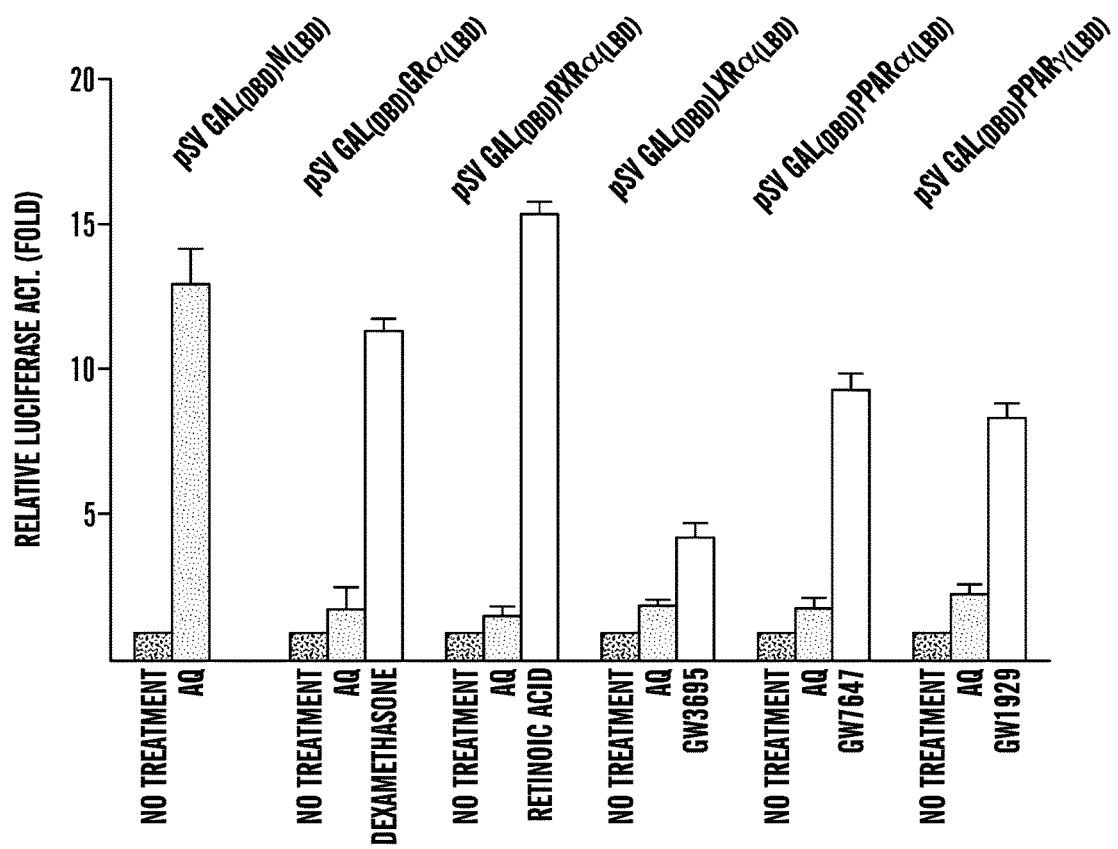
FIG. 19 shows the target selectivity of AQ for LBDs of various NRs. 30 μM AQ robustly activates LBD function of Nurr1, but not other NRs tested here, indicating a high specificity. The positive reactivity of these NR constructs was confirmed by the known activators (2 nM dexamethasone, 20 nM retinoic acid, 2 μM GW3965, 50 nM GW7647, and 5 nM GW1929 for GR, RXR, LXR, PPARα, and PPARγ, respectively). The basal level of transcriptional activity was normalized to 1. Bars represent means±SEM from three independent experiments. (Nur77; NR4A1; nuclear receptor subfamily 4 group A member 1, GR; glucocorticoid receptor, LXR; liver X receptor-alpha, RXR; retinoid X receptor-alpha, PPARα; peroxisome proliferator-activated receptor-alpha, PPARγ; peroxisome proliferator-activated receptor-gamma)

To test if AQ and CQ act through Nurr1, the inventors treated cells with Nurr1-specific siRNA. Nurr1 siRNA, but not scrambled RNAs, reduced luciferase activation by >60%, suggesting that transcriptional activation by AQ and CQ is indeed through modulation of Nurr1 function (FIGS. 3C and 17). The inventors next tested if various quinoline compounds have similar Nurr1-activating function. Remarkably, none of these compounds showed any detectable transactivation function in a wide range of concentrations (FIG. 18). Since only AQ and CQ contain the 4-amino-7-chloroquinoline entity, these results further support its SAR. In addition, AQ and CQ were unable to induce the transcriptional activity of other nuclear receptors (NRs), showing high selectivity (FIG. 19).

A crucial mechanism of NRs is the recruitment of transcriptional coregulators as seen with steroid receptor coactivators (SRCs)[13]. To test if AQ and CQ modulate Nurr1's interaction with SRC, a co-immunoprecipitation assay was performed. We found that Nurr1's weak interactions with SRC-1 and SRC-3 were significantly enhanced by AQ and CQ (FIG. 13D). We next tested the effects of AQ and CQ on Nurr1 transcriptional function following SRC-1 or SRC-3 overexpression. While SRC-1/SRC-3 overexpression itself did not greatly influence Nurr1 function, AQ and CQ further enhanced Nurr1's transcriptional function in the presence of SRC-1/SRC-3 overexpression (FIG. 13E), suggesting that AQ and CQ induce Nurr1's trans activation function through its Nurr1 LBD by facilitating the recruitment of coactivators like SRC-1/SRC-3.

To investigate whether AQ and CQ physically interact with Nurr1's LBD, the inventors purified the Nurr1 LBD polypeptide (amino acid 328-598) and analyzed their physical binding using the Biacore S51 SPR sensor, which has a higher sensitivity and improved fluidics, enabling the monitoring of small signal changes derived from binding of compounds to proteins.

Figure 13F:
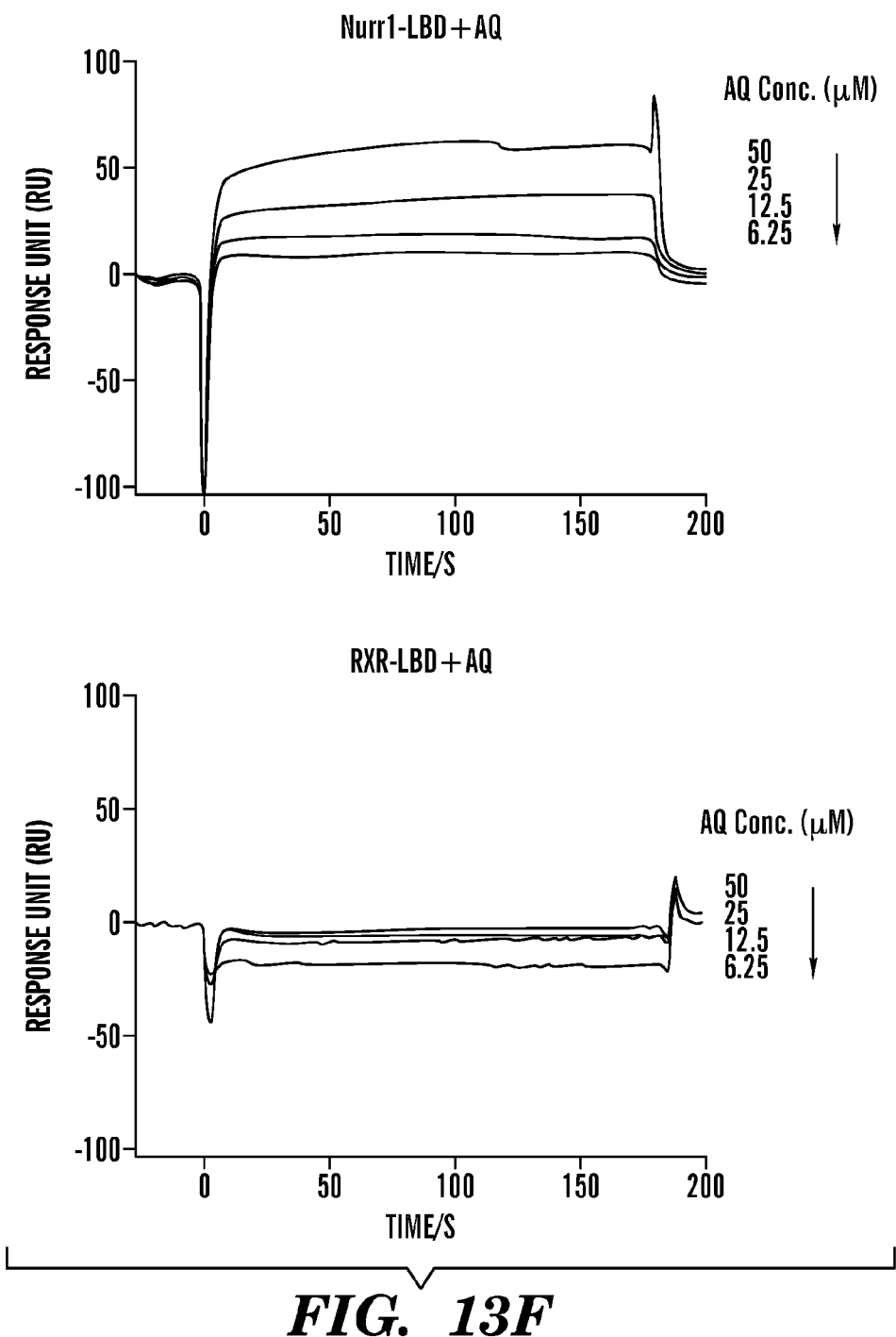
Figure 13G:
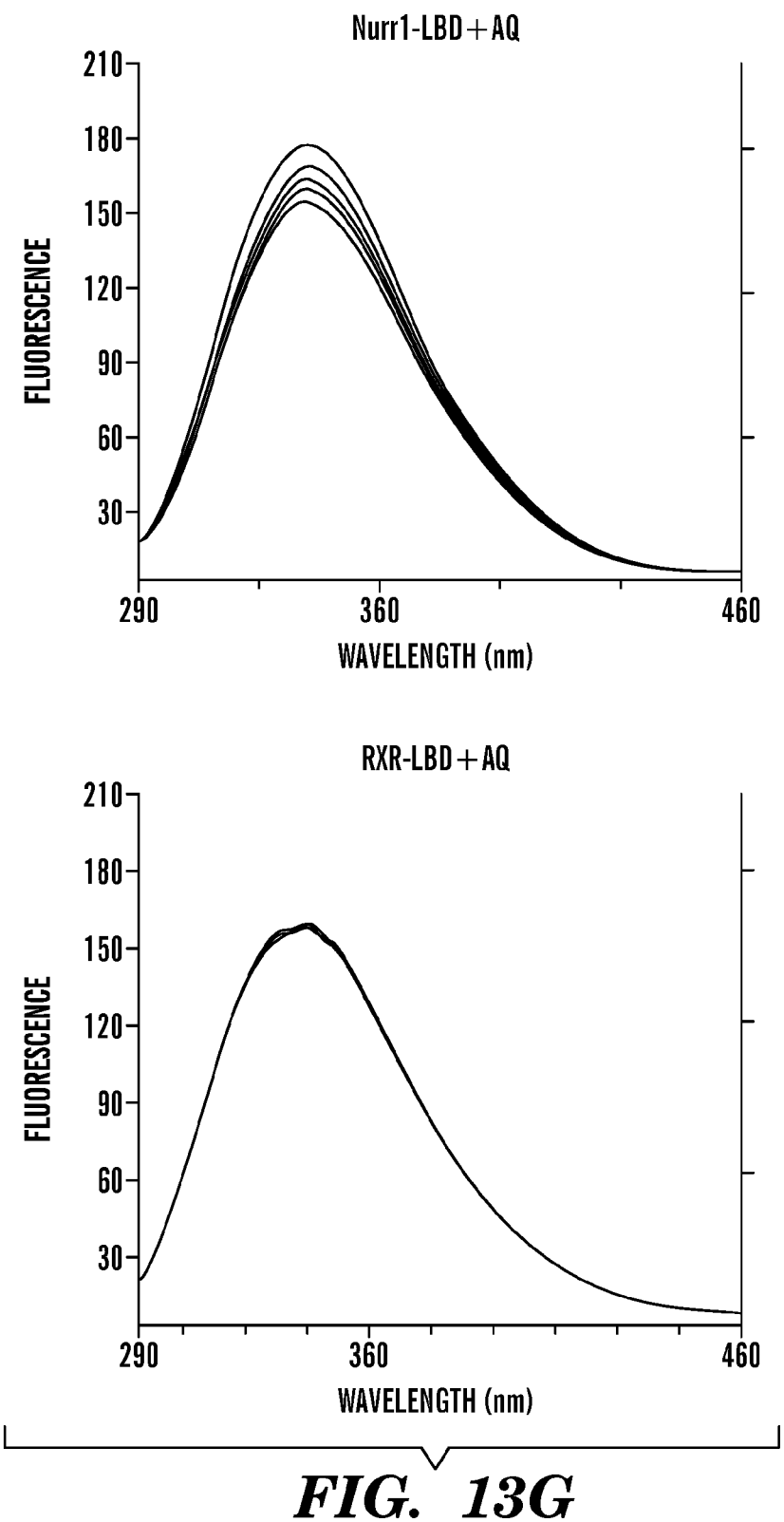
Figure 13H:
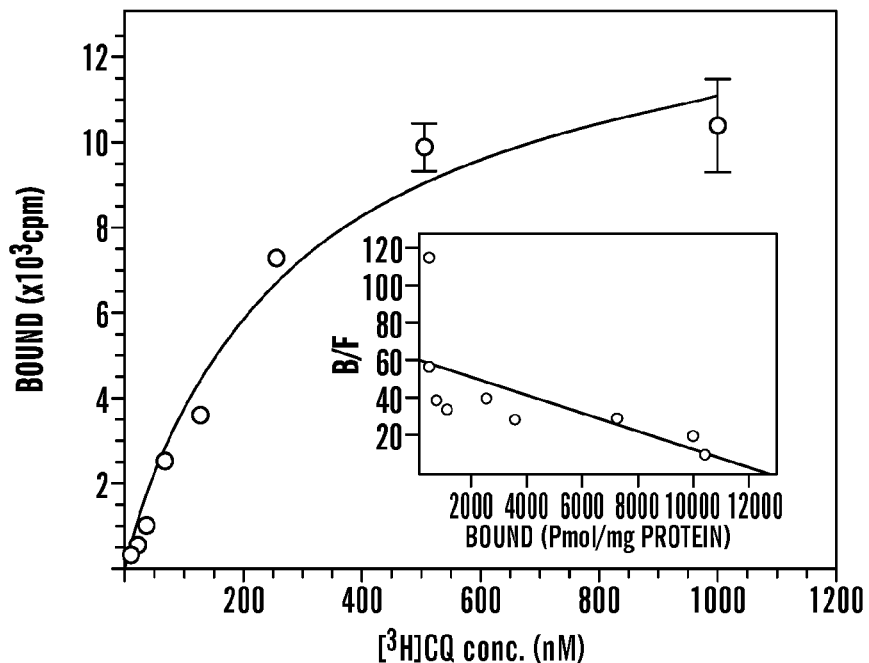
Figure 13I:
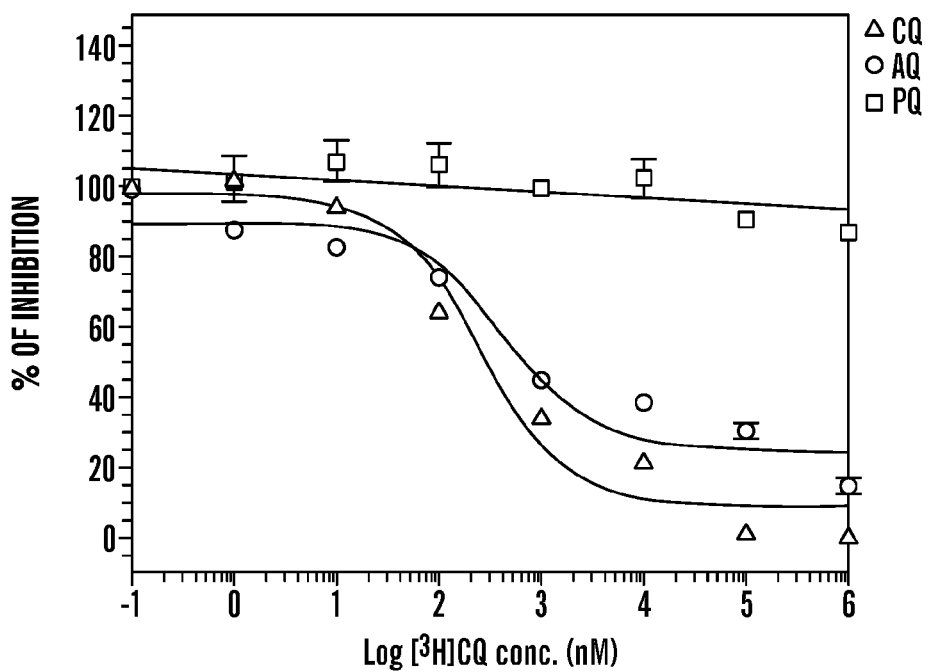
Figure 20A:
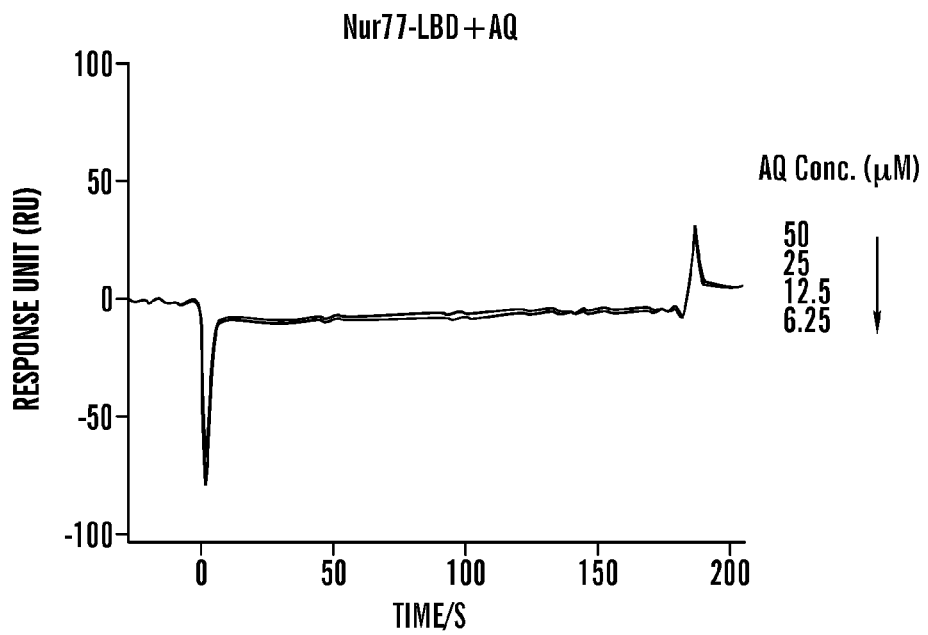
FIGS. 20A-20C shows that AQ does not interact with Nur77-LBD.
Figure 20B:
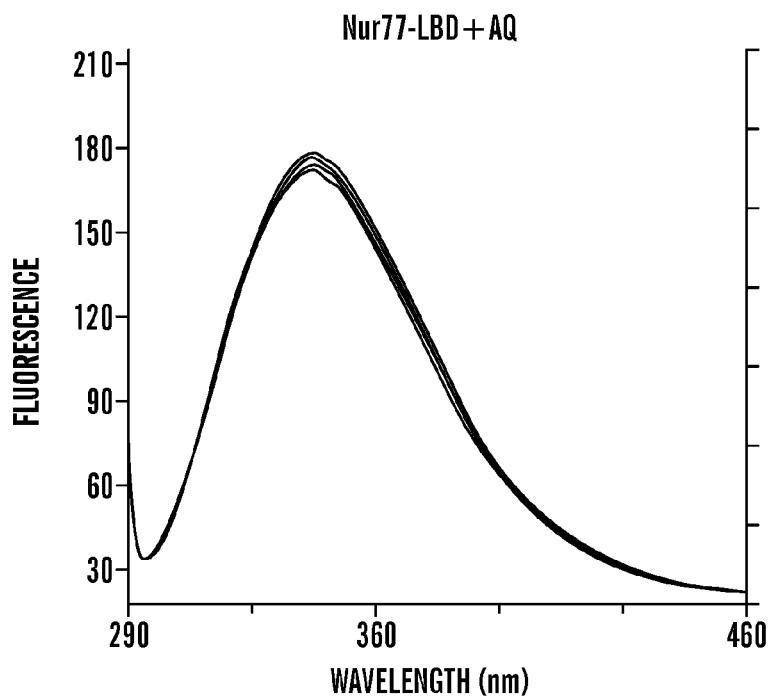
Figure 20C:
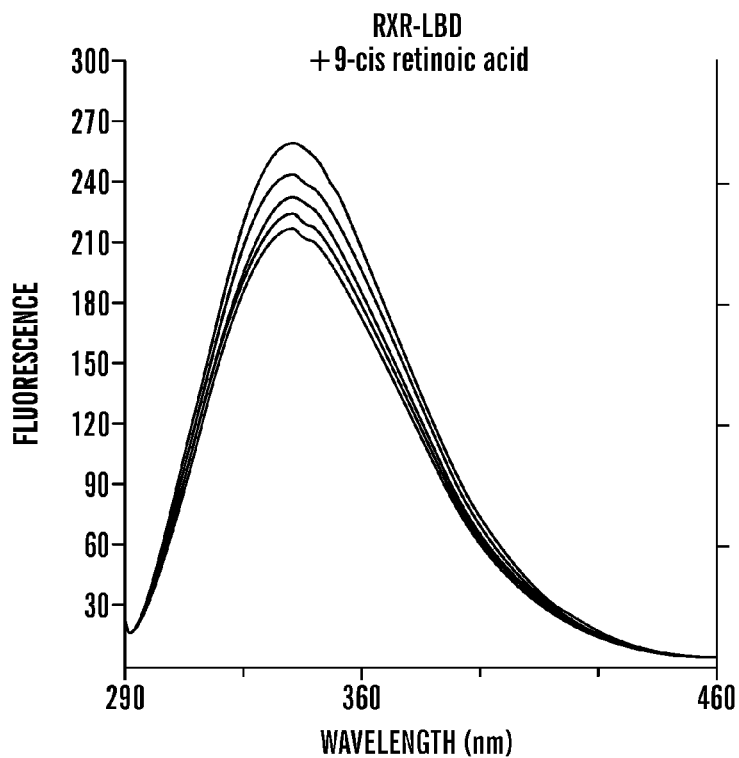

As shown in FIGS. 13F and 20A, AQ specifically bound to Nurr1-LBD in a dose-dependent manner but not to the LBDs of other NRs such as Nur77 or RXR. Next, we performed fluorescence quenching analysis. The Nurr1-LBD displayed maximal fluorescence at 336 nm whereas AQ itself had no fluorescence at this wavelength. When the Nurr1-LBD was incubated with increasing amounts of AQ, fluorescence intensity gradually decreased (FIG. 3G). In contrast, Nur77-LBD and RXR-LBD's fluorescence emission was not quenched by AQ over a wide range of concentrations (FIGS. 3G and 20B). In addition, the inventors performed a radioligand binding assay using [$^3$H]-CQ. The [$^3$H]-CQ showed saturable binding to Nurr1-LBD with a dissociation constant ($K_d$) of 0.27 μM and a maximal binding capacity ($B_{max}$) of 13.9 μM (FIG. 13H). Furthermore, competition-binding assay showed that unlabeled AQ/CQ can compete for binding with [$^3$H]-CQ with $K_i$ values of 246 and 88 nM for AQ and CQ, respectively (FIG. 13I). As expected, unlabeled primaquine which couldn't enhance the Nurr1 transcriptional function (FIG. 18) was unable to compete. Together, these data strongly suggest that AQ/CQ activate Nurr1 function via direct and specific binding to Nurr1's LBD.

Figure 14A:
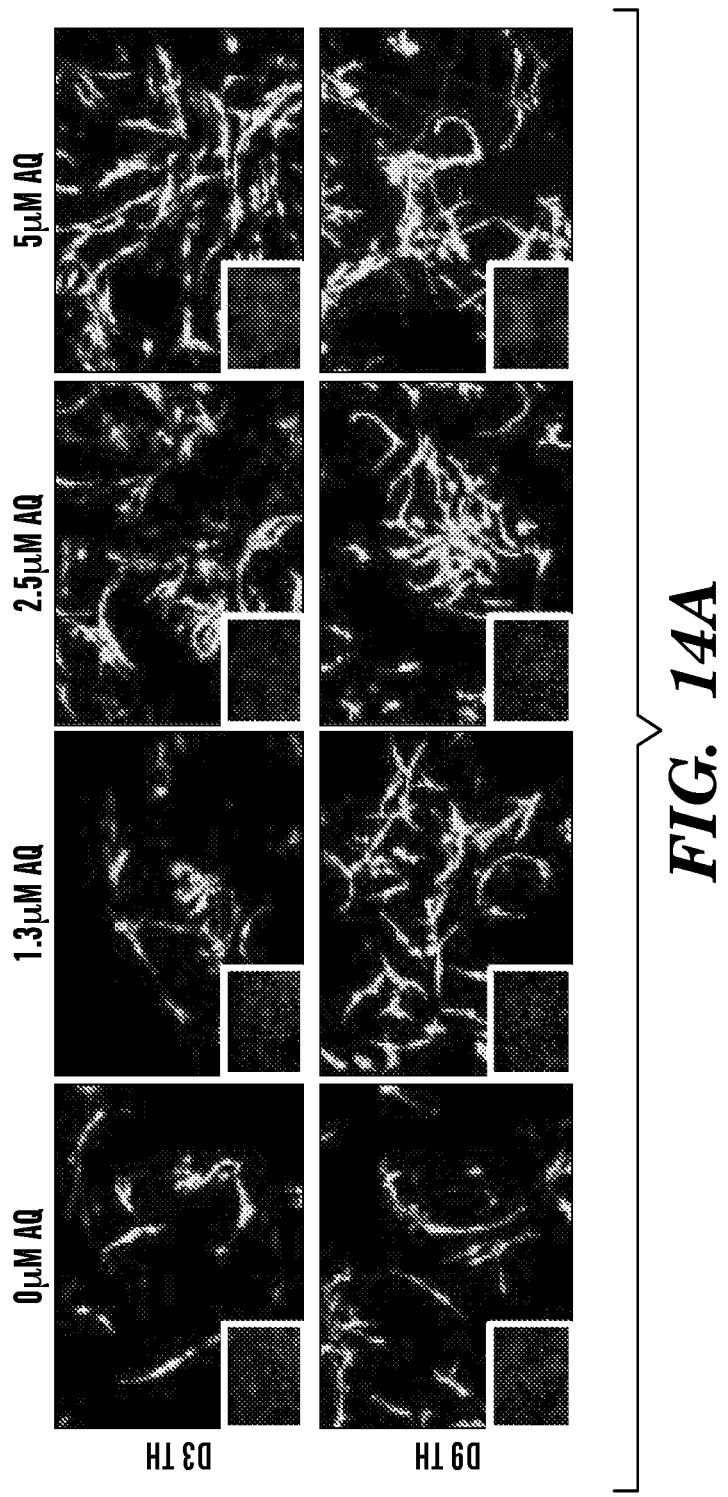
FIGS. 14A-14G show functional effects of AQ and CQ.
Figure 14B:
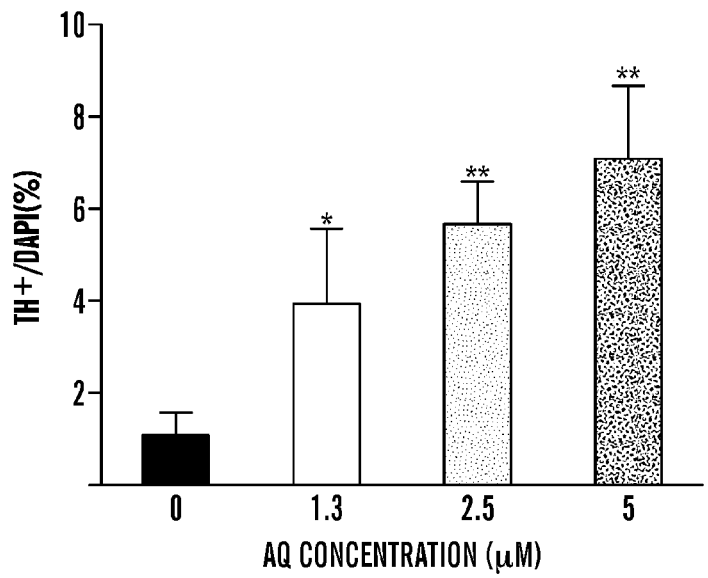
Figure 14C:
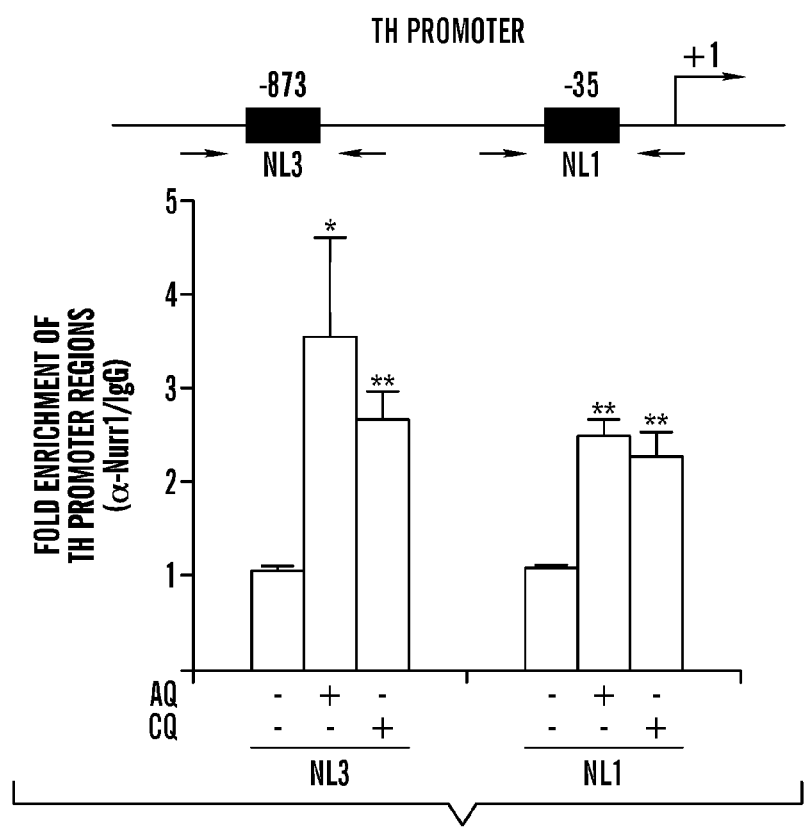
Figures 14D, 14E, 14F:
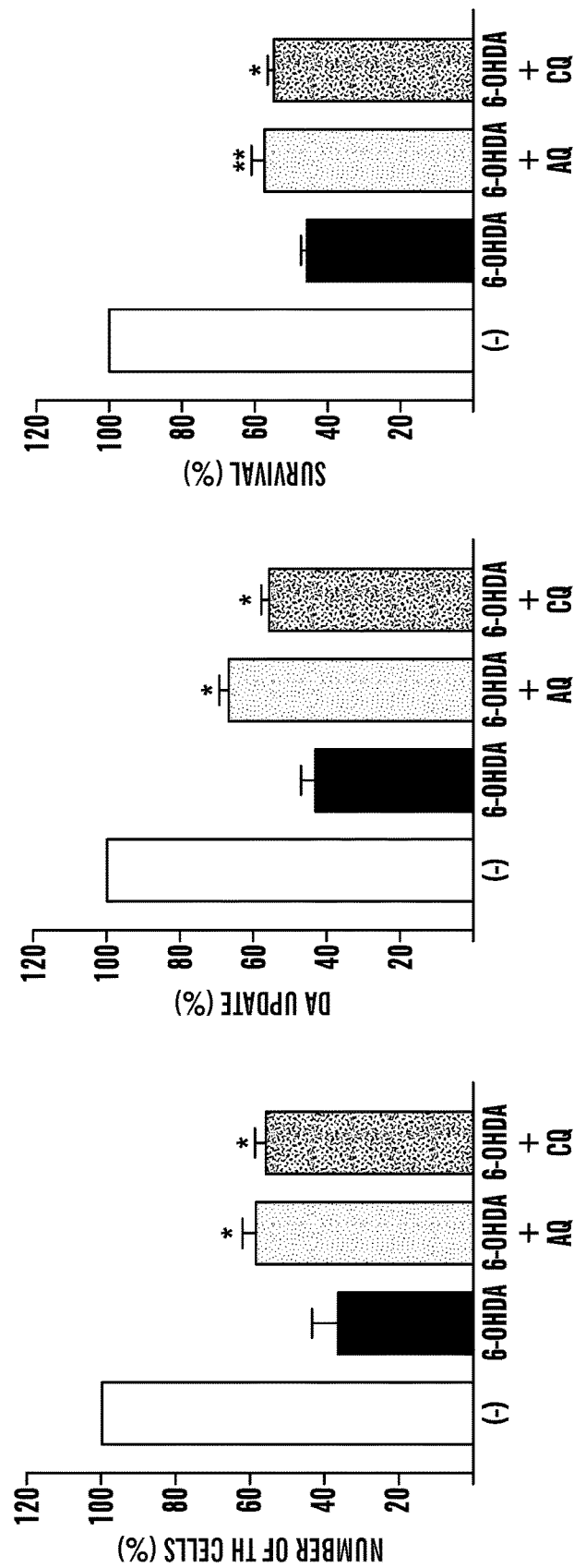
Figure 14G:
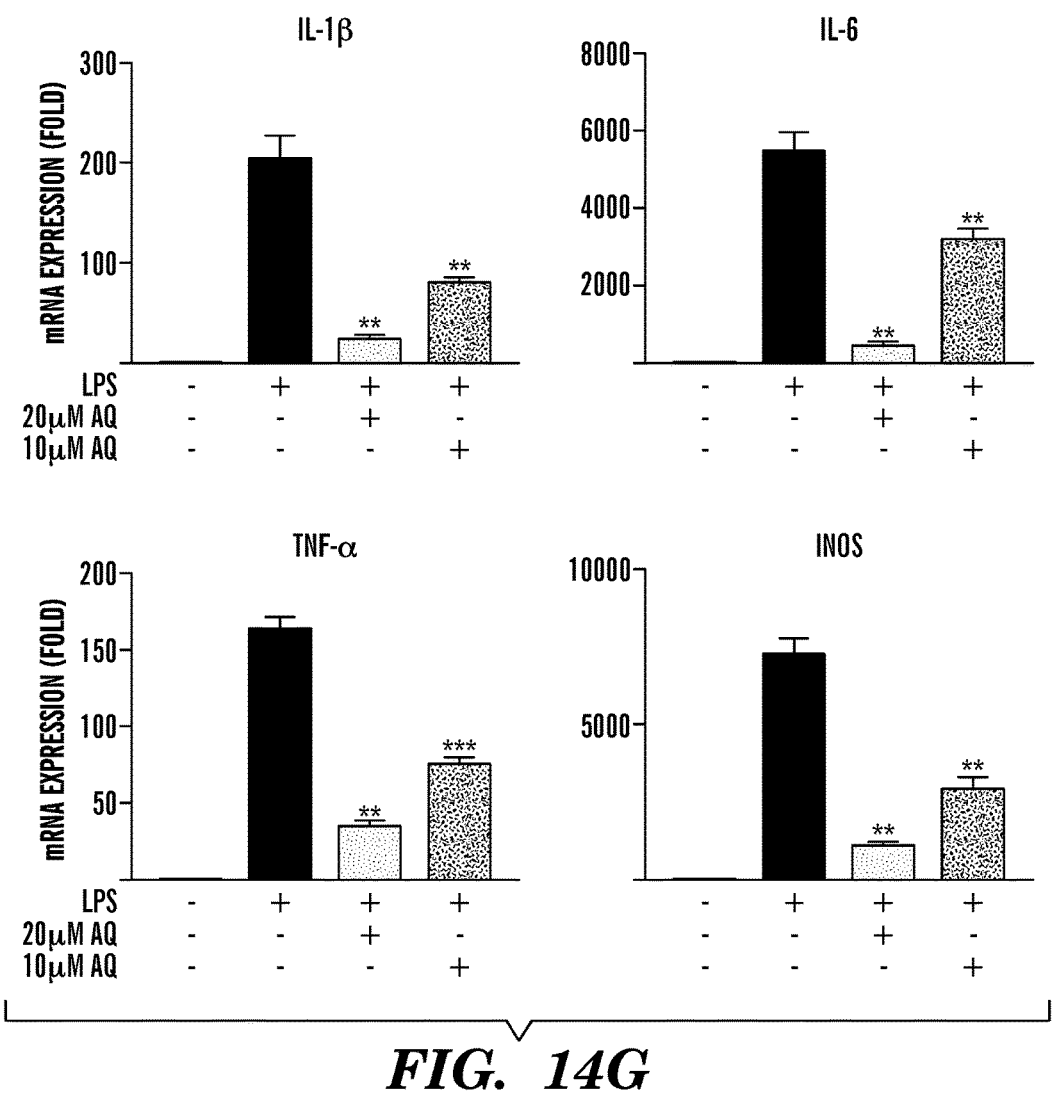
Figure 21:
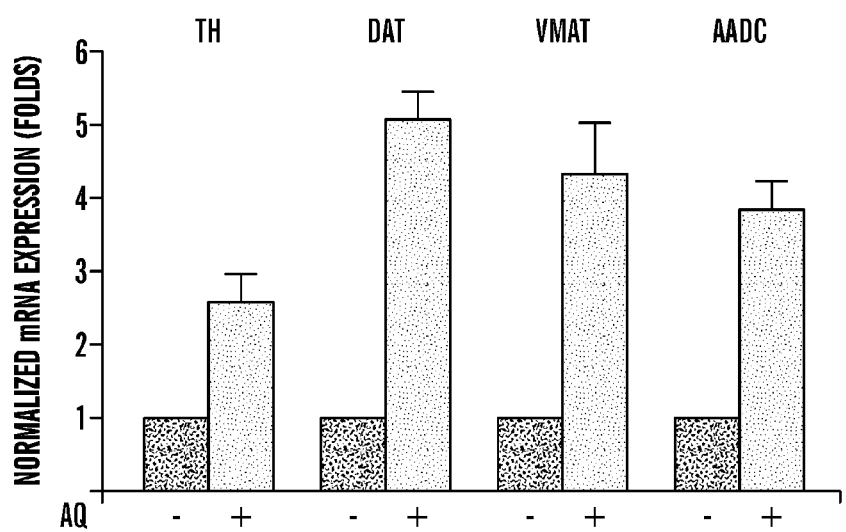
FIG. 21 shows results of real time PCR analysis showing that AQ treatment enhances expression of the mDA-specific genes (e.g., tyrosine hydroxylase (TH), dopamine transporter (DAT), vesicular monoamine transporter (VMAT), and aromatic amino acid decarboxylase (AADC)) during in vitro differentiation of neural stem cells. mRNAs from each treatment group were obtained following in vitro differentiation for 9d.
Figure 22A:
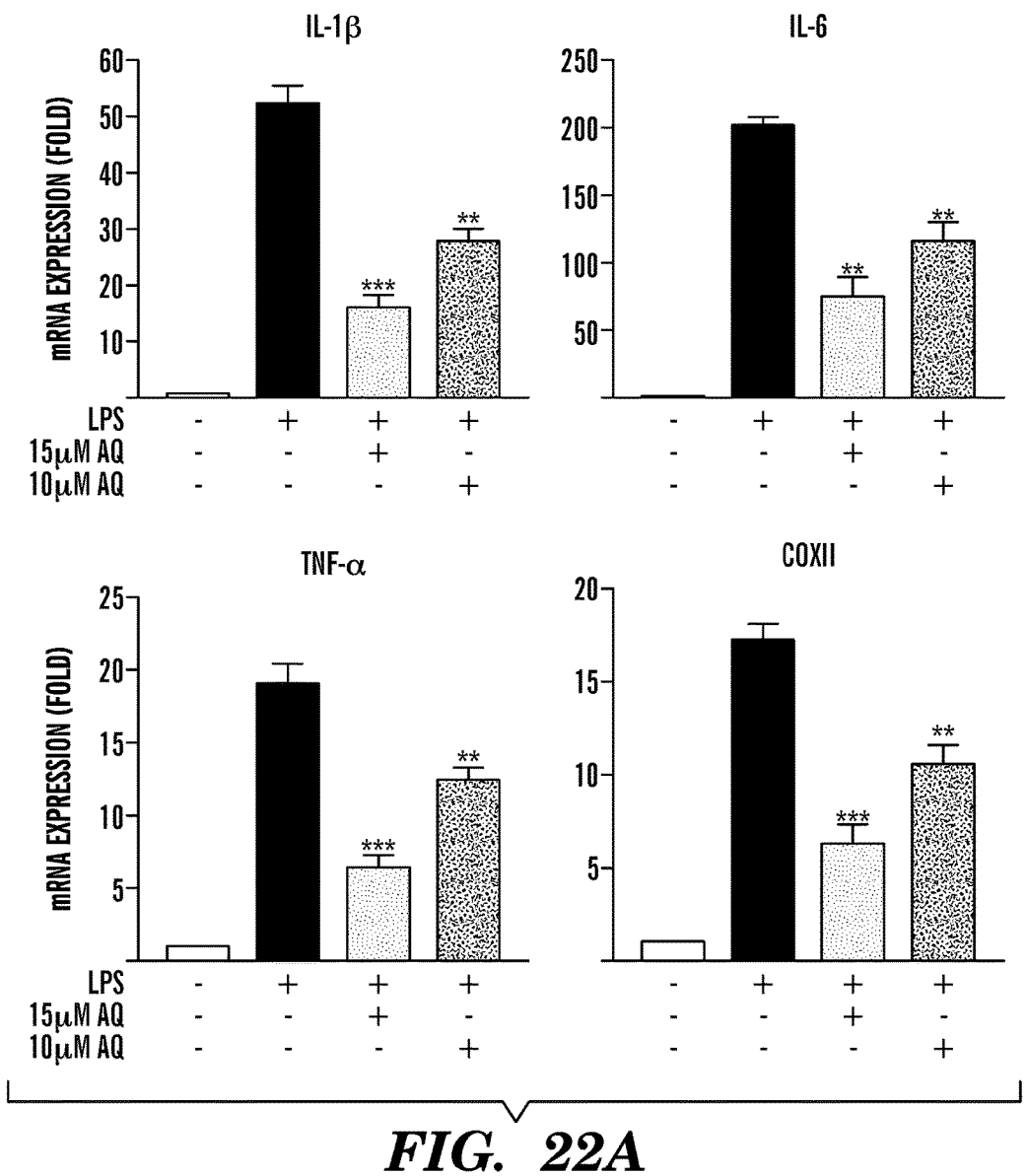
FIGS. 22A and 22B shows effect of AQ and CQ on expression of pro-inflammatory cytokine genes.
Figure 22B:
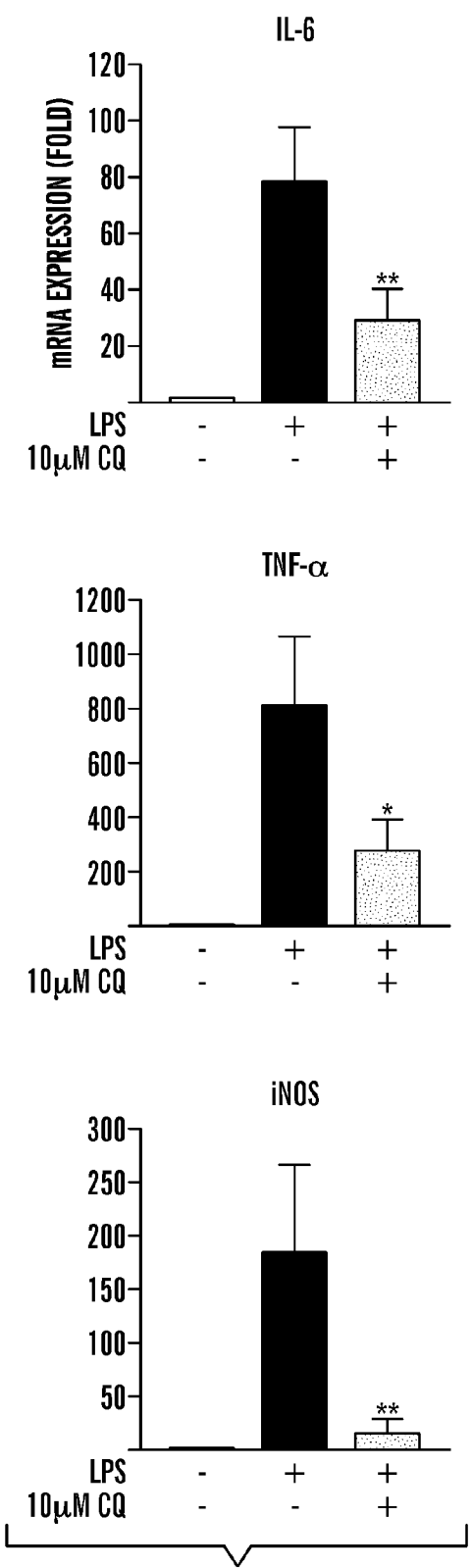

We next sought to test whether these compounds exhibit biological effects on mDA neurons in more physiological contexts. First, we tested if they can increase the generation of TH$^+$ neurons and/or expression of mDA-specific genes during in vitro differentiation of neural stem cells. We found that AQ enhanced Nurr1's function both in terms of the number of TH$^+$ neurons generated from neural stem cells and mRNA expression levels of the TH, dopamine transporter (DAT), vesicular monoamine transporter (VMAT), and aromatic amino acid decarboxylase (AADC) genes (FIGS. 14A, 14B, and 21). In vivo chromatin immunoprecipitation (ChIP) assay clearly showed that Nurr1 was recruited to both NL1 and NL3 sites of the TH promoter in AQ- and CQ-treated cells, suggesting that Nurr1 is directly involved in AQ- and CQ-mediated induction of TH expression (FIG. 14C). Second, we found that AQ and CQ significantly inhibit neurotoxin (6-OHDA)-induced death in primary DA neurons, as examined by the number of TH$^+$ neurons (FIG. 14D) and DA uptake (FIG. 14E). The neuroprotective effect of AQ and CQ was also observed in rat PC12 cells (FIG. 14F). Since Nurr1 has opposite transrepression activity in microglia and astrocytes[8], the inventors also analyzed the effect of AQ on expression of pro-inflammatory cytokine genes in primary microglia derived from P1 rat brains. When these cells were treated with the inflammation-inducing lipopolysaccharide (LPS; 10 ng/ml) for 8 hrs, expression of all cytokine genes tested (IL-1β, IL-6, TNF-α and iNOS) was dramatically induced (FIG. 14G). Remarkably, AQ treatment prominently reduced the expression of all these genes in a dose dependent manner (>10-fold). AQ and CQ showed very similar effects for repressing these cytokine genes in both primary microglia and BV-2 microglial cell line (FIG. 22). Taken together, our data show that AQ and CQ are able to enhance the contrasting dual roles of Nurr1: (1) they increase Nurr1's transactivation of mDA-specific genes in mDA neurons and (2) they also further enhance Nurr1's transrepression of pro-inflammatory cytokine gene expression in microglia.

Figure 15B:
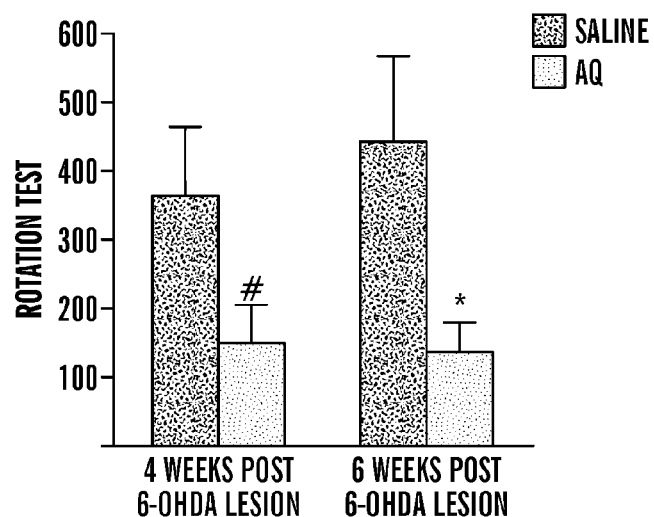
Figure 15C:
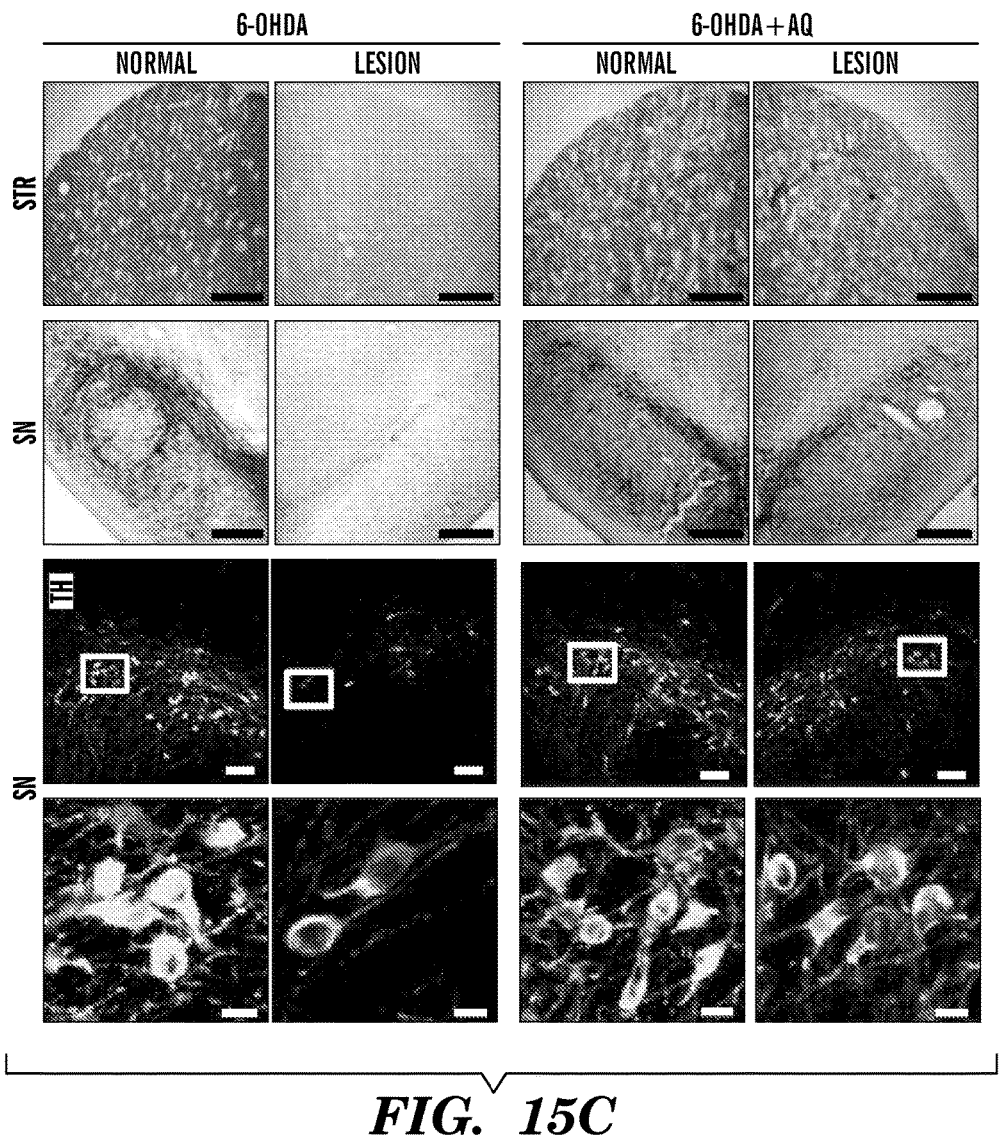
Figure 23:
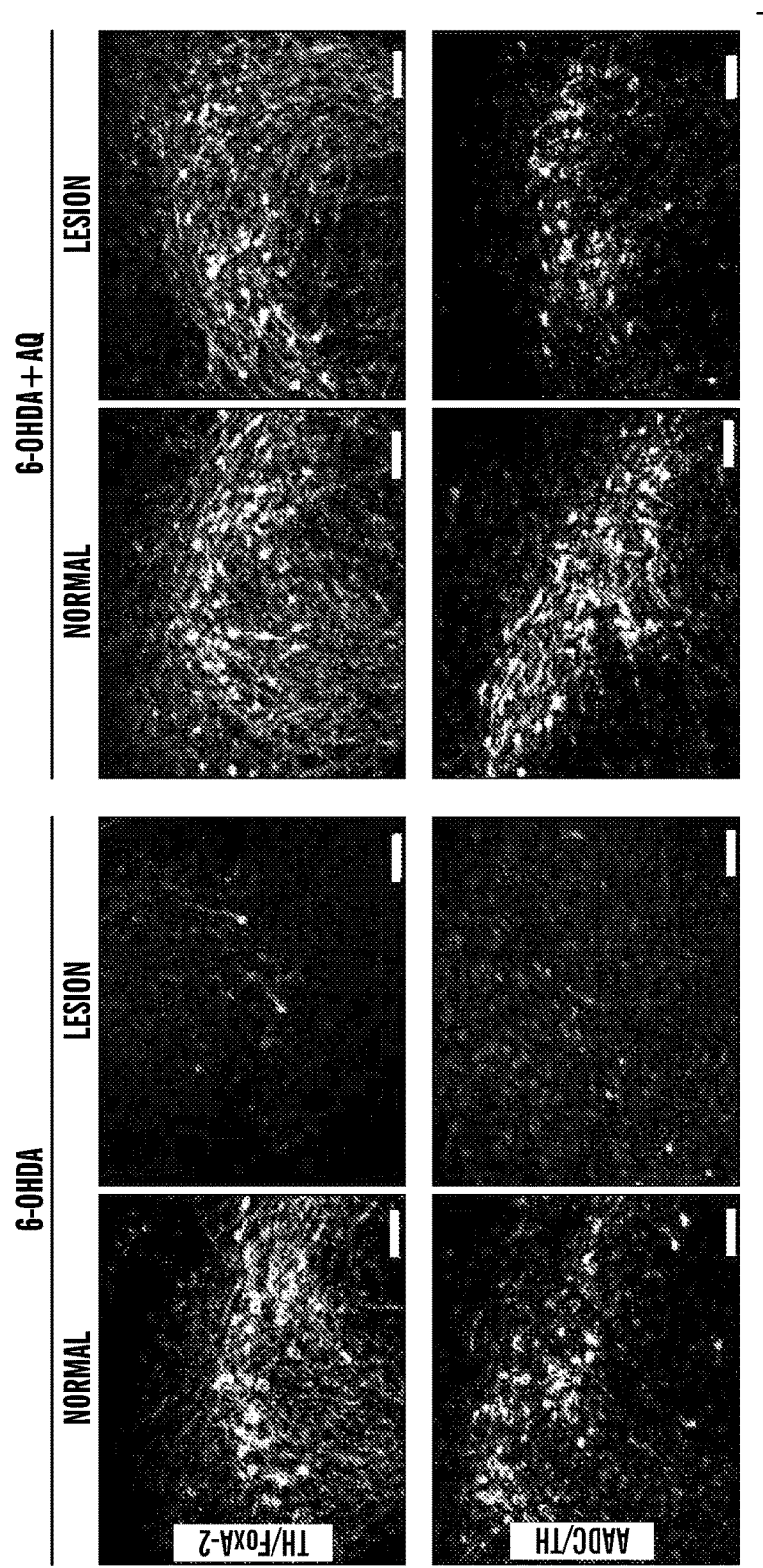
FIG. 23 shows that spared TH+ cells in the lesioned hemisphere of 6-OHDA rats following AQ treatments co-expressed mature DA neuronal markers such as FoxA2 and AADC. Scale bar=100 μm.
Figure 24I:
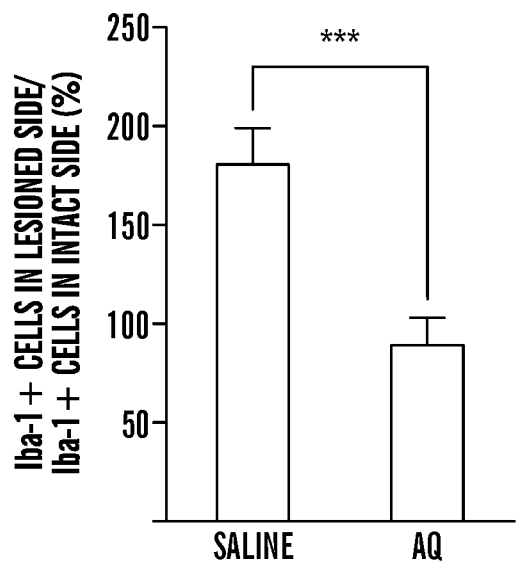
Figure 24J:
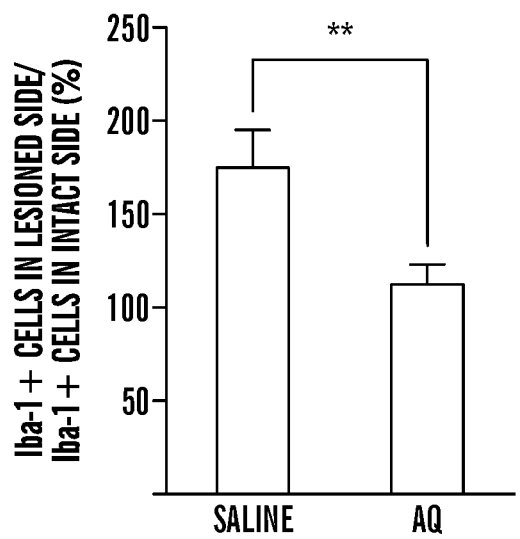
Figure 25A:
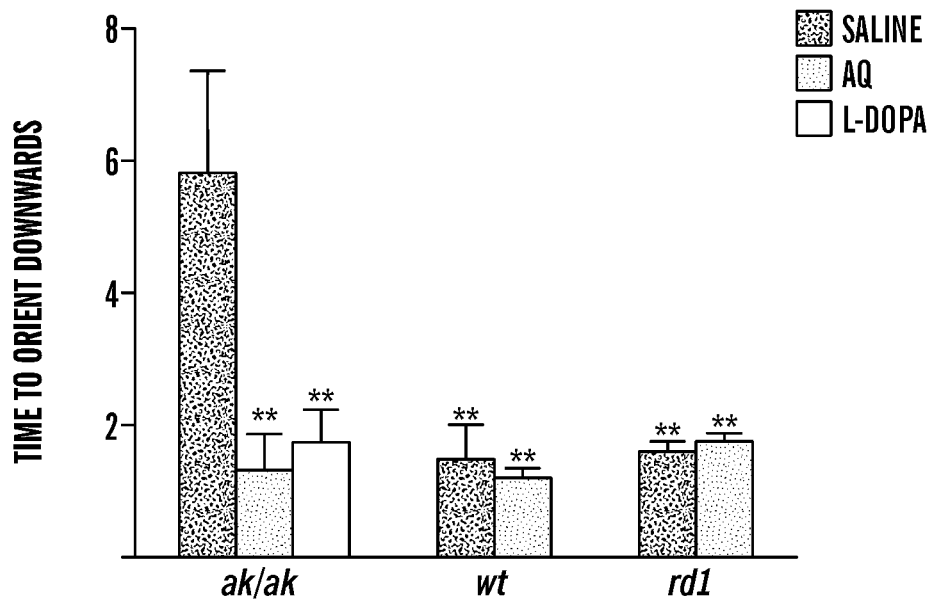
FIGS. 25A-25D show that AQ treatment to ak/ak mice resulted in functional improvements in nigrostriatal-specific motor behavior tests such as Pole Test (FIG. 25A), Beam Test (FIG. 25B), Cylinder Test (FIG. 25C), and Rotarod Test (FIG. 25D). L-Dopa treatment was used as positive control. Bars represent the mean±SEM (*p<0.05, p<0.01, *p<0.001).
Figure 25B:
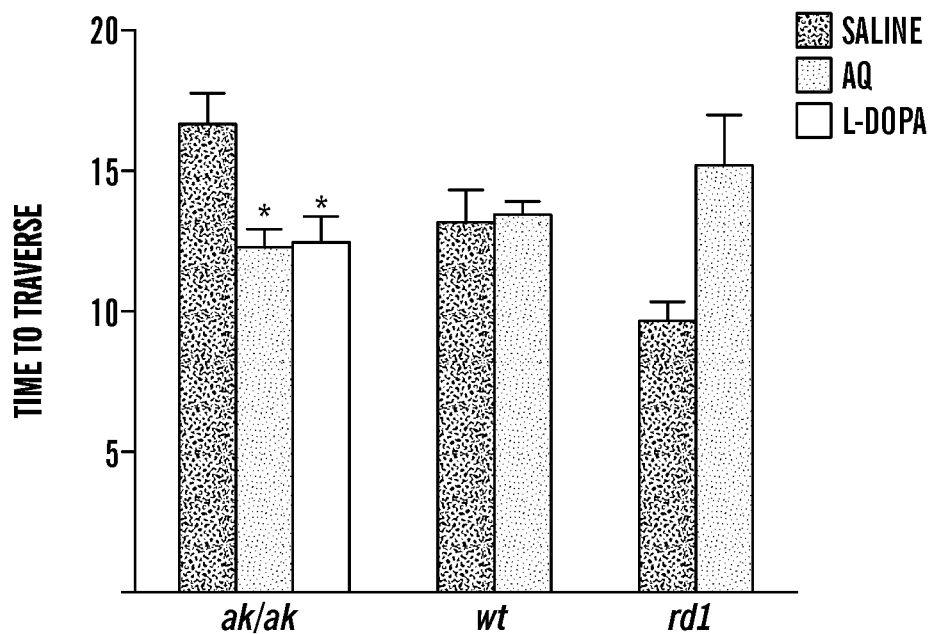
Figure 25C:
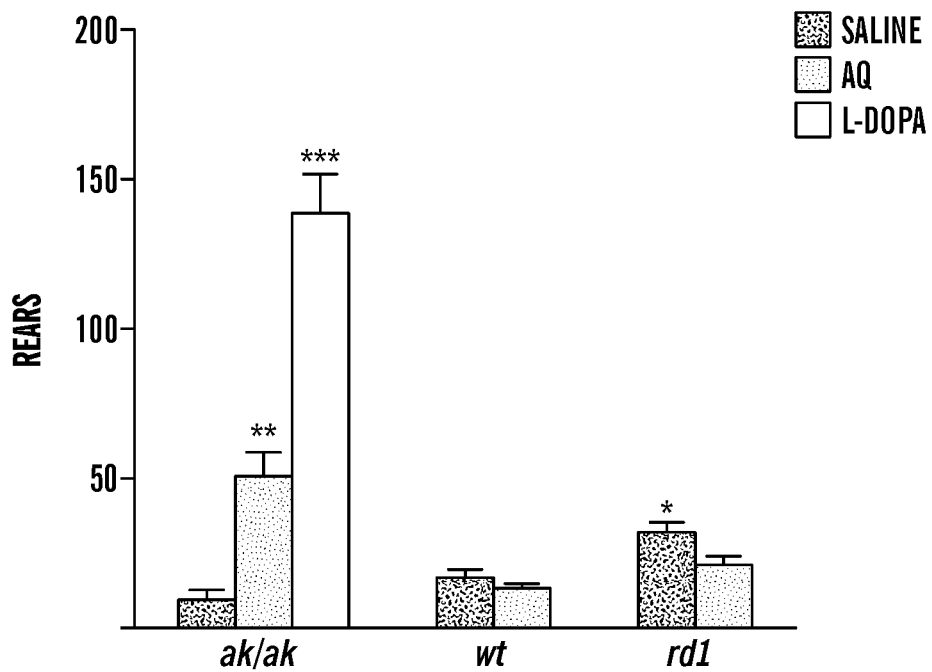
Figure 25D:
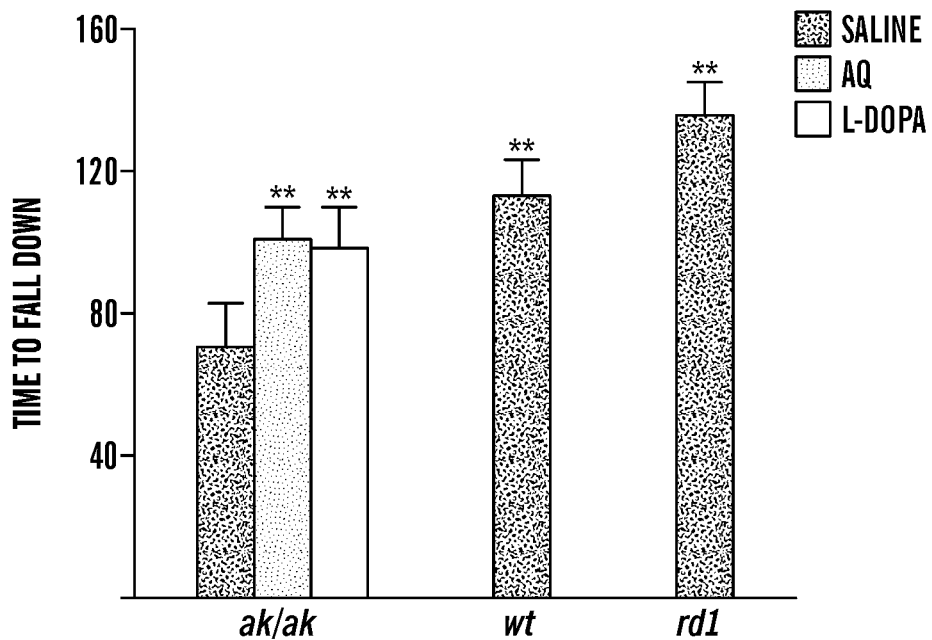

The above findings prompted the inventors to test whether these compounds can ameliorate motor behavior deficits by neuroprotective mechanism(s) in PD animal models. Toward this goal, we tested the effects of AQ administration in an animal model of PD, 6-OHDA lesioned rats. Rats with unilateral intrastriatal 6-OHDA lesion were administered with saline or AQ for two weeks, starting from 1 day prior to intrastriatal 6-OHDA lesion (FIG. 15A). As expected, amphetamine administration produced rotation behavior toward the lesion side in control rats, when measured at 4 and 6 weeks post 6-OHDA lesion, indicating unilateral damage to the right striatum (FIGS. 15A and 15B). Remarkably, AQ administration significantly ameliorated 6-OHDA-induced rotation behavior at 4 and 6 weeks post 6-OHDA lesion ($p<0.06$ and $p<0.0003$, respectively). Immunohistochemistry of the substantia nigra (SN) and the striatum (STR) of these animals showed that AQ-treated rats retained a significant number of TH$^+$ cells in the lesion side SN while saline-treated control rats lost the great majority of TH$^+$ cells (FIG. 15C). Similarly, abundant TH$^+$ fibers were spared in the STR of AQ-treated brains while they were mostly lost in the STR of control brains To quantitatively analyze these data, TH$^+$ cells in the SN were stereologically counted in a blind manner. As shown in FIG. 15D, the number of TH$^+$ neurons in the lesion side of AQ-treated rats was approximately 60% of those from the intact side at 6 weeks post 6-OHDA lesion ($p<0.0003$), whereas it remained less than 20% in saline-treated animals. Importantly, these spared TH$^+$ cells co-expressed other DA markers such as FoxA2 and AADC (FIG. 23). The inventors also examined microglial activation by immunohistochemistry of the microglial marker Iba-1. As shown in FIGS. 15E and 24, microglial activation was prominently observed in the ipsilateral SN and STR regions of 6-OHDA lesioned rats. In contrast, following AQ treatment, the numbers of Iba-1$^+$ microglia in the ipsilateral SN and STR regions decreased to the levels of the contralateral sides, indicating a robust suppression of neuroinflammation by Nurr1 activation[8]. Without wishing to be bound by a theory, it is believed that Nurr1-based neuroprotective mechanism, unlike the L-dopa treatment, may not trigger dyskinesia-like side effects. To address this, the inventors tested if AQ treatment triggers abnormal involuntary movements (AIMs), well validated dyskinesia-like behaviors[14]. Toward this end, the inventors measured AIM scores such as axial, limb, locomotive, and orolingual dyskinesias. In L-DOPA-treated rats (8 mg/kg for two weeks prior to scoring; FIG. 15A). The animals showed dramatically increased AIMs scores ($F_{(2,71)}=33$, $p<0.0001$), classified as the axial, limb, locomotive, and orolingual dyskinesias (FIG. 15F). In contrast, both saline- and AQ-treated 6-OHDA rats did not show any detectable AIMs behavior.

Figure 26:
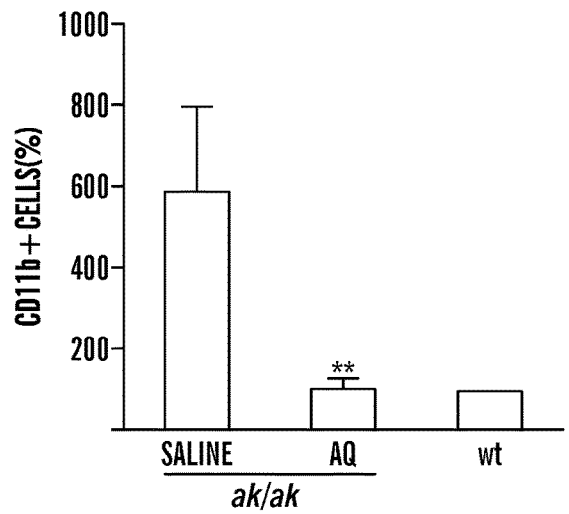
FIG. 26 shows that AQ reduces inflammation in the SN of ak/ak mice. ak/ak mice were administered saline or AQ for 2 weeks. Mice were sacrificed and their brains sectioned. Sections of SN regions from wild type and ak/ak mice were immunostained with anti-CD11b and anti-THantibodies. Stereological counting of CD11b+ microglia was performed in the SN area of ak/ak mice and presented as a percentage of the cell number in the wild type. Data represent the mean±SEM (**p<0.01).
Figure 27:
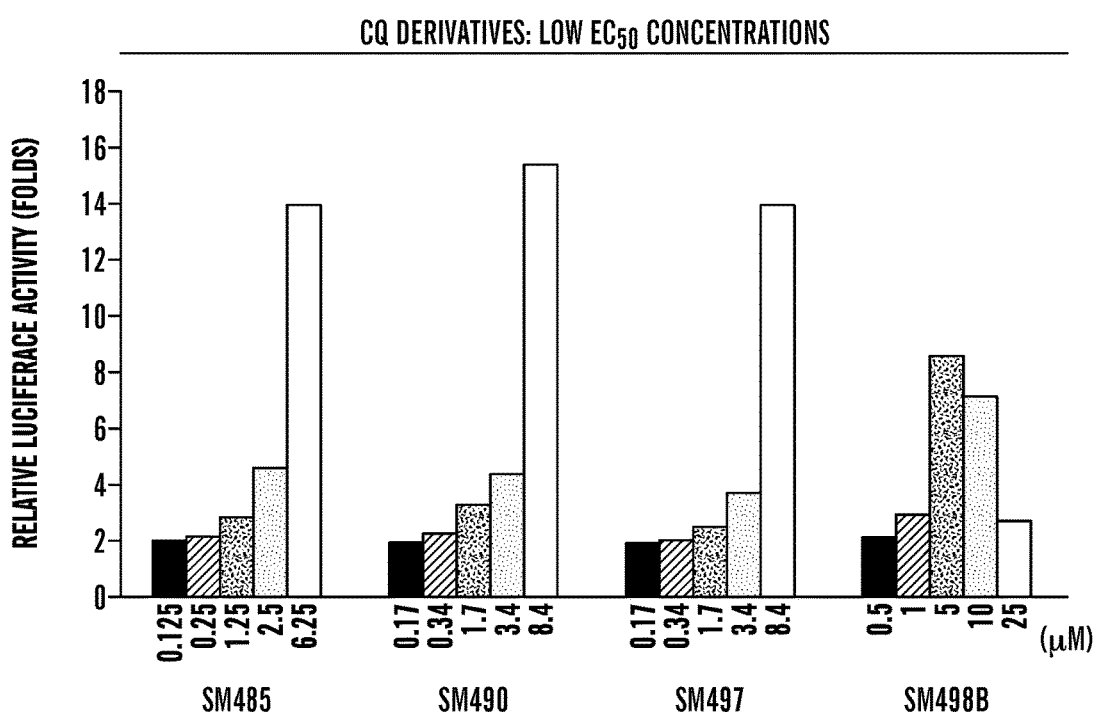
FIG. 27 show that some derivatives of CQ retaining the 4-amino-7-chloro quinolone structure, as shown in FIG. 2, exhibit significantly higher efficacy than the starting compound, CQ. While the $EC_{50}$ of CQ is approximately 60 μM (see FIG. 16), these four derivatives' $EC_{50}$ is less than one-tenth of CQ.

The inventors next tested if AQ treatment can also improve motor dysfunction in the aphakia mouse (ak/ak), that was shown to be a valid mouse model of PD[22,23]. Since the great majority of A9 dopamine neurons (>80%) are selectively degenerated in the SN of the ak/ak mouse starting from birth, it can be considered to be a severe PD situation. Following 2 weeks of AQ treatment, the inventors performed a battery of behavioral tests sensitive to nigrostriatal impairment[22]. Remarkably, the inventors discovered that ak/ak mice's motor deficits were significantly improved in all these tests (i.e., Pole, Challenging Beam, Cylinder, and Rotarod tests) by AQ treatment (FIGS. 25A-25D). Notably, there was no group difference between AQ- and L-DOPA treated animals indicating that AQ had similar effects as L-DOPA treatment on functional recovery in most tests, except the Cylinder test, in which L-DOPA treatment dramatically induced rearing activity, as previously reported[22]. The number of TH+ neurons was not detectably altered in the AQ-treated ak/ak mice (data not shown). In contrast, the inventors observed robust microglial activation as examined by activated microglial marker CD11b in the SN, which was reduced to the level of wild type mice (FIG. 26). Thus, albeit no increased TH+ neurons in the SN, suppression of activated microglia appears to improve motor deficits in ak/ak mice.

In summary, using the novel high throughput cell-based assay described herein, the inventors identified two small molecules, AQ and CQ, which can activate Nurr1 through direct interaction with its LBD. Furthermore, AQ administration significantly improved motor impairments in 6-OHDA lesioned rodent models of PD without dyskinesia-like side effects. The data presented herein shows that these compounds enhanced the contrasting dual functions of Nurr1-activation of mDA neuron-specific function (e.g., TH expression) and repression of microglial activation and neurotoxic cytokine gene expression—leading to a significant neuroprotective effect in a rodent model of PD. These findings are surprising because Nurr1 lacks a 'classical' binding pocket due to the presence of bulky hydrophobic side chain residues, and is thought to be a ligand-independent and constitutively active NR[15,16]. However, certain ligands are able to "worm" their way into the interior of proteins and to squeeze into buried LBD by inducing or exploiting transient conformational changes, thus creating a cavity[17,18], suggesting the possibility that Nurr1 may become an "adopted" NR[19]. Notably, based on selective binding to neuromelanin of an MPTP metabolite[20], a previous study demonstrated that administration of CQ to monkeys protected them from MPTP-induced parkinsonian motor abnormalities[21]. Our findings are in line with this study showing CQ's neuroprotective effect in a rodent or monkey model, and further suggest the involvement of additional and/or alternate mechanisms related to Nurr1 activation. Taken together, our results provide a preclinical "proof-of-concept" that Nurr1 could serve as a valid target for further development of mechanism-based, disease-modifying therapeutics of PD.

REFERENCES

1. Dauer, W. & Przedborski, S. Parkinson's disease: mechanisms and models. *Neuron* 39, 889-909 (2003).
2. Meissner, W. G. et al. Priorities in Parkinson's disease research. *Nat Rev Drug Discov* 10, 377-93 (2011).
3. Obeso, J. A. et al. Missing pieces in the Parkinson's disease puzzle. *Nat Med* 16, 653-61 (2010).
4. Zetterstrom, R. H. et al. Dopamine neuron agenesis in Nurr1-deficient mice. *Science* 276, 248-50 (1997).
5. Kadkhodaei, B. et al. Nurr1 is required for maintenance of maturing and adult midbrain dopamine neurons. *J Neurosci* 29, 15923-32 (2009).
6. Castillo, S. O. et al. Dopamine biosynthesis is selectively abolished in substantia nigra/ventral tegmental area but not in hypothalamic neurons in mice with targeted disruption of the Nurr1 gene. *Mol Cell Neurosci* 11, 36-46 (1998).
7. Saucedo-Cardenas, O. et al. Nurr1 is essential for the induction of the dopaminergic phenotype and the survival of ventral mesencephalic late dopaminergic precursor neurons. *Proc Natl Acad Sci USA* 95, 4013-8 (1998).
8. Saijo, K. et al. A Nurr1/CoREST pathway in microglia and astrocytes protects dopaminergic neurons from inflammation-induced death. *Cell* 137, 47-59 (2009).
9. Chu, Y. et al. Nurr1 in Parkinson's disease and related disorders. *J Comp Neurol* 494, 495-514 (2006).
10. Le, W. D. et al. Mutations in NR4A2 associated with familial Parkinson disease. *Nat Genet* 33, 85-9 (2003).
11. Glass, C. K., Saijo, K., Winner, B., Marchetto, M. C. & Gage, F. H. Mechanisms underlying inflammation in neurodegeneration. *Cell* 140, 918-34 (2010).
12. Kim, K. S. et al. Orphan nuclear receptor Nurr1 directly transactivates the promoter activity of the tyrosine hydroxylase gene in a cell-specific manner. *J Neurochem* 85, 622-34 (2003).
13. Glass, C. K. & Rosenfeld, M. G. The coregulator exchange in transcriptional functions of nuclear receptors. *Genes Dev* 14, 121-41 (2000).
14. Dekundy, A., Lundblad, M., Danysz, W. & Cenci, M. A. Modulation of L-DOPA-induced abnormal involuntary movements by clinically tested compounds: further validation of the rat dyskinesia model. *Behav Brain Res* 179, 76-89 (2007).
15. Wang, Z. et al. Structure and function of Nurr1 identifies a class of ligand-independent nuclear receptors. *Nature* 423, 555-60 (2003).
16. McMorrow, J. P. & Murphy, E. P. Inflammation: a role for NR4A orphan nuclear receptors? *Biochem Soc Trans* 39, 688-93 (2011).
17. Ringe, D., Petsko, G. A., Kerr, D. E. & Ortiz de Montellano, P. R. Reaction of myoglobin with phenylhydrazine: a molecular doorstop. *Biochemistry* 23, 2-4 (1984).
18. Schlichting, I. et al. The catalytic pathway of cytochrome p450cam at atomic resolution. *Science* 287, 1615-22 (2000).
19. Hummasti, S. & Tontonoz, P. Adopting new orphans into the family of metabolic regulators. *Mol Endocrinol* 22, 1743-53 (2008).
20. D'Amato, R. J., Lipman, Z. P. & Snyder, S. H. Selectivity of the parkinsonian neurotoxin MPTP: toxic metabolite MPP+ binds to neuromelanin. *Science* 231, 987-9 (1986).
21. D'Amato, R. J. et al. Evidence for neuromelanin involvement in MPTP-induced neurotoxicity. *Nature* 327, 324-6 (1987).
22. Hwang, D. Y., et al. 3,4-dihydroxyphenylalanine reverses the motor deficits in Pitx3-deficient aphakia mice: behavioral characterization of a novel genetic model of Parkinson's disease. *J Neurosci* 25, 2132-2137 (2005).
23. Chung, S., et al. ES cell-derived renewable and functional midbrain dopaminergic progenitors. *Proc Natl Acad Sci USA* 108, 9703-9708 (2011).

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A compound selected from the group consisting of Formula (I)-Formula (X):

Formula (I):

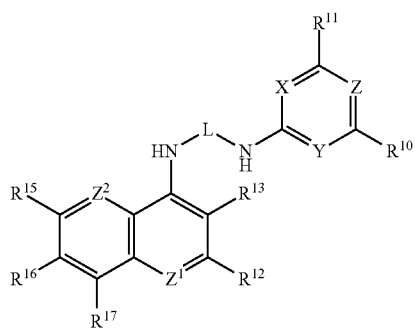

Formula (I)

wherein:

X, Y, and Z are independently CR$^{18}$, N, O, or S, provided that two of X, Y, and Z are N;

one of Z$^1$ and Z$^2$ is N and the other is CR$^{14}$;

R and R$^{10}$-R$^{18}$ are independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted; and L is a linker Formula (II):

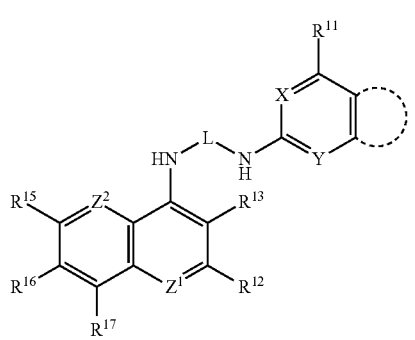

Formula (II)

wherein:

X and Y are independently CR$^{18}$, N, O, or S;

A and B are independently CR$^{18}$, N, O, or S;

one of Z$^1$ and Z$^2$ is N and the other is CR$^{14}$;

R and R$^{10}$-R$^{18}$ are independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted;

----- forms a cyclyl, heterocyclyl, aryl, or heteroaryl, each of which can be optionally substituted; and L is a linker;

Formula (III):

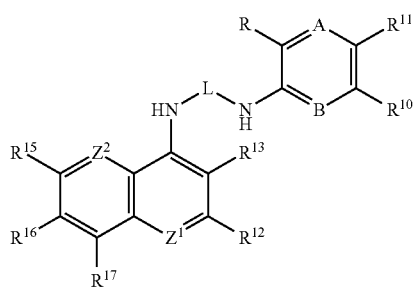

Formula (III)

wherein:

A and B are independently CR$^{18}$ or N;

one of Z$^1$ and Z$^2$ is N and the other is CR$^{14}$;

R and R$^{10}$-R$^{18}$ are independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted; and L is a linker;

Formula (IV):

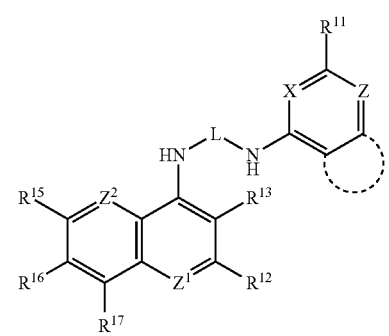

Formula (IV)

wherein:

X and Z are independently CR$^{18}$, N, O, or S;

one of Z$^1$ and Z$^2$ is N and the other is CR$^{14}$;

R and R$^{11}$-R$^{18}$ are independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted;

----- forms a cyclyl, heterocyclyl, aryl, or heteroaryl, each of which can be optionally substituted; and L is a linker;

Formula (V):

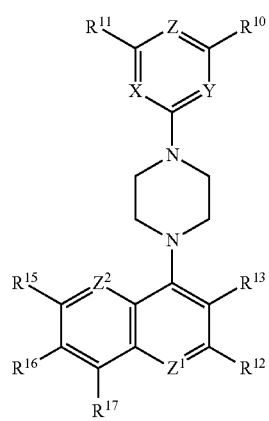

Formula (V)

wherein:
X, Y, and Z are independently $CR^{18}$, N, O, or S, provided that X and Y are N or Y and Z are N;
one of $Z^1$ and $Z^2$ is N and the other is $CR^{14}$;
R and $R^{11}$-$R^{18}$ are independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted; and
$R^{10}$ is linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted;

Formula (VI):

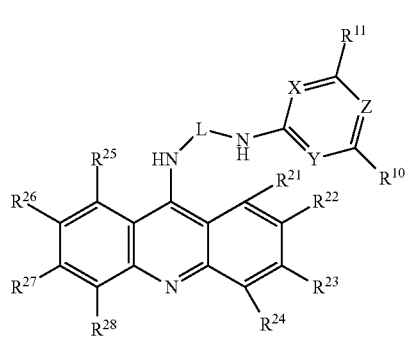

Formula (VI)

wherein:
X, Y, and Z are independently $CR^{18}$, N, O, or S;
$R^{10}$, $R^{11}$ and $R^{21}$-$R^{28}$ are independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted; and
L is a linker;

Formula (VII):

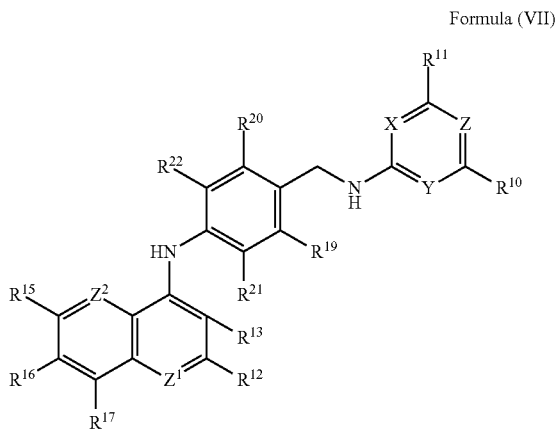

Formula (VII)

wherein:
X, Y, and Z are independently $CR^{18}$, N, O, or S;
one of $Z^1$ and $Z^2$ is N and the other is $CR^{14}$; and
R and $R^{10}$-$R^{22}$ are independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted;

Formula (VIII):

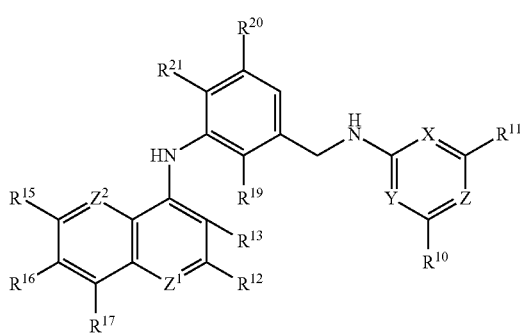

Formula (VIII)

wherein:
X, Y, and Z are independently $CR^{18}$, N, O, or S;
one of $Z^1$ and $Z^2$ is N and the other is $CR^{14}$; and
R and $R^{10}$-$R^{21}$ are independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted;

Formula (IX):

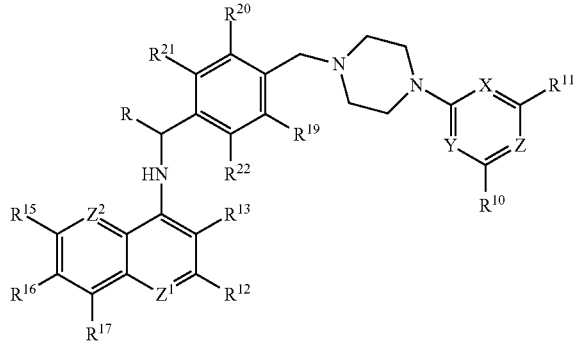

wherein:

X, Y, and Z are independently $CR^{18}$, N, O, or S;

one of $Z^1$ and $Z^2$ is N and the other is $CR^{14}$; and

R and $R^{10}$-$R^{22}$ are independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted;

Formula (X):

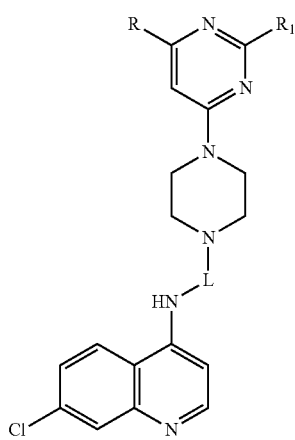

wherein:

R is hydrogen, $CH_3$, Cl, $CF_3$ or CN;

$R_1$ is cyclic or acrylic amine; and

L is an optionally substituted $C_2$-$C_{30}$ alkyl, optionally substituted aromatic ring, optionally substituted heteroaryl ring, saturated cyclic ring; amino acid, or peptide;

and any pharmaceutically acceptable salt, hydrate, solvate, ester, stereoisomer mixture, or enantiomer thereof.

2. The compound of claim 1, wherein the compound is selected from the group consisting of

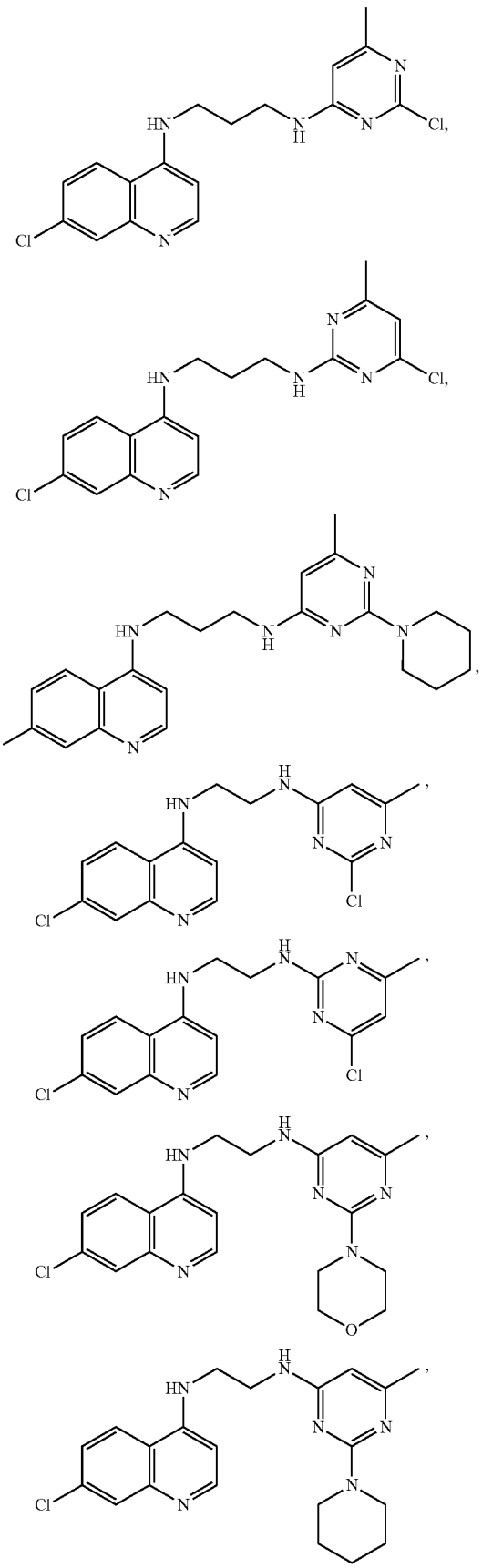

279
-continued
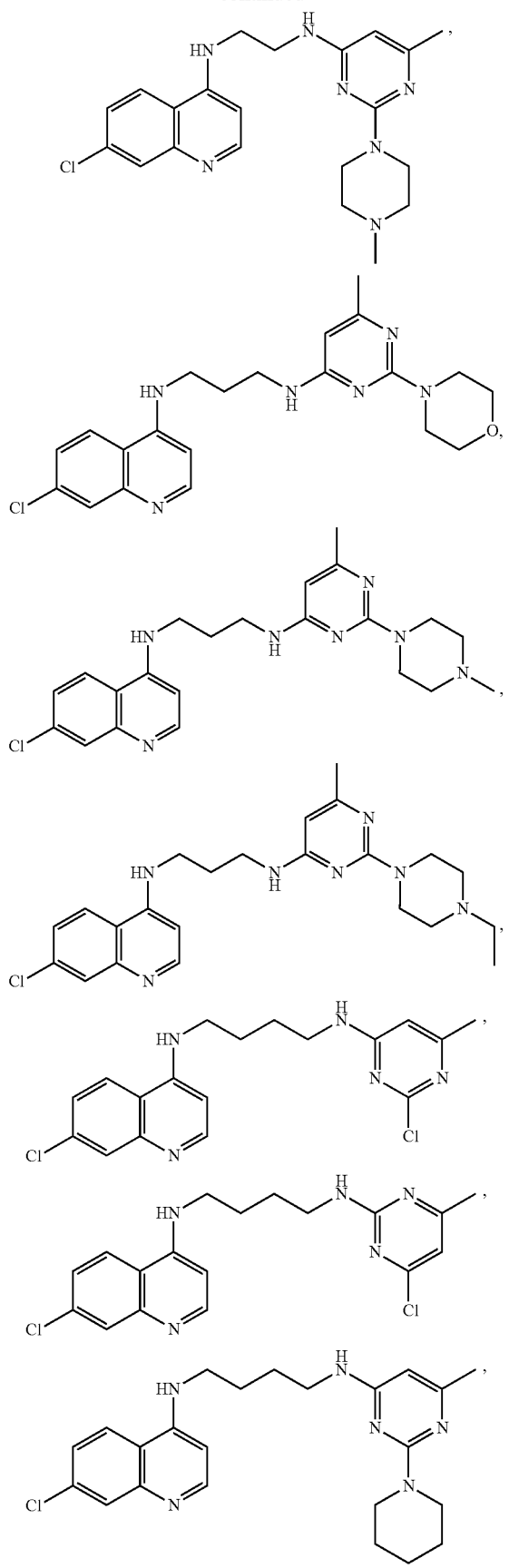
280
-continued
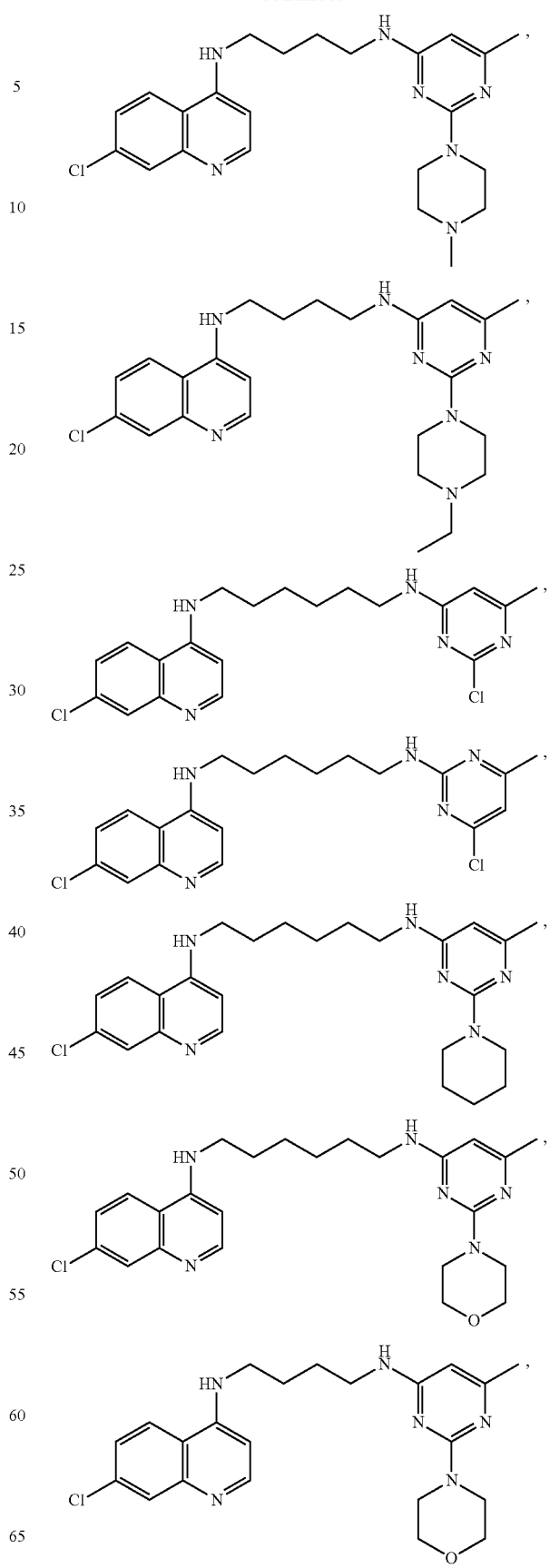

281
-continued
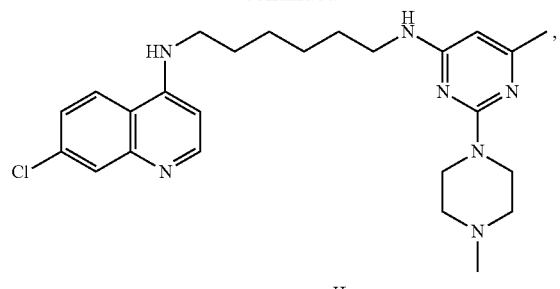
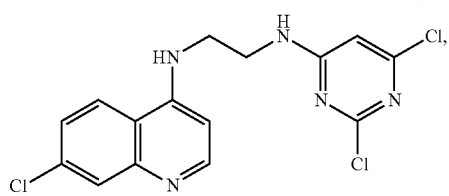
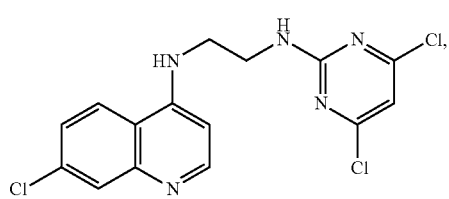
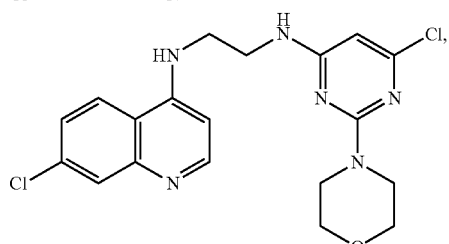
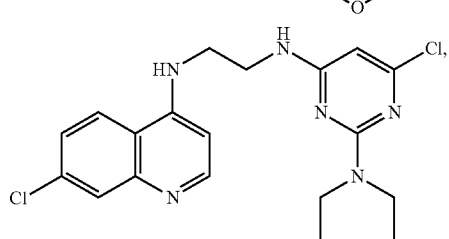
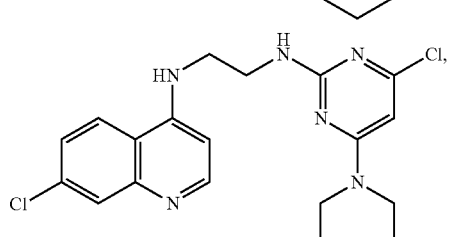
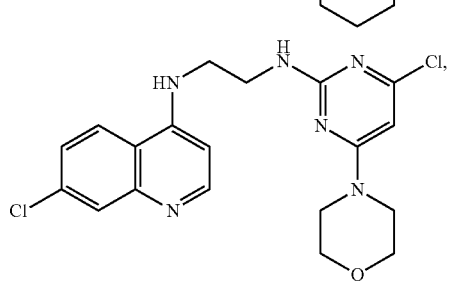
282
-continued
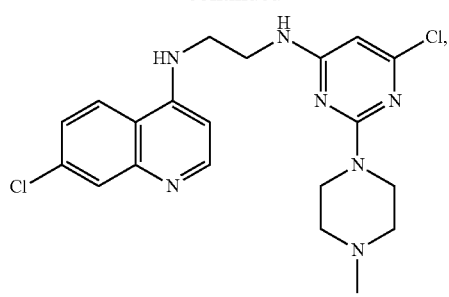
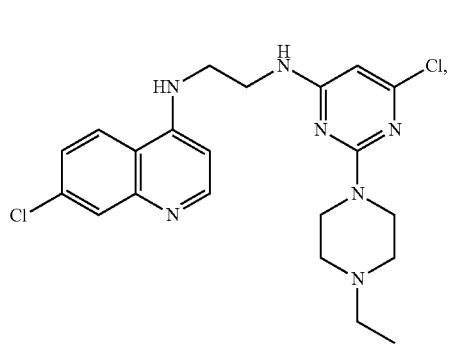
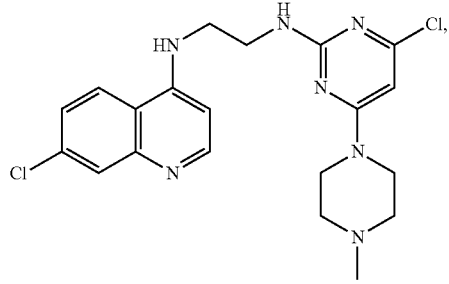
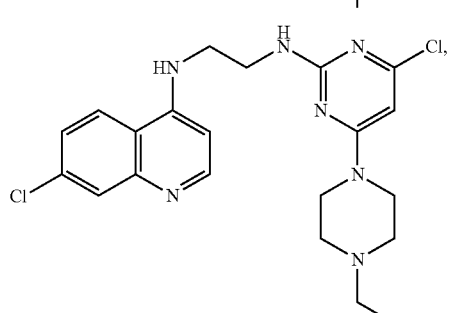
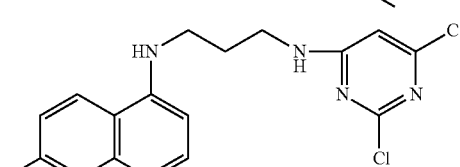
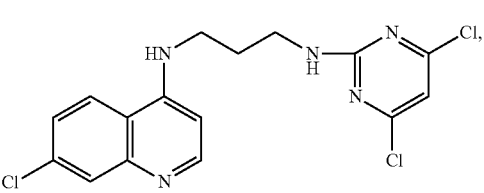

-continued
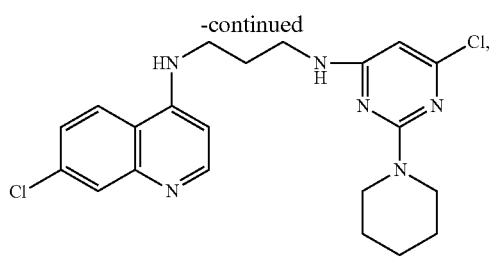
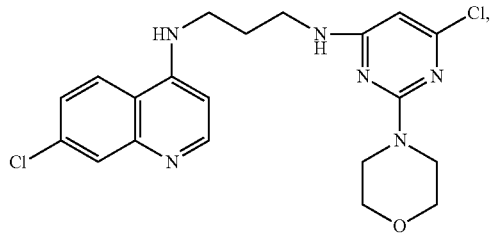
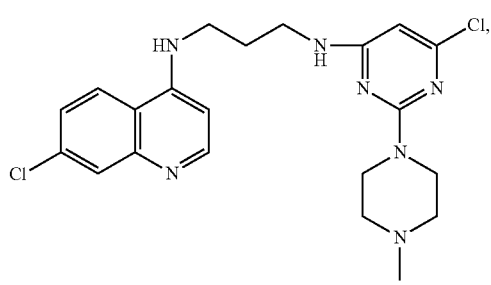
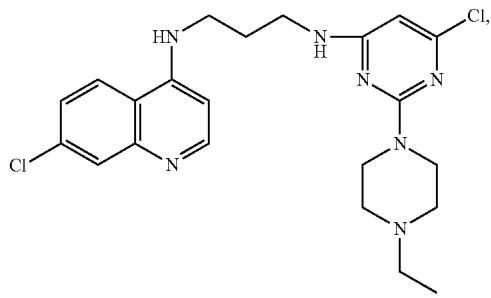
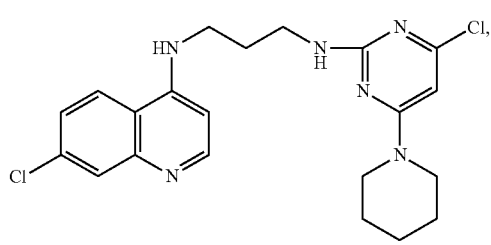
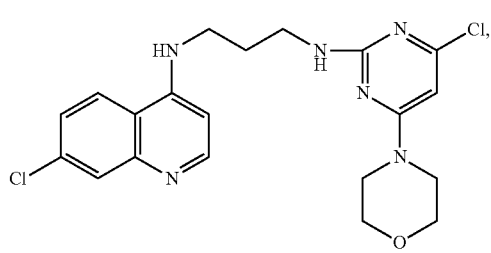
-continued
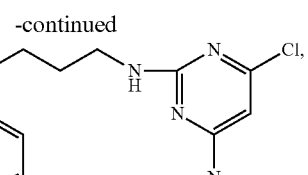
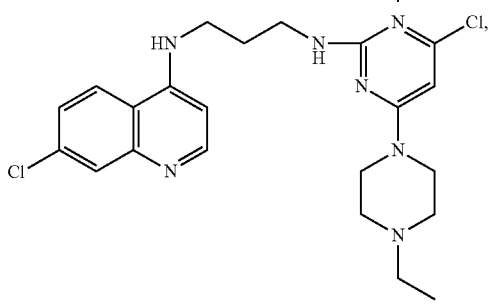
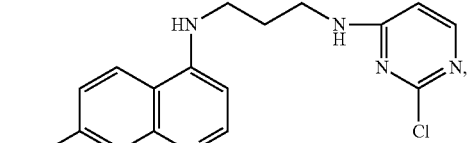
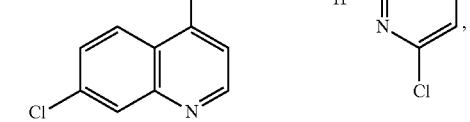
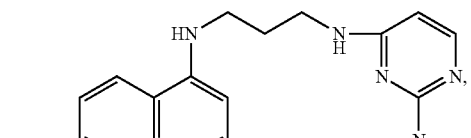
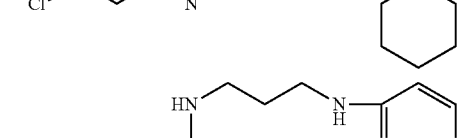
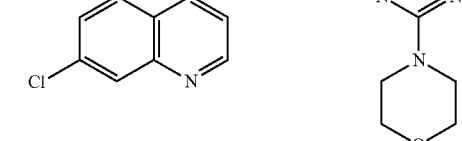

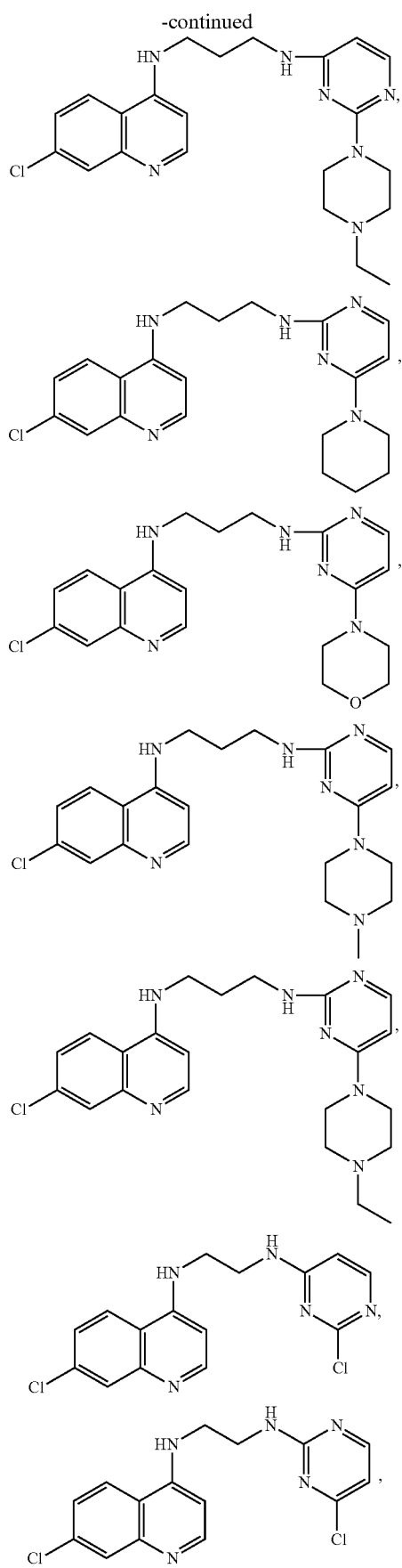
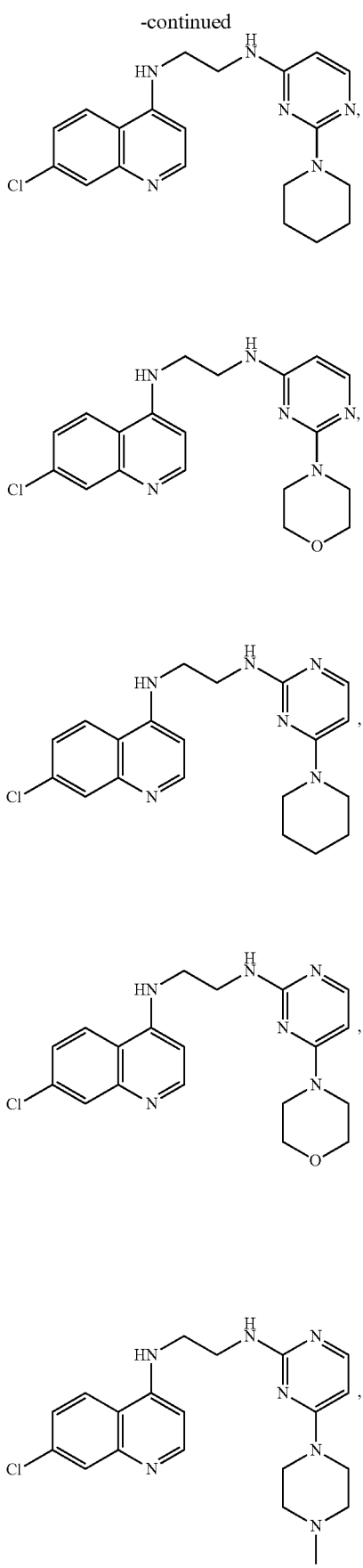

287
-continued
288
-continued
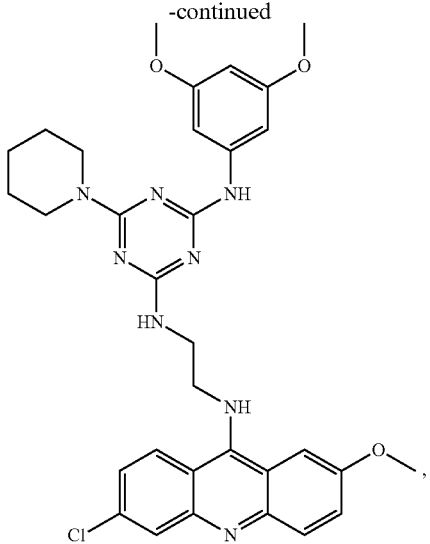
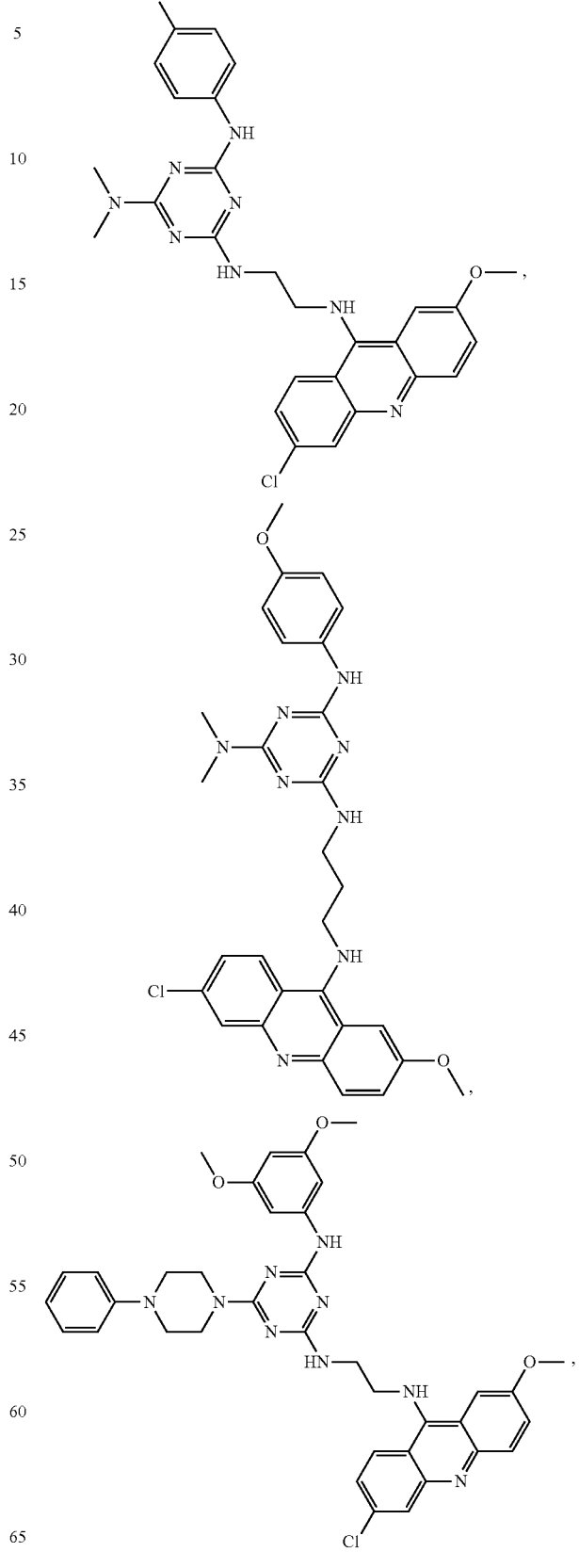
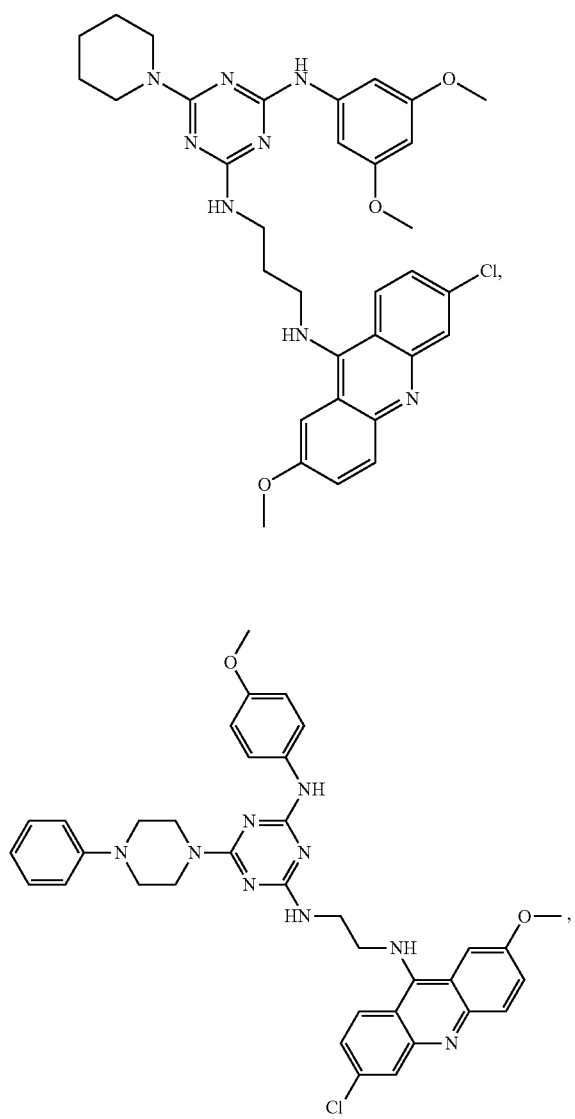

289
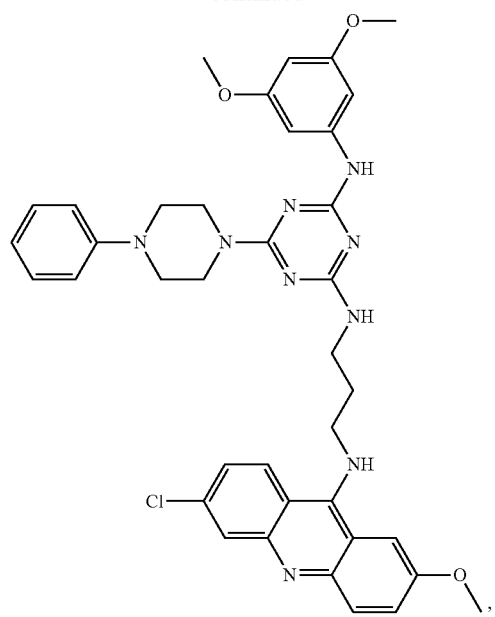
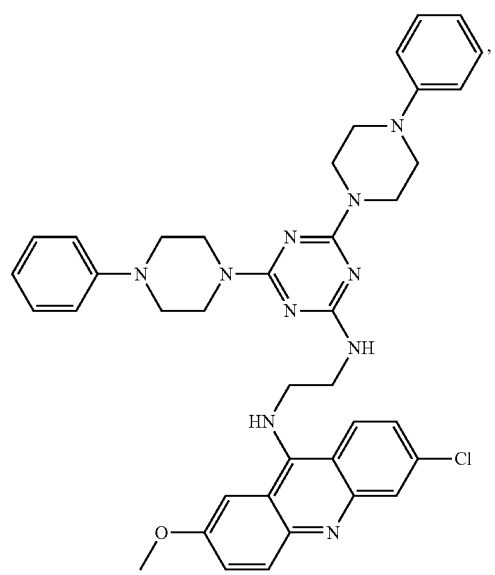
290
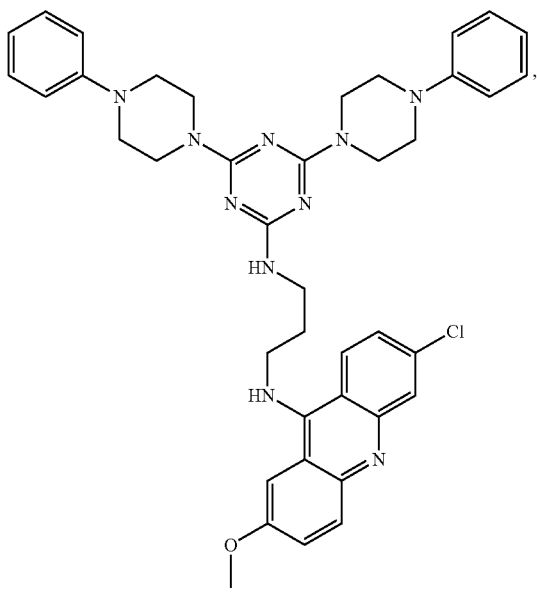
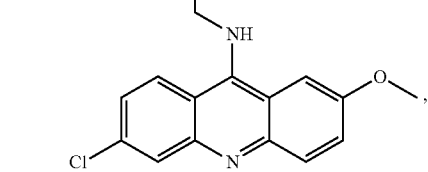

291
-continued
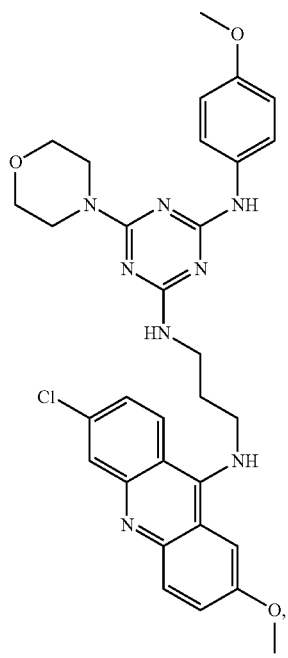
292
-continued
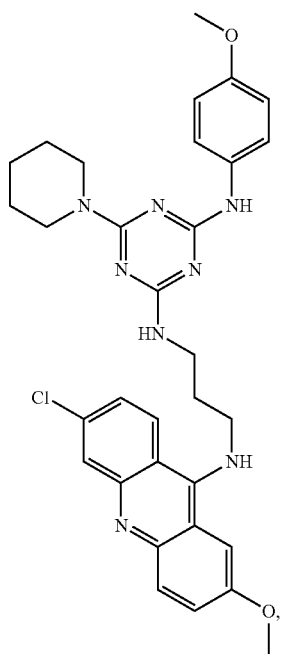
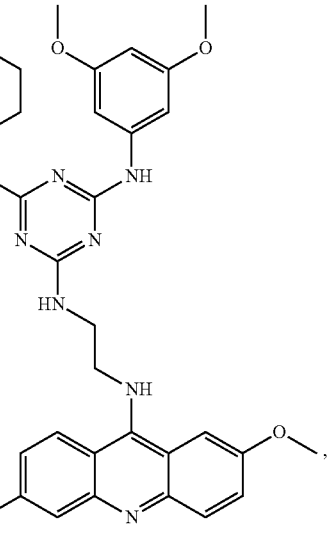

293
-continued
294
-continued
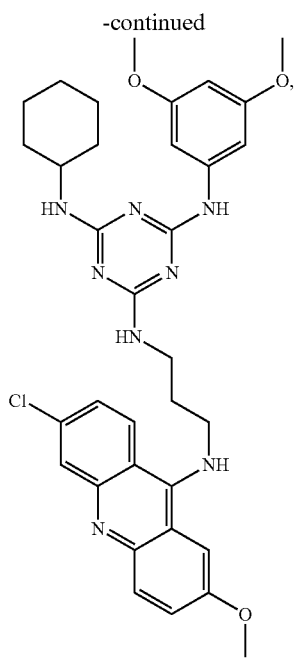
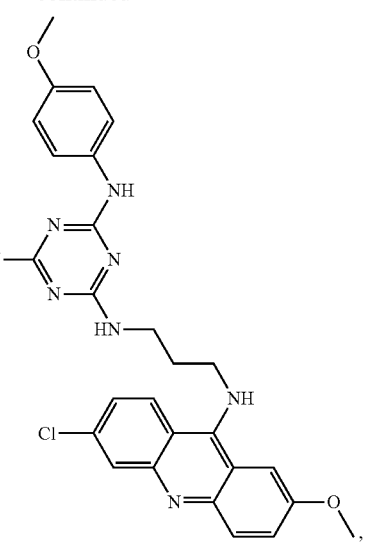
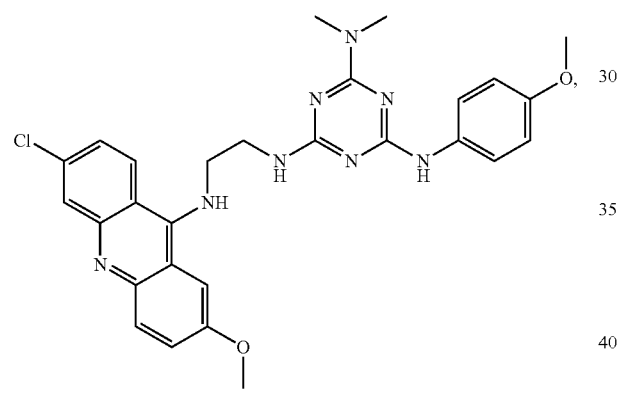
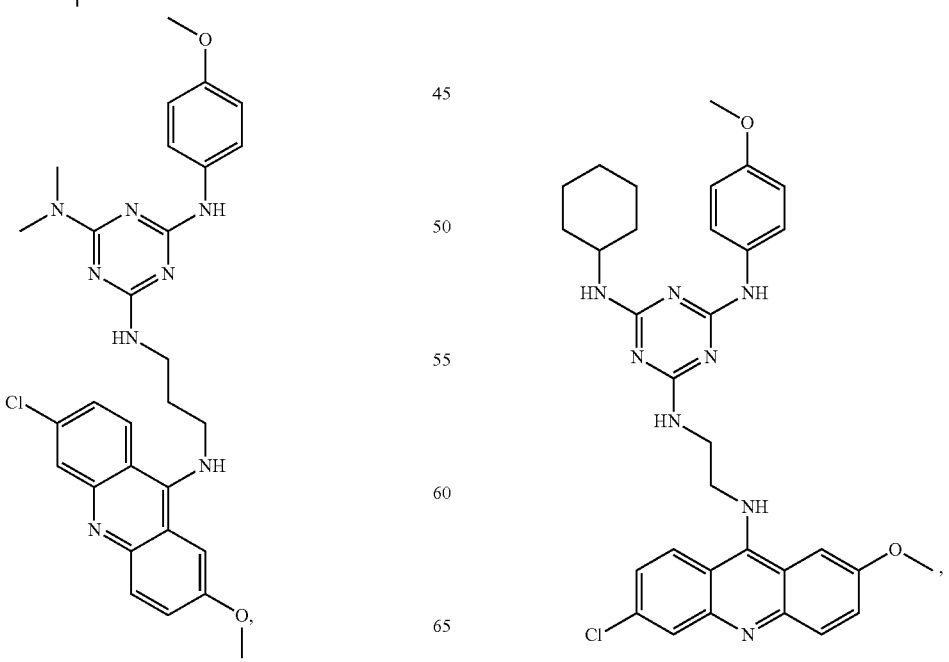

-continued
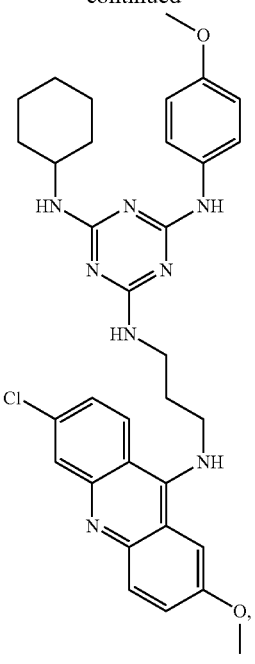
-continued
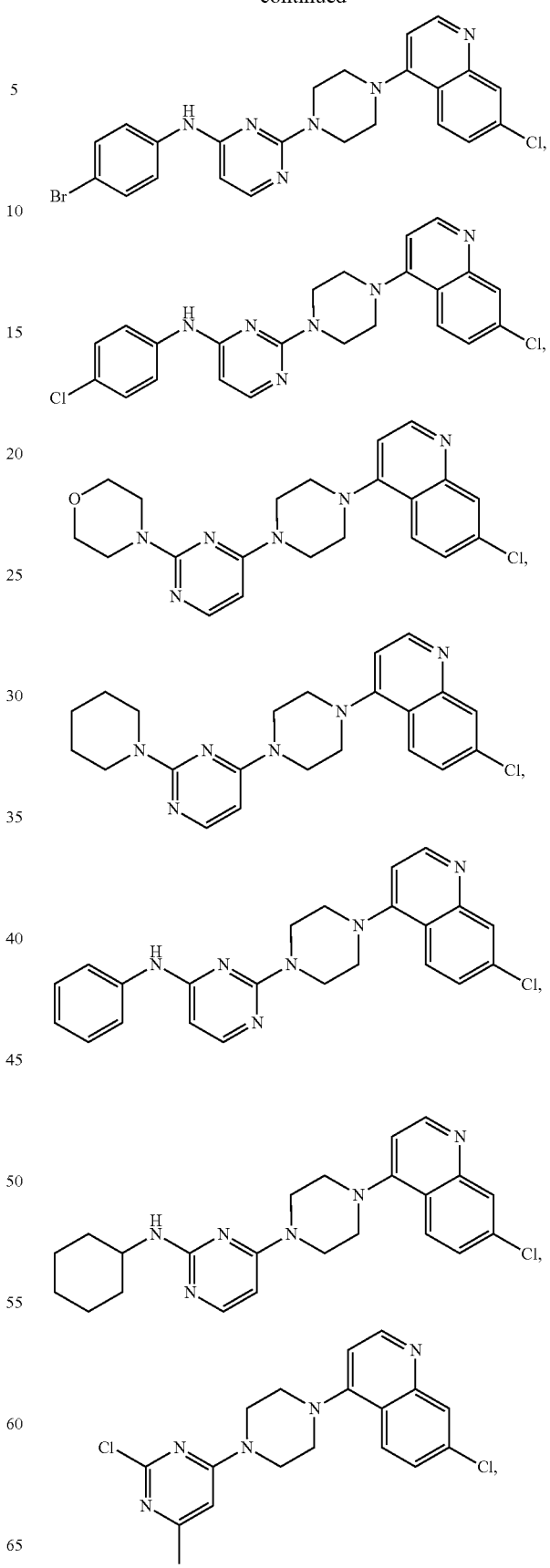

297
-continued
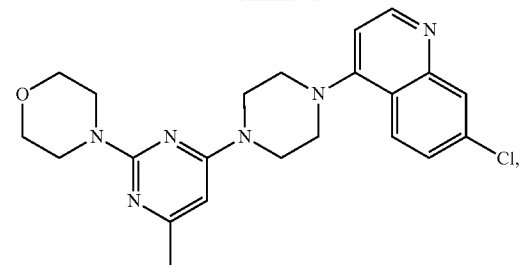
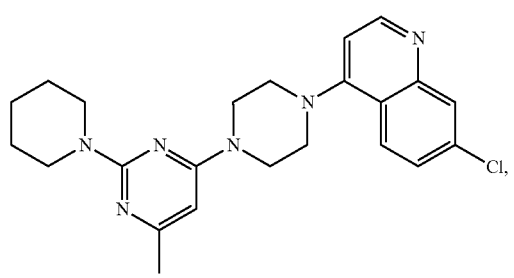
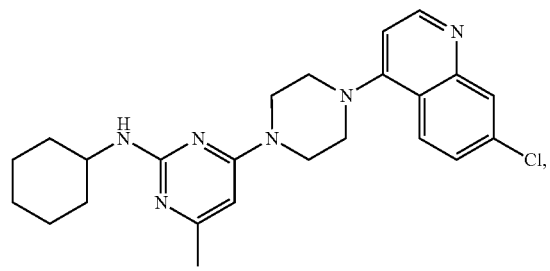
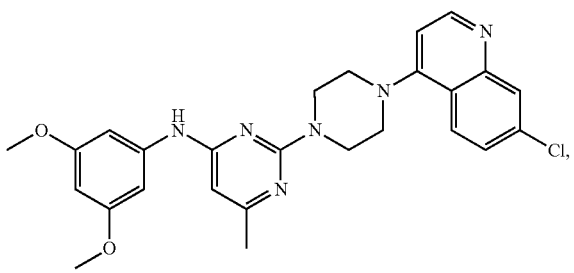
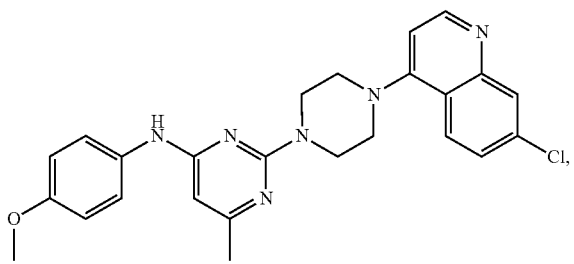
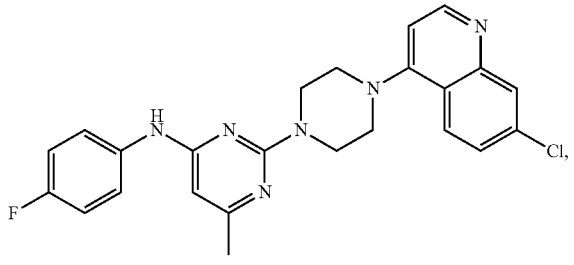
298
-continued
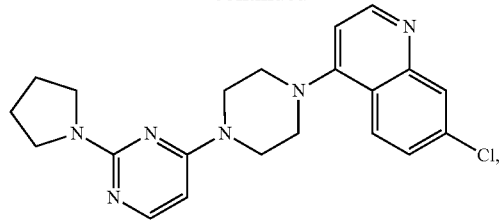
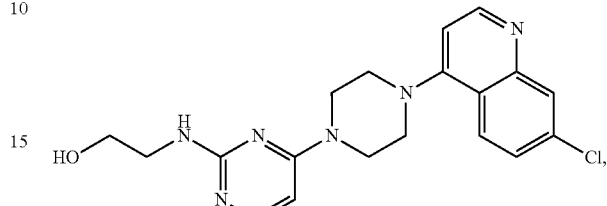
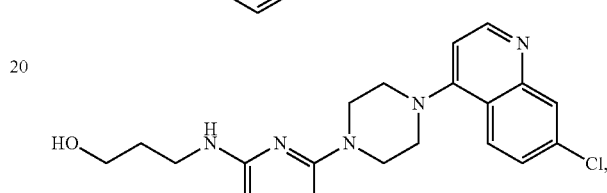
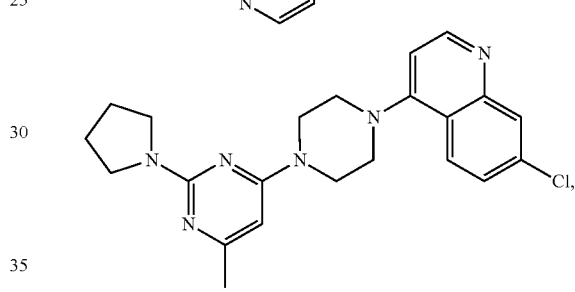
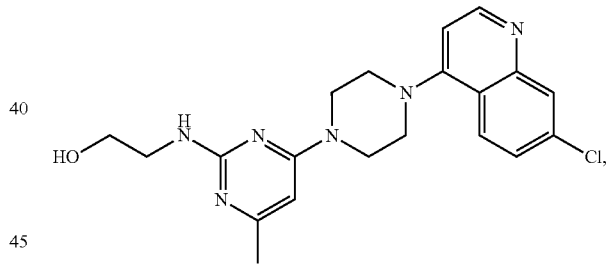
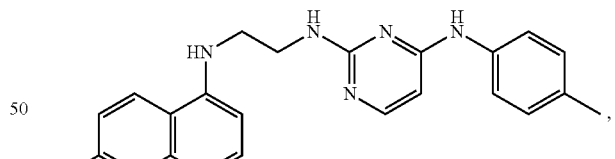
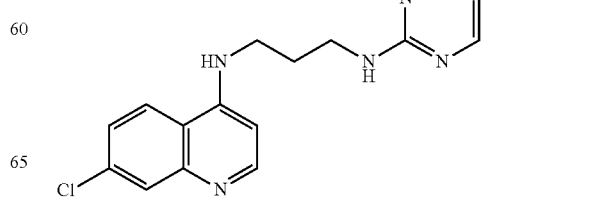

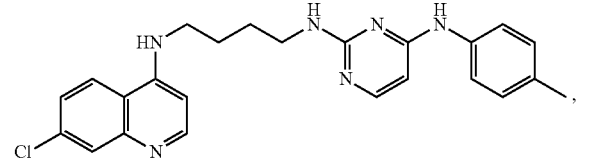
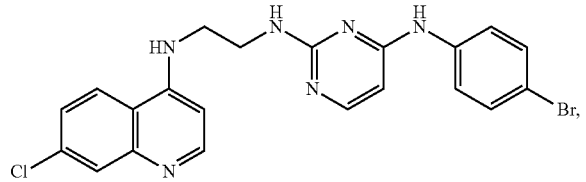
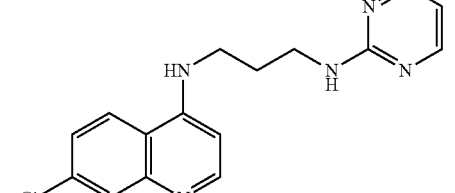
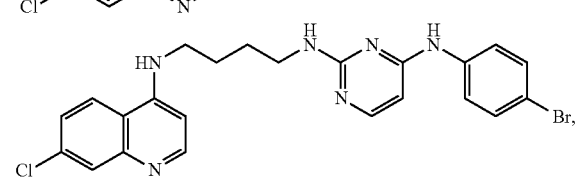
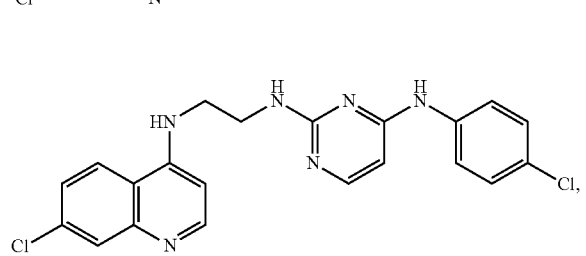
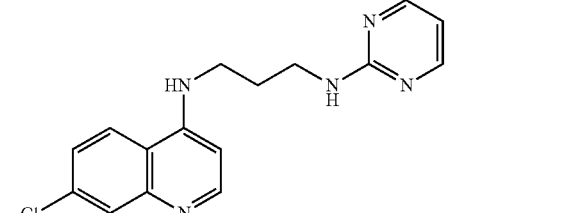
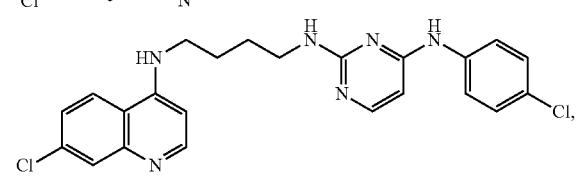
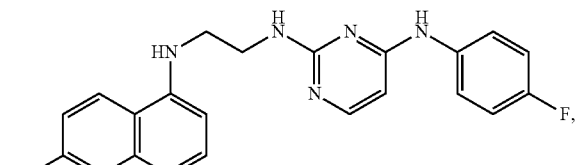
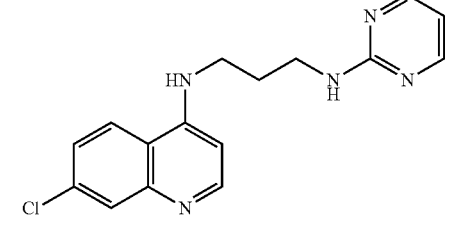
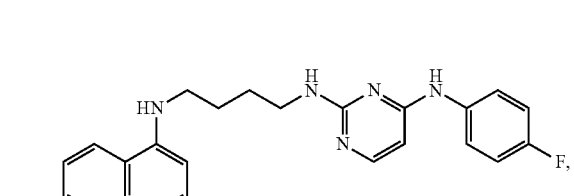
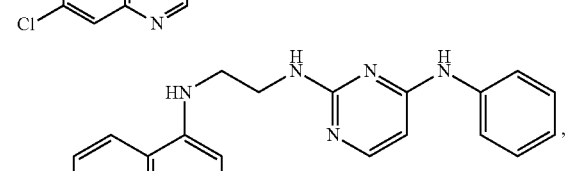
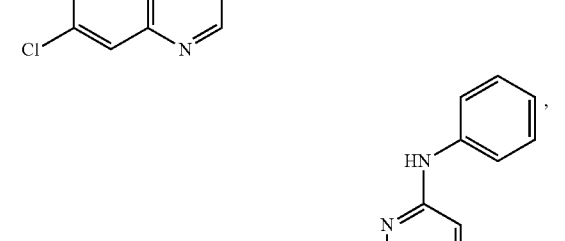
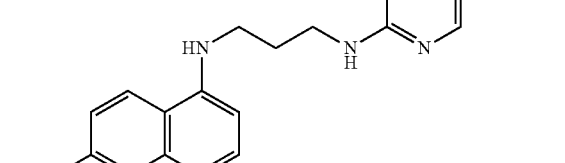
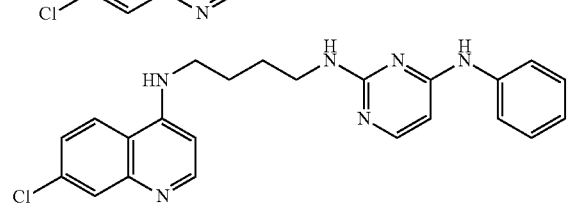
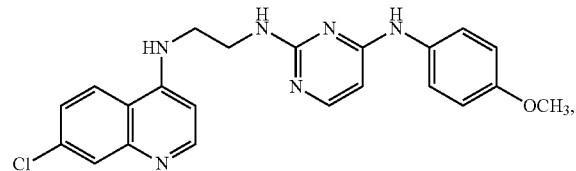

301
-continued
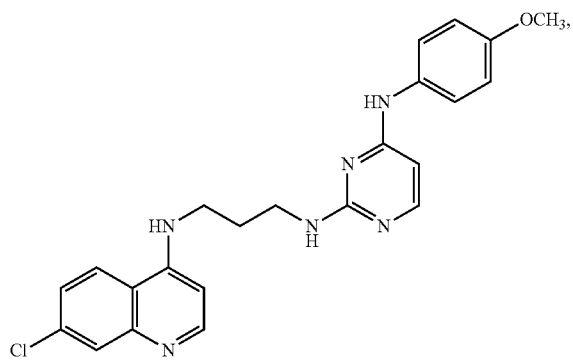
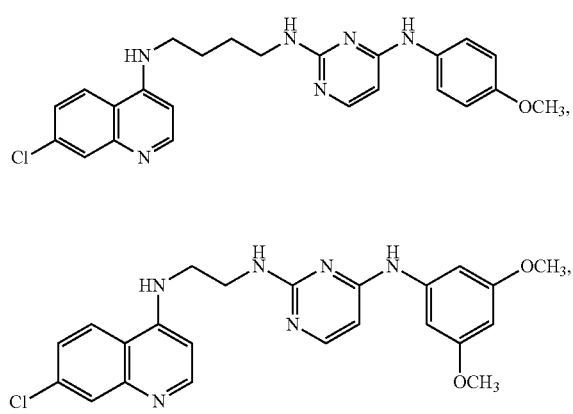
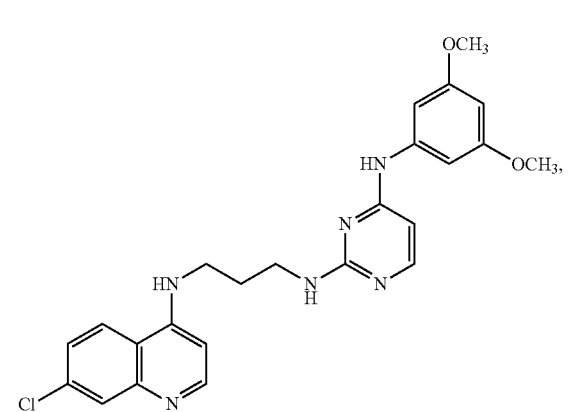
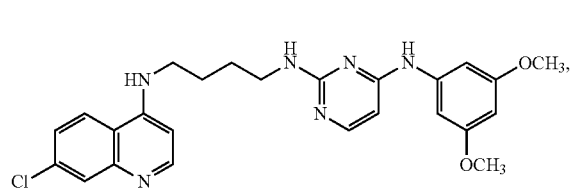
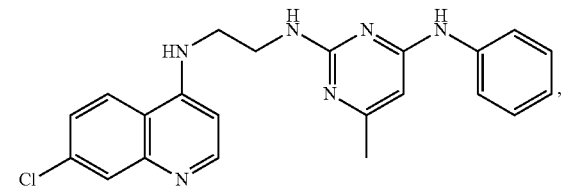
302
-continued
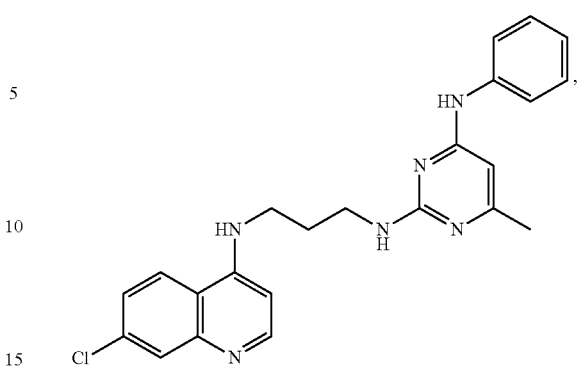
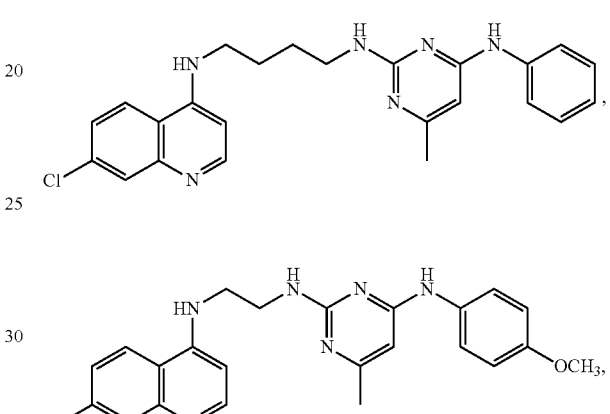
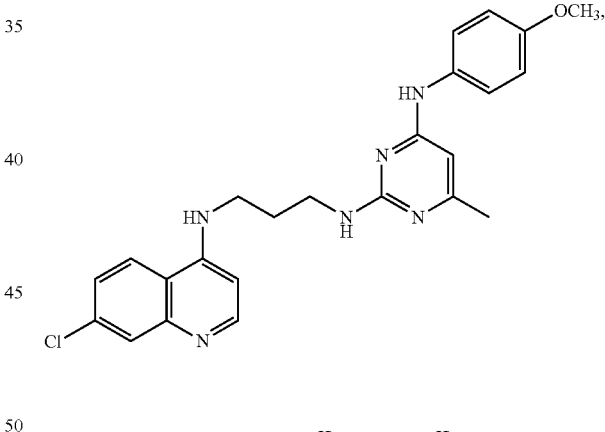
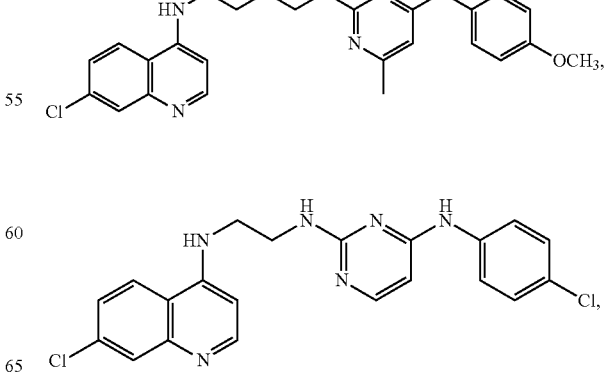

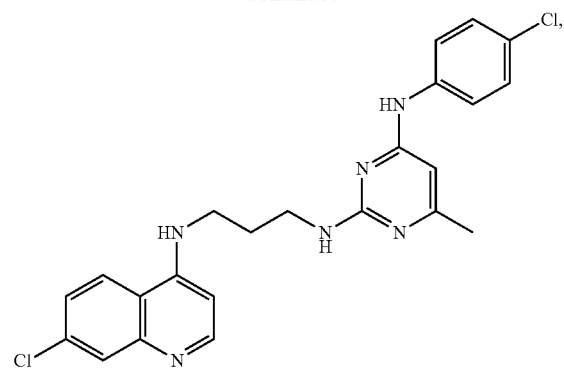
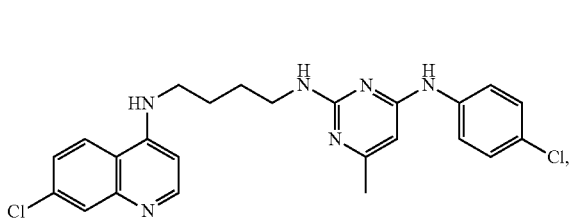
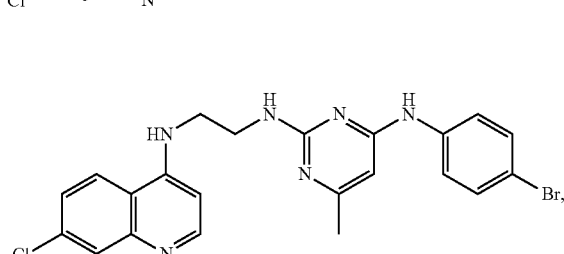
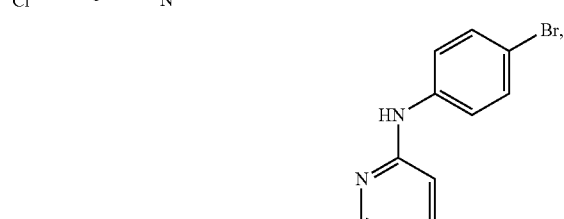
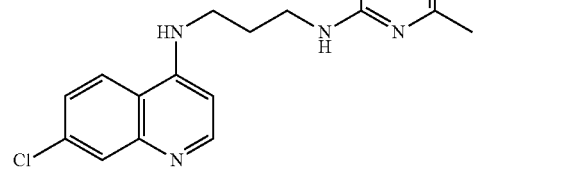
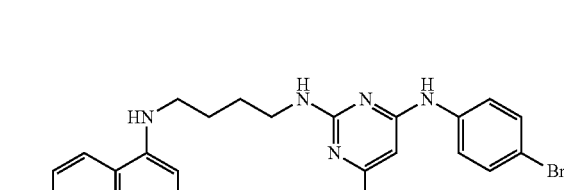
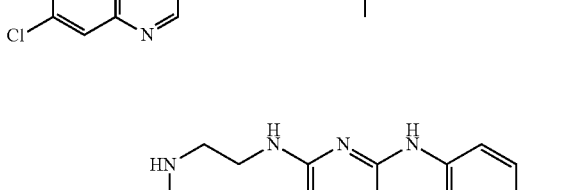
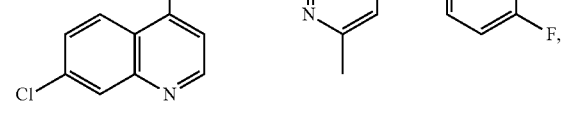
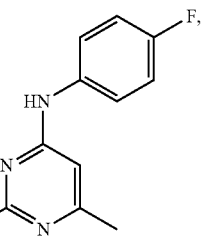
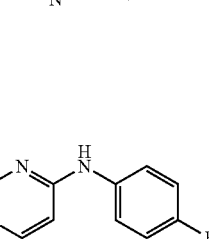
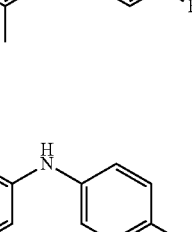
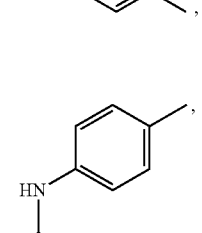
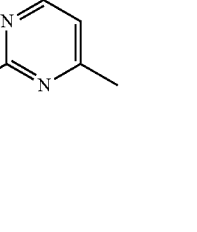
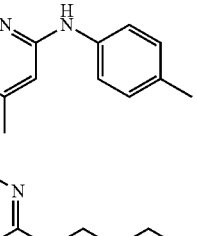
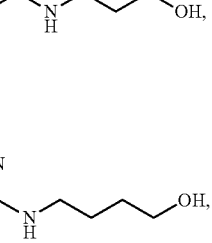

305
-continued
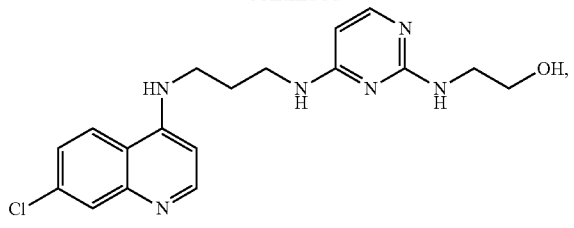
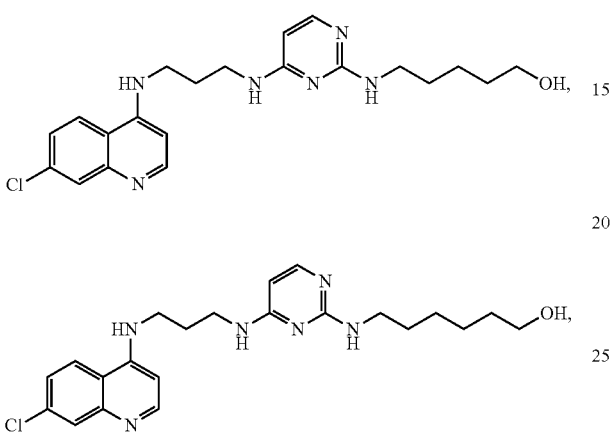
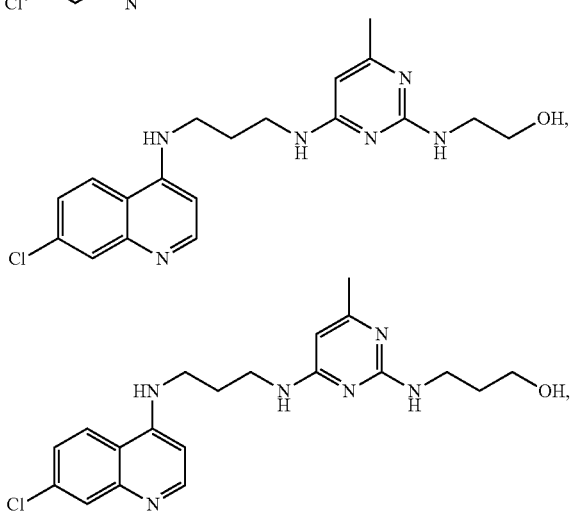
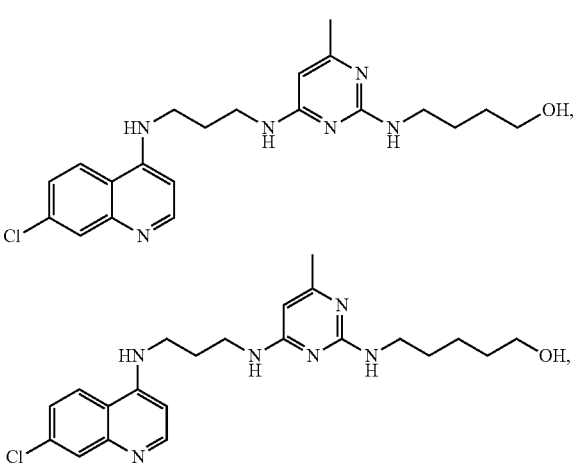
306
-continued
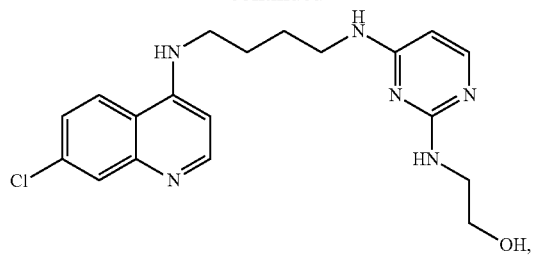
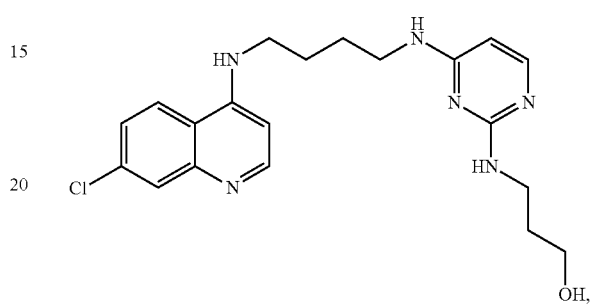
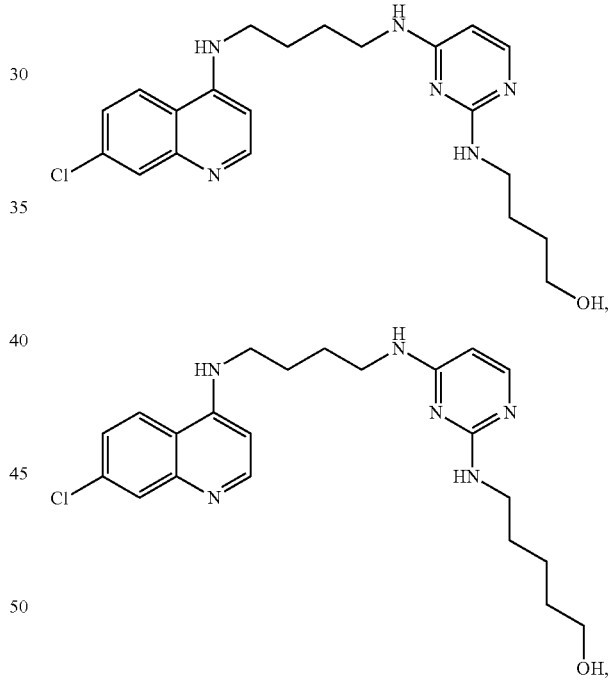
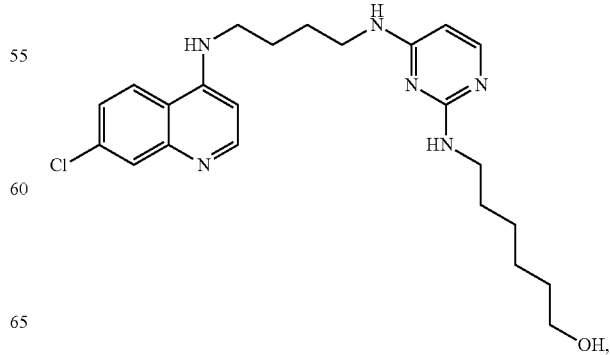

307
-continued
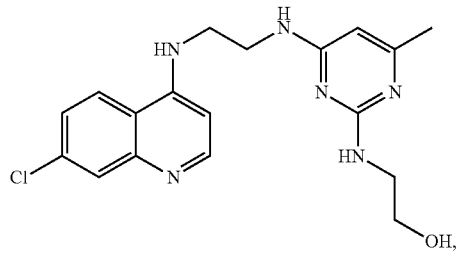
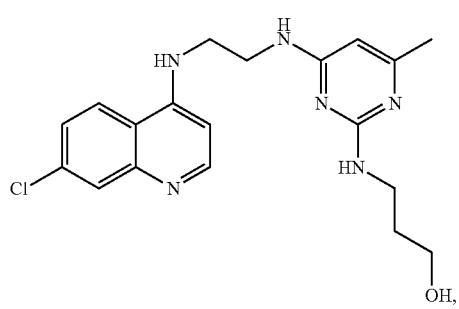
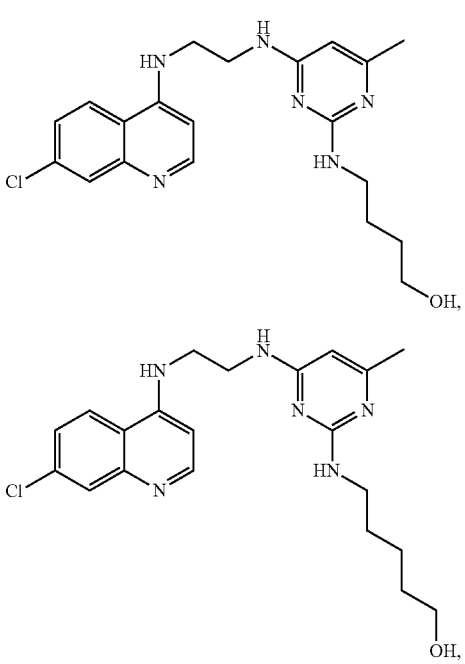
308
-continued
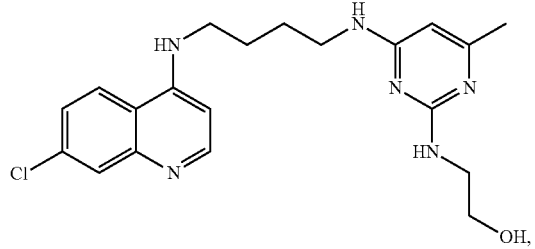
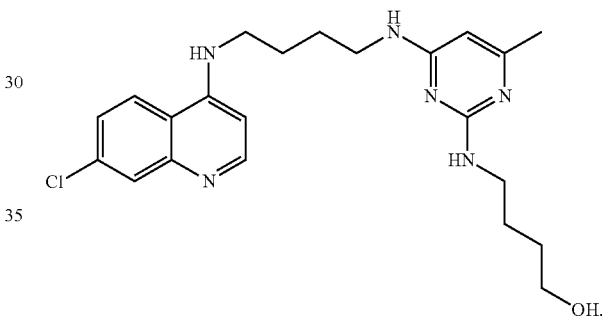
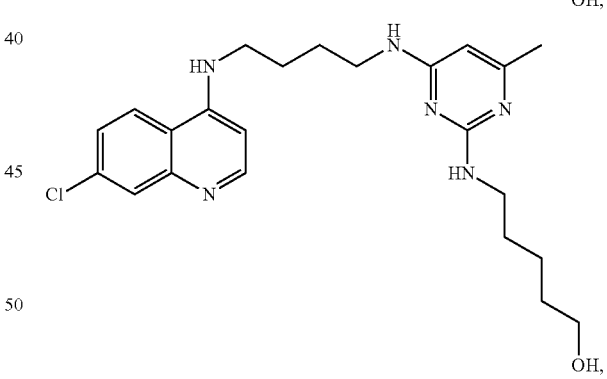
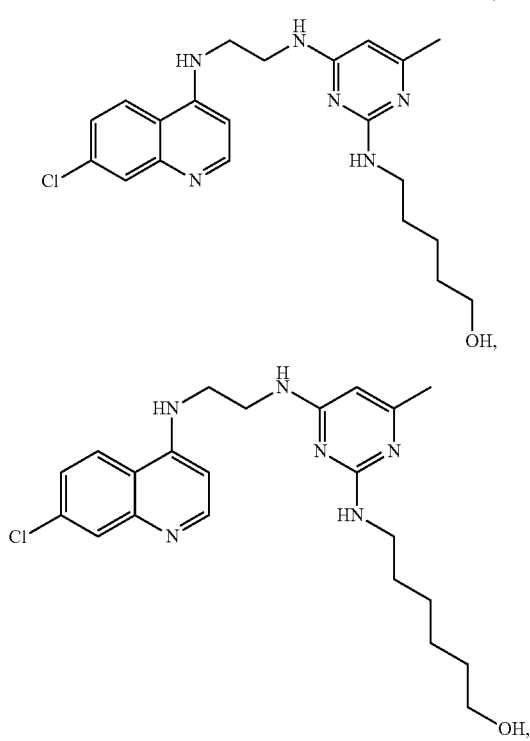

309
-continued
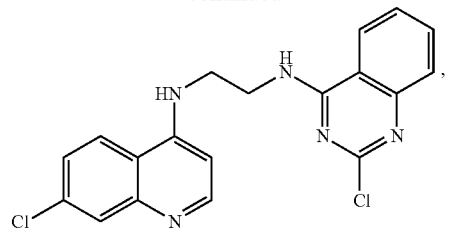
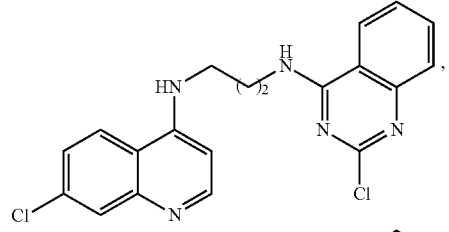
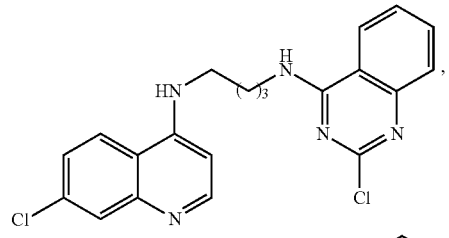
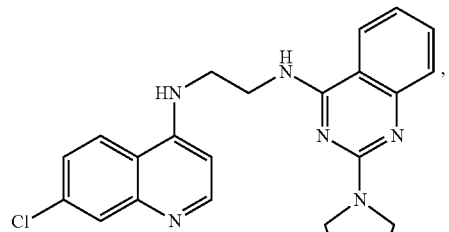
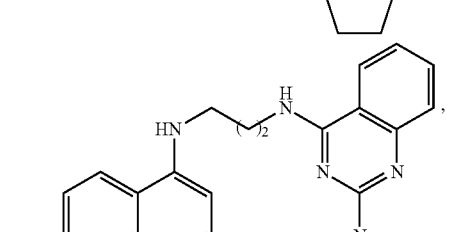
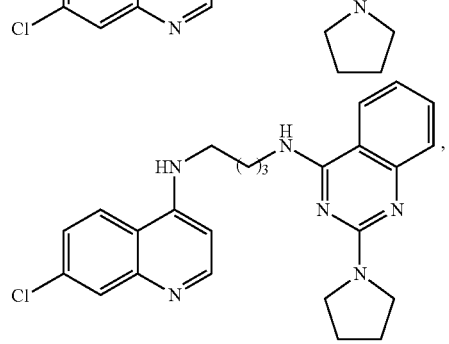
310
-continued
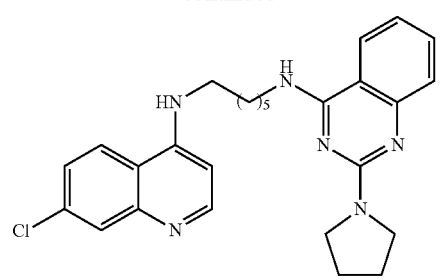
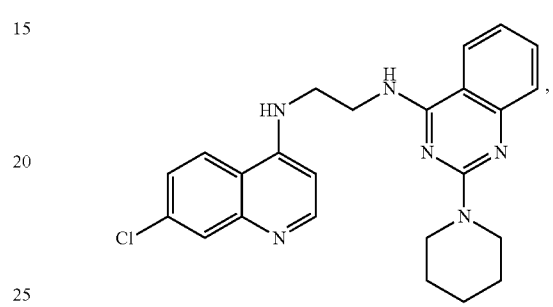
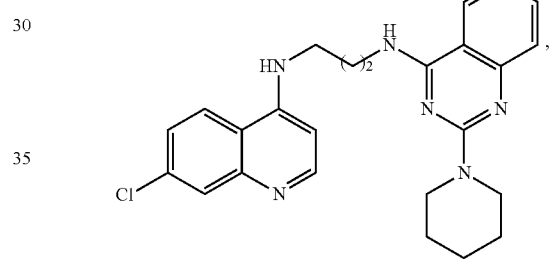
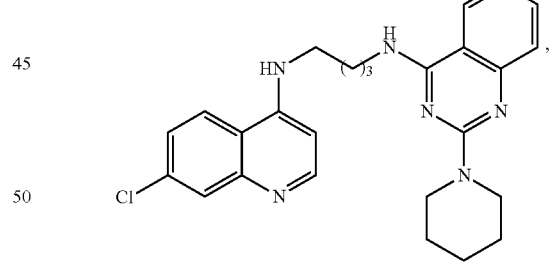
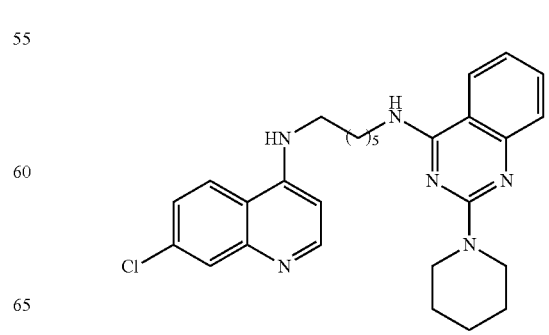

311
-continued
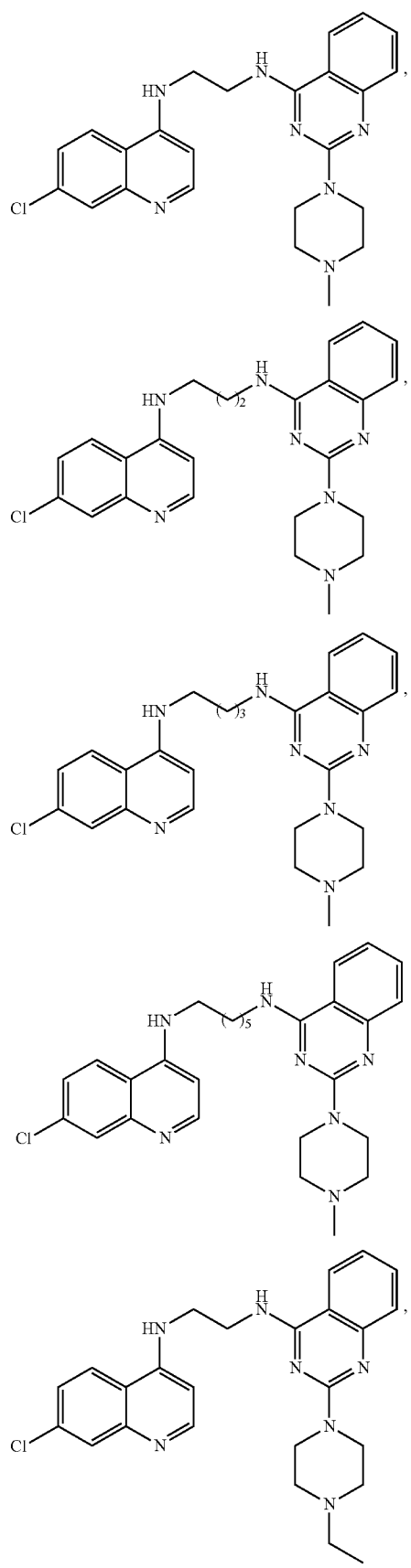
312
-continued
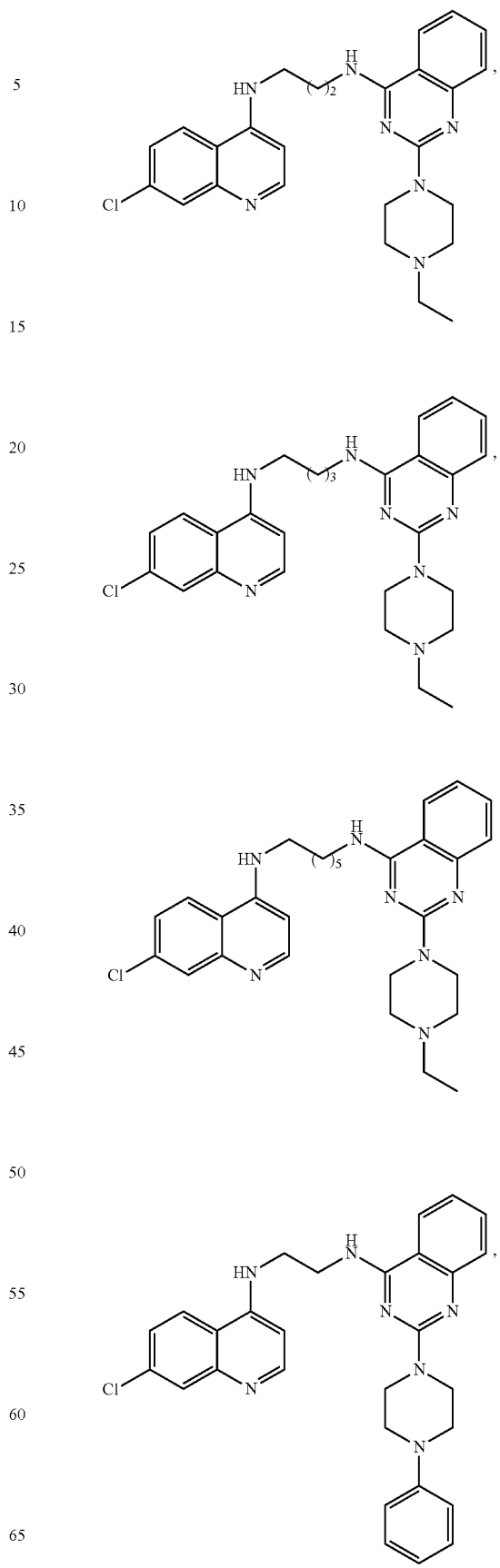

313
-continued
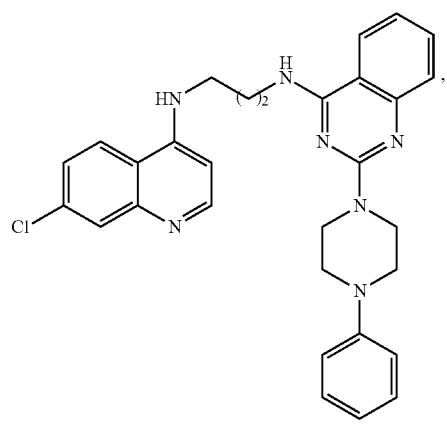
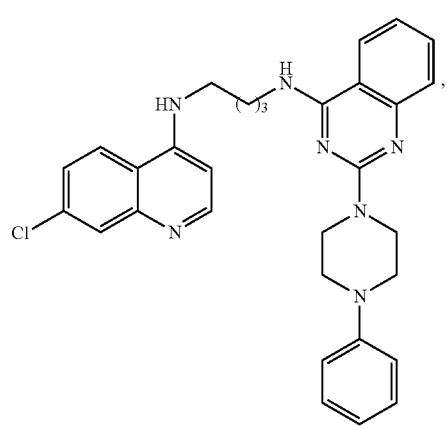
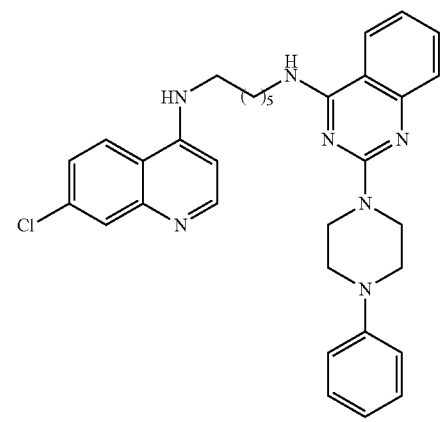
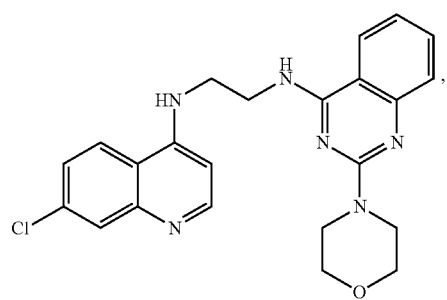
314
-continued
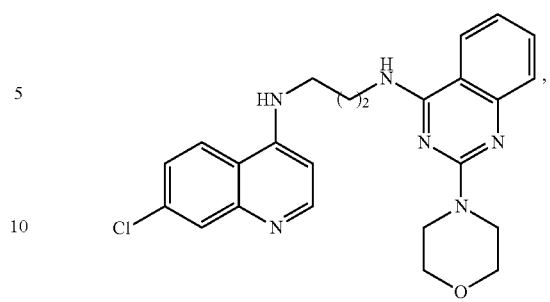
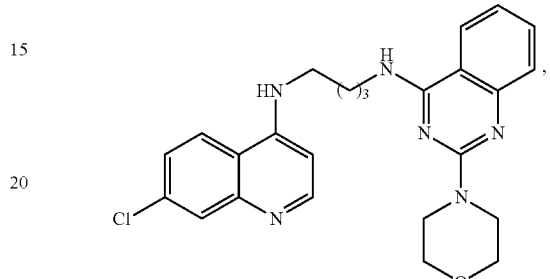
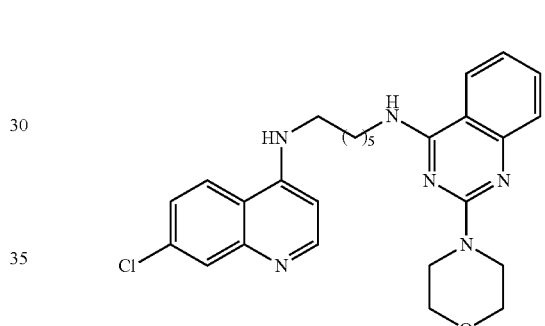
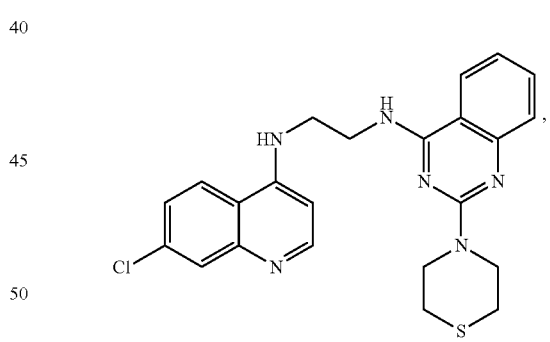
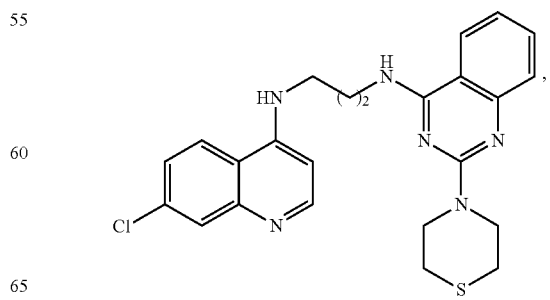

-continued
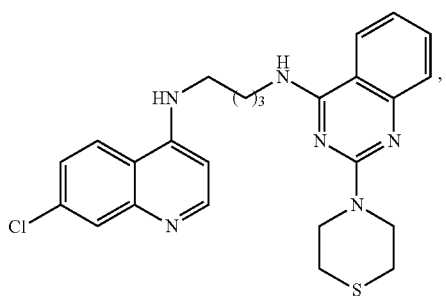
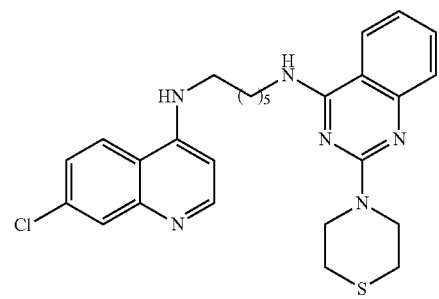
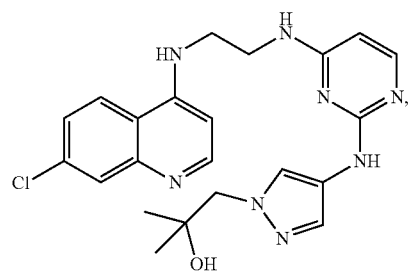
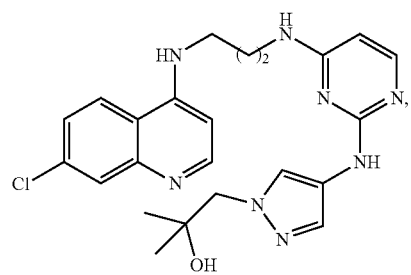
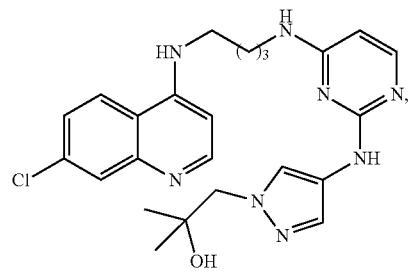
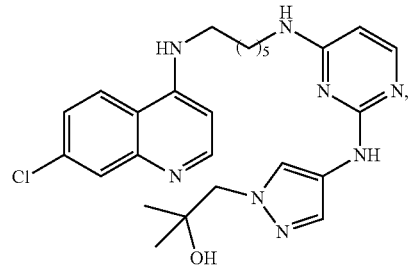
-continued
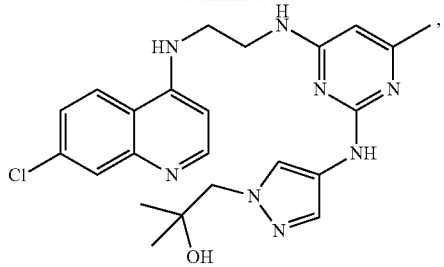
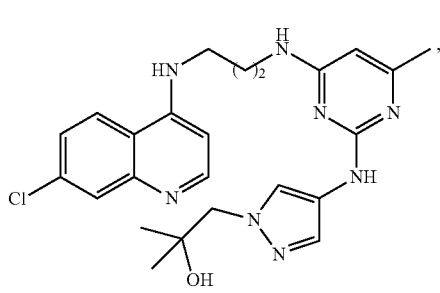
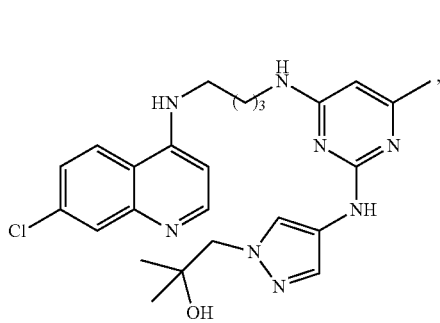
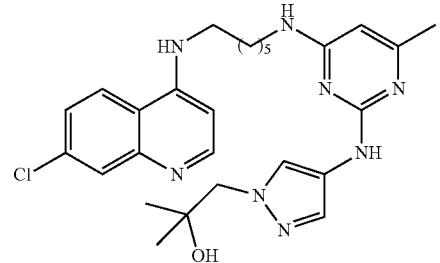
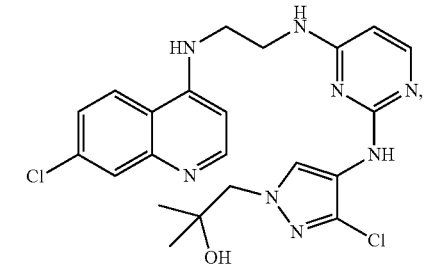
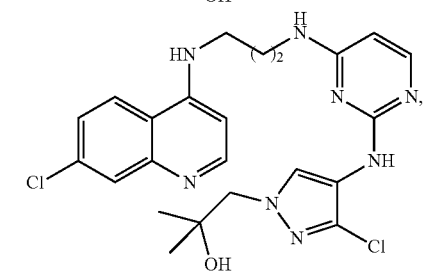

317
-continued
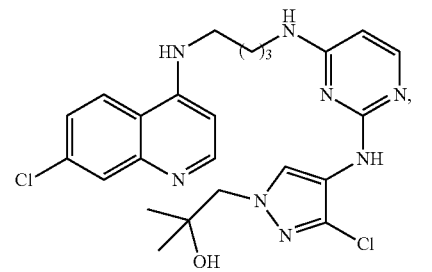
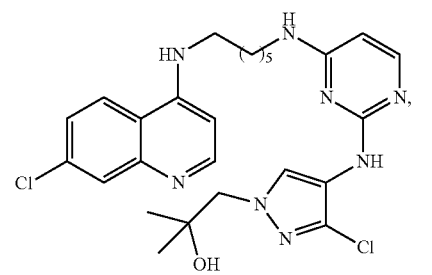
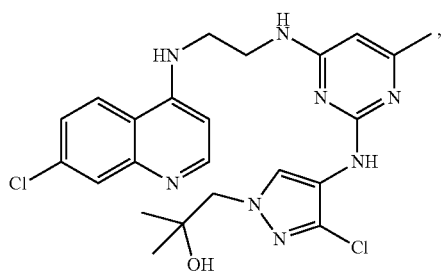
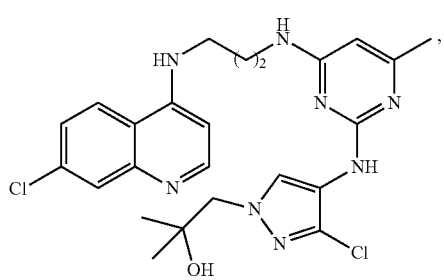
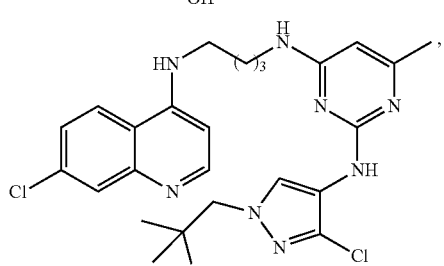
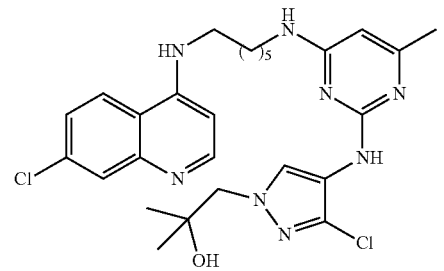
318
-continued
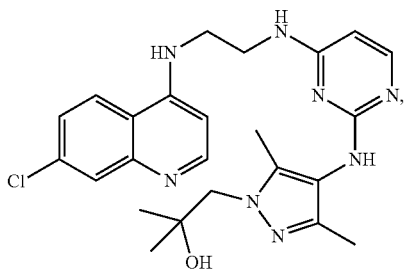
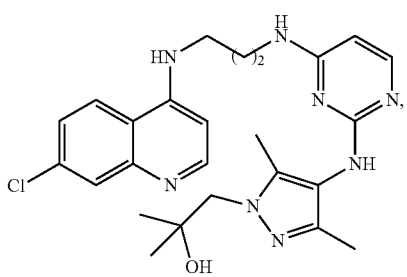
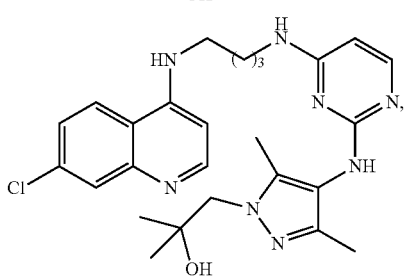
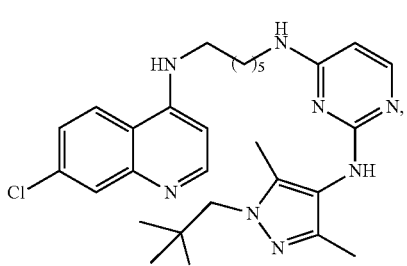
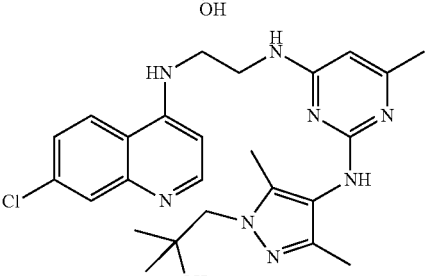
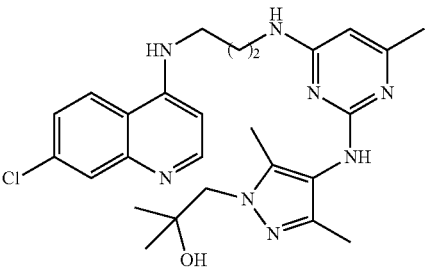

319
-continued
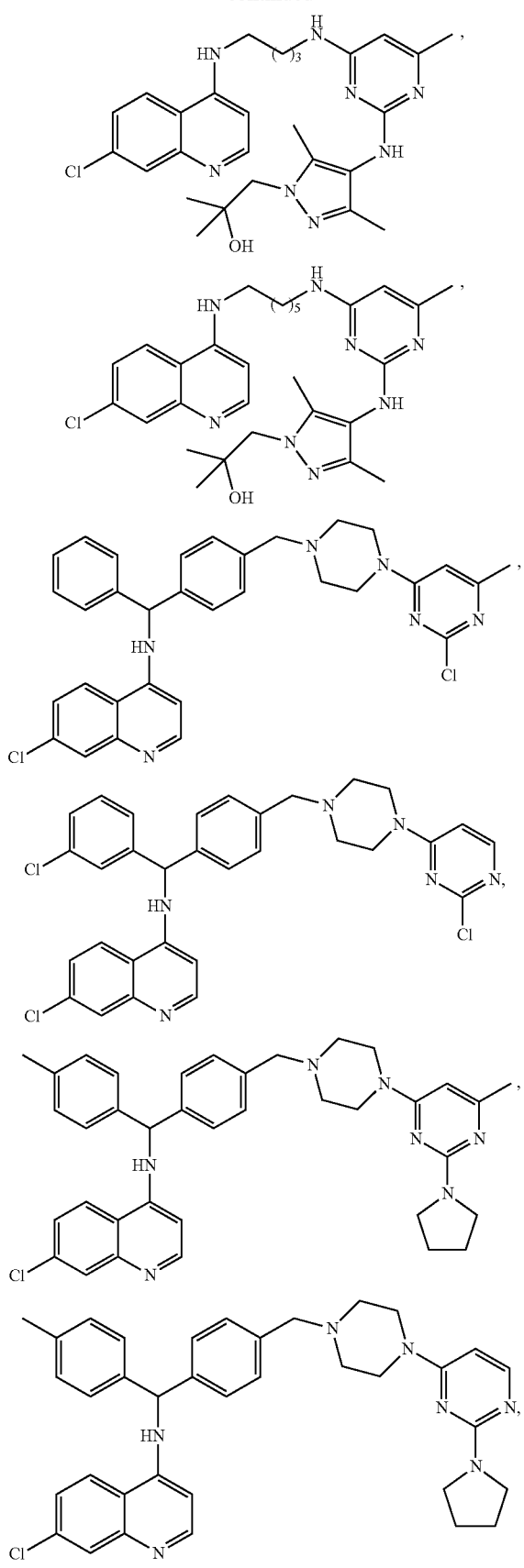
320
-continued
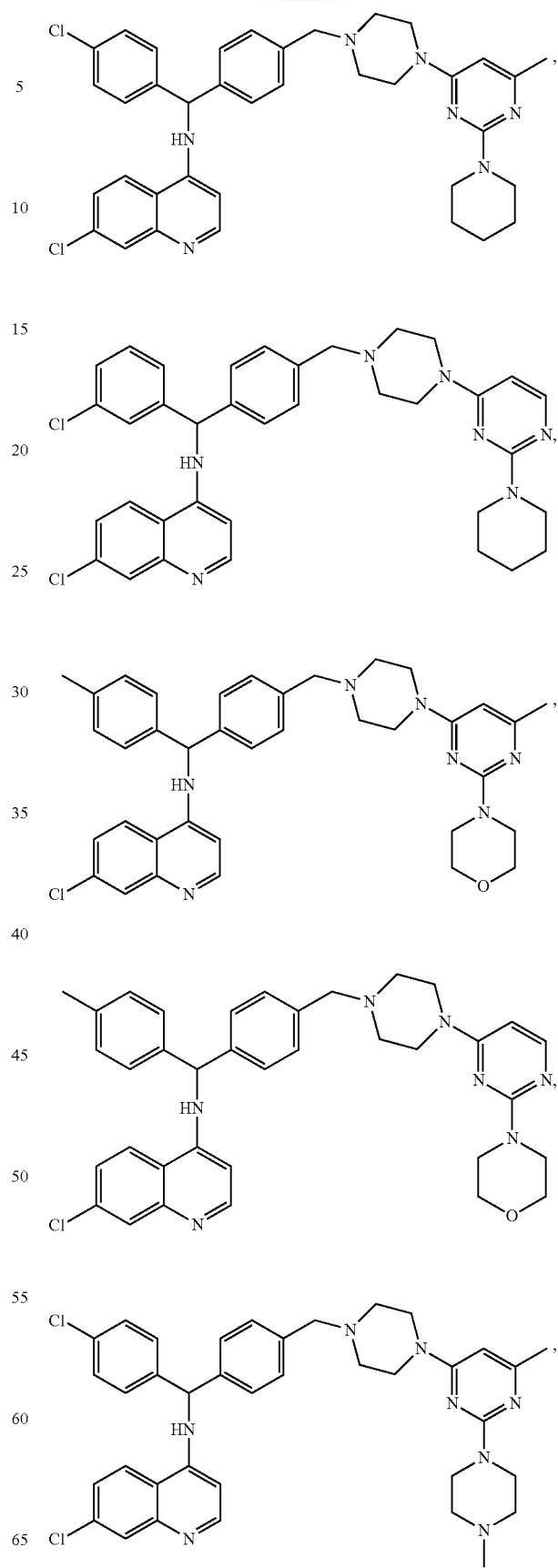

321
-continued
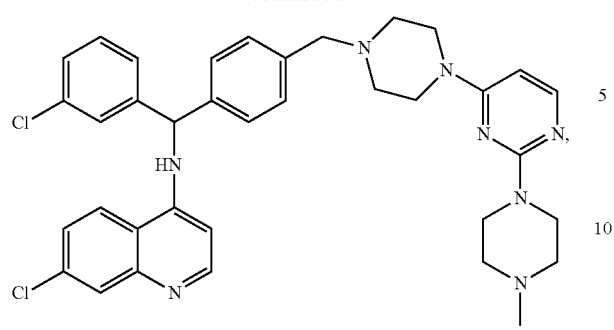
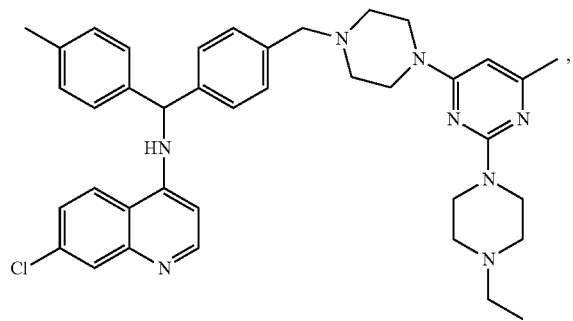
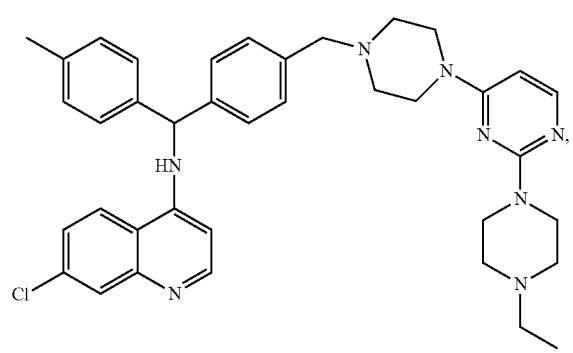
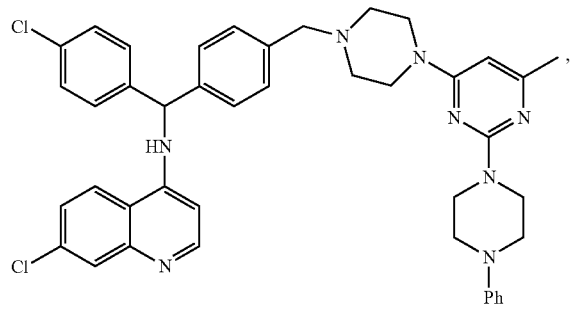
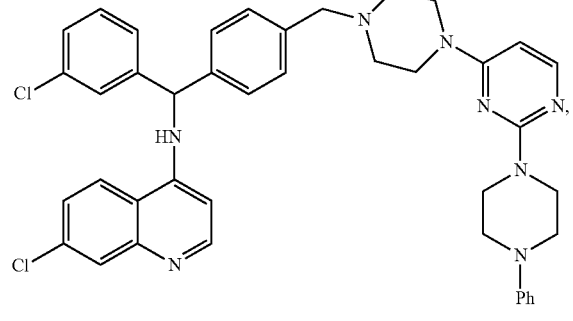
322
-continued
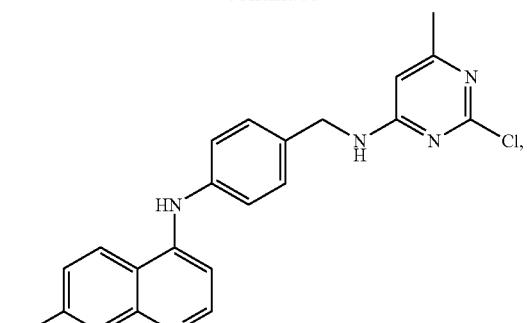
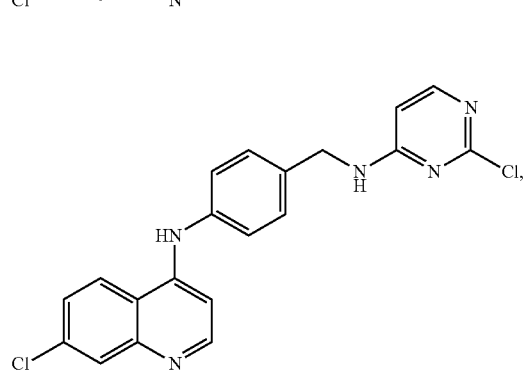
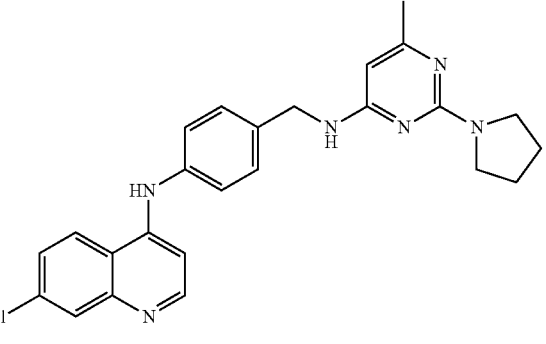
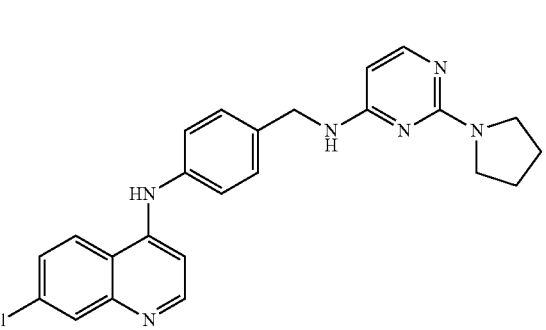
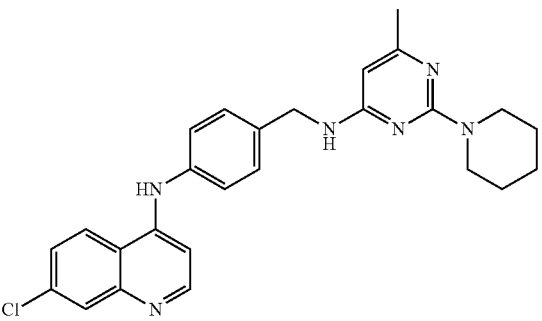

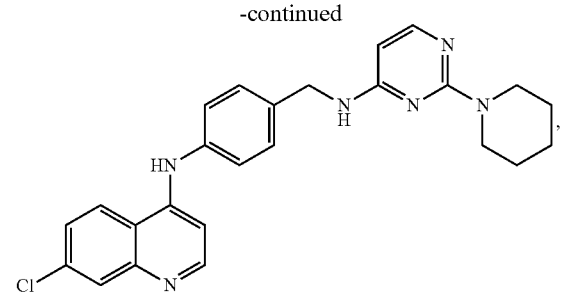
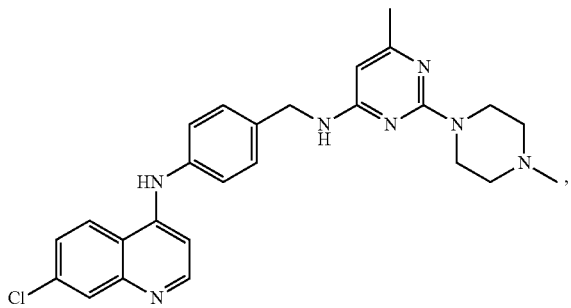
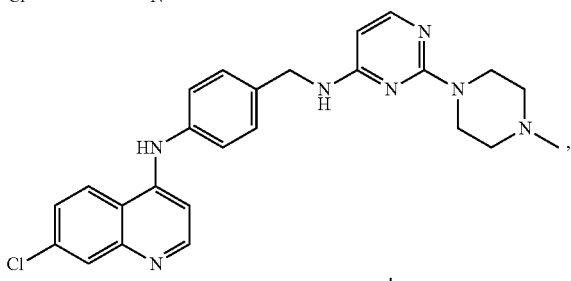
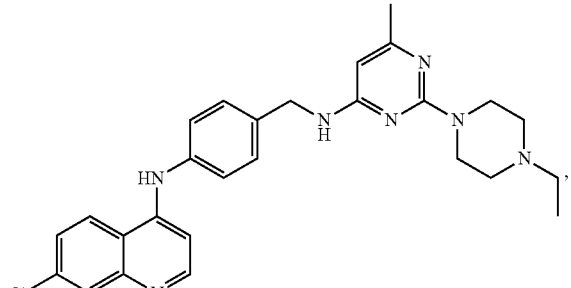
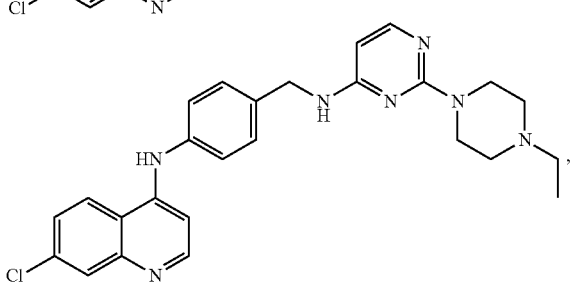
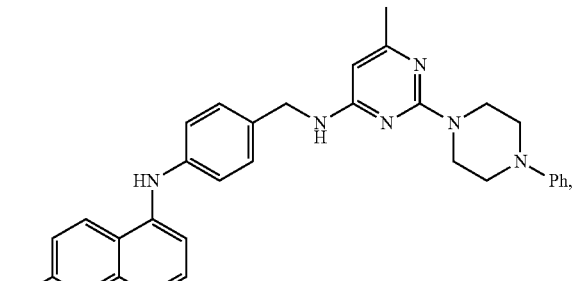
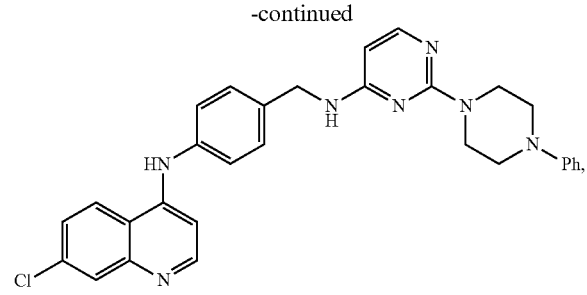
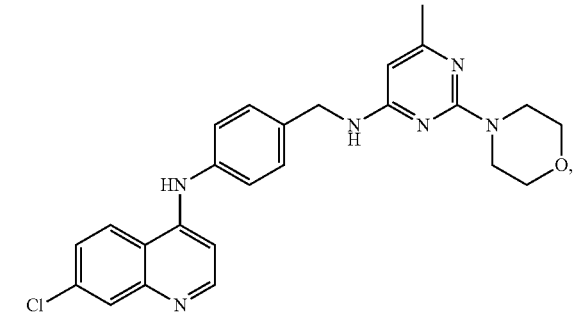
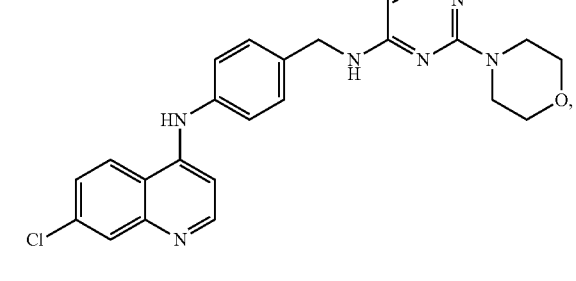
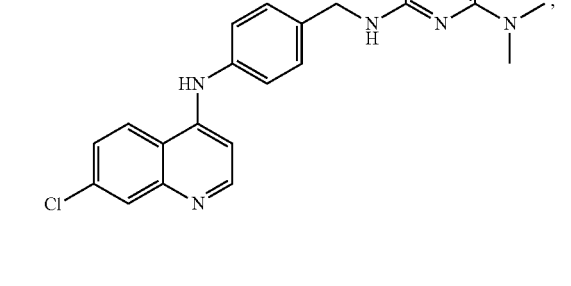
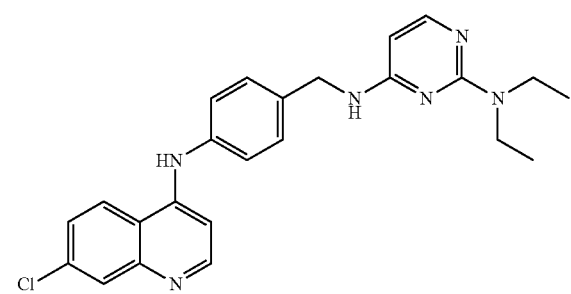

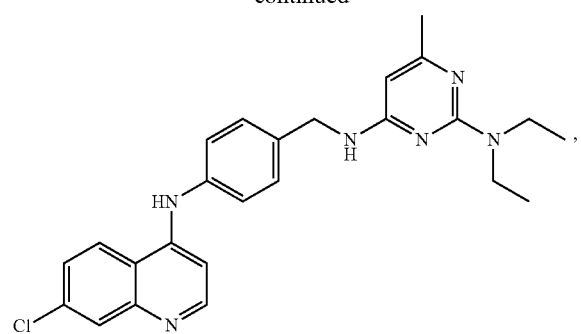
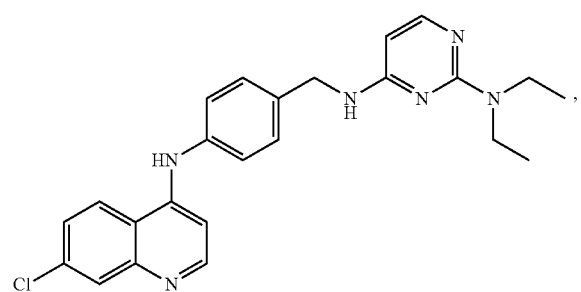
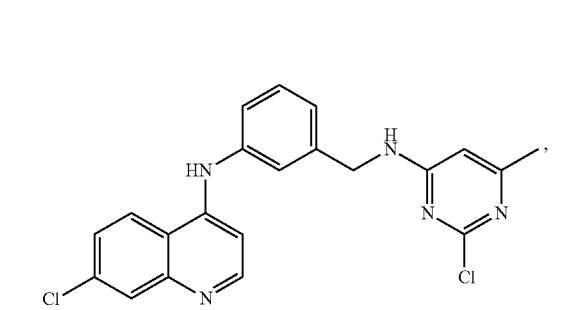
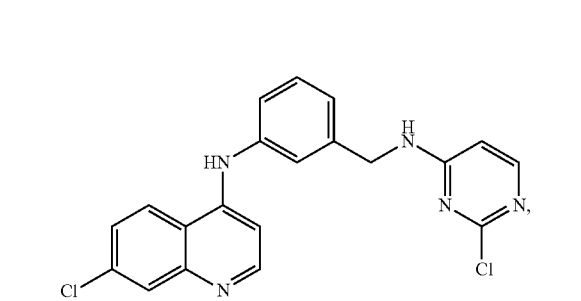
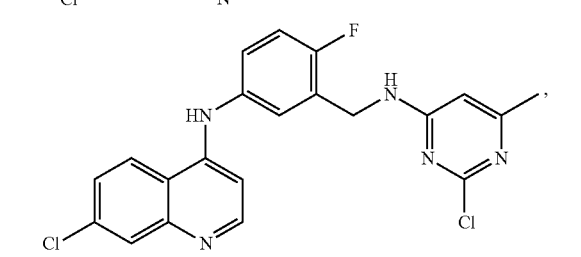
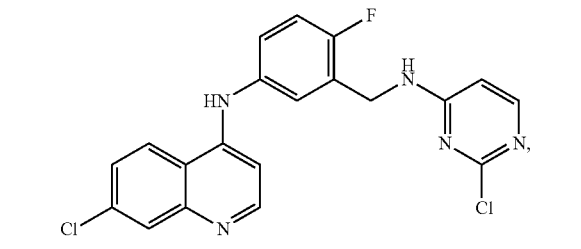
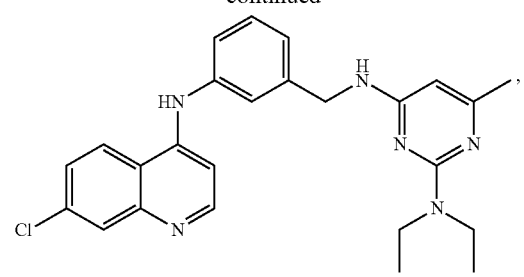
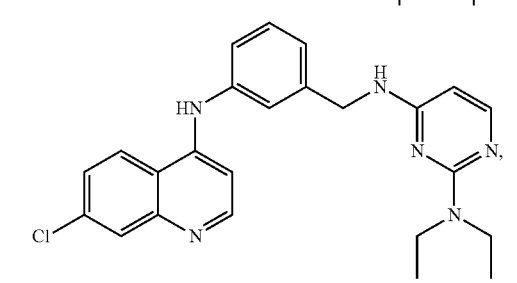
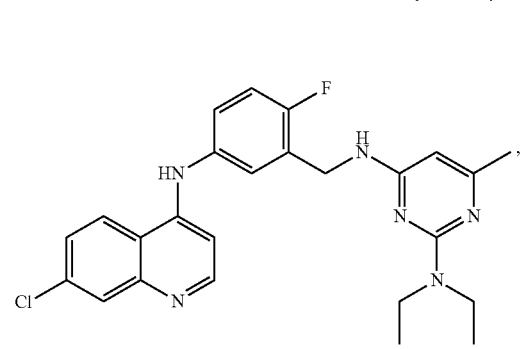
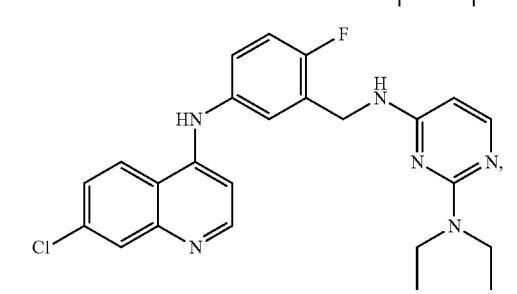
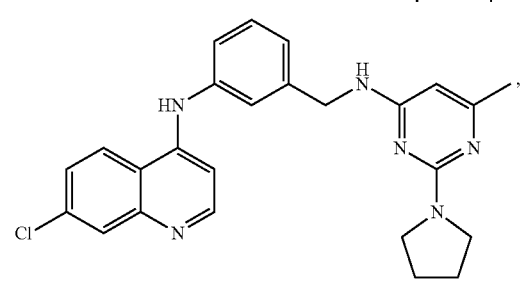
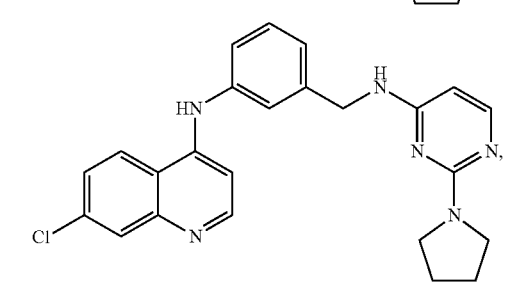

327
-continued
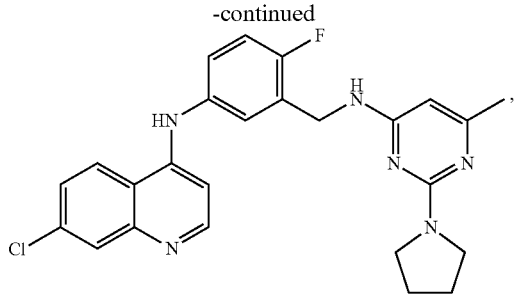
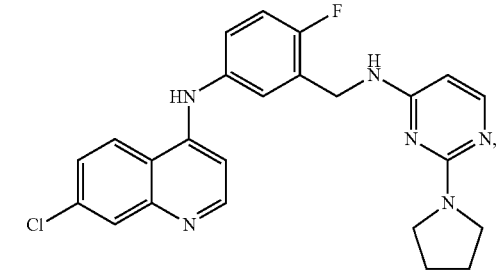
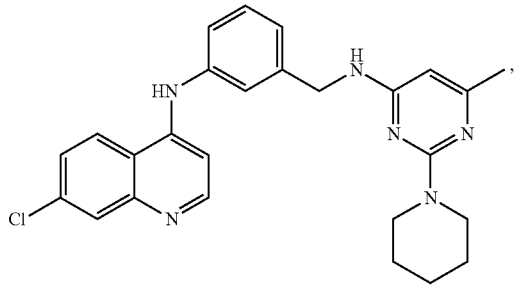
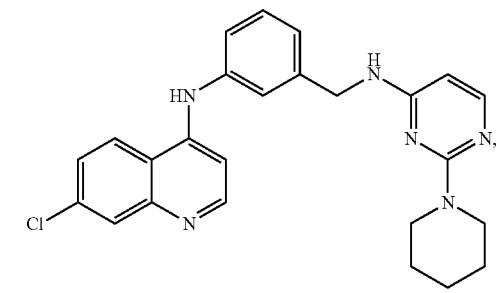
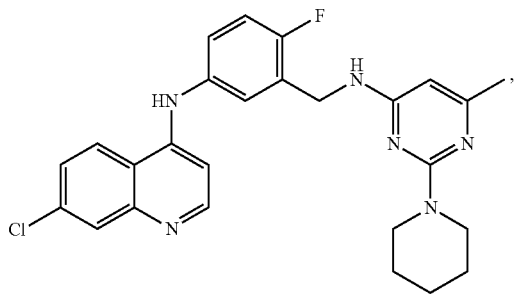
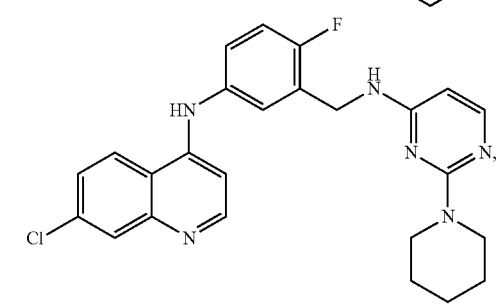
328
-continued
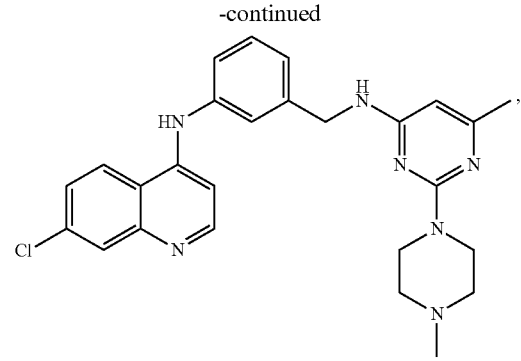
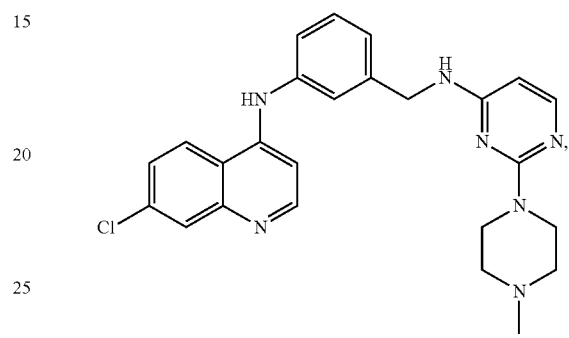
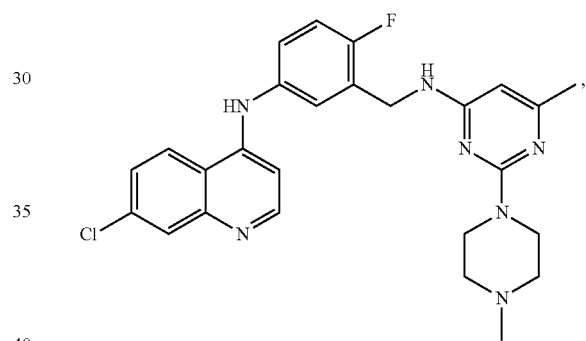
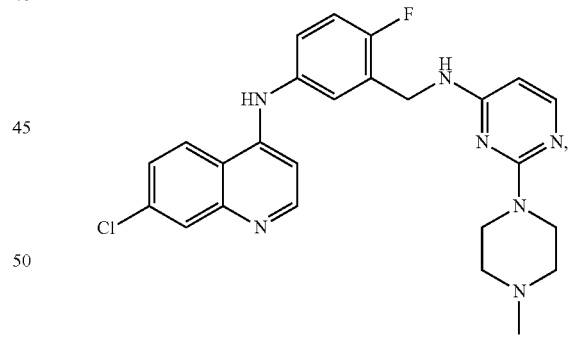
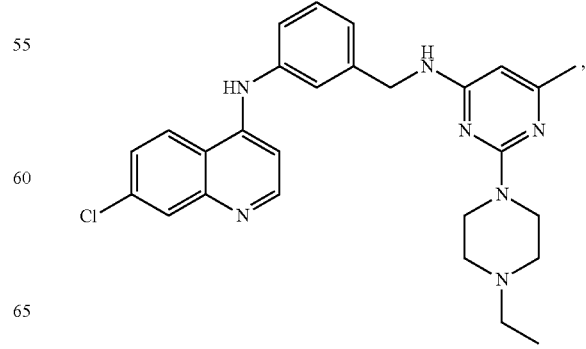

329
-continued
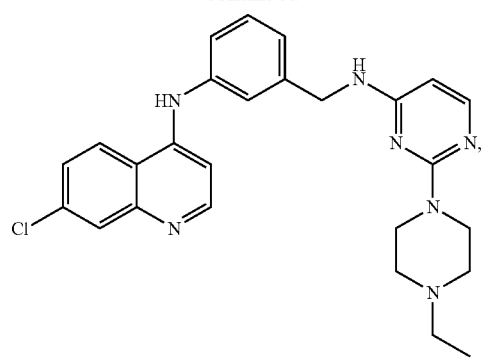
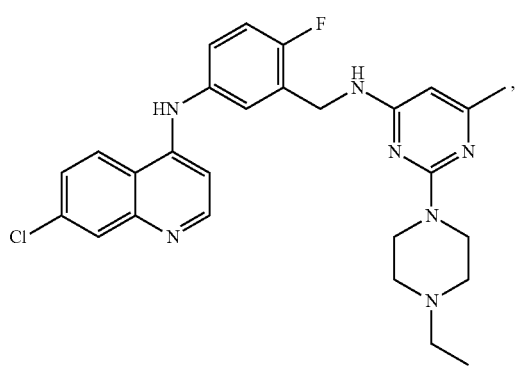
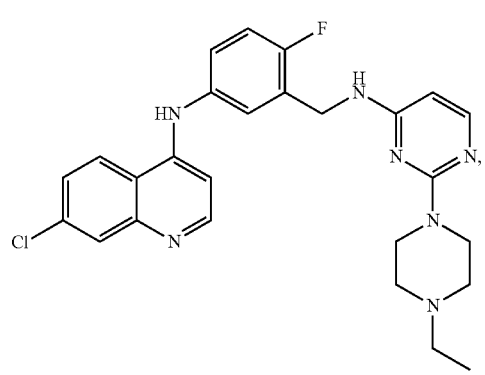
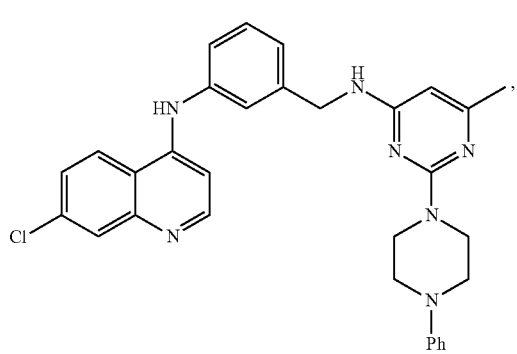
330
-continued
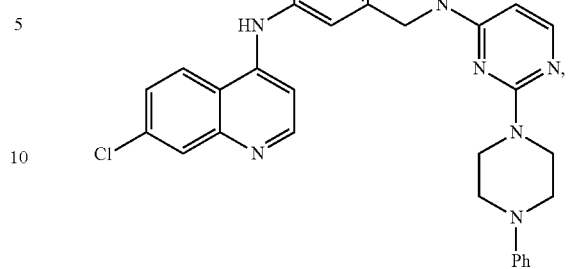
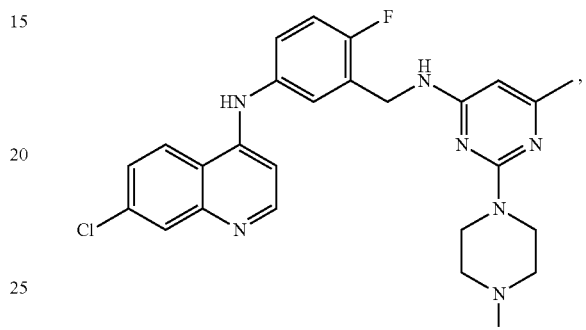
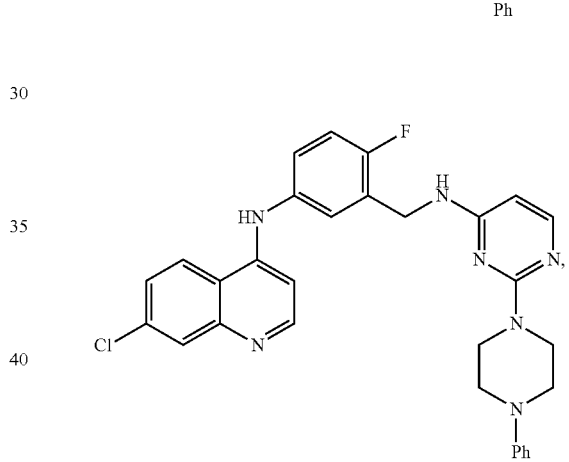
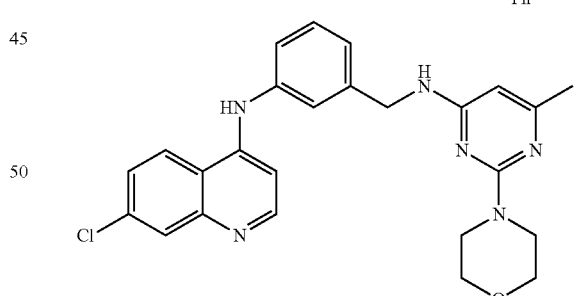
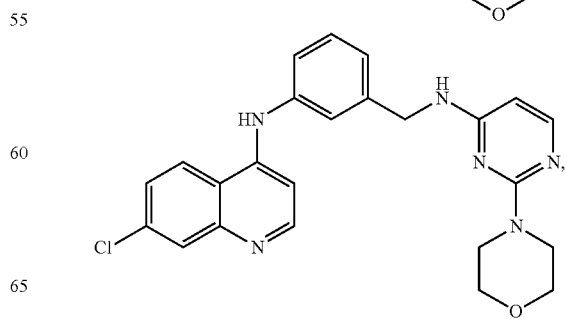

331
-continued
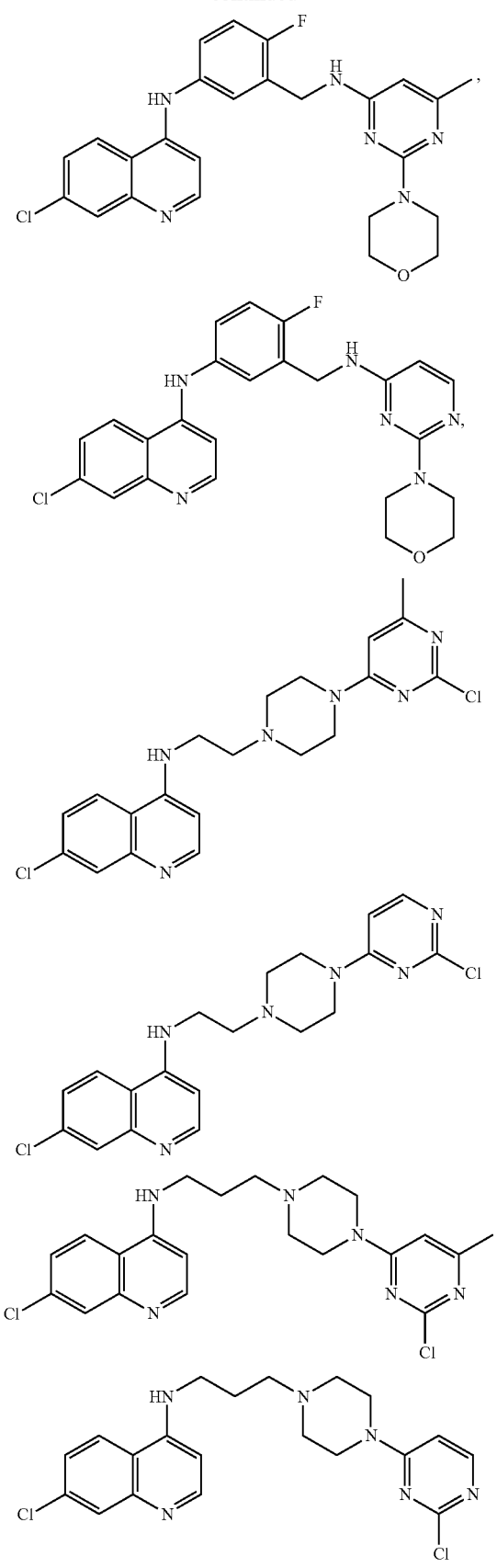
332
-continued
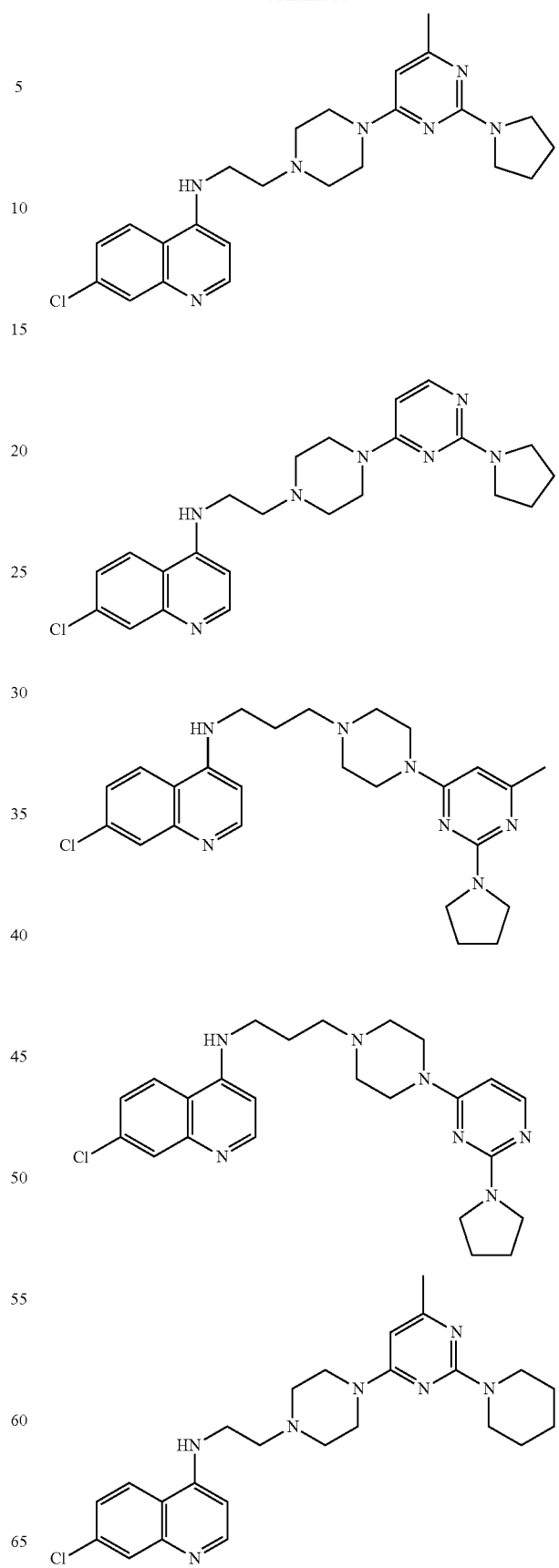

333
-continued
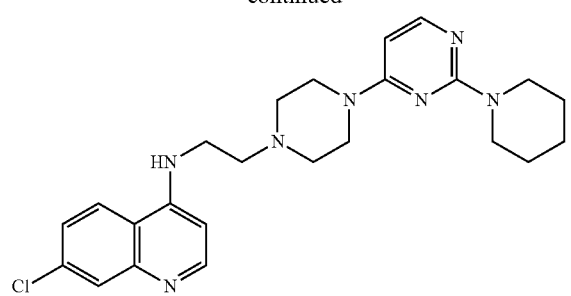
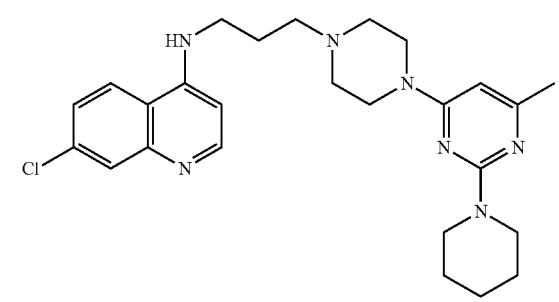
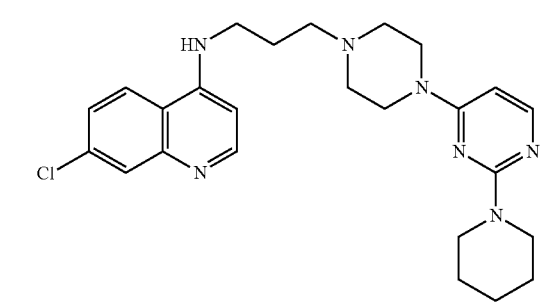
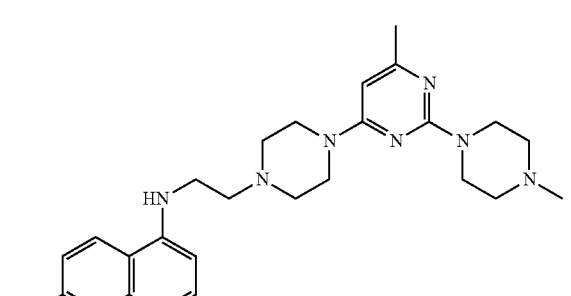
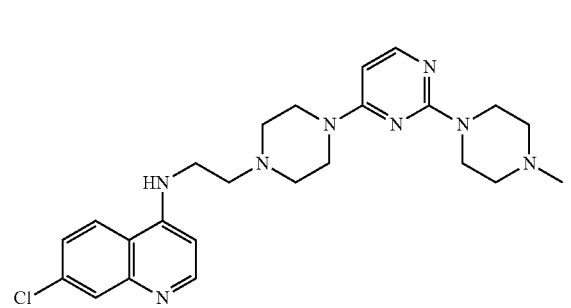
334
-continued
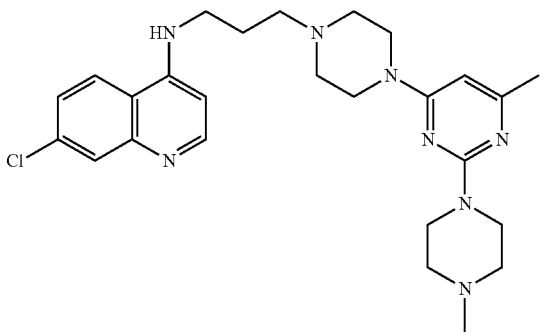
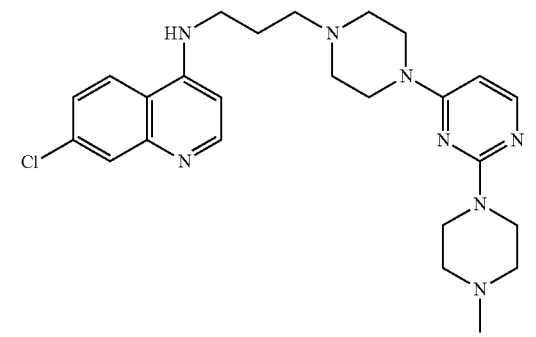
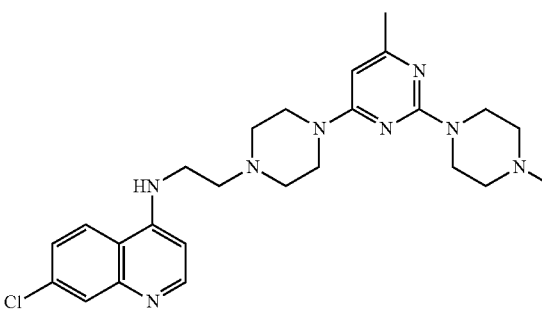
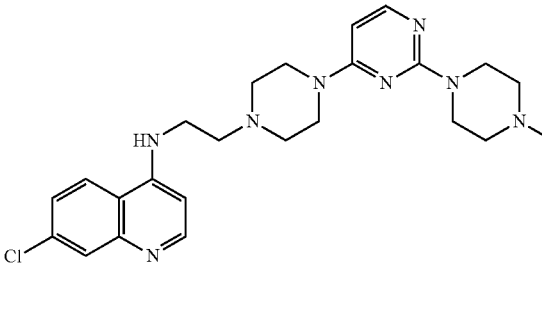
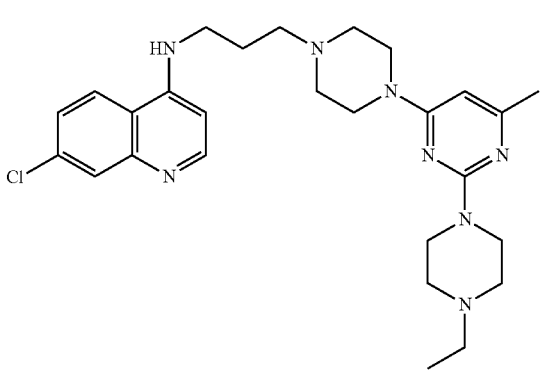

335
-continued
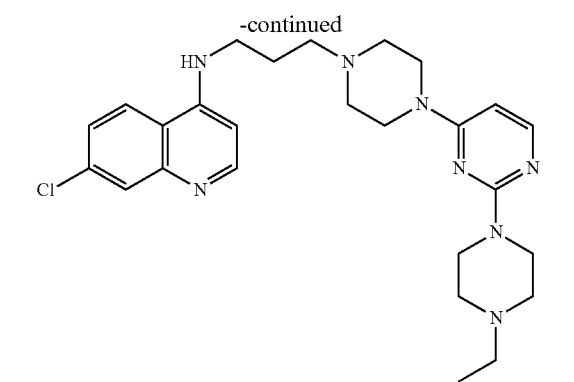
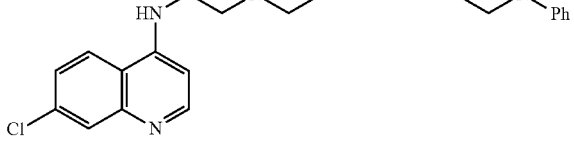
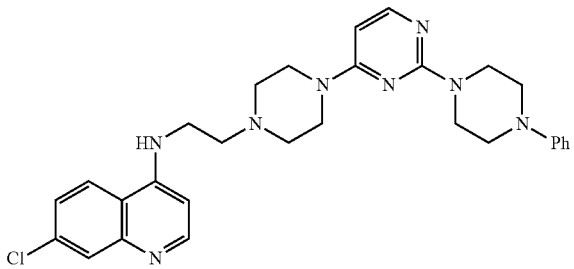
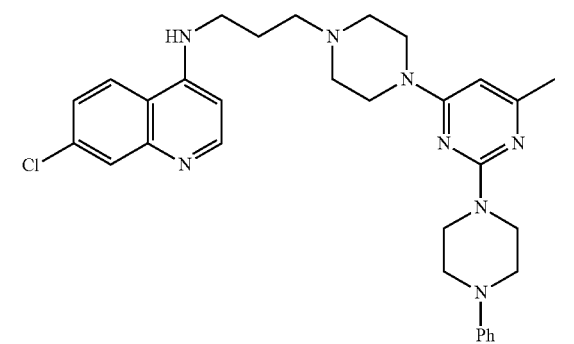
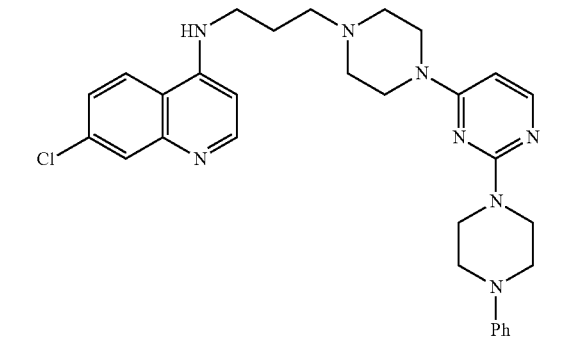
336
-continued
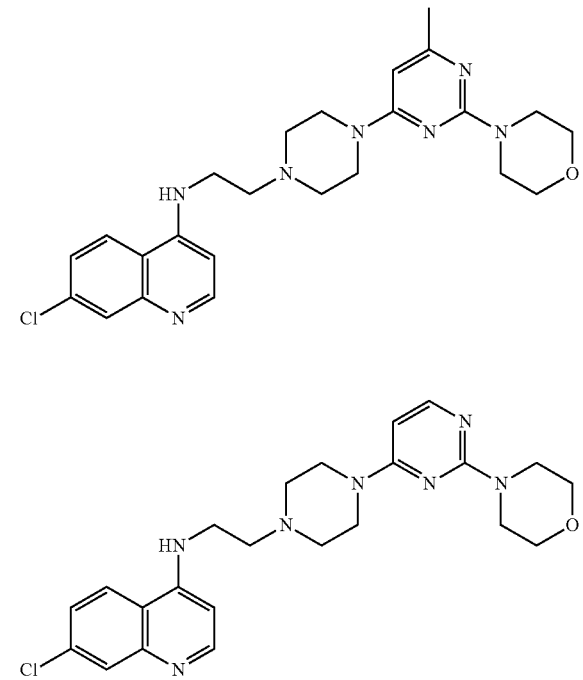
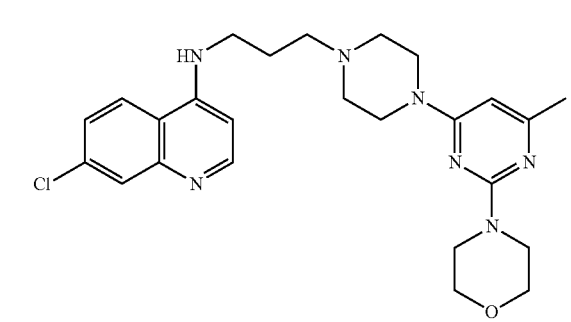
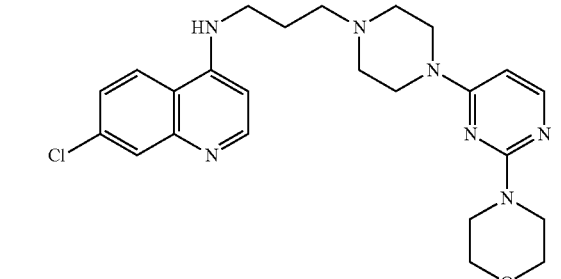
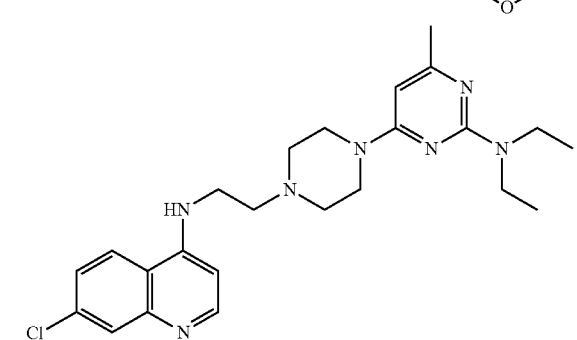

-continued

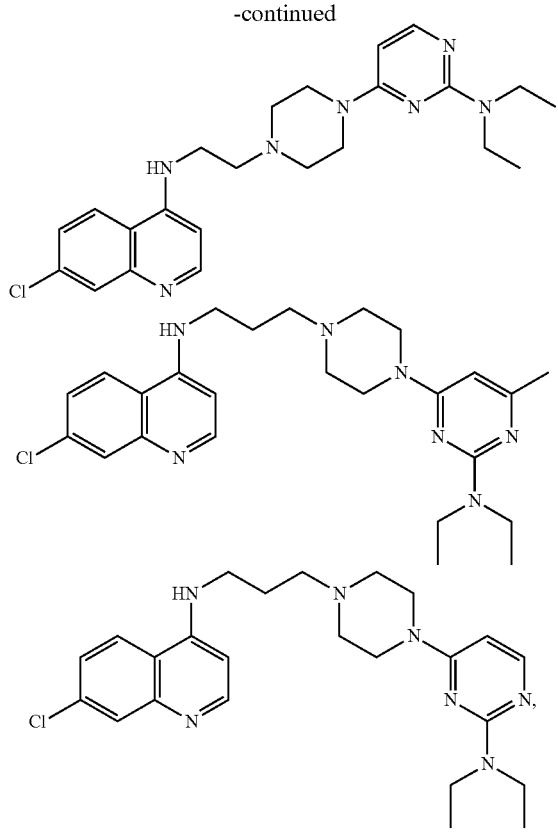

and any pharmaceutically acceptable salt, hydrate, solvate, ester, stereoisomer mixture, or enantiomer thereof.

3. The compound of claim 1, wherein the compound is

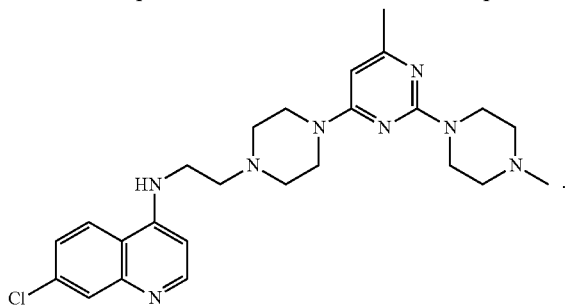

4. A composition comprising a compound of claim 1 and a stem cell.

5. The composition of claim 4, wherein the stem cell is a human embryonic stem cell.

6. A compound of Formula (I):

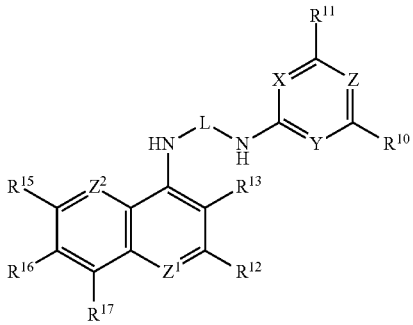

Formula (I)

wherein:

X, Y, and Z are independently $CR^{18}$, N, O, or S, provided that at least one of X, Y, and Z is N;

$Z^1$ is $CR^{14}$;

$Z^2$ is N;

R and $R^{10}$-$R^{18}$ are independently H, linear or branched alkyl, linear or branched alkenyl, linear or branched alkynyl, cyclyl, heterocyclyl, aryl, heteroaryl, halogen, trifluoromethyl, alkoxy, nitro, cyano, carbonyl, hydroxyl, phenoxy, amino, alkylamino, thiol, or alkylthio, each of which can be optionally substituted; and L is a linker, and any pharmaceutically acceptable salt, hydrate, solvate, ester, stereoisomer mixture, or enantiomer thereof.

\* \* \* \* \*

UNITED STATES PATENT AND TRADEMARK OFFICE
CERTIFICATE OF CORRECTION

PATENT NO. : 9,567,316 B2
APPLICATION NO. : 14/382727
DATED : February 14, 2017
INVENTOR(S) : Diwan S. Rawat et al.

It is certified that error appears in the above-identified patent and that said Letters Patent is hereby corrected as shown below:

In the Specification

In Column 1, Line 5, delete "Grant Number MH048866" and insert -- Grant Numbers MH048866 and NS084869 --

Signed and Sealed this
Sixteenth Day of August, 2022

Katherine Kelly Vidal
Director of the United States Patent and Trademark Office

SEQUENCE LISTING

```
<160> NUMBER OF SEQ ID NOS: 35

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gctttcaagc ttatgccttg tgttcaggcg cagtatgg                              38

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtcaatctcg aggaaaggta aggtgtccag gaaaag                                36

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctcggaggac agtactccg                                                   19

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gatcgaaaac aaaaggtcac ttac                                             24

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaaaaacata tggttaaaga agtggttcg                                        29
```

```
<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtcaatctcg agttagaaag gtaaggtgtc caggaaaag                              39

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaggtgcata tgaccagcag cgccaacgag gacatg                                 36

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaaaaactcg agctaagtca tttggtgcgg cgcctc                                 36

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9 aaacccccata tgaagcagcc cccagatgcc                                       30

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaaaaactcg agtcagaagg gcagcgt                                           27

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcaactgttc ctgaactcaa ct                                                22
```

```
<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atcttttggg gtccgtcaac t                                                  21

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tagtccttcc taccccaatt tcc                                                23

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ttggtcctta gccactcctt c                                                  21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acatcgaccc gtccacagta t                                                  21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cagaggggta ggcttgtctc                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atgtcggctc caggacctta                                                    20

<210> SEQ ID NO 18
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggtagtaact gttgacaccc act                                            23

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aggtcggtgt gaacggattt g                                              21

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgtagaccat gtagttgagg tca                                            23

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agcccccacc tggagtattt tg                                             22

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agcaatctct tccgctgtgt attc                                           24

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcctttatct gtcctgagtt ccg                                            23

<210> SEQ ID NO 24
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgatgagtcc tgagtcctgg tgac                                            24

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gctggcacat ctatcctctt tgg                                             23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
caatgctgac cacgaccaca tac                                             23

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcacacaaaa tgggaaggtg gc                                              22

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cattttttcc tccttagcag gtgg                                            24

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgacatcaag aaggtggtga agc                                             23

<210> SEQ ID NO 30
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 30
ggaagaatgg gagttgctgt tg                                              22

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcgtggagag gatgcgcagg                                                 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agtgcaagct ggtggtcccg                                                 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tccttagaga tcctgtttcc                                                 20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcagctggtc cccatgtaag                                                 20

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tttttttttt tttttttt                                                   18
```